(12) United States Patent  (10) Patent No.: US 8,809,342 B2
Aspnes et al.                (45) Date of Patent:    Aug. 19, 2014

(54) GLUCAGON RECEPTOR MODULATORS

(75) Inventors: Gary Erik Aspnes, Rockville, RI (US); Mary Theresa Didiuk, Madison, CT (US); Kevin James Filipski, Ivoryton, CT (US); Angel Guzman-Perez, Belmont, MA (US); Jeffrey Allen Pfefferkorn, Mystic, CT (US); Benjamin Dawson Stevens, Manchester, CT (US); Meihua Mike Tu, Mystic, CT (US)

(73) Assignee: Pfizer Inc., New York, NY (US)

( * ) Notice: Subject to any disclaimer, the term of this patent is extended or adjusted under 35 U.S.C. 154(b) by 187 days.

(21) Appl. No.: 13/334,202

(22) Filed: Dec. 22, 2011

(65) Prior Publication Data

US 2012/0165343 A1    Jun. 28, 2012

Related U.S. Application Data

(60) Provisional application No. 61/562,008, filed on Nov. 21, 2011, provisional application No. 61/426,600, filed on Dec. 23, 2010.

(51) Int. Cl.
*C07D 401/12* (2006.01)
*A61K 31/4427* (2006.01)

(52) U.S. Cl.
CPC .......... *C07D 401/12* (2013.01); *A61K 31/4427* (2013.01)
USPC ........... 514/256; 514/332; 514/340; 514/352; 544/333; 546/262; 546/268.4; 546/310

(58) Field of Classification Search
CPC ................... C07D 401/12; A61K 31/4427
USPC ........ 544/333; 546/262, 268.4, 310; 514/256, 514/332, 340, 352
See application file for complete search history.

(56) References Cited

U.S. PATENT DOCUMENTS

| | | | |
|---|---|---|---|
| 5,776,954 A | 7/1998 | de Laszlo et al. | |
| 5,837,719 A | 11/1998 | de Laszlo et al. | |
| 5,880,139 A | 3/1999 | Chang | |
| 5,939,359 A | 8/1999 | Engel et al. | |
| 6,103,720 A | 8/2000 | Lubisch et al. | |
| 6,211,242 B1 | 4/2001 | Setoi et al. | |
| 6,218,431 B1 | 4/2001 | Schoen et al. | |
| 7,151,114 B2 | 12/2006 | Streicher et al. | |
| 7,687,534 B2 | 3/2010 | Stelmach et al. | |
| 2003/0203946 A1 | 10/2003 | Behrens et al. | |
| 2004/0097552 A1 | 5/2004 | Duffy et al. | |
| 2004/0097557 A1 | 5/2004 | Duffy et al. | |
| 2004/0209928 A1 | 10/2004 | Kurukulasuriya et al. | |
| 2004/0209943 A1 | 10/2004 | Erickson et al. | |
| 2004/0266856 A1 | 12/2004 | Chu et al. | |
| 2005/0272794 A1 | 12/2005 | Parmee et al. | |
| 2006/0094764 A1 | 5/2006 | Anderskewitz et al. | |
| 2006/0122236 A1* | 6/2006 | Wood et al. .................. | 514/352 |
| 2006/1222256 | 6/2006 | Gillespie et al. | |
| 2007/0088070 A1 | 4/2007 | Parmee et al. | |
| 2007/0088071 A1 | 4/2007 | Kim et al. | |
| 2012/0053173 A1 | 3/2012 | Banno et al. | |
| 2012/0059012 A1 | 3/2012 | Fujii et al. | |

FOREIGN PATENT DOCUMENTS

| | | |
|---|---|---|
| CN | 102206172 | 10/2011 |
| DE | 10300398 | 1/2003 |
| GB | 2292149 | 2/1996 |
| JP | 10259176 | 9/1998 |
| JP | 200560835 | 3/2005 |
| JP | 2009040702 | 2/2009 |
| WO | 9219210 | 11/1992 |
| WO | 9414427 | 7/1994 |
| WO | 9421590 | 9/1994 |
| WO | 9609818 | 4/1996 |
| WO | 9716442 | 5/1997 |
| WO | 9804528 | 2/1998 |
| WO | 9822109 | 5/1998 |
| WO | 9824780 | 6/1998 |
| WO | 9824782 | 6/1998 |
| WO | 9901423 | 1/1999 |
| WO | 9924404 | 5/1999 |
| WO | 9932448 | 7/1999 |
| WO | 0064876 | 11/2000 |

(Continued)

OTHER PUBLICATIONS

Djuric, et al., "Glucagon receptor antagonists for the treatment of type II diabetes: current prospects", Current Opinion in Investigational Drugs vol. 3(11), pp. 1617-1623 (2002).
Potent and Orally Available 3-Cyano-4-hydroxybenzoic Acid [1-(2,3,5,6-Tetramethylbenzyl)-1H-indol-4-ylmethylene]hydrazide. Journal of Medicinal Chemistry", vol. 45(26), pp. 5755-5775 (2002).
Lau, et al., "New b-alanine derivatives are orally available glucagon receptor antagonists", Journal of Medicinal Chemistry, vol. 50(1), pp. 113-128 (2007).

(Continued)

*Primary Examiner* — Deepak Rao
(74) *Attorney, Agent, or Firm* — James T. Wasicak

(57) ABSTRACT

The present invention provides a compound of Formula (I)

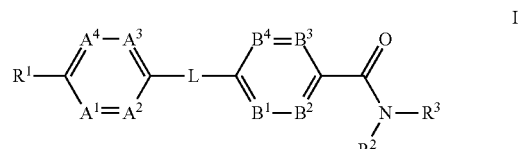

or a pharmaceutically acceptable salt thereof wherein $R^1$, $R^2$, $R^3$, $A^1$, $A^2$, $A^3$, $A^4$, L, $B^1$, $B^2$, $B^3$ and $B^4$ are as defined herein. The compounds of Formula I have been found to act as glucagon antagonists or inverse agonists. Consequently, the compounds of Formula I and the pharmaceutical compositions thereof are useful for the treatment of diseases, disorders, or conditions mediated by glucagon.

8 Claims, No Drawings

(56) References Cited

FOREIGN PATENT DOCUMENTS

| | | |
|---|---|---|
| WO | 0064888 | 11/2000 |
| WO | 0069810 | 11/2000 |
| WO | 0200612 | 1/2002 |
| WO | 0240446 | 5/2002 |
| WO | 02070462 | 9/2002 |
| WO | 03047626 | 6/2003 |
| WO | 03048109 | 6/2003 |
| WO | 03051357 | 6/2003 |
| WO | 03053938 | 7/2003 |
| WO | 03055482 | 7/2003 |
| WO | 03064404 | 8/2003 |
| WO | 03080545 | 10/2003 |
| WO | 03087044 | 10/2003 |
| WO | 03097619 | 11/2003 |
| WO | 2004002480 | 1/2004 |
| WO | 2004002481 | 1/2004 |
| WO | 2004024066 | 3/2004 |
| WO | 2004050039 | 6/2004 |
| WO | 2004056763 | 7/2004 |
| WO | 2004063147 | 7/2004 |
| WO | 2004069158 | 8/2004 |
| WO | 2004092146 | 10/2004 |
| WO | 2004099170 | 11/2004 |
| WO | 2004100875 | 11/2004 |
| WO | 2005014534 | 2/2005 |
| WO | 2005058845 | 6/2005 |
| WO | 2005065680 | 7/2005 |
| WO | 2005 118542 | 12/2005 |
| WO | 2005 123668 | 12/2005 |
| WO | 2006014618 | 2/2006 |
| WO | 2006017055 | 2/2006 |
| WO | 2006042850 | 4/2006 |
| WO | 2006086488 | 8/2006 |
| WO | 2006102067 | 9/2006 |
| WO | 2006104826 | 10/2006 |
| WO | 2007015999 | 2/2007 |
| WO | 2007022380 | 2/2007 |
| WO | 2007040445 | 4/2007 |
| WO | 2007059195 | 5/2007 |
| WO | 2007072179 | 6/2007 |
| WO | 2007091396 | 8/2007 |
| WO | 2007 106181 | 9/2007 |
| WO | 2007 114855 | 10/2007 |
| WO | 2007 120270 | 10/2007 |
| WO | 2007111864 | 10/2007 |
| WO | 2007120284 | 10/2007 |
| WO | 2007 123581 | 11/2007 |
| WO | 2007136577 | 11/2007 |
| WO | 2008042223 | 4/2008 |
| WO | 2008098244 | 8/2008 |
| WO | 2009035558 | 3/2009 |
| WO | 2009057784 | 5/2009 |
| WO | 2009110520 | 9/2009 |
| WO | 2009111700 | 9/2009 |
| WO | 2009125424 | 10/2009 |
| WO | 2009140342 | 11/2009 |
| WO | 2010 019828 | 2/2010 |
| WO | 2010019830 | 2/2010 |
| WO | 2010030722 | 3/2010 |
| WO | 2010039789 | 4/2010 |
| WO | 2010071750 | 6/2010 |
| WO | 2010080971 | 7/2010 |
| WO | 2010088061 | 8/2010 |
| WO | 2010098948 | 9/2010 |
| WO | 2010098994 | 9/2010 |
| WO | 2010131669 | 11/2010 |
| WO | 2010144664 | 12/2010 |
| WO | 2011007722 | 1/2011 |
| WO | 2011037815 | 3/2011 |
| WO | 2011119541 | 9/2011 |
| WO | 2011119559 | 9/2011 |
| WO | 2011027849 | 10/2011 |

OTHER PUBLICATIONS

Kodra, et al., "Novel Glucagon Receptor Antagonists with Improved Selectivity over the Glucose-Dependent Insulinotropic Polypeptide Receptor", Journal of Medicinal Chemistry, vol. 51(17), pp. 5387-5396 (2008).

Madsen, et al., "Human Glucagon Receptor Antagonists with Thiazole Cores. A Novel Series with Superior Pharmacokinetic Properties", Journal of Medicinal Chemistry, vol. 52(9), pp. 2989-3000 (2009).

Rivera, et al., "A novel glucagon receptor antagonist, NNC 25-0926, blunts hepatic glucose production in the conscious dog", Journal of Pharmacology and Experimental Therapeutics, vol. 321(2), pp. 743-752 (2007).

Chen, et al., "Insight into the bioactivity and metabolism of human glucagon receptor antagonists from 3D-QSAR analyses", QSAR & Combinatorial Science, vol. 23(8), pp. 603-620 (2004).

Kurukulasuriya, et al., "Towards a potent small molecule Glucagon receptor antagonist", Abstracts of Papers, 228th ACS National Meeting, Philadelphia, PA, United States, Aug. 22-26, 2004, MEDI-035.

Sinz, et al., "Discovery of 2-acylindoles as potent, orally active human glucagon receptor antagonists." Abstracts of Papers, 235th ACS National Meeting, New Orleans, LA, United States, Apr. 6-10, 2008, MEDI-016.

Collins, et al., CP-99,711: A nonpeptide glucagon receptor antagonist. Bioorganic & Medicinal Chemistry Letters, vol. 2(9), pp. 915-918 (1992).

Kumar, et al., "Quantitative Structure-Activity Relationships of Selective Antagonists of Glucagon Receptor Using QuaSAR Descriptors", Chem. Pharm. Bull., vol. 54(11), pp. 1586-1591 (2006).

Madsen, et al., "Advances in Non-Peptide Glucagon Receptor Antagonists", Current Pharm. Design, vol. 5(9), pp. 683-691 (1999).

Parker, et al., "Effects of skyrin, a receptor-selective glucagon antagonist, in rat and human hepatocytes", Diabetes vol. 49(12), pp. 2079-2086 (2000).

Qureshi, et al., "A novel glucagon receptor antagonist inhibits glucagon-mediated biological effects", Diabetes, vol. 53(12), pp. 3267-3273 (2004).

Petersen, et al., "Effects of a novel glucagon receptor antagonist (Bay 27-9955) on glucagon-stimulated glucose production in humans", Diabetologia, vol. 44(11), pp. 2018-2024 (2001).

Winzell, et al., "Glucagon receptor antagonism improves islet function in mice with insulin resistance induced by a high-fat diet", Diabetologia, vol. 50(7), pp. 1453-1462 (2007).

Mu, et al., "Chronic treatment with a glucagon receptor antagonist lowers glucose and moderately raises circulating glucagon and glucagon-like peptide 1 without severe alpha cell hypertrophy in diet-induced obese mice", Diabetologia, vol. 54(9), pp. 2381-2391 (2011).

Ling, et al., "Small-molecule glucagon receptor antagonists", Drugs of the Future, vol. 27(10), pp. 987-993 (2002).

Guillon, et al., "Synthesis of new pyrrolo[1,2-a]quinoxalines: potential non-peptide glucagon receptor antagonists", European Journal of Medicinal Chemistry, vol. 33(4), pp. 293-308 (1998).

Dallas-Yang, et al., Hepatic glucagon receptor binding and glucose-lowering in vivo by peptidyl and non-peptidyl glucagon receptor antagonists. European Journal of Pharmacology, vol. 501(1-3), pp. 225-234 (2004).

Yang, et al., "Cloning and expression of canine glucagon receptor and its use to evaluate glucagon receptor antagonists in vitro and in vivo", European Journal of Pharmacology, vol. 555(1), pp. 8-16 (2007).

Sloop, et al., "Glucagon as a target for the treatment of Type 2 diabetes", Expert Opinion on Therapeutic Targets, vol. 9(3), pp. 593-600 (2005).

Ling, et al., "Approaches to glucagon receptor antagonists", Expert Opinion on Therapeutic Patents, vol. 13(1), pp. 15-22 (2003).

Kurukulasuriya, et al., "Progress towards glucagon receptor antagonist therapy for Type 2 diabetes", Expert Opinion on Therapeutic Patents, vol. 15(12), pp. 1739-1749 (2005).

Shen, et al., "A survey of small molecule glucagon receptor antagonists from recent patents (2006-2010)", Expert Opinion on Therapeutic Patents, vol. 21(8), pp. 1211-1240 (2011).

(56) References Cited

OTHER PUBLICATIONS

Cascieri, et al., "Characterization of a novel, non-peptidyl antagonist of the human glucagon receptor", Journal of Biological Chemistry, vol. 274(13), pp. 8694-8697 (1999).

Johansen, et al., "Labelling of a potent glucagon receptor antagonist with tritium, carbon-14 and stable isotopes", Journal of Labelled Compounds and Radiopharmaceuticals, vol. 50(5-6), pp. 466-467 (2007).

Madsen, et al., "Discovery and Structure-Activity Relationship of the First Non-Peptide Competitive Human Glucagon Receptor Antagonists", Journal of Medicinal Chemistry, vol. 41(26), pp. 5150-5157 (1998).

Ling, et al., Identification of Alkylidene Hydrazides as Glucagon Receptor Antagonists, Journal of Medicinal Chemistry, vol. 44(19), pp. 3141-3149 (2001).

Madsen, et al., "Optimization of Alkylidene Hydrazide Based Human Glucagon Receptor Antagonists. Discovery of the Highly Ladouceur, et al., "4-Phenylpyridine glucagon receptor antagonists: synthetic approaches to the sterically hindered chiral hydroxy group", Tetrahedron Letters, vol. 43(25), pp. 4455-4458 (2002).

Filipski, et al., "A novel series of glucagon receptor antagonists with reduced molecular weight and lipophilicity", Bioorganic & Medicinal Chemistry Letters, vol. 22(1), pp. 415-420 (2012).

Sinz, et al., "Discovery of cyclic guanidines as potent, orally active, human glucagon receptor antagonists", Bioorganic & Medicinal Chemistry Letters, vol. 21(23), pp. 7131-7136 (2011).

Sinz, et al., "Discovery of N-Aryl-2-acylindole human glucagon receptor antagonists", Bioorganic & Medicinal Chemistry Letters, vol. 21(23), pp. 7124-7130 (2011).

Shen, et al., "Discovery of novel, potent, selective, and orally active human glucagon receptor antagonists containing a pyrazole core", Bioorganic & Medicinal Chemistry Letters, vol. 21(1), pp. 76-81 (2011).

Kim, et al., "Discovery of potent, orally active benzimidazole glucagon receptor antagonists", Bioorganic & Medicinal Chemistry Letters, vol. 18(13), pp. 3701-3705 (2008).

DeMong, et al., "Glucagon receptor antagonists for type II diabetes", Annual Reports in Medicinal Chemistry, vol. 43, pp. 119-137 (2008).

Liang, et al., "Design and synthesis of conformationally constrained tri-substituted ureas as potent antagonists of the human glucagon receptor", Bioorganic & Medicinal Chemistry Letters, vol. 17(3), pp. 587-592 (2007).

Karthikeyan, et al., "Quantitative structure activity relationships of some selective inhibitors of glucagon receptor: a Hansch approach", Asian Journal of Biochemistry, vol. 1(4), pp. 307-315 (2006).

Cohen, et al., "Direct observation (NMR) of the efficacy of glucagon receptor antagonists in murine liver expressing the human glucagon receptor", Bioorganic & Medicinal Chemistry, vol. 14(5), pp. 1506-1517 (2006).

Shen, et al., "Discovery of novel, potent, and orally active spiro-urea human glucagon receptor antagonists", Bioorganic & Medicinal Chemistry Letters, vol. 15(20), pp. 4564-4569 (2005).

Duffy, et al., "Discovery and investigation of a novel class of thiophene-derived antagonists of the human glucagon receptor", Bioorganic & Medicinal Chemistry Letters, vol. 15(5), pp. 1401-1405 (2005).

Kurukulasuriya, et al., "Biaryl amide glucagon receptor antagonists", Bioorganic & Medicinal Chemistry Letters, vol. 14(9), pp. 2047-2050 (2004).

Smith, et al., "Optimization of the 4-aryl group of 4-aryl-pyridine glucagon antagonists: development of an efficient, alternative synthesis", Bioorganic & Medicinal Chemistry Letters, vol. 12(9), pp. 1303-1306 (2002).

Ling, et al., "Human glucagon receptor antagonists based on alkylidene hydrazides", Bioorganic & Medicinal Chemistry Letters, vol. 12(4), pp. 663-666 (2002).

Ladouceur, et al., "Integration of optimized substituent patterns to produce highly potent 4-aryl-pyridine glucagon receptor antagonists", Bioorganic & Medicinal Chemistry Letters, vol. 12(23), pp. 3421-3424 (2002).

Ladouceur, et al., "Discovery of 5-Hydroxyalkyl-4-phenylpyridines as a New Class of Glucagon Receptor Antagonists", Bioorganic & Medicinal Chemistry Letters, vol. 12(3), pp. 461-464 (2002).

Chang, et al., "Substituted Imidazoles as Glucagon Receptor Antagonists", Bioorganic & Medicinal Chemistry Letters, vol. 11(18), pp. 2549-2553 (2001).

deLaszlo, et al., "Potent, orally absorbed glucagon receptor antagonists", Bioorganic & Medicinal Chemistry Letters, vol. 9(5), pp. 641-646 (1999).

Kodra, et al., "Nonpeptide orally bioavailable glucagon receptor antagonists", Abstracts of Papers, 237th ACS National Meeting, Salt Lake City, UT, United States, Mar. 22-26, 2009, MEDI-166.

Dai, et al., "Discovery of a highly potent and selective imidazolone-based glucagon receptor antagonist", Abstracts of Papers, 241st ACS National Meeting & Exposition, Anaheim, CA, United States, Mar. 27-31, 2011, MEDI-22.

Parmee, "Discovery of MK-0893: A glucagon receptor antagonist for the treatment of type II diabetes", Abstracts of Papers, 241st ACS National Meeting & Exposition, Anaheim, CA, United States, Mar. 27-31, 2011, MEDI-31.

Handlon, et al., Glucagon receptor antagonists for the treatment of type 2 diabetes. Abstracts of Papers, 226th ACS National Meeting, New York, NY, United States, Sep. 7-11, 2003, MEDI-164.

Marsham, et al., "Qunazoline antifolate thymidylate synthase inhibitors: bridge modifications and conformationally restricted analogs in the C2-methyl series", Journal of Medicinal Chemistry, vol. 34(7), pp. 2209-2218 (1991).

JPET Fast Forward, Published on Feb. 16, 2007 as DOI:10.1124/JPET.106.115717, "A novel glucagon receptor antagonist, NNC25,0926, blunts hepatic glucose production in the conscious dog".

Business Wire, Sep. 17, 2007, "Metabasis Therapeutics Presents Promising Preclinical Results with Its Novel Glucagon Antagonist for the Treatment of Type 2 Diabetes", http://findarticles.com/p/articles/mi_m0EIN/is_2007_Sept_17/ai_n19522058/, downloaded Oct. 19, 2010.

* cited by examiner

GLUCAGON RECEPTOR MODULATORS

This application claims the benefit of U.S. Provisional Application No. 61/562,008, filed Nov. 21, 2011, and U.S. Provisional Application No. 61/426,600, filed Dec. 23, 2010, both applications are hereby incorporated by reference.

FIELD OF THE INVENTION

The present invention relates to compounds that are antagonists, mixed agonists/antagonists, partial agonists, negative allosteric modulators or inverse agonists of the glucagon receptor, pharmaceutical compositions comprising the compounds, and the uses of the compounds or compositions.

BACKGROUND

Diabetes is a major public health concern because of its increasing prevalence and associated health risks. The disease is characterized by metabolic defects in the production and utilization of carbohydrates which result in the failure to maintain appropriate blood glucose levels. Two major forms of diabetes are recognized. Type I diabetes, or insulin-dependent diabetes mellitus (IDDM T1 DM), is the result of an absolute deficiency of insulin. Type II diabetes, or non-insulin dependent diabetes mellitus (NIDDM T2DM), often occurs with normal, or even elevated levels of insulin and appears to be the result of the inability of tissues and cells to respond appropriately to insulin. Aggressive control of NIDDM T2DM with medication is essential; otherwise it can progress into β-cell failure and insulin dependence.

Glucagon is a twenty nine amino acid peptide which is secreted from the α cells of the pancreas into the hepatic portal vein thereby exposing the liver to higher levels of this hormone than non-hepatic tissues. Plasma glucagon levels decrease in response to hyperglycemia, hyperinsulinemia, elevated plasma non-esterified fatty acid levels and somatostatin whereas glucagon secretion is increased in response to hypoglycemia and elevated plasma amino acid levels. Glucagon, through activation of its receptor, is a potent activator of hepatic glucose production by activating glycogenolysis and gluconeogenesis.

The glucagon receptor is a 62 kDa protein that is activated by glucagon and is a member of the class B G-protein coupled family of receptors. Other closely related G-protein coupled receptors include glucagon-like peptide-1 receptor (GLP-1), glucagon-like peptide-2 receptor (GLP-2) and gastric inhibitory polypeptide receptor. The glucagon receptor is encoded by the GCGR gene in humans and these receptors are mainly expressed in the liver with lesser amounts found in the kidney, heart, adipose tissue, spleen, thymus, adrenal glands, pancreas, cerebral cortex and gastrointestinal tract. Stimulation of the glucagon receptor results in activation of adenylate cyclase and increased levels of intracellular cAMP.

Reports have indicated that an uncommon missense mutation in the GCGR gene is correlated with diabetes mellitus type 2 and one reported inactivating mutation of the glucagon receptor in humans causes resistance to glucagon and is associated with pancreatic α-cell hyperplasia, nesidioblastosis, hyperglucagonemia and pancreatic neuroendocrine tumors. In rodent studies with GCGR knockout mice and mice treated with GCGR antisense oligonucleotides the mice exhibited improved fasting glucose, glucose tolerance and pancreatic β-cell function. In both healthy control animals and animal models of type 1 and type 2 diabetes, removal of circulating glucagon with selective and specific antibodies has resulted in a reduction of the glycemic level. More specifically, treatment of both mice and cynomolgus monkeys with GCGR-antagonizing antibodies (mAb B and mAb Ac) has been shown to improve glycemic control without causing hypoglycemia. Recent mice studies have further shown that antagonism of the glucagon receptor results in improved glucose homeostasis through a mechanism which requires a functional GLP-1 receptor. Antagonism of the glucagon receptor resulted in compensatory overproduction of GLP-1, likely from the pancreatic α-cells, and this may play an important role in intraislet regulation and maintenance of β-cell function.

A promising area of diabetes research involves the use of small molecule antagonists, mixed agonists/antagonists, partial agonists, negative allosteric modulators or inverse agonists of the glucagon receptor to lower the level of circulating glucagon and thereby lower the glycemic level. Therapeutically, it is anticipated that inactivation of the glucagon receptor would be an effective strategy for lowering blood glucose by reducing hepatic glucose output and normalizing glucose stimulated insulin secretion. Consequently, a glucagon antagonist, mixed agonist/antagonist, partial agonist, negative allosteric modulator or inverse agonist may provide therapeutic treatment for NIDDM T2DM and associated complications, inter alia, hyperglycemia, dyslipidemia, insulin resistance syndrome, hyperinsulinemia, hypertension, and obesity.

Several drugs in five major categories, each acting by different mechanisms, are available for treating hyperglycemia and subsequently, NIDDM T2DM (Moller, D. E., "New drug targets for Type 2 diabetes and the metabolic syndrome" *Nature* 414; 821-827, (2001)): (A) Insulin secretagogues, including sulphonyl-ureas (e.g., glipizide, glimepiride, glyburide) and meglitinides (e.g., nateglidine and repaglinide) enhance secretion of insulin by acting on the pancreatic beta-cells. While this therapy can decrease blood glucose level, it has limited efficacy and tolerability, causes weight gain and often induces hypoglycemia. (B) Biguanides (e.g., metformin) are thought to act primarily by decreasing hepatic glucose production. Biguanides often cause gastrointestinal disturbances and lactic acidosis, further limiting their use. (C) Inhibitors of alpha-glucosidase (e.g., acarbose) decrease intestinal glucose absorption. These agents often cause gastrointestinal disturbances. (D) Thiazolidinediones (e.g., pioglitazone, rosiglitazone) act on a specific receptor (peroxisome proliferator-activated receptor-gamma) in the liver, muscle and fat tissues. They regulate lipid metabolism subsequently enhancing the response of these tissues to the actions of insulin. Frequent use of these drugs may lead to weight gain and may induce edema and anemia. (E) Insulin is used in more severe cases, either alone or in combination with the above agents.

Ideally, an effective new treatment for NIDDM T2DM would meet the following criteria: (a) it would not have significant side effects including induction of hypoglycemia; (b) it would not cause weight gain; (c) it would at least partially replace insulin by acting via mechanism(s) that are independent from the actions of insulin; (d) it would desirably be metabolically stable to allow less frequent usage; and (e) it would be usable in combination with tolerable amounts of any of the categories of drugs listed herein.

A number of publications have appeared which disclose non-peptide compounds which act at the glucagon receptor. For example, WO 03/048109, WO 2004/002480, WO 2005/123668, WO 2005/118542, WO 2006/086488, WO 2006/102067, WO 2007/106181, WO 2007/114855, WO 2007/120270, WO 2007/123581 and Kurukulasuriya et al. *Bioorganic & Medicinal Chemistry Letters*, 2004, 14(9), 2047-2050 each disclose non-peptide compounds that act as glucagon receptor antagonists. Although investigations are on-going, there still exists a need for a more effective and safe therapeutic treatment for diabetes, particularly NIDDM.

SUMMARY OF THE INVENTION

The present invention provides compounds of Formula I that act as glucagon receptor modulators, in particular, glucagon antagonists; therefore, may be used in the treatment of diseases mediated by such antagonism (e.g., diseases related to Type 2 diabetes, and diabetes-related and obesity-related co-morbidities). A first embodiment of the present invention are compounds of Formula (I)

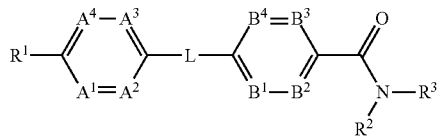

or a pharmaceutically acceptable salt thereof, wherein
$R^1$ is phenyl optionally substituted with one to four substituents each independently selected from halo, $—S(O)_2—(C_{1-3})$alkyl, hydroxy, $—C(O)NR^aR^b$, $(C_3-C_5)$cycloalkyl, cyano, $(C_1-C_6)$alkyl optionally substituted with one to three fluoro, or $(C_1-C_6)$alkoxy optionally substituted with one to three fluoro;
or a 6-membered heteroaryl group which is optionally fused with a $(C_4-C_7)$cycloalkyl, phenyl or 5 to 6 membered heteroaryl, and wherein the optionally fused 6-membered heteroaryl group is optionally substituted with one to four substituents each independently selected from halo, $—S(O)_2—(C_{1-3})$alkyl, hydroxy, $—C(O)NR^aR^b$, cyano, $(C_1-C_6)$alkyl optionally substituted with one to three fluoro, or $(C_1-C_6)$alkoxy optionally substituted with one to three fluoro;
$R^a$ and $R^b$ are each independently H or $(C_1-C_3)$alkyl;
$R^2$ is H or $(C_1-C_3)$alkyl;
$R^3$ is tetrazolyl, $—CH_2$-tetrazolyl, $—(CH_2)_2SO_3H$ or $—(CH_2)_2CO_2H$ optionally substituted with a hydroxy or fluoro;
$A^1, A^2, A^3$ and $A^4$ are each independently $CR^4$ or N, with the proviso that no more than two of $A^1, A^2, A^3$ and $A^4$ are N;
$R^4$ at each occurrence is independently H, halo, cyano, $(C_1-C_3)$alkyl optionally substituted with one to three fluoro, or $(C_1-C_3)$alkoxy optionally substituted with one to three fluoro;
L is $—X—CH(R^5)—$ or $—CH(R^5)—X—$;
X is $CH_2$, O or NH;
$R^5$ is $(C_1-C_6)$alkyl which is optionally substituted with one to three fluoro, hydroxy or methoxy;
$(C_3-C_7)$cycloalkyl which is optionally substituted with one to two $(C_1-C_3)$alkyl which are optionally substituted with one to three fluoro or one to two $(C_1-C_3)$alkyl and wherein one to two carbons of the $(C_3-C_7)$cycloalkyl can be replaced with a NH, $N(C_1-C_3)$alkyl, O or S; or $(C_3-C_7)$cycloalkyl-$(C_1-C_6)$alkyl wherein the $(C_3-C_7)$cycloalkyl group of said $(C_3-C_7)$cycloalkyl-$(C_1-C_6)$alkyl is optionally substituted with one to two $(C_1-C_3)$alkyl which are optionally substituted with one to three fluoro;
$B^1, B^2, B^3$ and $B^4$ are each independently $CR^6$ or N, with the proviso that no more than two of $B^1, B^2, B^3$ and $B^4$ are N;
$R^6$ at each occurrence is independently H, halo, $(C_1-C_3)$alkyl optionally substituted with one to three fluoro, or $(C_1-C_3)$ alkoxy optionally substituted with one to three fluoro; and further provided that when L is $—X—CH(R^5)—$ and X is $CH_2$ or O then at least one of $B^1, B^2, B^3$ and $B^4$ is N; when L is $—X—CH(R^5)—$ and X is NH then at least one of $A^1, A^2, A^3, A^4$ is N; and when L is $—CH(R^5)—X—$ then at least one of $B^1, B^2, B^3$ and $B^4$ is N.

A second embodiment the present invention is the compound of the first embodiment or a pharmaceutically acceptable salt thereof, wherein $R^2$ is hydrogen or methyl and $R^3$ is $—(CH_2)_2CO_2H$, $—CH_2CH(F)CO_2H$, or $—CH_2CH(OH)CO_2H$.

A third embodiment of the present invention is the compound of the first or second embodiments or a pharmaceutically acceptable salt thereof, wherein X is O. A fourth embodiment of the present invention is the compound of the first or second embodiments or a pharmaceutically acceptable salt thereof, wherein X is NH. A fifth embodiment of the present invention is the compound of the first or second embodiment or a pharmaceutically acceptable salt thereof, wherein X is $CH_2$. A sixth embodiment of the present invention is the compound of the fourth embodiment or a pharmaceutically acceptable salt thereof wherein L is $—X—CH(R^5)—$ and one or two of $B^1, B^2, B^3$ and $B^4$ are N. A seventh embodiment of the present invention is the compound of the fourth embodiment or a pharmaceutically acceptable salt thereof wherein L is $—CH(R^5)—X—$ and one or two of $A^1, A^2, A^3$ and $A^4$ is N.

An eighth embodiment of the present invention is the compound of any of the first through seventh embodiments or a pharmaceutically acceptable salt thereof wherein $R^5$ is ethyl, propyl, isopropyl, isobutyl, t-butyl, pentyl, neopentyl, cyclopropyl, cyclobutyl, cyclopentyl, cyclohexyl or cyclopropylmethyl each optionally substituted with 1 to 3 fluoro and wherein said cyclopropyl, cyclobutyl, cyclopentyl, cyclohexyl are each optionally substituted with 1 to 2 methyl.

A ninth embodiment of the present invention is the compound of the sixth embodiment or a pharmaceutically acceptable salt thereof wherein $R^1$ is phenyl substituted with a trifluoromethyl or halo; $R^2$ is H; and provided that $A^1$ and $A^2$ are not both N and further provided that $A^2$ and $A^3$ are not both N. A tenth embodiment of the present invention is the compound of the seventh embodiment or a pharmaceutically acceptable salt thereof wherein $R^1$ is phenyl substituted with a trifluoromethyl or halo; $R^2$ is H; and provided that one or two of $A^1, A^2, A^3$ and $A^4$ are N and further provided that $A^2$ and $A^3$ are not both N. An eleventh embodiment of the present invention is the compound of the tenth embodiment or a pharmaceutically acceptable salt thereof wherein $R^3$ is $—(CH_2)_2CO_2H$. A twelfth embodiment of the present invention is the compound of the eleventh embodiment or a pharmaceutically acceptable salt thereof wherein $R^1$ is 4-trifluoromethylphenyl or 4-chlorophenyl; and $R^4$ and $R^6$ at each occurrence are H. A thirteenth embodiment of the present invention is the compound of the twelfth embodiment or a pharmaceutically acceptable salt thereof wherein $B^1$ is N and $B^2, B^3$ and $B^4$ are each $CR^6$; $B^2$ is N and $B^1, B^3$ and $B^4$ are each $CR^6$; $B^1$ and $B^4$ are each N and $B^2$ and $B^3$ are each $CR^6$; $B^2$ and $B^3$ are each N and $B^1$ and $B^4$ are each $CR^6$; or $B^1$ and $B^3$ are each N and $B^2$ and $B^4$ are each $CR^6$. A fourteenth embodiment of the present invention is the compound of the first embodiment or a pharmaceutically acceptable salt thereof wherein $A^1$ is N and $A^2, A^3$ and $A^4$ are each $CR^4$; $A^2$ is N and $A^1, A^3$ and $A^4$ are each $CR^4$; $A^1$ and $A^4$ are each N and $A^2$ and $A^3$ are each $CR^4$; or $A^1$ and $A^3$ are each N and $A^2$ and $A^4$ are each $CR^4$.

A fifteenth embodiment of the present invention is a compound selected from the group consisting of: (+)-(R)-3-(6-(3-methyl-1-(4'-(trifluoromethyl)biphenyl-4-yl)butylamino)

nicotinamido) propanoic acid; 3-(6-(3-methyl-1-(4'-(trifluoromethyl)biphenyl-4-yl)butylamino)nicotinamido) propanoic acid; (−)-(S)-3-(6-(3-methyl-1-(4'-(trifluoromethyl)biphenyl-4-yl)butylamino)nicotinamido) propanoic acid; 3-(2-(3-methyl-1-(4'-(trifluoromethyl)biphenyl-4-yl)butylamino)pyrimidine-5-carboxamido) propanoic acid; (R)-3-(2-(3-methyl-1-(4'-(trifluoromethyl)biphenyl-4-yl)butylamino)pyrimidine-5-carboxamido) propanoic acid; (S)-3-(2-(3-methyl-1-(4'-(trifluoromethyl)biphenyl-4-yl)butylamino)pyrimidine-5-carboxamido) propanoic acid; 3-(6-(1-(4'-(trifluoromethyl)biphenyl-4-yl)butylamino) nicotinamido)propanoic acid; (R)-3-(6-(1-(4'-(trifluoromethyl)biphenyl-4-yl)butylamino)nicotinamido) propanoic acid; (S)-3-(6-(1-(4'-(trifluoromethyl)biphenyl-4-yl)butylamino)nicotinamido) propanoic acid; 3-(6-(2-methyl-1-(4'-(trifluoromethyl)biphenyl-4-yl)propylamino) nicotinamido) propanoic acid; 3-(6-(1-(4'-(trifluoromethyl)biphenyl-4-yl)propylamino) nicotinamido)propanoic acid; (R)-3-(6-(1-(4'-(trifluoromethyl)biphenyl-4-yl)propylamino)nicotinamido)propanoic acid; (S)-3-(6-(1-(4'-(trifluoromethyl) biphenyl-4-yl)propylamino)nicotinamido)propanoic acid; (+)-3-(6-(2-methyl-1-(4'-(trifluoromethyl)biphenyl-4-yl)propylamino)nicotinamido) propanoic acid; (+3-(6-(2-methyl-1-(4'-(trifluoromethyl)biphenyl-4-yl)propylamino)nicotinamido) propanoic acid; 3-(5-(3-methyl-1-(4'-(trifluoromethyl)biphenyl-4-yl)butylamino)pyrazine-2-carboxamido) propanoic acid; (R)-3-(5-(3-methyl-1-(4'-(trifluoromethyl)biphenyl-4-yl)butylamino)pyrazine-2-carboxamido) propanoic acid; (S)-3-(5-(3-methyl-1-(4'-(trifluoromethyl)biphenyl-4-yl)butylamino)pyrazine-2-carboxamido) propanoic acid;

2-(3-methyl-1-(4'-(trifluoromethyl)biphenyl-4-yl)butylamino)-N-(1H-tetrazol-5-yl)pyrimidine-5-carboxamide; N-(3-(1H-tetrazol-5-ylamino)-3-oxopropyl)-6-(3-methyl-1-(4'-(trifluoromethyl) biphenyl-4-yl)butylamino)nicotinamide; N-((2H-tetrazol-5-yl)methyl)-6-(3-methyl-1-(4'-(trifluoromethyl)biphenyl-4-yl)butylamino) nicotinamide; 2-(6-(3-methyl-1-(4'-(trifluoromethyl) biphenyl-4-yl)butylamino) nicotinamido) ethanesulfonic acid; 3-(N-methyl-6-(3-methyl-1-(4'-(trifluoromethyl)biphenyl-4-yl) butylamino) nicotinamido)propanoic acid; (2R)-2-hydroxy-3-(6-(3-methyl-1-(4'-(trifluoromethyl)biphenyl-4-yl)butylamino) nicotinamido) propanoic acid; 3-(6-(3-methyl-1-(2-methyl-4'-(trifluoromethyl)biphenyl-4-yl) butylamino) nicotinamido)propanoic acid; 3-(2-(3-methyl-1-(2-methyl-4'-(trifluoromethyl)biphenyl-4-yl) butylamino)pyrimidine-5-carboxamido)propanoic acid; 3-(2-(1-(2,6-dimethyl-4'-(trifluoromethyl)biphenyl-4-yl)-3-methylbutylamino) pyrimidine-5-carboxamido)propanoic acid; 3-(6-(1-(2,6-dimethyl-4'-(trifluoromethyl)biphenyl-4-yl)-3-methylbutylamino) nicotinamido) propanoic acid; 3-(6-(3-methyl-1-(6-(4-(trifluoromethyl) phenyl)pyridin-3-yl)butylamino)nicotinamido) propanoic acid; 3-(5-(1-(4'-(trifluoromethyl)biphenyl-4-yl)butylamino)pyrazine-2-carboxamido) propanoic acid; 3-(5-(1-(4'-(trifluoromethyl)biphenyl-4-yl)propylamino)pyrazine-2-carboxamido) propanoic acid; 3-(6-(cyclobutyl(4'-(trifluoromethyl)biphenyl-4-yl)methylamino) nicotinamido) propanoic acid; 3-(6-(3,3-dimethyl-1-(4'-(trifluoromethyl)biphenyl-4-yl)butylamino)nicotinamido) propanoic acid; 3-(6-(cyclopropyl(4'-(trifluoromethyl)biphenyl-4-yl)methylamino)nicotinamido) propanoic acid; 3-(6-(cyclopentyl(4'-(trifluoromethyl)biphenyl-4-yl)methylamino) nicotinamido) propanoic acid; 3-(6-(3-methyl-1-(4-(6-methylpyridin-3-yl)phenyl)butylamino)nicotinamido)propanoic acid; 3-(6-(1-(biphenyl-4-yl)-3-methylbutylamino)nicotinamido)propanoic acid; 3-(6-(1-(2'-fluorobiphenyl-4-yl)-3-methylbutylamino) nicotinamido)propanoic acid; 3-(6-(1-(3'-chlorobiphenyl-4-yl)-3-methylbutylamino)nicotinamido)propanoic acid; 3-(6-(3-methyl-1-(4-(pyridin-3-yl)phenyl)butylamino) nicotinamido)propanoic acid; 3-(6-(1-(3'-fluorobiphenyl-4-yl)-3-methylbutylamino)nicotinamido)propanoic acid; 3-(6-(3-methyl-1-(2'-methylbiphenyl-4-yl)butylamino) nicotinamido)propanoic acid; 3-(6-(1-(2'-methoxybiphenyl-4-yl)-3-methylbutylamino)nicotinamido)propanoic acid; 3-(6-(1-(2'-chlorobiphenyl-4-yl)-3-methylbutylamino)nicotinamido)propanoic acid; 3-(6-(1-(4'-cyanobiphenyl-4-yl)-3-methylbutylamino)nicotinamido)propanoic acid; 3-(6-(1-(4'-ethoxybiphenyl-4-yl)-3-methylbutylamino)nicotinamido)propanoic acid; 3-(6-(1-(3'-methoxybiphenyl-4-yl)-3-methylbutylamino) nicotinamido)propanoic acid; 3-(6-(1-(2',6'-dimethylbiphenyl-4-yl)-3-methylbutylamino) nicotinamido)propanoic acid; 3-(6-(1-(2',5'-dimethylbiphenyl-4-yl)-3-methylbutylamino) nicotinamido)propanoic acid; 3-(6-(3-methyl-1-(4'-methylbiphenyl-4-yl)butylamino)nicotinamido) propanoic acid; 3-(6-(1-(4'-fluorobiphenyl-4-yl)-3-methylbutylamino)nicotinamido)propanoic acid; 3-(6-(1-(4'-methoxybiphenyl-4-yl)-3-methylbutylamino) nicotinamido)propanoic acid; 3-(6-(1-(4'-chlorobiphenyl-4-yl)-3-methylbutylamino)nicotinamido)propanoic acid; 3-(6-(1-(4'-ethylbiphenyl-4-yl)-3-methylbutylamino) nicotinamido)propanoic acid; 3-(6-(3-methyl-1-(4-(pyridin-2-yl)phenyl)butylamino)nicotinamido)propanoic acid; 3-(6-(1-(4'-(dimethylcarbamoyl)biphenyl-4-yl)-3-methylbutylamino)nicotinamido) propanoic acid; 3-(6-(1-(4'-isopropylbiphenyl-4-yl)-3-methylbutylamino)nicotinamido)propanoic acid; 3-(6-(3-methyl-1-(4'-(trifluoromethoxy)biphenyl-4-yl)butylamino) nicotinamido) propanoic acid; 3-(6-(3-methyl-1-(4'-(methylsulfonyl)biphenyl-4-yl)butylamino)nicotinamido) propanoic acid; 3-(6-(3-methyl-1-(4-(6-(trifluoromethyl) pyridin-3-yl)phenyl)butylamino)nicotinamido) propanoic acid; 3-(6-(1-(2,6-dimethyl-4'-(trifluoromethyl)biphenyl-4-ylamino)-3-methylbutyl)nicotinamido)propanoic acid; (R)-3-(6-(1-(2,6-dimethyl-4'-(trifluoromethyl)biphenyl-4-ylamino)-3-methylbutyl)nicotinamido)propanoic acid; (S)-3-(6-(1-(2,6-dimethyl-4'-(trifluoromethyl)biphenyl-4-ylamino)-3-methylbutyl)nicotinamido)propanoic acid; 3-(6-(3-methyl-1-(4'-(trifluoromethyl)biphenyl-4-ylamino)butyl)nicotinamido) propanoic acid; (R)-3-(6-(3-methyl-1-(4'-(trifluoromethyl)biphenyl-4-ylamino)butyl) nicotinamido) propanoic acid; (S)-3-(6-(3-methyl-1-(4'-(trifluoromethyl)biphenyl-4-ylamino)butyl)nicotinamido) propanoic acid; 3-(6-(3-methyl-1-(6-(4-(trifluoromethyl) phenyl)pyridin-3-ylamino)butyl)nicotinamido) propanoic acid; 3-(6-(3-methyl-1-(5-methyl-6-(4-(trifluoromethyl) phenyl)pyridin-3-ylamino)butyl)nicotinamido)propanoic acid; 3-(6-(1-(5-methyl-6-(4-(trifluoromethyl)phenyl)pyridin-3-ylamino)butyl)nicotinamido) propanoic acid; 3-(6-(1-(4'-(trifluoromethyl)biphenyl-4-ylamino)ethyl) nicotinamido) propanoic acid; 3-(6-(1-(5-methyl-6-(4-(trifluoromethyl)phenyl)pyridin-3-ylamino)propyl)nicotinamido)propanoic acid; N-((1H-tetrazol-5-yl)methyl)-6-(3-methyl-1-(4'-(trifluoromethyl)biphenyl-4-ylamino) butyl) nicotinamide; 6-(3-methyl-1-(4'-(trifluoromethyl) biphenyl-4-ylamino)butyl)-N-(2H-tetrazol-5-yl) nicotinamide;

3-(4-(1-(6-(4-(trifluoromethyl)phenyl)pyridazin-3-ylamino) butyl)benzamido)propanoic acid; 3-(4-(1-(2-(4-(trifluoromethyl)phenyl)pyrimidin-5-ylamino)butyl)benzamido) propanoic acid; (R)-3-(4-(1-(2-(4-(trifluoromethyl)phenyl)pyrimidin-5-ylamino)butyl)benzamido) propanoic acid; (S)-3-(4-(1-(2-(4-(trifluoromethyl)phenyl)pyrimidin-5-ylamino)butyl)benzamido) propanoic acid; 3-(6-(3-methyl-1-(4'-(trifluoromethyl)biphenyl-4-yloxy)butyl)nicotinamido)propanoic acid; 3-(6-(3-methyl-1-(4'-(trifluoromethyl)biphenyl-4-yl)butoxy)nicotinamido)propanoic acid; and 3-(6-(1-(4'-(trifluoromethyl)biphenyl-4-yloxy)ethyl)nicotinamido)propanoic acid;
or a pharmaceutically acceptable salt thereof.

A sixteenth embodiment of the present invention is a compound selected from the group consisting of: (−)-(S)-3-(6-(3-methyl-1-(4'-(trifluoromethyl)biphenyl-4-yl)butylamino)nicotinamido) propanoic acid; 3-(2-(3-methyl-1-(4'-(trifluoromethyl) biphenyl-4-yl)butylamino)pyrimidine-5-carboxamido)propanoic acid; 3-(6-(1-(4'-(trifluoromethyl)biphenyl-4-yl)propylamino)nicotinamido) propanoic acid; 3-(5-(3-methyl-1-(4'-(trifluoromethyl)biphenyl-4-yl)butylamino) pyrazine-2-carboxamido) propanoic acid; (+/−)-3-(4-(1-(2-(4-(trifluoromethyl)phenyl)pyrimidin-5-ylamino)butyl)benzamido) propanoic acid; (−)-3-(6-(2-methyl-1-(4'-(trifluoromethyl)biphenyl-4-yl)propylamino)nicotinamido) propanoic acid; or a pharmaceutically acceptable salt thereof.

A further embodiment of the present invention is a compound of Formula I

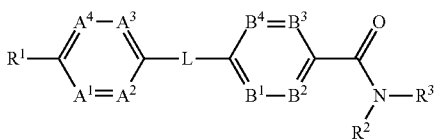

or a pharmaceutically acceptable salt thereof, wherein
$R^1$ is phenyl optionally substituted with one to four substituents each independently selected from halo, —S(O)$_2$—(C$_{1-3}$)alkyl, hydroxy, —C(O)NR$^a$R$^b$, (C$_3$-C$_5$)cycloalkyl, cyano, (C$_1$-C$_6$)alkyl optionally substituted with one to three fluoro, or (C$_1$-C$_6$)alkoxy optionally substituted with one to three fluoro;
or a 6-membered heteroaryl group which is optionally fused with a (C$_4$-C$_7$)cycloalkyl, phenyl
or 5 to 6 membered heteroaryl, and wherein the optionally fused 6-membered heteroaryl group is optionally substituted with one to four substituents each independently selected from halo, —S(O)$_2$—(C$_{1-3}$)alkyl, hydroxy, —C(O)NR$^a$R$^b$, cyano, (C$_1$-C$_6$)alkyl optionally substituted with one to three fluoro, or (C$_1$-C$_6$)alkoxy optionally substituted with one to three fluoro;
$R^a$ and $R^b$ are each independently H or (C$_1$-C$_3$)alkyl;
$R^2$ is H or (C$_1$-C$_3$)alkyl;
$R^3$ is tetrazolyl, —CH$_2$-tetrazolyl, —(CH$_2$)$_2$SO$_3$H or —(CH$_2$)$_2$CO$_2$H optionally substituted with a hydroxy or fluoro;
$A^1$, $A^2$, $A^3$ and $A^4$ are each independently CR$^4$ or N, with the proviso that no more than two of $A^1$, $A^2$, $A^3$ and $A^4$ are N;
$R^4$ at each occurrence is independently H, halo, cyano, (C$_1$-C$_3$)alkyl optionally substituted with one to three fluoro, or (C$_1$-C$_3$)alkoxy optionally substituted with one to three fluoro;
L is —X—CH(R$^5$)— or —CH(R$^5$)—X—;
X is CH$_2$, O or NH;
$R^5$ is (C$_1$-C$_6$)alkyl which is optionally substituted with one to three fluoro, hydroxy or methoxy;
(C$_3$-C$_7$)cycloalkyl which is optionally substituted with one to two (C$_1$-C$_3$)alkyl which are optionally substituted with one to three fluoro or one to two (C$_1$-C$_3$)alkyl, or (C$_1$-C$_3$)alkoxy which are optionally substituted with one to three fluoro, and wherein one or two carbons of the (C$_3$-C$_7$)cycloalkyl can be replaced with a NH, N(C$_1$-C$_3$)alkyl, O or S; or (C$_3$-C$_7$)cycloalkyl-(C$_1$-C$_6$)alkyl wherein the (C$_3$-C$_7$)cycloalkyl group of said (C$_3$-C$_7$)cycloalkyl-(C$_1$-C$_6$)alkyl is optionally substituted with one to two (C$_1$-C$_3$)alkyl which are optionally substituted with one to three fluoro;
$B^1$, $B^2$, $B^3$ and $B^4$ are each independently CR$^6$ or N, with the proviso that no more than two of $B^1$, $B^2$, $B^3$ and $B^4$ are N;
$R^6$ at each occurrence is independently H, halo, (C$_1$-C$_3$)alkyl optionally substituted with one to three fluoro, or (C$_1$-C$_3$)alkoxy optionally substituted with one to three fluoro; and further provided that when L is —X—CH(R$^5$)— and X is CH$_2$ or O then at least one of $B^1$, $B^2$, $B^3$ and $B^4$ is N; when L is —X—CH(R$^5$)— and X is NH then at least one of $A^1$, $A^2$, $A^3$, $A^4$ is N; and when L is —CH(R$^5$)—X— then at least one of $B^1$, $B^2$, $B^3$ and $B^4$ is N.

Yet another embodiment of the present invention is a compound selected from the group consisting of (S)-N-({6-[(3-methyl-1-{4-[5-(trifluoromethyl)pyridin-2-yl]phenyl}butyl)amino]pyridin-3-yl}carbonyl)-beta-alanine; (+/−)-N-({6-[(cyclohexyl{2-[4-(trifluoromethyl)phenyl]pyrimidin-5-yl}methyl)amino]pyridin-3-yl}carbonyl)-beta-alanine; (±)-3-(4-(1-((5-(4-(trifluoromethyl)phenyl)pyrazin-2-yl)amino)butyl)benzamido) propanoic acid;
(S)-3-(4-(1-((5-(4-(trifluoromethyl)phenyl)pyrazin-2-yl)amino)butyl)benzamido) propanoic acid;
(R)-3-(4-(1-((5-(4-(trifluoromethyl)phenyl)pyrazin-2-yl)amino)butyl)benzamido) propanoic acid; 3-(N-methyl-6-((3-methyl-1-(4'-(trifluoromethyl)-[1,1'-biphenyl]-4-yl)butyl)amino)nicotinamido)propanoic acid; (±)-3-(6-(((tetrahydro-2H-pyran-4-yl)(4'-(trifluoromethyl)-[1,1'-biphenyl]-4-yl)methyl)amino)nicotinamido)propanoic acid; (±)-3-(6-((1-(2-cyano-4'-(trifluoromethyl)-[1,1'-biphenyl]-4-yl)butyl)amino) nicotinamido) propanoic acid; (+/−)-3-({5-[3-methyl-1-(4'-trifluoromethyl-biphenyl-4-yl)-butylamino]-pyrimidine-2-carbonyl}-amino)-propionic acid; 3-({5-[(R)-3-methyl-1-(4'-trifluoromethyl-biphenyl-4-yl)-butylamino]-pyrimidine-2-carbonyl}-amino)-propionic acid; 3-({5-[(S)-3-methyl-1-(4'-trifluoromethyl-biphenyl-4-yl)-butylamino]-pyrimidine-2-carbonyl}-amino)-propionic acid; 3-[(6-{(S)-3-methyl-1-[2-(4-trifluoromethyl-phenyl)-pyrimidin-5-yl]-butylamino}-pyridine-3-carbonyl)-amino]-propionic acid; (+/−)-3-(6-(4,4,4-trifluoro-1-(4'-(trifluoromethyl)biphenyl-4-yl)butylamino) nicotinamido) propanoic acid; 3-(6-(2-cyclopropyl-1-(4'-(trifluoromethyl)biphenyl-4-yl)ethylamino)nicotinamido) propanoic acid; 3-(6-(3-methyl-1-(5-methyl-6-(4-(trifluoromethyl)phenyl)pyridin-3-yl)butylamino) nicotinamido)propanoic acid; 3-(6-(1-(6-(4-chlorophenyl)-5-methylpyridin-3-ylamino)-3-methylbutyl)nicotinamido) propanoic acid; 3-(2-(1-(4'-(trifluoromethyl)biphenyl-4-yl)butylamino)pyrimidine-5-carboxamido)propanoic acid; 3-(4-(1-(6-(4-(trifluoromethyl)phenyl)pyridin-3-ylamino)butyl)benzamido)propanoic acid; (+/−)-3-(6-(3-methyl-1-(2-(4-(trifluoromethyl)phenyl)pyrimidin-5-yl)butylamino) nicotinamido)propanoic acid; (R)-3-(6-(3-methyl-1-(6-(4-(trifluoromethyl)phenyl)pyridin-3-yl)butylamino) nicotinamido)propanoic acid; (S)-3-(6-(3-methyl-1-(6-(4-(trifluoromethyl)phenyl)pyridin-3-yl)butylamino) nicotinamido)propanoic acid; (+/−)-3-(6-(3-methyl-1-(4-(5-(trifluoromethyl)pyridin-2-yl)phenyl)butylamino) nicotinamido)propanoic acid; 3-(6-(1-(2-methoxy-4'-(trifluoromethyl)biphenyl-4-yl)butylamino)nicotinamido) propanoic acid; 3-(6-(1-(3-methoxy-4'-(trifluoromethyl)

biphenyl-4-yl)butylamino)nicotinamido) propanoic acid; 3-(6-(1-(2-(4-(trifluoromethoxy)phenyl)pyrimidin-5-yl)butylamino)nicotinamido) propanoic acid; (R)-3-(6-(cyclopentyl(4'-fluorobiphenyl-4-yl)methylamino)nicotinamido)propanoic acid; (S)-3-(6-(cyclopentyl(4'-fluorobiphenyl-4-yl)methylamino)nicotinamido) propanoic acid; 3-(6-(cyclopentyl(2-(4-(trifluoromethyl)phenyl)pyrimidin-5-yl)methylamino) nicotinamido) propanoic acid; (R)-3-(6-((tetrahydro-2H-pyran-4-yl)(4'-(trifluoromethyl)biphenyl-4-yl)methylamino) nicotinamido)propanoic acid; (S)-3-(6-((tetrahydro-2H-pyran-4-yl)(4'-(trifluoromethyl)biphenyl-4-yl)methylamino) nicotinamido)propanoic acid; 3-(4-(3-methyl-1-(2-(4-(trifluoromethyl)phenyl)pyrimidin-5-ylamino)butyl)benzamido) propanoic acid; 3-(3-(3-methyl-1-(2-(4-(trifluoromethyl)phenyl)pyrimidin-5-ylamino)butyl)picolinamido)propanoic acid; 3-(6-((3-methoxycyclobutyl)(4'-(trifluoromethyl)biphenyl-4-yl)methylamino) nicotinamido)propanoic acid; 3-(6-((tetrahydro-2H-pyran-3-yl)(4'-(trifluoromethyl)biphenyl-4-yl)methylamino) nicotinamido)propanoic acid; (R)-3-(6-(cyclopentyl(2-(4-(trifluoromethyl)phenyl)pyrimidin-5-yl)methylamino) nicotinamido)propanoic acid; (S)-3-(6-(cyclopentyl(2-(4-(trifluoromethyl)phenyl)pyrimidin-5-yl)methylamino) nicotinamido)propanoic acid; (R)-3-(6-(1-(2-(4-(trifluoromethyl)phenyl)pyrimidin-5-yl)butylamino) nicotinamido) propanoic acid; and (S)-3-(6-(1-(2-(4-(trifluoromethyl)phenyl)pyrimidin-5-yl)butylamino)nicotinamido) propanoic acid; or a pharmaceutically acceptable salt thereof.

Another aspect of the present invention is a pharmaceutical composition that comprises (1) a compound of the present invention, and (2) a pharmaceutically acceptable excipient, diluent, or carrier. Preferably, the composition comprises a therapeutically effective amount of a compound of the present invention. The composition may also contain at least one additional pharmaceutical agent (described herein). Preferred agents include anti-obesity agents and/or anti-diabetic agents (described herein below).

In yet another aspect of the present invention is a method for treating a disease, condition, or disorder mediated by glucagon, in particular, deactivation of the glucagon receptor, in a mammal that includes the step of administering to a mammal, preferably a human, in need of such treatment a therapeutically effective amount of a compound of the present invention, or a pharmaceutical composition thereof.

Diseases, disorders, or conditions mediated by glucagon include Type II diabetes, hyperglycemia, metabolic syndrome, impaired glucose tolerance, glucosuria, cataracts, diabetic neuropathy, diabetic nephropathy, diabetic retinopathy, obesity, dyslipidemia, hypertension, hyperinsulinemia, and insulin resistance syndrome. Preferred diseases, disorders, or conditions include Type II diabetes, hyperglycemia, impaired glucose tolerance, obesity, and insulin resistance syndrome. More preferred are Type II diabetes, hyperglycemia, and obesity. Most preferred is Type II diabetes.

In yet another aspect of the present invention is a method of reducing the level of blood glucose in a mammal, preferably a human, which includes the step of administering to a mammal in need of such treatment a therapeutically effective amount of a compound of the present invention, or a pharmaceutical composition thereof.

Compounds of the present invention may be administered in combination with other pharmaceutical agents (in particular, anti-obesity and anti-diabetic agents described herein below). The combination therapy may be administered as (a) a single pharmaceutical composition which comprises a compound of the present invention, at least one additional pharmaceutical agent described herein and a pharmaceutically acceptable excipient, diluent, or carrier; or (b) two separate pharmaceutical compositions comprising (i) a first composition comprising a compound of the present invention and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions may be administered simultaneously or sequentially and in any order.

Definitions

As used herein, the term "alkyl" refers to a hydrocarbon radical of the general formula $C_nH_{2n+1}$. The alkane radical may be straight or branched. For example, the term "$(C_1-C_6)$ alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion (i.e., alkyl moiety) of an alkoxy, acyl (e.g., alkanoyl), alkylamino, dialkylamino, alkylsulfonyl, and alkylthio group have the same definition as above. When indicated as being "optionally substituted", the alkane radical or alkyl moiety may be unsubstituted or substituted with one or more substituents (generally, one to three substituents except in the case of halogen substituents such as perchloro or perfluoroalkyls).

The term "cycloalkyl" refers to nonaromatic rings that are fully hydrogenated and may exist as a single ring, bicyclic ring or a spiral ring. Unless specified otherwise, the carbocyclic ring is generally a 3- to 8-membered ring. For example, $(C_3-C_7)$cycloalkyl include groups such as cyclopropyl, cyclobutyl, cyclopentyl, cyclohexyl, cyclohexenyl, cycloheptyl, norbornyl (bicyclo[2.2.1]heptyl) and the like.

The phrase "5 to 6 membered heteroaryl" means a radical of a 5 or 6 membered heteroaromatic ring. The heteroaromatic ring can contain 1 to 4 heteroatoms selected from N, O and S. 5 to 6 membered heteroaryl groups include pyrrolyl, furanyl, thienyl, imidazolyl, thiazolyl, oxazolyl, triazolyl, tetrazolyl, pyridinyl, pyrimidinyl, pyrazinyl, triazinyl and the like. Preferred 5 to 6 membered heteroaryl groups include pyridinyl, pyrimidinyl or pyrazinyl. The phrase "6 membered heteroaryl" wherein the ring is a 6 membered heteroaromatic ring.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The terms "modulated" or "modulating", or "modulate(s)", as used herein, unless otherwise indicated, refers to the changes in activity of the glucagon receptor as a result of action of the compounds of the present invention.

The terms "mediated" or "mediating" or "mediate(s)", as used herein, unless otherwise indicated, refers to the treatment or prevention the particular disease, condition, or disorder, (ii) attenuation, amelioration, or elimination of one or more symptoms of the particular disease, condition, or disorder, or (iii) prevention or delay of the onset of one or more symptoms of the particular disease, condition, or disorder described herein, by modulation of glucagon.

The term "compounds of the present invention" (unless specifically identified otherwise) refer to compounds of Formula I and any pharmaceutically acceptable salts of the compounds, as well as, all stereoisomers (including diastereoisomers and enantiomers), tautomers, conformational isomers, and isotopically labeled compounds. Hydrates and solvates of the compounds of the present invention are considered compositions of the present invention, wherein the compound is in association with water or solvent, respectively.

DETAILED DESCRIPTION

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements (also available via the *Beilstein* online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). Similarly, a "hydroxy-protecting group" refers to a substituent of a hydroxy group that blocks or protects the hydroxy functionality. Suitable hydroxyl-protecting groups (O-Pg) include for example, allyl, acetyl, silyl, benzyl, para-methoxybenzyl, trityl, and the like. The need for such protection is readily determined by one skilled in the art. For a general description of protecting groups and their use, see T. W. Greene, *Protective Groups in Organic Synthesis*, John Wiley & Sons, N.Y., 1991.

Reaction Scheme I outlines the general procedures that can be used to provide compounds of the present invention of Formula I.

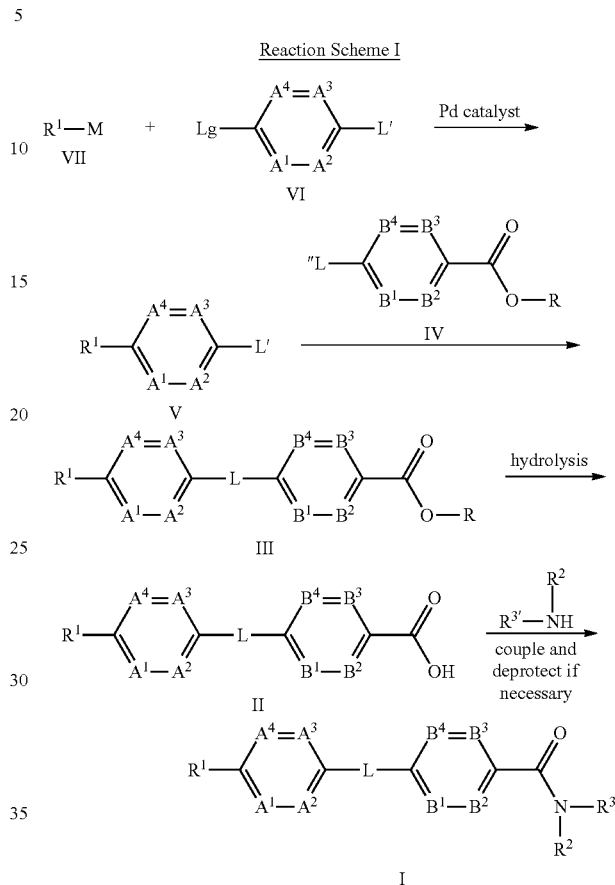

Reaction Scheme I provides a general route which can be employed to prepare compounds of Formula I. More specific details of the transformations depicted are provided in Reaction Schemes II-VI below. In step one of Reaction Scheme I a metallated compound $R^1$-M of Formula VII and the compound of Formula VI are coupled using a palladium catalyzed coupling reaction. In the compound of Formula VII M represents a metal and in the compound of Formula VI Lg is an appropriate leaving group, such as a halide or triflate. The compound of Formula V can then be reacted with the compound of Formula IV to provide the compound of Formula III. In the compound of Formula V L' represents a precursor group which is, along with R'" in the compound of Formula IV, covered into the linker L in the compound of Formula III. The compound of Formula III can then be hydrolyzed to provide the free acid of Formula II which can then be subjected to an amide coupling reaction with the amine $R^{3'}R^2NH$, followed by deprotection if necessary to provide the compound of Formula I. The group $R^{3'}$ in the amine $R^{3'}R^2NH$ can represent either $R^3$ itself or a protected version of $R^3$ which can be subsequently deprotected to provide $R^3$.

Reaction Scheme II outlines the general procedures that can be used to provide compounds of the present invention having Formula Ia. The compounds of Formula Ia are of Formula I wherein L is —C($R^5$)—X—, X is NH and $R^2$ is H.

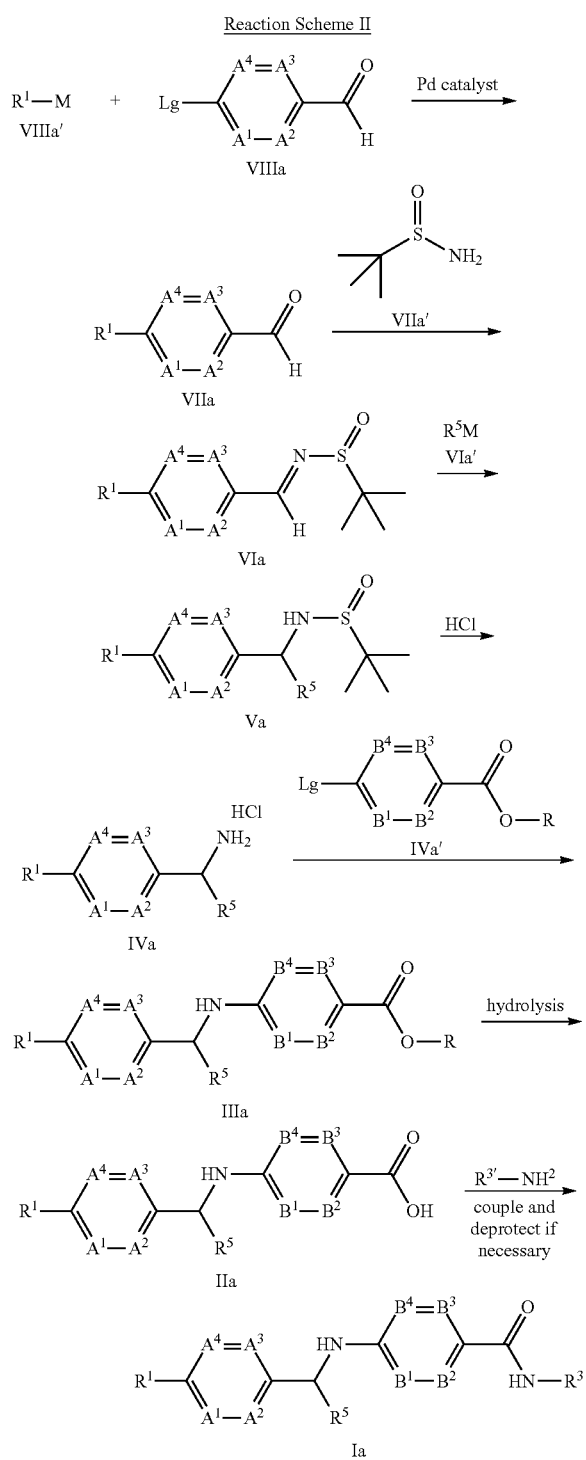

Reaction Scheme II

The substituted aldehyde of Formula VIIIa may be formed by a palladium catalysed coupling between a metallated compound $R^1$-M of Formula VIIIa' and the aldehyde derivative of general Formula VIIIa. Preferably, the reaction is carried out between the boronate ester VIIIa' (where M is B(OR')$_2$ and R' is H or lower alkyl) and an aldehyde derivative VIIIa (wherein Lg is OSO$_2$CF$_3$, Cl, Br or I) using a suitable palladium catalyst, a suitable phosphine ligand and a suitable base in the presence of a suitable solvent at a temperature of typically from room temperature up to around reflux (or at temperatures above the boiling point of the solvent e.g. 120° C. using microwave conditions).

A suitable palladium catalyst is tris(dibenzylideneacetone) dipalladium, bis (dibenzylideneacetone) palladium, palladium acetate or (1,1'-bis(diphenylphosphino) ferrocene) dichloropalladium. A suitable phosphine ligand is tricyclohexylphosphine, triphenylphosphine or 2-dicyclohexylphosphino-2',6'-dimethoxybiphenyl. A suitable base is sodium carbonate, potassium carbonate, potassium phosphate or sodium hydrogen carbonate and solvents are DME, 1,4-dioxane or THF/water.

Alternatively, the cross coupling may be carried out between the trimethyl stannane of general Formula VIIIa' (wherein M is SnMe$_3$) and aldehyde derivative of Formula VIIIa using a suitable catalyst, such as tetrakis(triphenylphosphine)palladium, an optional copper (I) source, such as copper (I) chloride, a suitable base, such as cesium fluoride, and a suitable solvent, such as N,N-dimethylformamide, at a temperature of typically around 80° C. to 120° C. Further alternative methods using metallated compounds $R^1$-M (where M is MgX' or ZnX' and X' is a halide) with the derivative VIIIa using a suitable palladium catalyst, a suitable phosphine base, an optional copper (I) source, and a suitable base in the presence of a suitable solvent at a temperature of typically around reflux, can also be employed.

Suitable palladium catalysts are tris(dibenzylideneacetone)dipalladium, bis(dibenzylidene acetone)palladium, palladium acetate or (1,1'-bis(diphenylphosphino) ferrocene) dichloropalladium. Suitable phosphine bases are tricyclohexylphosphine or 2-dicyclohexylphosphino-2',6'-dimethoxybiphenyl. A suitable copper (I) source is copper (I) chloride. Suitable bases are potassium carbonate or sodium hydrogen carbonate. Suitable solvents are DME, 1,4-dioxane or THF/water.

The substituted aldehyde of Formula VIIIa can then be reacted with an alkylsulfinamide such as 2-methylpropane-2-sulfinamide VIIa' in an appropriate solvent such as dichloromethane in the presence of titanium(IV)ethoxide, typically at a temperature from room temperature up to reflux for a period of 1 to 24 hours to provide the compound of Formula VIa. The compound of Formula VIa is then alkylated using an appropriate alkylating agent $R^5$-M (VIa'), such as a Grignard reagent wherein M represents a magnesium halide, or a reagent where M represents a zinc halide or an organolithium reagent wherein M represent lithium. The reaction is typically carried out in an appropriate solvent such as THF at a temperature of −78° C. to room temperature for a period of 30 minutes to 24 hours to provide the compound of Formula Va. The sulfinamide compound of Formula Va can then be treated with an acid, such as HCl in an appropriate solvent such as diethyl ether, dioxane or methanol typically at room temperature for a period of 1 to 24 hours to provide the amine compound of Formula IVa (depicted as the hydrochloride salt).

The amine of Formula IVa can then be reacted with an appropriately substituted compound of Formula IVa'. The compound of Formula IVa' is one in which the group Lg represents an appropriate leaving group such as a halide or triflate and the group R typically represents lower alkyl such as methyl, ethyl or t-butyl, although other groups which provide hydrolyzable esters can be employed. The reaction of the compound of Formula IVa with the compound of Formula IVa' is carried out in an appropriate solvent, such as N,N-dimethylformamide, in the presence of a base, such as potassium carbonate, at a temperature of room temperature to 120° C. for a period of 1 to 24 hours to provide the compound of Formula IIIa.

The compound of Formula IIIa then undergoes hydrolysis to provide the compound of Formula IIa. Depending on which R group is present in the ester of Formula IIIa, appropriate acid or base catalyzed hydrolysis can be carried out to provide the corresponding free acid in the compound of Formula IIa. For example, when R represents methyl, hydrolysis is typically carried out with aqueous sodium hydroxide or lithium hydroxide in a mixture of methanol and tetrahydrofuran at a temperature from room temperature up to 80° C. for 15 minutes to 24 hours.

Conversion of the compound of Formula IIa to provide the compound of Formula Ia can be carried out using standard amide coupling conditions. Amide coupling is carried out using standard literature conditions. The acid of Formula IIa can be converted to the corresponding acid chloride using a suitable chlorinating agent, such as oxalyl chloride or thionyl chloride, in a suitable solvent, such as dichloromethane or toluene, optionally in the presence of catalytic DMF, at a suitable temperature, typically of between 0° C. and room temperature. The acid chloride can then be reacted with the amine of generic formula $R^{3'}$—NH2 in the presence of a base, such as triethylamine or diisopropylethylamine, in a suitable solvent, such as dichloromethane or toluene, at a temperature of between 0° C. and room temperature. $R^{3'}$ can represent either $R^3$ itself or a protected version of $R^3$ which can be subsequently deprotected to provide $R^3$. Alternatively, the acid (IIa) can be converted to a suitable activated species with a coupling agent, such as EDCI.HCl, HBTU, HATU, PyBop, DCC, or CDI, in a suitable solvent, such as dichloromethane, acetonitrile or DMF. In the presence of EDCI.HCl, HOBT is typically added. EDCI is 1-ethyl-3-(3-dimethylaminopropyl) carbodiimide; HBTU is O-Benzotriazole-N,N,N',N'-tetramethyluronium hexafluorophosphate; HATU is O-(7-Azabenzotriazol-1-yl)-N,N,N',N'-tetramethyluronium hexafluorophosphate; PyBop is Benzotriazol-1-yloxytripyrrolidinophosphonium hexafluorophosphate; DCC is dicyclohexylcarbodiimide; CDI is N,N'-carbonyldiimidazole and HOBT is 1-hydroxy benzotriazole. A suitable base, such as triethylamine or diisopropylethylamine, is also used and the reaction is typically carried out at room temperature. In the instance where $R^{3'}$ represents a protected version of $R^3$, subsequent deprotection can then be carried out by methods known in the art to provide $R^3$. For example, when $R^3$ is an ester, appropriate acid or base catalyzed hydrolysis can be carried out to provide the corresponding free acid in the compound of Formula Ia.

Reaction Scheme III outlines the general procedures one could use to provide compounds of the present invention having Formula Ib. The compounds of Formula Ib are of Formula I wherein L is —X—C($R^5$)—, X is NH and $R^2$ is H.

Reaction Scheme IIA provides an alternative method for the preparation of the compounds of Formula Ia wherein the amine compound of Formula IVa is prepared from the corresponding nitrile of Formula Va.

Reaction Scheme IIA

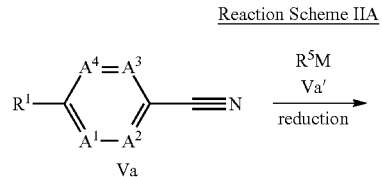

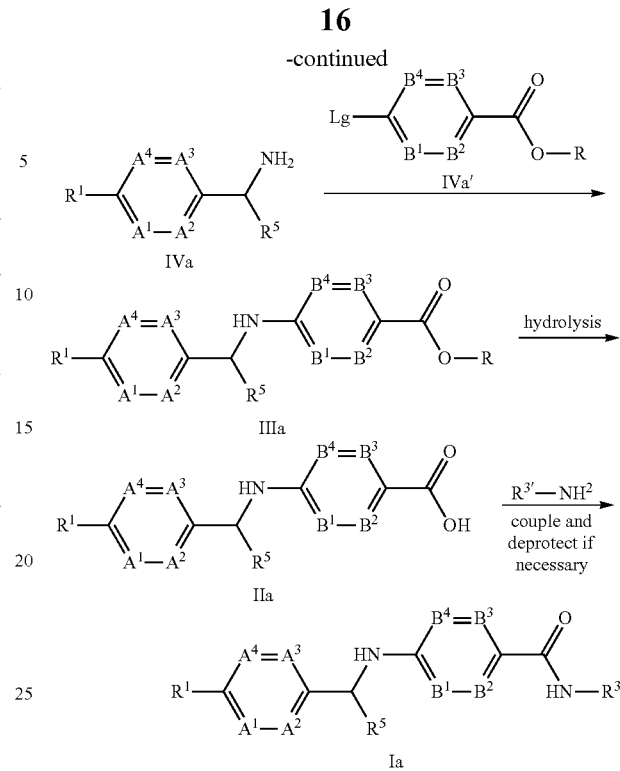

The nitrile of Formula Va is reacted with an appropriate Grignard reagent $R^5$-M wherein M represents a magnesium halide such as magnesium chloride or magnesium bromide. The reaction is carried out in an appropriate solvent such as tetrahydrofuran or a mixture of tetrahydrofuran and diethyl ether. The reaction is typically carried out at 0° C. to 100° C. and microwave irradiation of the reaction mixture is preferred. Upon completion of the Grignard reaction the reaction mixture is then subjected to reduction using an appropriate reducing agent such as sodium borohydride in an appropriate solvent such as methanol to provide the amine compound of Formula IVa. The compound of Formula IVa is then converted to the compound of Formula Ia as previously described for Reaction Scheme II.

Reaction Scheme III

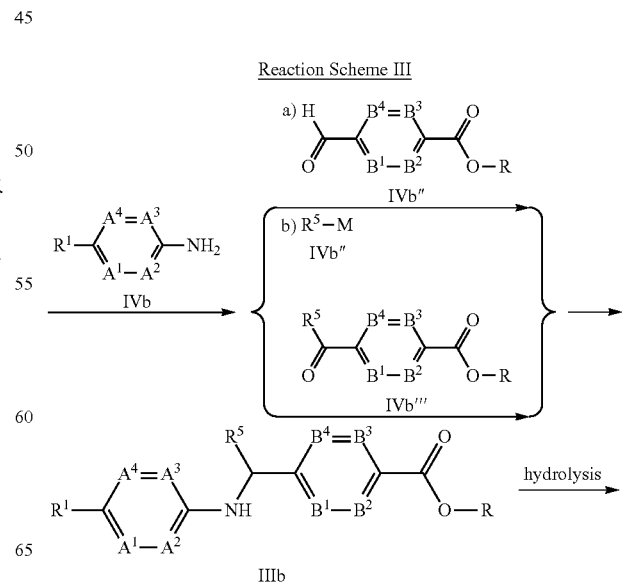

-continued

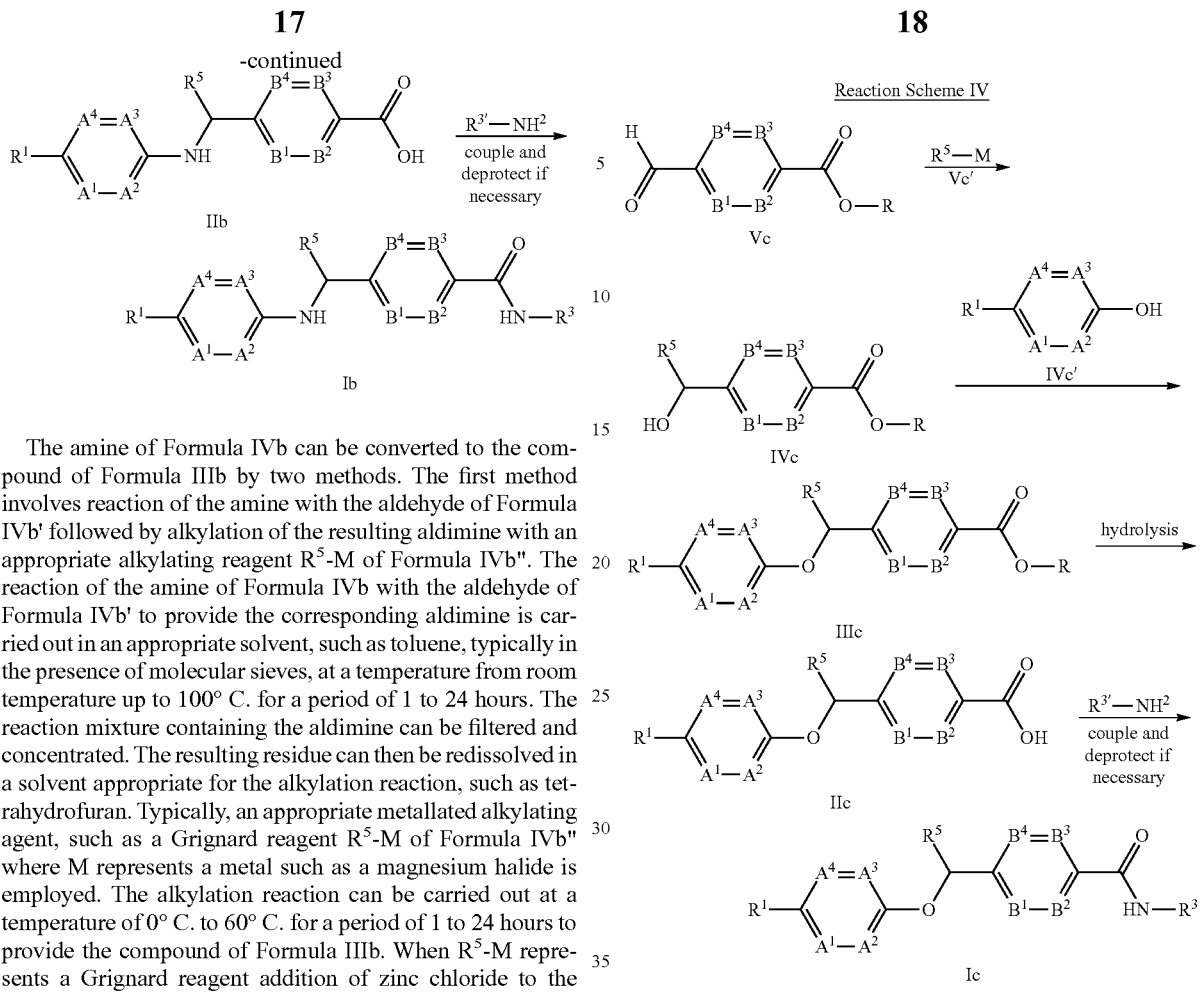

The amine of Formula IVb can be converted to the compound of Formula IIIb by two methods. The first method involves reaction of the amine with the aldehyde of Formula IVb' followed by alkylation of the resulting aldimine with an appropriate alkylating reagent $R^5$-M of Formula IVb". The reaction of the amine of Formula IVb with the aldehyde of Formula IVb' to provide the corresponding aldimine is carried out in an appropriate solvent, such as toluene, typically in the presence of molecular sieves, at a temperature from room temperature up to 100° C. for a period of 1 to 24 hours. The reaction mixture containing the aldimine can be filtered and concentrated. The resulting residue can then be redissolved in a solvent appropriate for the alkylation reaction, such as tetrahydrofuran. Typically, an appropriate metallated alkylating agent, such as a Grignard reagent $R^5$-M of Formula IVb" where M represents a metal such as a magnesium halide is employed. The alkylation reaction can be carried out at a temperature of 0° C. to 60° C. for a period of 1 to 24 hours to provide the compound of Formula IIIb. When $R^5$-M represents a Grignard reagent addition of zinc chloride to the reaction mixture may be desirable to increase the yield of the compound of Formula IIIb (see Ishihara, K. et al.; JACS, 2006, 128, 9998).

Alternatively, the compound of Formula IIIb can be prepared by reaction of an amine of Formula IVb and a ketone of Formula IVb''' followed by reduction of the resulting imine. The reaction can be carried out under typical reductive amination conditions to provide the compound of Formula IIIb. For example, the amine of Formula IVb and ketone IVb''' in an appropriate solvent such as dimethoxyethane and in the presence of molecular sieves and para-toluene sulfonic acid can be reacted at room temperature up to 120° C. (sealed tube) for 1 to 24 hours. The reaction mixture can then be allowed to cool to room temperature and be treated with an appropriate reducing agent, such as sodium cyanoborohydride in methanol, and in the presence of acetic acid for 1 to 24 hours to provide the compound of Formula IIIb.

The compound of Formula IIIb can be hydrolyzed to provide the free acid compound of Formula IIb by methods as previously described for the preparation of the compound of Formula IIa in Reaction Scheme II. The free acid compound of Formula IIb can then undergo amide coupling conditions followed by deprotection if necessary to provide the compound of Formula Ib as previously described for the conversion of the compound of Formula IIa to Formula Ia in Reaction Scheme II.

Reaction Scheme IV outlines the general procedures that can be used to provide compounds of the present invention having Formula Ic. The compounds of Formula Ic are of Formula I wherein L is —X—C($R^5$)—, X is O and $R^2$ is H.

The compound of Formula IVc is prepared by reaction of an aldehyde of Formula Vc with an appropriate metallated alkylating compound $R^5$-M (Vc'). Typically, $R^5$-M is a Grignard reagent in which M represents a magnesium halide, such as magnesium chloride or magnesium bromide. The reaction is carried out in an appropriate solvent, such as tetrahydrofuran, at a temperature from about −78° C. to room temperature for a period of 15 minutes to 24 hours to provide the alcohol of Formula IVc. The alcohol IVc is then coupled with the phenol of Formula IVc' using phenolic ether Mitsunobu reaction conditions (see e.g. Mitsunobu, O.; Synthesis, 1981, 1; Lepore, S. D. et al. J. Org. Chem., 2003, 68(21), 8261-8263) to provide the compound of Formula IIIc. This reaction is typically carried out in an appropriate solvent such as tetrahydrofuran in the presence of an appropriate coupling reagent such as diethylazodicarboxylate (DEAD) or diisopropylazodicarboxylate (DIAD) and a phosphine ligand such as triphenylphosphine. The reaction is typically run at a temperature from about 0° C. to room temperature for 1 to 24 hours. The compound IIIc can then be hydrolyzed to the compound of Formula IIc followed by amide formation and deprotection, as necessary, to provide the compound of Formula Ic as previously described for the corresponding steps in Reaction Scheme II.

Reaction Scheme V outlines the general procedures that can be used to provide compounds of the present invention having Formula Id. The compounds of Formula Id are of Formula I wherein L is —C($R^5$)—X—, X is O and $R^2$ is H.

Reaction Scheme V

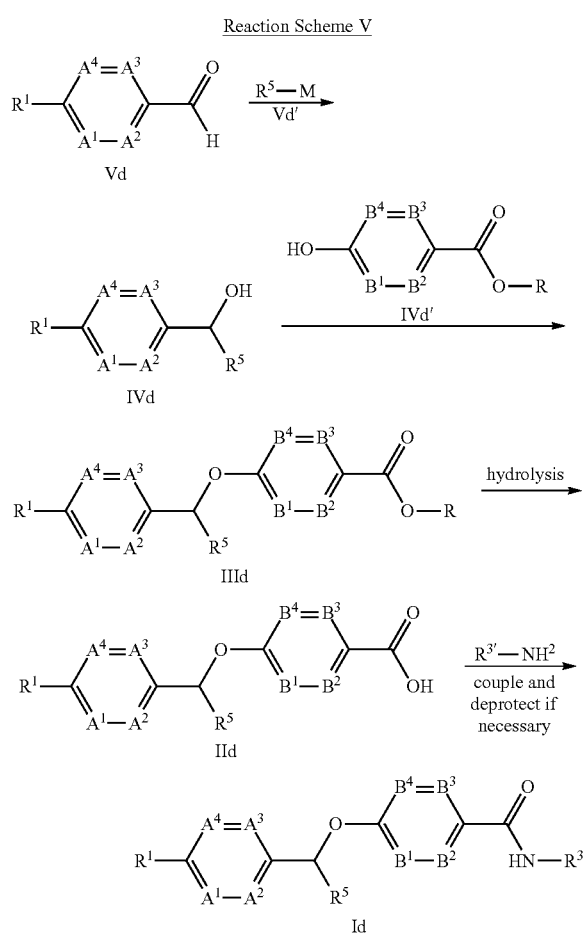

The compound of Formula Id is prepared in an analogous manner to the preparation of the compound of Formula Ic in Reaction Scheme IV by substituting the compounds of Formula Vd, Vd', IVd, IVd', IIId and IIId for the compounds Vc, Vc', IVc, IVc', IIIc and IIIc as previously described.

Reaction Scheme VI outlines the general procedures one could use to provide compounds of the present invention having Formula Ia. The compounds of Formula Ia are of Formula I wherein L is —X—C(R⁵)—, X is CH₂ and R² is H.

Reaction Scheme VI

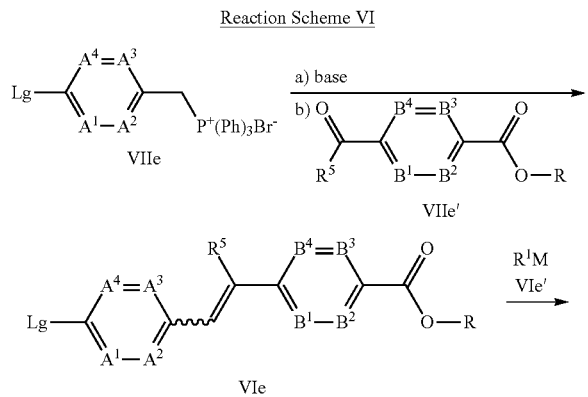

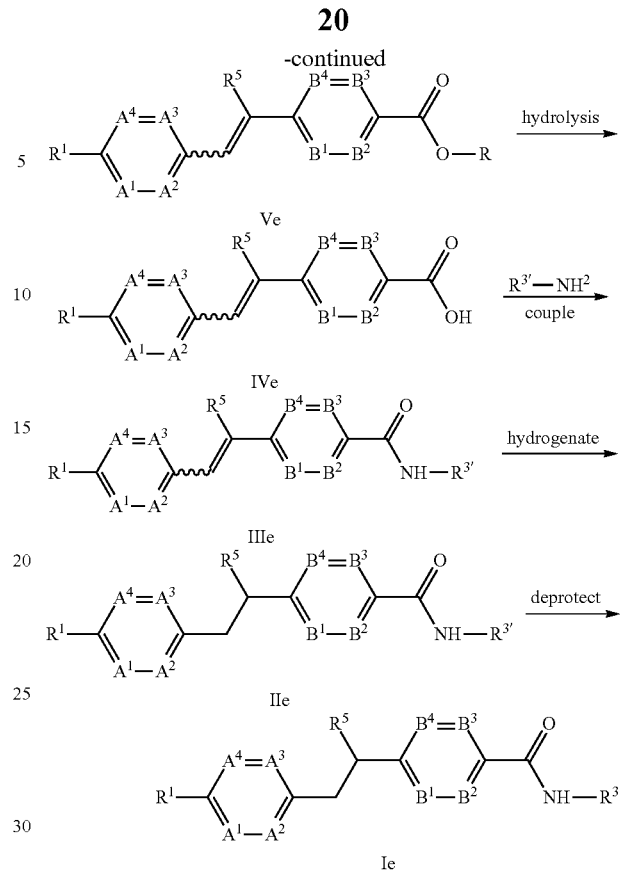

The phosphonium bromide compound of Formula VIIIe may be treated with an appropriate base and then reacted with the ketone derivative of Formula VIIIe' to provide the olefinic compound of Formula VIe. The compound of Formula VIIIe is typically treated with a base such as lithium bis(trimethylsilyl)amide (LHMDS) in an appropriate solvent such as toluene at −78° C. up to room temperature. Other bases that can be employed include lithium amides such as lithium diisopropylamide (LDA), lithium 2,2,6,6-tetramethyl piperidine (LiTMP) or lithium diethyl amide as well as alkyl lithiums such as methyl lithium or n-butyl lithium.

The compound of Formula VIe can then be reacted with the metallated compound R¹-M (VIe'), typically by a palladium catalyzed coupling reaction, as was described previously for the first step in Reaction Scheme II to provide the compound of Formula Ve. The compound of Formula Ve is then subjected to hydrolysis, typically in methanol and tetrahydrofuran using sodium hydroxide as base at 0° C. to room temperature for a period of 1 to 24 hours to provide the free acid of formula IVe. The free acid of Formula IVe can then be reacted with the amine R³'—NH₂ using the amide coupling conditions previously described for Reaction Scheme II to provide the compound of Formula IIIe. The compound of Formula IIIe is then subjected to hydrogenation to reduce the olefinic moiety and provide the compound of Formula IIe. The hydrogenation is typically carried out in the presence of an appropriate hydrogenation catalyst, such as 10% palladium on carbon (Pd/C), in an appropriate solvent such as methanol at a temperature from room temperature up to 50° C. Hydrogenation apparatus such as the ThalesNano H-Cube® hydrogenator (ThalesNano, Budapest, Hungary) with a 10% Pd/C cartridge can be employed for this step. The compound of Formula IIe can then be deprotected as necessary and as previously described for Reaction Scheme II to provide the compound of Formula Ie.

The compounds of the present invention may be isolated and used per se, or when possible, in the form of its pharmaceutically acceptable salt. The term "salts" refers to inorganic and organic salts of a compound of the present invention. These salts can be prepared in situ during the final isolation and purification of a compound, or by separately reacting the compound with a suitable organic or inorganic acid or base and isolating the salt thus formed. Representative salts include the hydrobromide, hydrochloride, hydroiodide, sulfate, bisulfate, nitrate, acetate, trifluoroacetate, oxalate, besylate, palmitinate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, e.g., Berge, et al., *J. Pharm. Sci.*, 66, 1-19 (1977).

The compounds of the present invention may contain asymmetric or chiral centers, and, therefore, exist in different stereoisomeric forms. Unless specified otherwise, it is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column. Alternatively, the specific stereoisomers may be synthesized by using an optically active starting material, by asymmetric synthesis using optically active reagents, substrates, catalysts or solvents, or by converting one stereoisomer into the other by asymmetric transformation.

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons. For example, the pyrimidone ring of this invention may also exist in its hydroxy pyrimidine form. Both such forms are included in the compounds of Formula I.

Certain compounds of the present invention may exist in different stable conformational forms which may be separable. Torsional asymmetry due to restricted rotation about an asymmetric single bond, for example, because of steric hindrance or ring strain, may permit separation of different conformers.

The present invention also embraces isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine, iodine, and chlorine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{123}I$, $^{125}I$ and $^{36}Cl$, respectively.

Certain isotopically-labeled compounds of the present invention (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, and $^{18}F$ are useful for positron emission tomography (PET) studies to examine substrate occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Certain compounds of the present invention may exist in more than one crystal form (generally referred to as "polymorphs"). Polymorphs may be prepared by crystallization under various conditions, for example, using different solvents or different solvent mixtures for recrystallization; crystallization at different temperatures; and/or various modes of cooling, ranging from very fast to very slow cooling during crystallization. Polymorphs may also be obtained by heating or melting the compound of the present invention followed by gradual or fast cooling. The presence of polymorphs may be determined by solid probe NMR spectroscopy, IR spectroscopy, differential scanning calorimetry, powder X-ray diffraction or such other techniques.

Compounds of the present invention are useful for treating diseases, conditions and/or disorders modulated by glucagon; therefore, another embodiment of the present invention is a pharmaceutical composition comprising a therapeutically effective amount of a compound of the present invention and a pharmaceutically acceptable excipient, diluent or carrier. The compounds of the present invention (including the compositions and processes used therein) may also be used in the manufacture of a medicament for the therapeutic applications described herein.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical compositions also include solvates and hydrates of the compounds of Formula I. The term "solvate" refers to a molecular complex of a compound represented by Formula I (including pharmaceutically acceptable salts thereof) with one or more solvent molecules. Such solvent molecules are those commonly used in the pharmaceutical art, which are known to be innocuous to the recipient, e.g., water, ethanol, ethylene glycol, and the like, The term "hydrate" refers to the complex where the solvent molecule is water. The solvates and/or hydrates preferably exist in crystalline form. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides a method of treating diseases, conditions and/or disorders modulated by glucagon in an animal that includes administering to an animal in need of such treatment a therapeutically effective amount of a compound of the present invention or a pharmaceutical composition comprising an effective amount of a compound of the present invention and a pharmaceutically acceptable excipient, diluent, or carrier. The method is particularly useful for treating diseases, conditions and/or disorders that benefit from the modulation of glucagon which include: eating disorders (e.g., binge eating disorder, anorexia, bulimia, weight loss or control and obesity), prevention of obesity and insulin resistance.

One aspect of the present invention is the treatment of obesity, and obesity-related disorders (e.g., overweight, weight gain, or weight maintenance).

Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

Another aspect of the present invention is for the treatment or delaying the progression or onset of diabetes or diabetes-related disorders including Type 1 (insulin-dependent diabetes mellitus, also referred to as "IDDM") and Type 2 (noninsulin-dependent diabetes mellitus, also referred to as "NIDDM") diabetes, impaired glucose tolerance, insulin resistance, hyperglycemia, and diabetic complications (such as atherosclerosis, coronary heart disease, stroke, peripheral vascular disease, nephropathy, hypertension, neuropathy, and retinopathy).

Yet another aspect of the present invention is the treatment of diabetes- or obesity-related co-morbidities, such as metabolic syndrome. Metabolic syndrome includes diseases, conditions or disorders such as dyslipidemia, hypertension, insulin resistance, diabetes (e.g., Type 2 diabetes), weight gain, coronary artery disease and heart failure. For more detailed information on Metabolic Syndrome, see, e.g., Zimmet, P. Z., et al., "The Metabolic Syndrome: Perhaps an Etiologic Mystery but Far From a Myth—Where Does the International Diabetes Federation Stand?," *Diabetes & Endocrinology,* 7(2), (2005); and Alberti, K. G., et al., "The Metabolic Syndrome—A New Worldwide Definition," *Lancet,* 366, 1059-62 (2005). Preferably, administration of the compounds of the present invention provides a statistically significant ($p<0.05$) reduction in at least one cardiovascular disease risk factor, such as lowering of plasma leptin, C-reactive protein (CRP) and/or cholesterol, as compared to a vehicle control containing no drug. The administration of compounds of the present invention may also provide a statistically significant ($p<0.05$) reduction in glucose serum levels.

In yet another aspect of the present invention, the condition treated is impaired glucose tolerance, hyperglycemia, diabetic complications such as sugar cataracts, diabetic neuropathy, diabetic nephropathy, diabetic retinopathy and diabetic cardiomyopathy, anorexia nervosa, bulimia, cachexia, hyperuricemia, hyperinsulinemia, hypercholesterolemia, hyperlipidemia, dyslipidemia, mixed dyslipidemia, hypertriglyceridemia, nonalcoholic fatty liver disease, atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis, vascular stenosis, solid tumors, skin cancer, melanoma, lymphoma, breast cancer, lung cancer, colorectal cancer, stomach cancer, esophageal cancer, pancreatic cancer, prostate cancer, kidney cancer, liver cancer, bladder cancer, cervical cancer, uterine cancer, testicular cancer and ovarian cancer.

The present invention also relates to therapeutic methods for treating the above described conditions in a mammal, including a human, wherein a compound of Formula I of this invention is administered as part of an appropriate dosage regimen designed to obtain the benefits of the therapy. The appropriate dosage regimen, the amount of each dose administered and the intervals between doses of the compound will depend upon the compound of formula (I) of this invention being used, the type of pharmaceutical compositions being used, the characteristics of the subject being treated and the severity of the conditions.

In general, an effective dosage for the compounds of the present invention is in the range of 0.01 mg/kg/day to 30 mg/kg/day, preferably 0.01 mg/kg/day to 5 mg/kg/day of active compound in single or divided doses. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. Practitioners will appreciate that "kg" refers to the weight of the patient measured in kilograms.

The compounds or compositions of this invention may be administered in single (e.g., once daily) or multiple doses or via constant infusion. The compounds of this invention may also be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents.

The compounds or compositions of the present invention may be administered to a subject in need of treatment by a variety of conventional routes of administration, including orally and parenterally, (e.g., intravenously, subcutaneously or intramedullary). Further, the pharmaceutical compositions of this invention may be administered intranasally, as a suppository, or using a "flash" formulation, i.e., allowing the medication to dissolve in the mouth without the need to use water.

It is also noted that the compounds of the present invention can be used in sustained release, controlled release, and delayed release formulations, which forms are also well known to one of ordinary skill in the art.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include anti-obesity agents (including appetite suppressants), anti-diabetic agents, anti-hyperglycemic agents, lipid lowering agents, and anti-hypertensive agents.

Suitable anti-diabetic agents include an acetyl-CoA carboxylase-2 (ACC-2) inhibitor, a diacylglycerol O-acyltransferase 1 (DGAT-1) inhibitor, a phosphodiesterase (PDE)-10 inhibitor, a sulfonylurea (e.g., acetohexamide, chlorpropamide, diabinese, glibenclamide, glipizide, glyburide, glimepiride, gliclazide, glisentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adipose, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone, rosiglitazone and troglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) agonist (e.g., exendin-3 and exendin-4), a protein tyrosine phosphatase-1B (PTP-1B) inhibitor (e.g., trodusquemine, hyrtiosal extract, and compounds disclosed by Zhang, S., et al., Drug Discovery Today, 12(9/10), 373-381 (2007)), SIRT-1 inhibitor (e.g., reservatrol), a dipeptidyl peptidease IV (DPP-IV) inhibitor (e.g., sitagliptin, vildagliptin, alogliptin and saxagliptin), an SGLT2 inhibitor (e.g. dapagliflozin, remogliflozin, sergliflozin and AVE2268), an insulin secreatagogue, a fatty acid oxidation inhibitor, an A2 antagonist, a c-jun amino-terminal kinase (JNK) inhibitor, insulin, an insulin mimetic, a glycogen phosphorylase inhibitor, and a VPAC2 receptor agonist. Preferred anti-diabetic agents for the combination aspects are metformin, SGLT2 inhibitors (e.g. dapagliflozin, remogliflozin, sergliflozin and AVE2268) and DPP-IV inhibitors (e.g., sitagliptin, vildagliptin, alogliptin and saxagliptin). Preferred combinations include the instant compounds of Formula I with metformin and a DPP-IV inhibitor or with metformin and an SGLT2 inhibitor.

Suitable anti-obesity agents include 11β-hydroxy steroid dehydrogenase-1 (11β-HSD type 1) inhibitors, stearoyl-CoA desaturase-1 (SCD-1) inhibitor, MCR-4 agonists, cholecystokinin-A (CCK-A) agonists, monoamine reuptake inhibitors (such as sibutramine), sympathomimetic agents, $β_3$ adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists), $PYY_{3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin antagonists, histamine 3 antagonists or inverse agonists, neuromedin U agonists, MTP/ApoB inhibitors (e.g., gut-selective MTP inhibitors, such as dirlotapide), opioid antagonist, orexin antagonist, and the like.

Preferred anti-obesity agents for use in the combination aspects of the present invention include gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818, 658), lipase inhibitor (e.g., Cetilistat), $PYY_{3-36}$ (as used herein "$PYY_{3-36}$" includes analogs, such as pegylated $PYY_{3-36}$ e.g., those described in US Publication 2006/0178501), opioid antagonists (e.g., naltrexone), oleoyl-estrone (CAS No. 180003-17-2), obinepitide (TM30338), pramlintide (Symlin®), tesofensine (NS2330), leptin, liraglutide, bromocriptine, orlistat, exenatide (Byetta®), AOD-9604 (CAS No. 221231-10-3) and sibutramine. Preferably, compounds of the present invention and combination therapies are administered in conjunction with exercise and a sensible diet.

All of the above recited U.S. patents and publications are incorporated herein by reference.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), and AstraZeneca Pharmaceuticals (London, England).

General Experimental Procedures

NMR spectra were recorded on a Varian Unity™ 400 (available from Varian Inc., Palo Alto, Calif.) at room temperature at 400 MHz for proton. Chemical shifts are expressed in parts per million (δ) relative to residual solvent as an internal reference. The peak shapes are denoted as follows: s, singlet; d, doublet; dd, doublet of doublet; t, triplet; q, quartet; m, multiplet; bs, broad singlet; 2s, two singlets. Atmospheric pressure chemical ionization mass spectra (APCI) were obtained on a Fisons™ Platform II Spectrometer (carrier gas: acetonitrile: available from Micromass Ltd, Manchester, UK). Chemical ionization mass spectra (CI) were obtained on a Hewlett-Packard™ 5989 instrument (ammonia ionization, PBMS: available from Hewlett-Packard Company, Palo Alto, Calif.). Electrospray ionization mass spectra (ES) were obtained on a Waters™ ZMD instrument (carrier gas: acetonitrile: available from Waters Corp., Milford, Mass.). High resolution mass spectra (HRMS) were obtained on an Agilent™ Model 6210 using time of flight method. Where the intensity of chlorine or bromine-containing ions are described, the expected intensity ratio was observed (approximately 3:1 for $^{35}Cl/^{37}Cl$-containing ions and 1:1 for $^{79}Br/^{81}Br$-containing ions) and the intensity of only the lower mass ion is given. In some cases only representative $^1H$ NMR peaks are given. Optical rotations were determined on a PerkinElmer™ 241 polarimeter (available from PerkinElmer Inc., Wellesley, Mass.) using the sodium D line (λ=589 nm) at the indicated temperature and are reported as follows $[α]_D^{temp}$, concentration (c=g/100 ml), and solvent.

Column chromatography was performed with either Baker™ silica gel (40 μm; J. T. Baker, Phillipsburg, N.J.) or Silica Gel 50 (EM Sciences™, Gibbstown, N.J.) in glass columns or in Flash 40 Biotage™ columns (ISC, Inc., Shelton, Conn.) or Biotage™ SNAP cartridge KPsil or Redisep Rf silica (from Teledyne™ ISCO™) under low nitrogen pressure. Chiral SFC (supercritical fluid chromatography) was performed on the chiral columns as specified.

Preparation of Starting Materials and Intermediates

The following materials are available from the corresponding sources: methyl 6-hydroxynicotinate—Fluorochem Ltd., Hadfield, Derbyshire, UK methyl 6-formylnicotinate—Ark Pharm, Inc., Libertyville, Ill., USA methyl 2-chloropyrimidine-5-carboxylate—Ark Pharm, Inc., Libertyville, Ill., USA (1H-tetrazol-5-yl)methanamine—Anichem LLC, North Brunswick, N.J., USA

Example 1.1

(R)-3-(6-(3-methyl-1-(4'-(trifluoromethyl)biphenyl-4-yl)butylamino) nicotinamido)propanoic acid

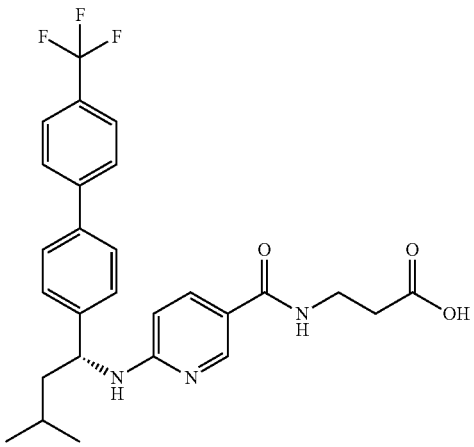 [SMILES: CC(C)C[C@@H](Nc1ccc(C(=O)NCCC(=O)O)cn1)c1ccc(-c2ccc(C(F)(F)F)cc2)cc1]

Step A: 4'-(trifluoromethyl)biphenyl-4-carbaldehyde

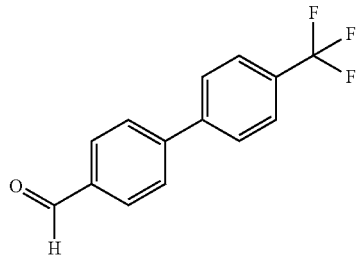 [SMILES: O=Cc1ccc(-c2ccc(C(F)(F)F)cc2)cc1]

A round bottom flask was charged with 4-bromobenzaldehyde (69.6 g, 376 mmol), 4-(trifluoromethyl)phenylboronic acid (75.0 g, 395 mmol) and 1-propanol (627 mL). The reaction mixture was stirred for 15 minutes at 70° C. until a clear solution was obtained. The resulting solution was treated with triphenylphosphine (888 mg, 3.38 mmol), palladium(II) acetate (256 mg, 1.13 mmol), 2M sodium carbonate (226 mL, 451 mmol) and water (138 mL). The reaction was heated at reflux for 1 hour, open to air. Water (900 mL) was then added and the reaction was cooled to 7° C. in an ice bath. The reaction was thoroughly stirred for 30 minutes until the title compound precipitated out. The mixture was then filtered and the solid washed with cold water (~600 mL). The solid was then solubilized in diethylether (500 mL) and filtered through a pad of celite and silica, rinsing with diethylether (2×500 mL). Removal of the solvent under reduced pressure afforded 4'-(trifluoromethyl) biphenyl-4-carbaldehyde (90.0 g, 96%)

as a pure white solid. $^1$H NMR (400 MHz, CDCl$_3$, δ): 7.75 (s, 4 H) 7.76-7.79 (m, 2 H) 7.96-8.04 (m, 2 H) 10.10 (s, 1 H). MS (M+1): 250.3.

Step B: (R,E)-2-methyl-N-((4'-(trifluoromethyl)biphenyl-4-yl)methylene)propane-2-sulfinamide

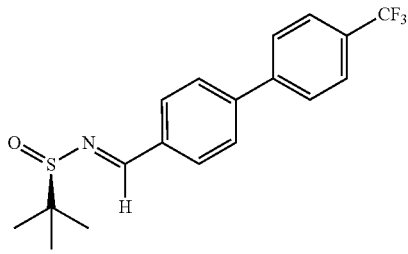 [SMILES: CC(C)(C)[S@@](=O)/N=C/c1ccc(-c2ccc(C(F)(F)F)cc2)cc1]

A round bottom flask equipped with a condenser was charged with 4'-(trifluoromethyl)biphenyl-4-carbaldehyde (20.0 g, 79.9 mmol), (R)-(+)-2-methylpropane-2-sulfinamide (9.69 g, 79.9 mmol) and dichloromethane (400 mL). Titanium(IV) ethoxide (33.2 mL, 160 mmol) was then added, and the mixture was heated to reflux for 3 hours. Methanol (50 mL) and saturated sodium bicarbonate (10 mL) were then added to the reaction, causing the titanium salts to precipitate. This mixture was stirred for 30 minutes and then filtered, rinsing with ethyl acetate. Sodium sulfate was added to the filtrate to remove the water and then filtered a second time. The solvent was removed under reduced pressure to afford (R,E)-2-methyl-N-((4'-(trifluoromethyl)biphenyl-4-yl)methylene)propane-2-sulfinamide (23.7 g, 84%) as a white solid. $^1$H NMR (400 MHz, CDCl$_3$, δ): 1.30 (s, 9 H) 7.70-7.74 (m, 2 H) 7.74 (s, 4 H) 7.95-7.99 (m, 2 H) 8.66 (s, 1 H). MS (M+1): 354.1.

Step C: (R)-2-methyl-N—((R)-3-methyl-1-(4'-(trifluoromethyl)biphenyl-4-yl)butyl)propane-2-sulfinamide

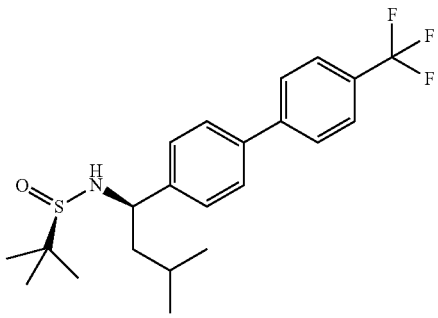 [SMILES: CC(C)C[C@@H](N[S@](=O)C(C)(C)C)c1ccc(-c2ccc(C(F)(F)F)cc2)cc1]

A round bottom flask was charged with (R,E)-2-methyl-N-((4'-(trifluoromethyl) biphenyl-4-yl)methylene)propane-2-sulfinamide (25.0 g, 70.7 mmol) and tetrahydrofuran (140 mL) and cooled down to −78° C. To this solution was added isobutyllithium (1.6M in heptane; 50.8 mL) dropwise over 20 minutes. The reaction was allowed to stir at −78° C. for 30 minutes. LC-MS analysis showed complete conversion of the starting material and the formation of two product diastereomers (4.6:1). The reaction was quenched with saturated ammonium chloride and extracted with ethyl acetate twice. The combined organic layers were washed with water and brine, dried over magnesium sulfate, filtered and concentrated under reduced pressure. Purification by column chromatography (1-10% ethyl acetate/dichloromethane) allowed isolation of the major isomer (the less polar isomer), (R)-2-methyl-N—((R)-3-methyl-1-(4'-(trifluoromethyl)biphenyl-4-yl)butyl)propane-2-sulfinamide (47.5 g, 74.2%) as a colorless gum. $^1$H NMR (400 MHz, CDCl$_3$, δ): 0.91 (d, 3 H) 0.96 (d, J=6.44 Hz, 3 H) 1.24 (s, 9 H) 1.49-1.59 (m, 1 H) 1.63-1.72 (m, 1 H) 1.84-1.94 (m, 1 H) 3.38 (br. s., 1 H) 4.46 (dd, J=8.19, 6.83 Hz, 1 H) 7.43-7.46 (m, 2 H) 7.56-7.60 (m, 2 H) 7.68-7.70 (m, 4 H). MS (M+1): 412.3.

Step D: (R)-3-methyl-1-(4'-(trifluoromethyl)biphenyl-4-yl)butan-1-amine hydrochloride

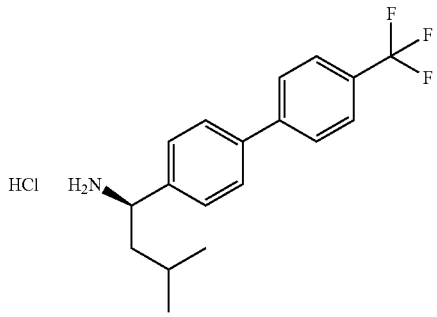 [SMILES: Cl ; CC(C)C[C@@H](N)c1ccc(-c2ccc(C(F)(F)F)cc2)cc1]

A round bottom flask was charged with (R)-2-methyl-N—((R)-3-methyl-1-(4'-(trifluoromethyl)biphenyl-4-yl)butyl)propane-2-sulfinamide (47.5 g, 115.5 mmol) and methanol (300 mL). The mixture was cooled to 0° C. and 2.0N HCl in ether (150 mL) was added. The reaction was stirred for 20 minutes. The reaction was then concentrated under reduced pressure. Trituration with ether provided (R)-3-methyl-1-(4'-(trifluoromethyl)biphenyl-4-yl)butan-1-amine hydrochloride (35.3 g, 89%), as a white solid. $^1$H NMR (400 MHz, CD$_3$OD, δ): 0.95 (d, 3 H) 0.99 (d, J=6.44 Hz, 3 H) 1.38-1.51 (m, 1 H) 1.78-1.91 (m, 1 H) 1.92-2.03 (m, 1 H) 4.40 (dd, J=10.15, 5.66 Hz, 1 H) 7.56-7.63 (m, 2 H) 7.74-7.88 (m, 6 H). MS (M+1): 291.2. [α]$_D$ =−11.9, c=1.8 (MeOH).

Step E: (R)-methyl-6-(3-methyl-1-(4'-(trifluoromethyl)biphenyl-4-yl)butylamino)nicotinate

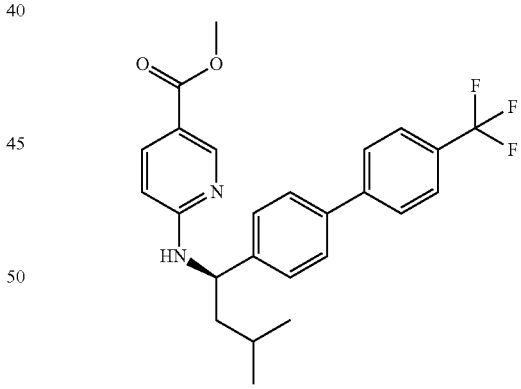

A 1.0 L round bottom flask was charged with methyl 6-fluoronicotinate (14.2 g, 91.6 mmol), (R)-3-methyl-1-(4'-(trifluoromethyl)biphenyl-4-yl)butan-1-amine hydrochloride (30.0 g, 87.3 mmol), potassium carbonate (36.2 g, 262 mmol) and N,N-dimethylformamide (300 mL). The reaction was heated to 110° C. and stirred for 15 hours. The reaction was cooled to room temperature and filtered. The filtrate was diluted with ethyl acetate and saturated ammonium chloride. The layers were separated and the aqueous was extracted with ethyl acetate. The combined organic layers were washed with water (5×) and brine (1×), dried over sodium sulfate, filtered and concentrated to provide (R)-methyl-6-(3-methyl-1-(4'-(trifluoromethyl)biphenyl-4-yl)butylamino)nicotinate (41.5 g) as a light brown solid. ¹H NMR (400 MHz, CDCl₃, δ): 0.98 (d, J=6.24 Hz, 3 H) 1.02 (d, J=6.24 Hz, 3 H) 1.67-1.92 (m, 3 H) 3.86 (s, 3 H) 4.68-4.84 (m, 1 H) 6.36 (d, J=8.97 Hz, 1 H) 6.65 (br. s., 1 H) 7.42-7.47 (m, 2 H) 7.55-7.59 (m, 2 H) 7.66-7.69 (m, 4 H) 8.00 (dd, J=8.97, 2.15 Hz, 1 H) 8.66 (d, J=1.95 Hz, 1 H). MS (M+1): 443.4.

Step F: (R)-6-(3-methyl-1-(4'-(trifluoromethyl)biphenyl-4-yl)butylamino)nicotinic acid

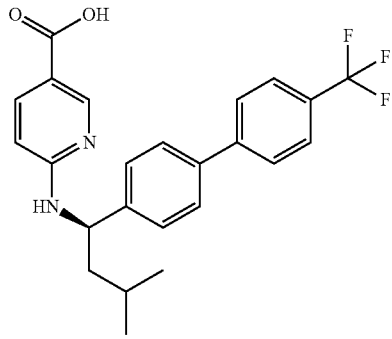 [SMILES: CC(C)C[C@@H](Nc1ccc(C(=O)O)cn1)c1ccc(-c2ccc(C(F)(F)F)cc2)cc1]

A round bottom flask was charged with (R)-methyl-6-(3-methyl-1-(4'-(trifluoromethyl)biphenyl-4-yl)butylamino) nicotinate (41.5 g, 93.8 mmol), methanol (200 mL) and tetrahydrofuran (200 mL). 1.0N NaOH (188 mL) was then added and the resulting solution was stirred at 50° C. for 3 hours. The reaction was cooled to room temperature and the organic solvents removed under reduced pressure. Water (300 mL) was added and the mixture was acidified with 10% citric acid to pH=3. A white precipitate formed and the heterogeneous mixture was stirred for 30 minutes at 0° C. The mixture was then filtered and the solid was dried under reduced pressure to afford (R)-6-(3-methyl-1-(4'-(trifluoromethyl)biphenyl-4-yl)butylamino)nicotinic acid (36.2 g, 90.0%). ¹H NMR (400 MHz, CDCl₃, δ): 0.98 (d, J=6.46 Hz, 3 H) 1.03 (d, J=6.46 Hz, 3 H) 1.66-1.78 (m, 1 H) 1.78-1.89 (m, 1 H) 1.96-2.05 (m, 1 H) 4.49-4.63 (m, 1 H) 6.44 (d, J=9.00 Hz, 1 H) 7.44-7.50 (m, 2 H) 7.53-7.58 (m, 2 H) 7.63-7.70 (m, 4 H) 8.17 (d, J=9.19 Hz, 1 H) 8.69-8.74 (m, 1 H) 9.44 (br. s., 1 H). MS (M+1): 429.4.

Step G: (R)-methyl 3-(6-(3-methyl-1-(4'-(trifluoromethyl)biphenyl-4-yl)butylamino)nicotinamido)propanoate

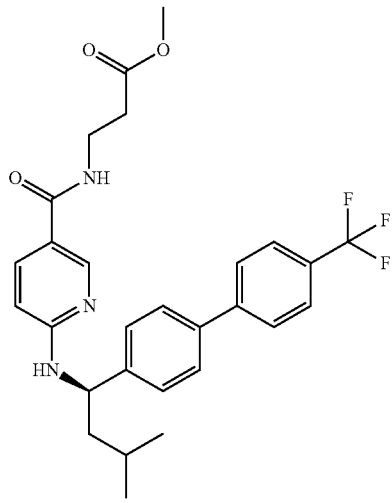 [SMILES: COC(=O)CCNC(=O)c1ccc(N[C@H](CC(C)C)c2ccc(-c3ccc(C(F)(F)F)cc3)cc2)nc1]

A round bottom flask was charged with (R)-6-(3-methyl-1-(4'-(trifluoromethyl)biphenyl-4-yl)butylamino)nicotinic acid (36.2 g, 84.4 mmol), 1-hydroxy-7-azabenzotriazole (12.6 g, 92.8 mmol), β-alanine methyl ester hydrochloride (14.3 g, 101 mmol), triethylamine (14.2 mL, 101 mmol) and dichloromethane (300 mL). 1-Ethyl-3-(3-dimethylaminopropyl)carbodiimide hydrochloride (18.0 g, 92.8 mmol) was then added and the reaction was stirred at room temperature for 1 hour. The reaction was diluted with dichloromethane and saturated ammonium chloride and water were added. The layers were separated, and the aqueous was extracted with dichloromethane. The combined organics were washed with brine, dried over sodium sulfate, filtered and concentrated to provide the crude compound as an orange gum. Purification by column chromatography (80% ethyl acetate/heptanes) provided (R)-methyl 3-(6-(3-methyl-1-(4'-(trifluoromethyl)biphenyl-4-yl)butylamino)nicotinamido) propanoate (34.6 g, 79.8%) as a white solid. ¹H NMR (400 MHz, CDCl₃, δ): 0.94-1.04 (m, 6 H) 1.65-1.85 (m, 4 H) 2.58-2.65 (m, 2 H) 3.64-3.72 (m, 4 H) 4.73-4.83 (m, 1 H) 5.33-5.41 (m, 1 H) 6.26 (d, J=8.78 Hz, 1 H) 6.53-6.63 (m, 1 H) 7.41-7.46 (m, 2 H) 7.53-7.58 (m, 2 H) 7.64-7.70 (m, 4 H) 7.76 (dd, J=8.78, 2.34 Hz, 1 H) 8.49 (d, J=2.34 Hz, 1 H). MS (M+1): 514.4.

Step H: (R)-3-(6-(3-methyl-1-(4'-(trifluoromethyl)biphenyl-4-yl)butylamino) nicotinamido)propanoic acid

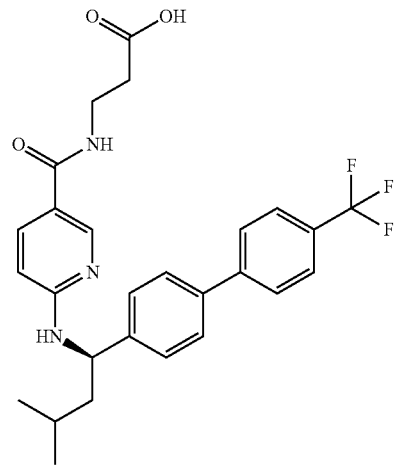 [SMILES: CC(C)C[C@@H](Nc1ccc(C(=O)NCCC(=O)O)cn1)c1ccc(-c2ccc(C(F)(F)F)cc2)cc1]

A round bottom flask was charged with (R)-methyl 3-(6-(3-methyl-1-(4'-(trifluoromethyl)biphenyl-4-yl)butylamino) nicotinamido)propanoate (6.26 g, 10.2 mmol), tetrahydrofuran (60 mL) and methanol (60 mL). 1.0N NaOH (18.3 mL, 18.3 mmol) was added and the resulting solution was stirred at room temperature for 15 min. The organic solvents were removed under reduced pressure and the resulting crude was diluted with water. 10% Citric acid was added to acidify the solution to pH~3. A white precipitate formed. After stirring for 30 minutes at room temperature, the solid was filtered off and dried under vacuum. Purification by column chromatography (0-10% methanol/dichloromethane) provided (R)-3-(6-(3-methyl-1-(4'-(trifluoromethyl)biphenyl-4-yl)butylamino)nicotinamido)propanoic acid (25.7 g, 76.4%) as a white solid. ¹H NMR (400 MHz, (CD₃)₂SO, δ): 0.91 (d, J=6.44 Hz, 3 H) 0.95 (d, J=6.44 Hz, 3 H) 1.48-1.59 (m, 1 H) 1.61-1.71 (m, 1 H) 1.72-1.82 (m, 1 H) 2.44 (t, J=7.12 Hz, 2 H) 3.34-3.42 (m, 2 H) 5.10 (br. s., 1 H) 6.52 (d, J=8.78 Hz, 1 H) 7.46-7.51 (m, 2 H) 7.57 (d, J=8.19 Hz, 1 H) 7.63-7.69 (m, 2 H) 7.74 (dd, J=8.88, 2.44 Hz, 1 H) 7.76-7.81 (m, 2 H) 7.83-7.89

(m, 2 H) 8.15 (t, J=5.46 Hz, 1 H) 8.40 (d, J=2.34 Hz, 1 H) 12.18 (br. s., 1 H). MS (M+1): 500.4.

Example 1.2

(+/−)-3-(6-(3-methyl-1-(4'-(trifluoromethyl)biphenyl-4-yl)butylamino) nicotinamido)propanoic acid

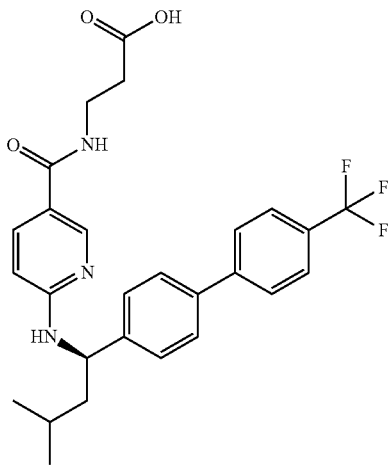 [SMILES: CC(C)C[C@@H](Nc1ccc(C(=O)NCCC(=O)O)cn1)c1ccc(-c2ccc(C(F)(F)F)cc2)cc1]

The title compound was prepared in a manner analogous to Example 1.1 using racemic 2-methylpropane-2-sulfinamide in Step B and without separation of diastereomers after Grignard addition in Step C. $^1$H NMR (400 MHz, (CD$_3$)$_2$SO, δ): 0.91 (d, J=6.44 Hz, 3 H) 0.95 (d, J=6.44 Hz, 3 H) 1.48-1.59 (m, 1 H) 1.61-1.71 (m, 1 H) 1.72-1.82 (m, 1 H) 2.44 (t, J=7.12 Hz, 2 H) 3.34-3.42 (m, 2 H) 5.10 (br. s., 1 H) 6.52 (d, J=8.78 Hz, 1 H) 7.46-7.51 (m, 2 H) 7.57 (d, J=8.19 Hz, 1 H) 7.63-7.69 (m, 2 H) 7.74 (dd, J=8.88, 2.44 Hz, 1 H) 7.76-7.81 (m, 2 H) 7.83-7.89 (m, 2 H) 8.15 (t, J=5.46 Hz, 1 H) 8.40 (d, J=2.34 Hz, 1 H) 12.18 (br. s., 1 H). MS (M+1): 500.4.

Example 1.3

(−)-(S)-3-(6-(3-methyl-1-(4'-(trifluoromethyl)biphenyl-4-yl)butylamino) nicotinamido)propanoic acid

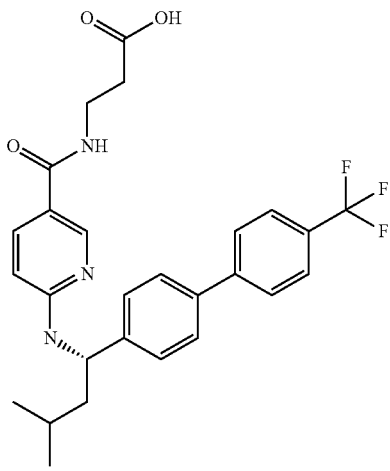 [SMILES: CC(C)C[C@H](Nc1ccc(C(=O)NCCC(=O)O)cn1)c1ccc(-c2ccc(C(F)(F)F)cc2)cc1]

The title compound is obtained by resolving racemic 3-(6-(3-methyl-1-(4'-(trifluoromethyl)biphenyl-4-yl)butylamino) nicotinamido) propanoic acid Example 1.2, by chiral SFC. Column: Chiralpak AD-H. Dimensions: 4.6 mm×25 cm. Mobile Phase: 65/35 CO$_2$/isopropanol. Flow Rate: 2.5 mL/min. Modifier: 0.2% diisopropyl amine. Retention time: 6.73 minutes. Optical Rotation: [α]$^D$=−12.4; c=0.42 (CHCl$_3$).

Example 1.1

(+)-(R)-3-(6-(3-methyl-1-(4'-(trifluoromethyl)biphenyl-4-yl)butylamino) nicotinamido)propanoic acid

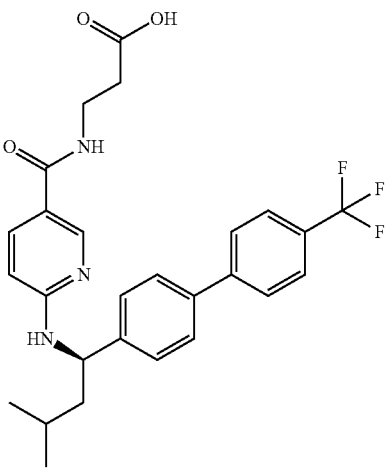 [SMILES: CC(C)C[C@@H](Nc1ccc(C(=O)NCCC(=O)O)cn1)c1ccc(-c2ccc(C(F)(F)F)cc2)cc1]

The title compound is obtained by resolving racemic 3-(6-(3-methyl-1-(4'-(trifluoromethyl)biphenyl-4-yl)butylamino) nicotinamido) propanoic acid Example 1.2, by chiral SFC. Column: Chiralpak AD-H. Dimensions: 4.6 mm×25 cm. Mobile Phase: 65/35 CO$_2$/isopropanol. Flow Rate: 2.5 mL/min. Modifier: 0.2% diisopropyl amine. Retention time: 5.28 min. Optical Rotation: [α]$^D$=+11.3; c=0.40 (CHCl$_3$).

Example 1.4

(+/−)-3-(2-(3-methyl-1-(4'-(trifluoromethyl)biphenyl-4-yl)butylamino)pyrimidine-5-carboxamido) propanoic acid

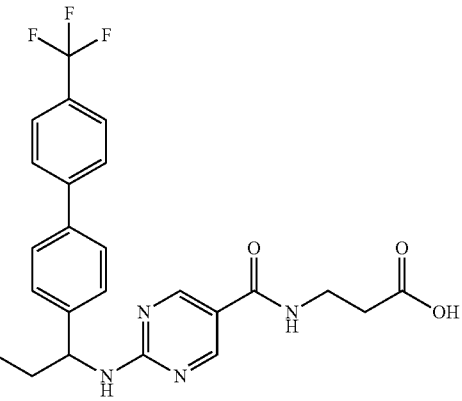

A solution of 3-methyl-1-(4'-(trifluoromethyl)biphenyl-4-yl)butan-1-amine (307 mg, 1 mmol), prepared as in example 1.1 using racemic 2-methylpropane-2-sulfinamide, methyl 2-chloropyrimidine-5-carboxylate (186 mg, 1 mmol) and diisopropylethylamine (516 mg, 4 mmol) in 2-propanol (3 mL) was heated to 100° C. for 3 hours. The mixture was concentrated under reduced pressure and the crude residue was purified by column chromatography to give methyl 2-(3-methyl-1-(4'-(trifluoromethyl)biphenyl-4-yl)butylamino)pyrimidine-5-carboxylate (500 mg, 87.3%).

The title compound was prepared from methyl 2-(3-methyl-1-(4'-(trifluoromethyl)biphenyl-4-yl)butylamino)pyrimidine-5-carboxylate by a method analogous to Example 1.1, steps F through H. $^1$H NMR (400 MHz, CD$_3$OD, δ): 8.67 (s, 2H), 7.81-7.78 (m, 1H), 7.73-7.71 (m, 1H), 7.65-7.63 (m, 1H), 7.52-7.50 (m, 1H), 5.27-5.23 (m, 1H), 3.60-3.56 (m, 2H), 2.62-2.59 (m, 2H), 1.95-1.85 (m, 1H), 1.80-1.60 (m, 2H), 1.03-0.98 (m, 6H). MS (M+1): 501.2.

Example 1.5

3-(2-(3-methyl-1-(4'-(trifluoromethyl)biphenyl-4-yl)butylamino)pyrimidine-5-carboxamido)propanoic acid, Isomer 1

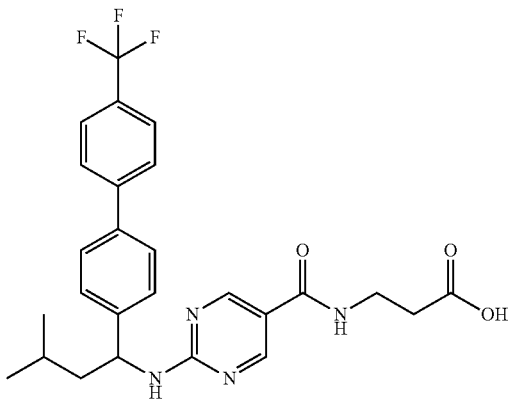 [SMILES: CC(C)CC(Nc1ncc(C(=O)NCCC(=O)O)cn1)c1ccc(-c2ccc(C(F)(F)F)cc2)cc1]

The title compound is obtained by resolving racemic 3-(2-(3-methyl-1-(4'-(trifluoromethyl)biphenyl-4-yl)butylamino)pyrimidine-5-carboxamido)propanoic acid Example 1.4, by chiral SFC. Column: Chiralpak AD-H. Dimensions: 4.6 mm×25 cm. Mobile Phase: 60/40 CO$_2$/propanol. Flow Rate: 2.5 mL/min. Modifier: 0.2% isopropyl amine. Retention time: 4.42 minutes.

Example 1.6

3-(2-(3-methyl-1-(4'-(trifluoromethyl)biphenyl-4-yl)butylamino)pyrimidine-5-carboxamido)propanoic acid, Isomer 2

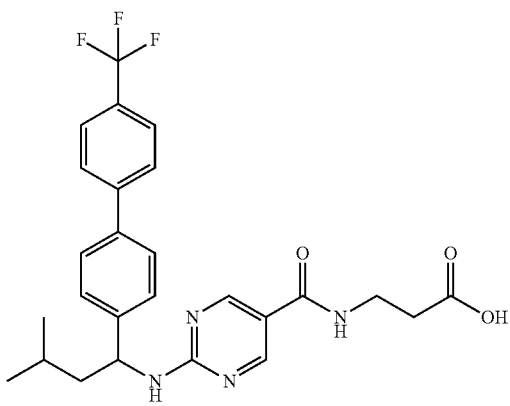 [SMILES: CC(C)CC(Nc1ncc(C(=O)NCCC(=O)O)cn1)c1ccc(-c2ccc(C(F)(F)F)cc2)cc1]

The title compound is obtained by resolving racemic 3-(2-(3-methyl-1-(4'-(trifluoromethyl)biphenyl-4-yl)butylamino)pyrimidine-5-carboxamido)propanoic acid Example 1.4, by chiral SFC. Column: Chiralpak AD-H. Dimensions: 4.6 mm×25 cm. Mobile Phase: 60/40 CO$_2$/propanol. Flow Rate: 2.5 mL/min. Modifier: 0.2% isopropyl amine. Retention time: 5.91 minutes.

Example 1.7

(+/−)-3-(6-(1-(4'-(trifluoromethyl)biphenyl-4-yl)butylamino) nicotinamido)propanoic acid

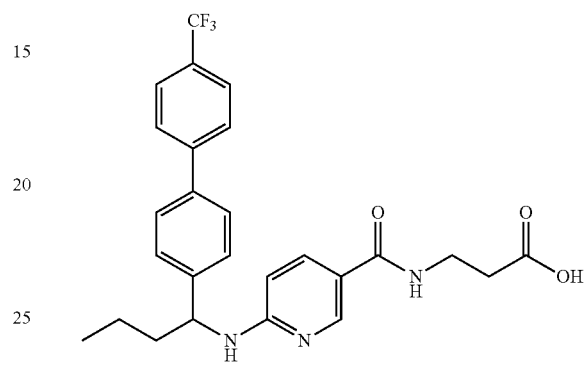

The title compound was prepared by a method analogous to Example 1.1 using racemic 2-methylpropane-2-sulfinamide in Step B and n-propylmagnesium bromide in Step C. $^1$H NMR (500 MHz, DMSO-d$_6$) δ ppm 0.90 (t, J=7.44 Hz, 3 H) 1.26-1.35 (m, 1 H) 1.36-1.45 (m, 1 H) 1.65-1.76 (m, 1 H) 1.75-1.86 (m, 1 H) 2.43 (t, J=7.07 Hz, 2 H) 3.34-3.40 (m, 2 H) 5.01 (br. s., 1 H) 6.51 (d, J=8.78 Hz, 1 H) 7.48 (d, J=8.29 Hz, 2 H) 7.57 (d, J=8.05 Hz, 1 H) 7.66 (d, J=8.29 Hz, 2 H) 7.73 (dd, J=8.90, 2.32 Hz, 1 H) 7.76-7.81 (m, 2 H) 7.82-7.88 (m, 2 H) 8.14 (t, J=5.49 Hz, 1 H) 8.39 (d, J=2.44 Hz, 1 H) 12.15 (br. s., 1 H). MS (M+1): 486.3.

Example 1.8

3-(6-(1-(4'-(trifluoromethyl)biphenyl-4-yl)butylamino)nicotinamido) propanoic acid, Isomer 1

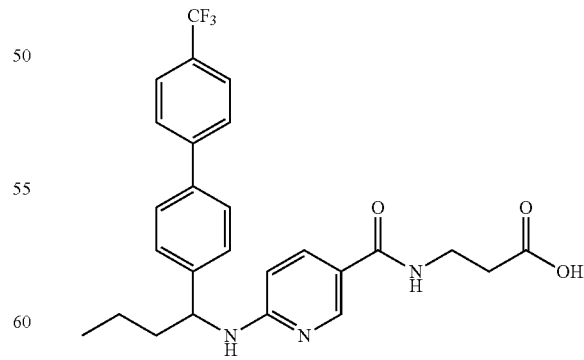

The title compound is obtained by resolving racemic 3-(6-(1-(4'-(trifluoromethyl)biphenyl-4-yl)butylamino)nicotinamido)propanoic acid Example 1.7, by chiral SFC. Column: Chiralpak AD-H. Dimensions: 10 mm×250 cm; Mobile Phase: 60/40 (CO$_2$/ethanol); Flow Rate: 10.0 ml/min.; Modifier: 0.2% diisopropylamine. Retention time: 3.08 minutes.

Example 1.9

3-(6-(1-(4'-(trifluoromethyl)biphenyl-4-yl)butylamino)nicotinamido) propanoic acid, Isomer 2

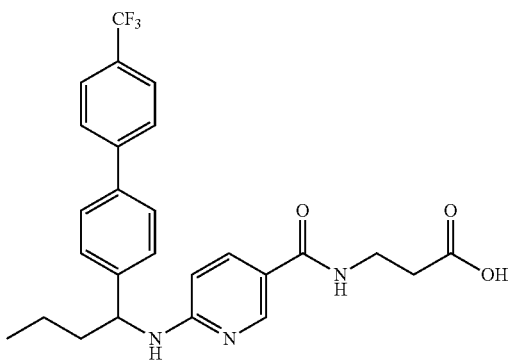 [SMILES: CCCC(Nc1ccc(C(=O)NCCC(=O)O)cn1)c1ccc(-c2ccc(C(F)(F)F)cc2)cc1]

The title compound is obtained by resolving racemic 3-(6-(1-(4'-(trifluoromethyl)biphenyl-4-yl)butylamino)nicotinamido)propanoic acid Example 1.7, by chiral SFC. Column: Chiralpak AD-H. Dimensions: 10 mm×250 cm; Mobile Phase: 60/40 (CO$_2$/ethanol); Flow Rate: 10.0 ml/min.; Modifier: 0.2% diisopropylamine. Retention time: 3.99 minutes.

Example 1.10

(+/−)-3-(6-(2-methyl-1-(4'-(trifluoromethyl)biphenyl-4-yl)propylamino) nicotinamido)propanoic acid

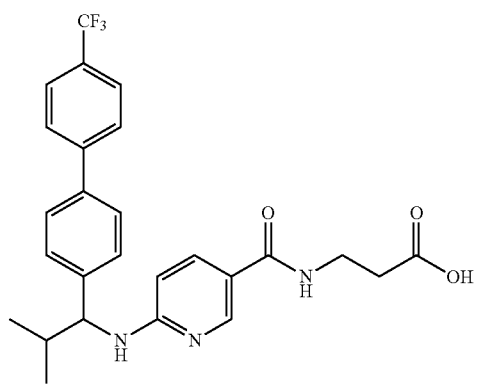 [SMILES: CC(C)C(Nc1ccc(C(=O)NCCC(=O)O)cn1)c1ccc(-c2ccc(C(F)(F)F)cc2)cc1]

The title compound was prepared by a method analogous to that described for Example 1.1 using racemic 2-methylpropane-2-sulfinamide in Step B and isopropylmagnesium chloride in step C. $^1$H NMR (400 MHz, (CD$_3$)$_2$SO, δ): 12.15 (s, 1 H), 8.39 (d, J=2.0 Hz, 1 H), 8.14 (t, J=5.4 Hz, 1 H), 7.84-7.94 (m, 2 H), 7.76-7.83 (m, 2 H), 7.73 (dd, J=8.8, 2.3 Hz, 1 H), 7.67 (d, J=8.2 Hz, 2 H), 7.53 (d, J=8.8 Hz, 2 H), 7.48 (d, J=8.2 Hz, 2 H), 6.57 (d, J=9.0 Hz, 1 H), 4.82 (br. s., 1 H), 3.37 (q, J=6.7 Hz, 2 H), 2.44 (t, J=7.1 Hz, 2 H), 2.08 (dq, J=13.8, 6.7 Hz, 1 H), 1.00 (d, J=6.6 Hz, 3 H), 0.81 (d, J=6.6 Hz, 3H). MS (M+1): 486.4.

Example 1.11

(+/−)-3-(6-(1-(4'-(trifluoromethyl)biphenyl-4-4Propylamino) nicotinamido)propanoic acid

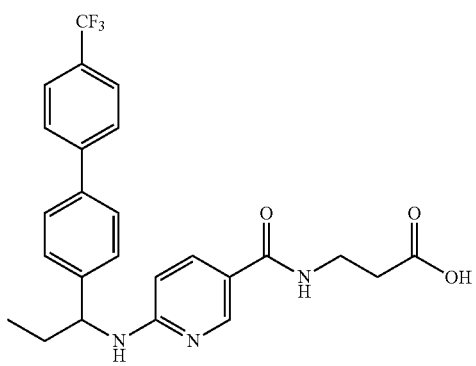 [SMILES: CCC(Nc1ccc(C(=O)NCCC(=O)O)cn1)c1ccc(-c2ccc(C(F)(F)F)cc2)cc1]

The title compound was prepared by a method analogous to that described for Example 1.1 using racemic 2-methylpropane-2-sulfinamide in Step B and ethylmagnesium bromide in step C. $^1$H NMR (400 MHz, CDCl$_3$, δ): 1.04 (t, J=7.32 Hz, 3 H) 1.86-2.01 (m, 1 H) 2.01-2.15 (m, 1 H) 2.57-2.69 (m, 2 H) 3.68-3.83 (m, 2 H) 4.32-4.44 (m, 1 H) 6.48 (d, J=8.78 Hz, 1 H) 7.44 (d, J=8.19 Hz, 2 H) 7.57 (d, J=8.19 Hz, 2 H) 7.63-7.72 (m, 4 H) 7.77-7.88 (m, 1 H) 8.01-8.30 (m, 2 H) 9.40 (br. s., 1 H). MS (M+1): 472.4.

Example 1.12

3-(6-(1-(4'-(trifluoromethyl)biphenyl-4-yl)propylamino)nicotinamido) propanoic acid, Isomer 1

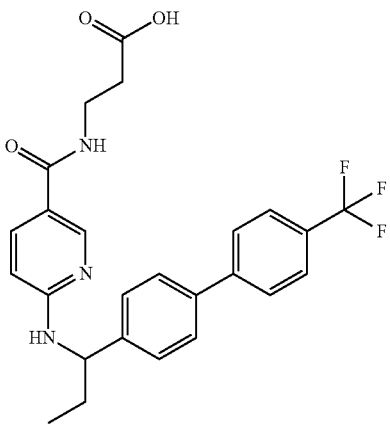 [SMILES: CCC(Nc1ccc(C(=O)NCCC(=O)O)cn1)c1ccc(-c2ccc(C(F)(F)F)cc2)cc1]

The title compound is obtained by resolving racemic 3-(6-(1-(4'-(trifluoromethyl)biphenyl-4-yl)propylamino)nicotinamido)propanoic acid Example 1.11, by chiral SFC. Column: Chiralpak AD-H. Dimensions: 10 mm×250 cm; Mobile Phase: 60/40 (CO$_2$/ethanol); Flow Rate: 10.0 ml/min.; Modifier: 0.2% diisopropylamine. Retention time: 3.86 minutes.

Example 1.13

3-(6-(1-(4'-(trifluoromethyl)biphenyl-4-yl)propylamino)nicotinamido) propanoic acid, Isomer 2

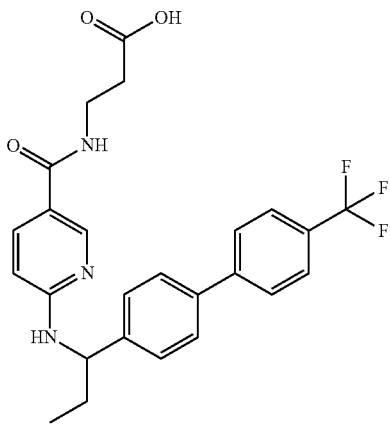 [SMILES: CCC(Nc1ccc(C(=O)NCCC(=O)O)cn1)c1ccc(-c2ccc(C(F)(F)F)cc2)cc1]

The title compound is obtained by resolving racemic 3-(6-(1-(4'-(trifluoromethyl)biphenyl-4-yl)propylamino)nicotinamido)propanoic acid Example 1.11, by chiral SFC. Column: Chiralpak AD-H. Dimensions: 10 mm×250 cm; Mobile Phase: 60/40 (CO$_2$/ethanol); Flow Rate: 10.0 ml/min.; Modifier: 0.2% diisopropylamine. Retention time: 7.90 minutes.

Example 1.14

(+)-3-(6-(2-methyl-1-(4'-(trifluoromethyl)biphenyl-4-yl)propylamino) nicotinamido)propanoic acid

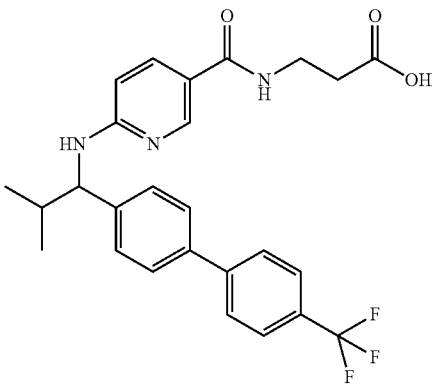 [SMILES: CC(C)C(Nc1ccc(C(=O)NCCC(=O)O)cn1)c1ccc(-c2ccc(C(F)(F)F)cc2)cc1]

The title compound was prepared by a method analogous to that described for Example 1.1 using (R)-(+)-2-methyl-2-propanesulfinamide in step B and isopropylmagnesium chloride in step C. $^1$H NMR (400 MHz, (CD$_3$)$_2$SO, δ): 12.15 (s, 1 H), 8.39 (d, J=2.0 Hz, 1 H), 8.14 (t, J=5.4 Hz, 1 H), 7.84-7.94 (m, 2 H), 7.76-7.83 (m, 2 H), 7.73 (dd, J=8.8, 2.3 Hz, 1 H), 7.67 (d, J=8.2 Hz, 2 H), 7.53 (d, J=8.8 Hz, 1 H), 7.48 (d, J=8.2 Hz, 2 H), 6.57 (d, J=9.0 Hz, 1 H), 4.82 (br. s., 1 H), 3.37 (q, J=6.7 Hz, 2 H), 2.44 (t, J=7.1 Hz, 2 H), 2.08 (dq, J=13.8, 6.7 Hz, 1 H), 1.00 (d, J=6.6 Hz, 3 H), 0.81 (d, J=6.6 Hz, 3 H). MS (M+1): 486.4. Optical Rotation: Dextrorotatory [α]$^D$ 20.0° C.=+234; c=0.26 (MeOH). Analytical Chiral SFC: Column: Chiralpak IA, 4.6 mm×25 cm, Mobile Phase: 70:30 CO$_2$:MeOH, Flow: 2.5 mL/min, Modifier: 0.2% isopropylamine; Retention time: 4.810 minutes, Peak 1.

Example 1.15

(−)-3-(6-(2-methyl-1-(4'-(trifluoromethyl)biphenyl-4-yl)propylamino) nicotinamido) propanoic acid

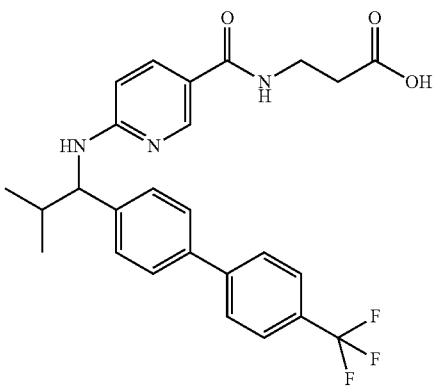 [SMILES: CC(C)C(Nc1ccc(C(=O)NCCC(=O)O)cn1)c1ccc(-c2ccc(C(F)(F)F)cc2)cc1]

The title compound was prepared by a method analogous to that described for Example 1.1 using (S)-(−)-2-methyl-2-propanesulfinamide in step B and isopropylmagnesium chloride in step C. $^1$H NMR (400 MHz, (CD$_3$)$_2$SO, δ): 12.16 (br. s., 1 H), 8.39 (d, J=1.6 Hz, 1 H), 8.16 (br. s., 1 H), 7.83-7.94 (m, 2 H), 7.72-7.83 (m, 3 H), 7.67 (d, J=8.0 Hz, 2 H), 7.54-7.64 (m, 1 H), 7.48 (d, J=8.0 Hz, 2 H), 6.59 (d, J=8.6 Hz, 1 H), 4.83 (br. s., 1 H), 3.16-3.53 (m, 2 H), 2.44 (t, J=7.0 Hz, 2 H), 2.08 (dq, J=13.8, 6.7 Hz, 1 H), 1.00 (d, J=6.4 Hz, 3 H), 0.81 (d, J=6.6 Hz, 3 H). MS (M+1): 486.4. Optical Rotation: Levorotatory [α]$^D$ 20.0° C.=−218; c=0.51 (MeOH). Analytical Chiral SFC: Column: Chiralpak IA, 4.6 mm×25 cm, Mobile Phase: 70:30 CO$_2$:MeOH, Flow: 2.5 mL/min, Modifier: 0.2% isopropylamine; Retention time: 7.910 min, Peak 2.

Example 1.16

(+/−)-3-(5-(3-methyl-1-(4'-(trifluoromethyl)biphenyl-4-yl)butylamino) pyrazine-2-carboxamido)propanoic acid

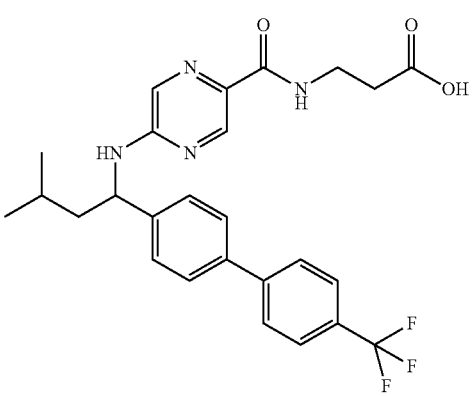 [SMILES: CC(C)CC(Nc1cnc(C(=O)NCCC(=O)O)cn1)c1ccc(-c2ccc(C(F)(F)F)cc2)cc1]

Step A: Preparation of methyl 5-(3-methyl-1-(4'-(trifluoromethyl)biphenyl-4-yl)butylamino)pyrazine-2-carboxylate

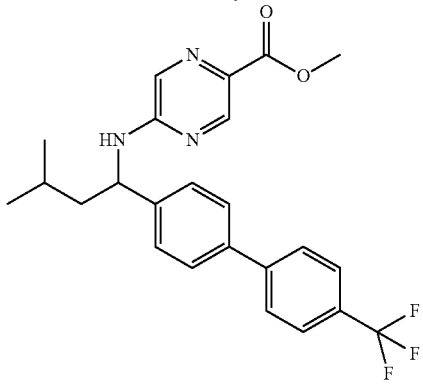

A solution of 3-methyl-1-(4'-(trifluoromethyl)biphenyl-4-yl)butan-1-amine (0.200 g, 0.651 mmol), methyl 5-chloropyrazine-2-carboxylate (124 mg, 0.716 mmol), and diisopropylethylamine (168 mg, 1.30 mmol) in 2-propanol (5 mL) was heated in a microwave reactor at 100° C. for 2 h. The mixture was cooled to room temperature and concentrated. The mixture was concentrated and purified by column chromatography to give methyl 5-(3-methyl-1-(4'-(trifluoromethyl)biphenyl-4-yl)butylamino)pyrazine-2-carboxylate (150 mg, 52%). $^1$H NMR (400 MHz, CDCl$_3$, δ): 8.75 (s, 1H), 7.87 (s, 1H), 7.68 (d, J=8.8 Hz, 2H), 7.64 (d, J=8.8 Hz, 2H), 7.55 (d, J=8.0 Hz, 2H), 7.43 (d, J=8.0 Hz, 2H), 5.46 (s, 1H), 5.04 (t, 1H), 4.12 (s, 3H), 1.87-1.80 (m, 1H), 1.80-1.60 (m, 2H), 1.02 (d, J=6.4 Hz, 3H), 0.98 (d, J=6.4 Hz, 3H).

Step B: (+/−)-3-(5-(3-methyl-1-(4'-(trifluoromethyl)biphenyl-4-yl)butylamino)pyrazine-2-carboxamido)propanoic acid The title compound was prepared from methyl 5-(3-methyl-1-(4'-(trifluoromethyl)biphenyl-4-yl)butylamino)pyrazine-2-carboxylate by a method analogous to Example 1.1, steps F through H. $^1$H NMR (400 MHz, CD$_3$OD, δ): 8.52 (s, 1H), 7.92 (s, 1H), 7.79 (d, J=8.4 Hz, 2H), 7.71 (d, J=8.4 Hz, 2H), 7.64 (d, J=8.4 Hz, 2H), 7.49 (d, J=8.4 Hz, 2H), 5.22-5.16 (m, 1H), 3.61 (m, J=6.4 Hz, 2H), 2.59 (m, J=6.4 Hz, 2H), 1.90-1.82 (m, 1H), 1.78-1.64 (m, 2H), 1.02 (d, 2H), 0.98 (d, 2H). MS (M+1): 501.5.

Example 1.17

3-(5-(3-methyl-1-(4'-(trifluoromethyl)biphenyl-4-yl) butylamino) pyrazine-2-carboxamido)propanoic acid, Isomer 1

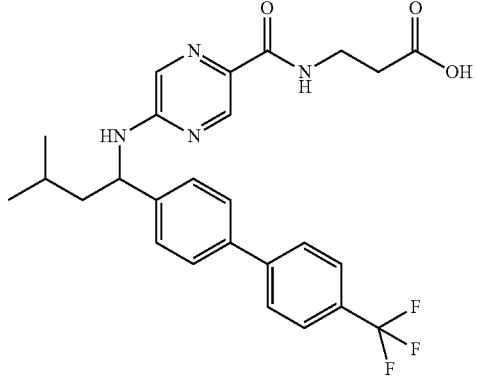 [SMILES: CC(C)CC(Nc1cnc(C(=O)NCCC(=O)O)cn1)c1ccc(-c2ccc(C(F)(F)F)cc2)cc1]

The title compound is obtained by resolving racemic 3-(5-(3-methyl-1-(4'-(trifluoromethyl)biphenyl-4-yl)butylamino) pyrazine-2-carboxamido)propanoic acid, by chiral SFC. Column: Chiralcel OJ-H. Dimensions: 10 mm×25 cm; Mobile Phase: 65/35 (CO$_2$/methanol); Flow Rate: 10.0 ml/min.; Modifier: none. Retention time: 2.63 minutes.

Example 1.18

3-(5-(3-methyl-1-(4'-(trifluoromethyl)biphenyl-4-yl) butylamino) pyrazine-2-carboxamido)propanoic acid, Isomer 2

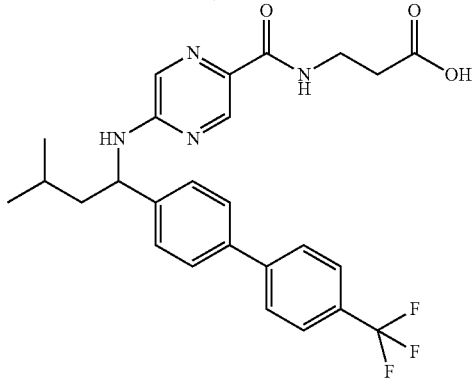 [SMILES: CC(C)CC(Nc1cnc(C(=O)NCCC(=O)O)cn1)c1ccc(-c2ccc(C(F)(F)F)cc2)cc1]

The title compound is obtained by resolving racemic 3-(5-(3-methyl-1-(4'-(trifluoromethyl)biphenyl-4-yl)butylamino) pyrazine-2-carboxamido)propanoic acid, by chiral SFC. Column: Chiralcel OJ-H. Dimensions: 10 mm×25 cm; Mobile Phase: 65/35 (CO$_2$/methanol); Flow Rate: 10.0 ml/min.; Modifier: none. Retention time: 3.45 minutes.

Example 1.19

(+/−)-2-(3-methyl-1-(4'-(trifluoromethyl)biphenyl-4-yl)butylamino)-N-(1H-tetrazol-5-yl)pyrimidine-5-carboxamide

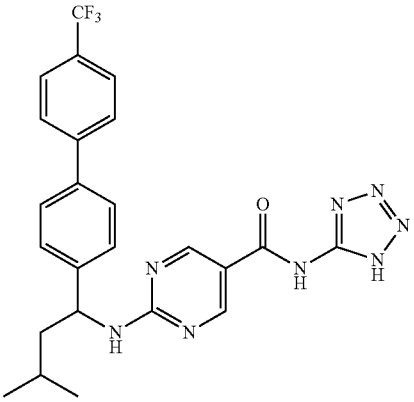 [SMILES: CC(C)CC(Nc1ncc(C(=O)Nc2nnn[nH]2)cn1)c1ccc(-c2ccc(C(F)(F)F)cc2)cc1]

To a solution of methyl 2-(3-methyl-1-(4'-(trifluoromethyl)biphenyl-4-yl)butylamino)pyrimidine-5-carboxylate (Example 1.4, step A) (0.220 g, 0.496 mmol) in anhydrous tetrahydrofuran (8 mL) was added 2M LiOH (8 mL) slowly at 0° C. The mixture was heated to 50° C. and stirred for 48 hours. The mixture was neutralized with 1N HCl and extracted with ethyl acetate (3×10 mL). The combined organic layers were dried over sodium sulfate, filtered, and concentrated. The residue was dissolved in N,N-dimethylformamide (20 mL) and 1,1'-carbonyldiimidazole (123 mg, 0.757 mmol) and diisopropylethylamine (113 mg, 0.873 mmol) were added. The mixture was stirred for 30 minutes at 80° C. 5-Aminotetrazole (148 mg, 1.75 mmol) was then added to the reaction mixture. The resulting mixture was stirred overnight at 80° C. The mixture was quenched with water and extracted with ethyl acetate (3×10 mL). The organic layer was washed with brine, dried over sodium sulfate, filtered, and concentrated. Purification by preparative HPLC gave (+/−)-2-(3-methyl-1-(4'-(trifluoromethyl)biphenyl-4-yl)butylamino)-N-(1H-tetrazol-5-yl)pyrimidine-5-carboxamide (11 mg, 3.8%) as a white solid. $^1$H NMR (400 MHz, CD$_3$OD, δ): 8.87 (s, 2H), 7.78 (d, 2H), 7.26 (d, 2H), 7.64 (d, 2H), 7.51 (d, 2H), 5.32-5.26 (m, 1H), 1.95-1.89 (m, 1H), 1.78-1.65 (m, 2H), 1.01 (d, 3H), 0.99 (d, 3H) ppm. MS (M+1): 495.1.

Example 1.20

(+/−)-N-(3-(1H-tetrazol-5-ylamino)-3-oxopropyl)-6-(3-methyl-1-(4'-(trifluoromethyl)biphenyl-4-yl)butylamino)nicotinamide

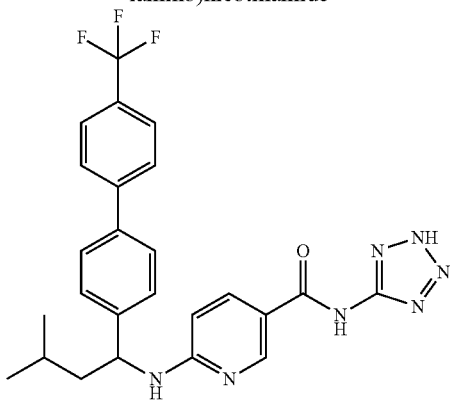

The title compound was prepared from 6-(3-methyl-1-(4'-(trifluoromethyl)biphenyl-4-yl)butylamino)nicotinic acid, as prepared in Example 1.1 using racemic 2-methylpropane-2-sulfinamide in Step B, and 5-aminotetrazole by a method analogous to example 1.19. $^1$H NMR (400 MHz, CD$_3$OD, δ): 8.58 (d, 1H), 7.90 (dd, 1H), 7.70 (d, 2H), 7.62 (d, 2H), 7.55 (d, 2H), 7.41 (d, 2H), 6.53 (d, 1H), 5.08 (m, 1H), 1.81-1.74 (m, 1H), 1.71-1.62 (m, 1H), 1.60-1.53 (m, 1H), 0.94 (d, 3H), 0.91 (d, 3H). MS (M+1): 496.3.

Example 1.21

(+/−)-N-((2H-tetrazol-5-yl)methyl)-6-(3-methyl-1-(4'-(trifluoromethyl)biphenyl-4-yl)butylamino)nicotinamide

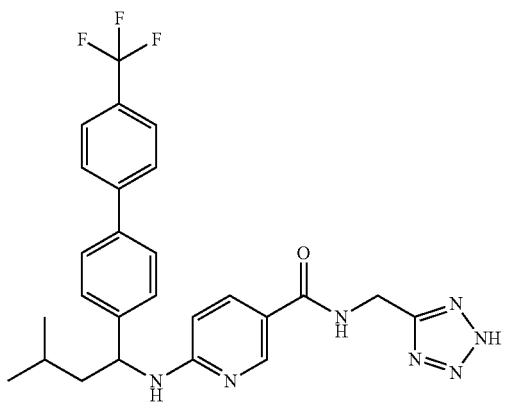 [SMILES: CC(C)CC(Nc1ccc(C(=O)NCc2nn[nH]n2)cn1)c1ccc(-c2ccc(C(F)(F)F)cc2)cc1]

A 5 mL vial equipped with a stir bar was charged with 6-(3-methyl-1-(4'-(trifluoromethyl)biphenyl-4-yl)butylamino)nicotinic acid (0.100 g, 0.233 mmol) as prepared in Example 1.1 using racemic 2-methylpropane-2-sulfinamide in Step B, O-(7-azabenzotriazol-1-yl)-N,N,N',N'-tetramethyl uronium hexafluorophosphate (133.0 mg, 0.350 mmol), N-methylmorpholine (118.0 mg, 1.167 mmol), N,N-dimethylformamide (1.2 mL). The mixture was purged with nitrogen, heated to 50° C. and stirred for 30 minutes. Then, (1H-tetrazol-5-yl)methanamine (39.9 mg, 0.233 mmol) was added. The mixture was stirred at 50° C. overnight. The reaction mixture was purified by prep-HPLC to give (+/−)-N-((2H-tetrazol-5-yl)methyl)-6-(3-methyl-1-(4'-(trifluoromethyl)biphenyl-4-yl)butylamino)nicotinamide (10 mg, 4.2%) as a white solid. $^1$H NMR (400 MHz, CD$_3$OD, δ): 8.50 (d, 1H), 7.86 (dd, 1H), 7.80 (d, 2H), 7.72 (d, 2H), 7.64 (d, 2H), 7.50 (d2H), 6.58 (d, 1H), 5.11 (m, 1H), 4.82 (s, 2H), 1.89-1.82 (m, 1H), 1.80-1.72 (m, 1H), 1.68-1.62 (m, 1H), 1.03 (d, 3H), 1.00 (d, 3H) ppm. MS (M+1): 510.3

Example 1.22

(+/−)-2-(6-(3-methyl-1-(4'-(trifluoromethyl) biphenyl-4-yl)butylamino) nicotinamido) ethanesulfonic acid

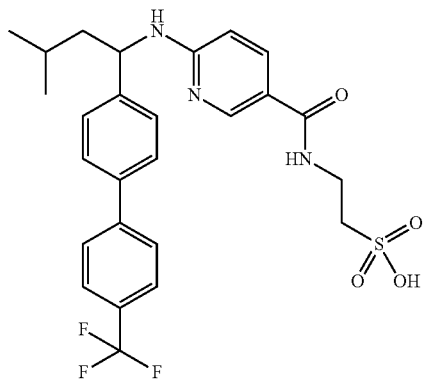 [SMILES: CC(C)CC(Nc1ccc(C(=O)NCCS(=O)(=O)O)cn1)c1ccc(-c2ccc(C(F)(F)F)cc2)cc1]

A 5 mL vial equipped with magnetic stirrer was charged with 6-(3-methyl-1-(4'-(trifluoromethyl)biphenyl-4-yl)butylamino)nicotinic acid (0.200 g, 0.467 mmol) as prepared in Example 1.1 using racemic 2-methylpropane-2-sulfinamide in Step B, O-(7-azabenzotriazol-1-yl)-N,N,N',N'-tetramethyl uronium hexafluorophosphate (266.0 mg, 0.700 mmol), N-methylmorpholine (236.1 mg, 2.334 mmol), N,N-dimethylformamide (2.4 mL). The mixture was purged with nitrogen, heated to 30° C. and stirred for 30 minutes. Then 2-aminoethanesulfonic acid (58.4 mg, 0.467 mmol) was added. The mixture was stirred at 30° C. for 2 h. The reaction mixture was diluted with water (20 mL) and extracted with ethyl acetate (3×20 mL). The combined organic layers were washed with water (2×20 mL) and dried over sodium sulfate, filtered and concentrated. Purification by prep-HPLC provided (+/−)-2-(6-(3-methyl-1-(4'-(trifluoromethyl)biphenyl-4-yl)butylamino)nicotinamido) ethanesulfonic acid (89.6 mg, 35.8%) as a white solid. $^1$H NMR (400 MHz, CD$_3$OD, δ): 8.41 (s, 1H), 8.29 (m, 1H), 8.25-8.19 (m, 1H), 7.88 (d, 2H), 7.78-7.70 (m, 4H), 7.54 (d, 2H), 7.13 (d, 1H), 5.05-4.92 (m, 1H), 3.76 (t, 2H), 3.06 (t, 2H), 1.88-1.82 (m, 1H), 1.72-1.62 (m, 2H), 1.07 (d, 3H), 1.04 (d, 3H) ppm. MS (M+1): 536.2.

Example 1.23

(+/−)-3-(N-methyl-6-(3-methyl-1-(4'-(trifluoromethyl)biphenyl-4-yl)butylamino)nicotinamido)propanoic acid

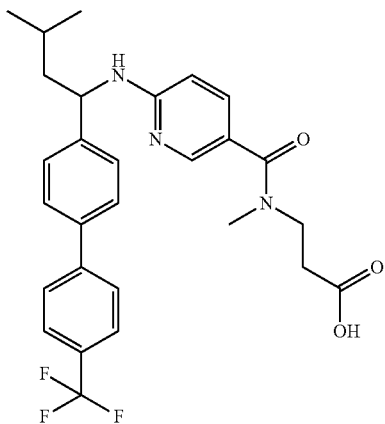 [SMILES: CC(C)CC(Nc1ccc(C(=O)N(C)CCC(=O)O)cn1)c1ccc(-c2ccc(C(F)(F)F)cc2)cc1]

Step A: Preparation of tert-butyl 3-(methylamino)propanoate

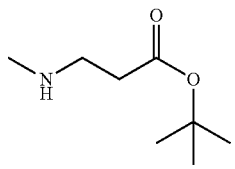

A 100 mL three-necked round bottom flask equipped with a stir bar was charged with tert-butyl acrylate (10.0 g, 78 mmol) and methanol (15.6 mL). The mixture was purged with nitrogen and cooled to 0° C. A solution of N-methyl-1-phenylmethanamine (10.4 g, 85.8 mmol) in methanol (15.6 mL) was then added. The reaction mixture was allowed to warm to room temperature and stir for 20 hr. Purification by column chromatography (ethyl acetate/petroleum ether 0-25%) gave the intermediate (18.4 g, 93.9%) as a light yellow oil.

To a solution of the above oil (17.5 g, 70.2 mmol) in methanol (120 mL) was added 10% palladium on carbon (5 g). The solution was degassed, then saturated with hydrogen and stirred for 70 h. The reaction mixture was filtered through Celite, and the solvent carefully removed under reduced pressure to give tert-butyl 3-(methylamino)propanoate (8 g, 69.6%) as a light yellow oil. $^1$H NMR (400 MHz, CDCl$_3$, δ): 2.73 (t, 2H), 2.39-2.34 (m, 5H), 1.38 (s, 9H). MS (M+1): 160.0.

Step B: Preparation of (+/−)-3-(N-methyl-6-(3-methyl-1-(4'-(trifluoromethyl)biphenyl-4-yl)butylamino) nicotinamido) propanoic acid A 5 mL vial equipped with a stir bar was charged with 6-(3-methyl-1-(4'-(trifluoromethyl)biphenyl-4-yl)butylamino)nicotinic acid (0.200 g, 0.467 mmol) as prepared in Example 1.1 using racemic 2-methylpropane-2-sulfinamide in Step B, O-(7-azabenzotriazol-1-yl)-N,N,N',N'-tetramethyl uronium hexafluorophosphate (266.0 mg, 0.700 mmol), N-methylmorpholine (236.1 mg, 2.334 mmol), and N,N-dimethylformamide (2.4 mL). The mixture was purged with nitrogen and stirred for 30 minutes at room temperature. Then tert-butyl-3-(methylamino)propanoate (74.4 mg, 0.467 mmol) was added and the mixture was stirred at room temperature overnight. The reaction mixture was diluted with water (20 mL) and extracted with ethyl acetate (3×20 mL). The combined organic layers were washed with water (3×20 mL), dried over sodium sulfate, filtered and concentrated to a pale yellow oil.

Dichloromethane (2 mL) was added to the crude oil (0.120 g, 0.211 mmol) and the mixture was cooled to 0° C. Trifluoroacetic acid (3 mL) was then added drop-wise. The reaction was allowed to warm to room temperature and stir for 3 hr. The reaction was concentrated. Purification by prep-HPLC gave (+/−)-3-(N-methyl-6-(3-methyl-1-(4'-(trifluoromethyl)biphenyl-4-yl)butylamino)nicotinamido)propanoic acid (56.5 mg, 52.3%) as a white solid. $^1$H NMR (400 MHz, CDCl$_3$, δ): 8.14-7.99 (m, 1H), 7.65-7.45 (m, 7H), 7.37 (d, 2H), 6.30 (d, 1H), 4.42 (m, 1H), 3.70 (m, 2H), 3.02 (s, 3H), 2.65-2.55 (m, 2H), 1.88-1.82 (m, 1H), 1.72-1.67 (m, 1H), 1.65-1.36 (m, 1H), 0.94 (d, 3H), 0.88 (d, 3H) ppm. MS (M+1): 514.3.

Example 1.24

(+/−)-(2R)-2-hydroxy-3-(6-(3-methyl-1-(4'-(trifluoromethyl)biphenyl-4-yl)butylamino)nicotinamido) propanoic acid

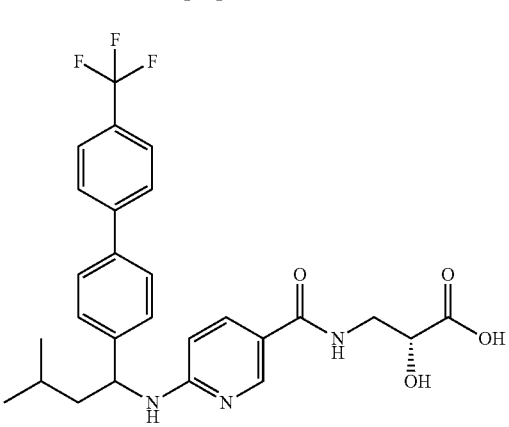

To a solution of 6-(3-methyl-1-(4'-(trifluoromethyl)biphenyl-4-yl)butylamino)nicotinic acid (0.200 g, 0.467 mmol), as prepared in Example 1.1 using racemic 2-methylpropane-2-sulfinamide in Step B, in N,N-dimethylformamide (2 mL) was added O-(7-azabenzotriazol-1-yl)-N,N,N',N'-tetramethyluronium hexafluorophosphate (444 mg, 1.17 mmol). The reaction was stirred at room temperature for 1 h. (R)-methyl-3-amino-2-hydroxypropanoate (111 mg, 0.934 mmol) and diisopropylethylamine (422 mg, 3.27 mmol) were then added and the reaction was stirred at room temperature for 15 h. The reaction mixture was diluted with saturated ammonium chloride (10 mL) and extracted with ethyl acetate (3×10 ml). The combined organics were washed with brine, dried over sodium sulfate, filtered and concentrated.

The crude residue (0.200 g, 0.543 mmol) was dissolved in tetrahydrofuran (4 mL) and 2N LiOH was added (4 mL). The reaction was stirred at room temperature for 1 h. The reaction was then acidified to pH 5-6 with 1N HCl, and extracted with ethyl acetate (4×20 mL). The combined organics were dried over sodium sulfate, filtered, and concentrated. Purification by prep-HPLC gave (+/−)-(2R)-2-hydroxy-3-(6-(3-methyl-1-(4'-(trifluoromethyl)biphenyl-4-yl)butylamino)nicotinamido)propanoic acid (152.7 mg, 78.3%) as a white solid. $^1$H NMR (400 MHz, CD$_3$OD, δ): 8.40 (s, 1H), 8.07 (d, 1H), 8.10 (d, 2H), 7.77-7.65 (m, 4H), 7.53 (d, 2H), 6.91 (d, 1H), 5.16 (s, 1H), 4.34 (t, 1H), 3.77-3.51 (m, 2H), 1.94-1.89 (m, 1H), 1.80-1.64 (m, 2H), 1.07-0.94 (m, 6H) ppm. MS (M+1): 516.3.

Example 1.25

(+/−)-3-(6-(3-methyl-1-(2-methyl-4'-(trifluoromethyl)biphenyl-4-yl) butylamino)nicotinamido)propanoic acid

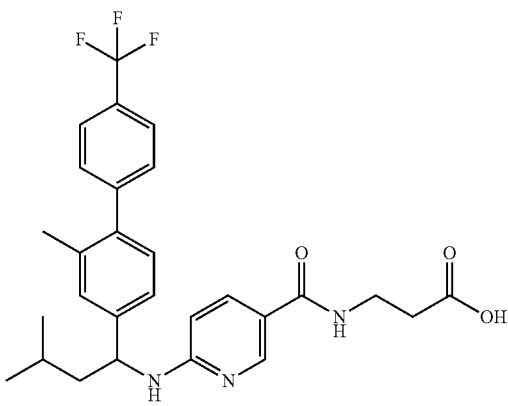

Step A: 2-methyl-4'-(trifluoromethyl)biphenyl-4-carbonitrile

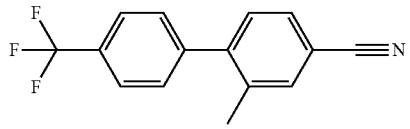 [SMILES: Cc1cc(C#N)ccc1-c1ccc(C(F)(F)F)cc1]

A mixture of 4-bromo-3-methylbenzonitrile (1.00 g, 5.10 mmol), 4-(trifluoromethyl)phenylboronic acid (0.969 g, 5.10 mmol), potassium carbonate (1.76 g, 12.8 mmol) and tetrakis(triphenylphosphine)palladium(0) (0.295 g, 0.255 mmol) in 1:1 dioxane:water (20 mL) was stirred at 80° C. overnight. The mixture was filtered through Celite. The filtrate was extracted with ethyl acetate. The organic layer was washed with water and brine, dried over sodium sulfate, filtered and concentrated. Purification by column chromatography gave 2-methyl-4'-(trifluoromethyl)biphenyl-4-carbonitrile (1.26 g, 95%). $^1$H NMR (400 MHz, CDCl$_3$, δ): 7.72 (d, 2H), 7.59 (s, 1H), 7.56 (d, 1H), 7.42 (d, 2H), 7.31 (d, 1H), 2.29 (s, 3H).

Step B: 3-methyl-1-(2-methyl-4'-(trifluoromethyl)biphenyl-4-yl)butan-1-amine

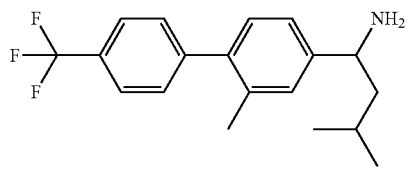

A microwave reaction vial was charged with 2-methyl-4'-(trifluoromethyl)biphenyl-4-carbonitrile (500 mg, 1.91 mmol) and tetrahydrofuran (5 mL). To the mixture was added isobutylmagnesium bromide (2.87 mL, 5.74 mmol, 2M in THF). The reaction was heated at 100° C. in a microwave for 30 minutes. The reaction mixture was then carefully added to a solution of sodium borohydride (145 mg, 3.83 mmol) in methanol (5 mL). After stirring for 5 minutes, the mixture was concentrated to dryness. Purification by column chromatography gave 3-methyl-1-(2-methyl-4'-(trifluoromethyl)biphenyl-4-yl)butan-1-amine (470 mg). $^1$H NMR (400 MHz, CD$_3$OD, δ): 7.72 (d, 2H), 7.50 (d, 2H), 7.24 (s, 1H), 7.19 (d, 2H), 3.94 (m, 1H), 2.27 (s, 3H), 1.65 (m, 2H), 1.49 (m, 1H), 0.95 (d, 3H), 0.92 (d, 3H).

Step C: Preparation of methyl 6-(3-methyl-1-(2-methyl-4'-(trifluoromethyl)biphenyl-4-yl)butylamino)nicotinate

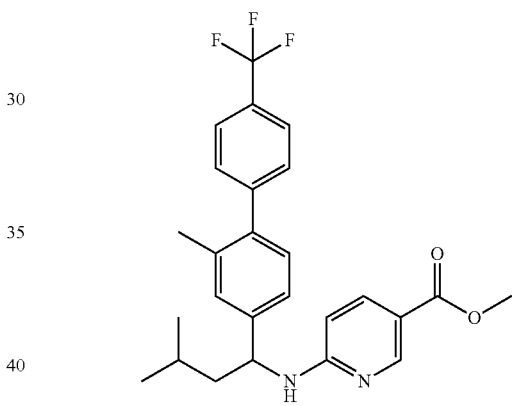

A mixture of 3-methyl-1-(2-methyl-4'-(trifluoromethyl)biphenyl-4-yl)butan-1-amine (250 mg, 0.778 mmol), methyl 6-fluoronicotinate (264 mg, 1.17 mmol), and potassium carbonate (323 mg, 2.33 mmol) in N,N-dimethylformamide (4 mL) was stirred for 12 hrs at 120° C. The reaction was concentrated and purification by column chromatography gave methyl 6-(3-methyl-1-(2-methyl-4'-(trifluoromethyl) biphenyl-4-yl)butylamino)nicotinate (300 mg). $^1$H NMR (400 MHz, CD$_3$OD, δ): 8.65 (s, 1H), 7.87 (d, 1H), 7.58 (d, 2H), 7.33 (d, 2H), 7.13 (d, 2H), 7.09 (s, 1H), 6.20 (d, 1H), 4.65 (m, 1H), 3.78 (s, 3H), 2.17 (s, 3H), 1.72 (m, 2H), 1.67 (m, 1H), 0.94 (d, 3H), 0.91 (d, 3H).

Step D: (+/−)-3-(6-(3-methyl-1-(2-methyl-4'-(trifluoromethyl)biphenyl-4-yl)butylamino)nicotinamido) propanoic acid The title compound was prepared from 6-(3-methyl-1-(2-methyl-4'-(trifluoromethyl)biphenyl-4-yl)butylamino)nicotinate by a method analogous to that described in Example 1.1 steps F-H. $^1$H NMR (400 MHz, CD$_3$OD, δ): 8.43 (s, 1H), 7.80 (d, 1H), 7.71 (d, 2H), 7.50 (d, 2H), 7.32 (d, 2H), 7.18 (s, 1H), 6.55 (d, 1H), 5.05 (m, 1H), 3.59 (m, 2H), 2.61 (m, 2H), 2.25

(s, 3H), 1.88-1.71 (m, 2H), 1.68-1.61 (m, 1H), 1.03 (d, 3H), 1.00 (d, 3H). MS (M+1): 514.7.

Example 1.26

(+/−)-3-(2-(3-methyl-1-(2-methyl-4'-(trifluoromethyl)biphenyl-4-yl)butylamino)pyrimidine-5-carboxamido)propanoic acid

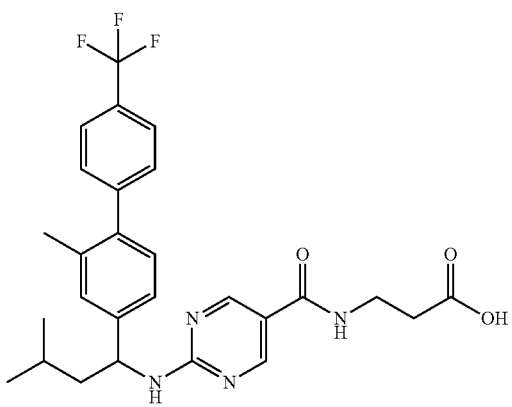 [SMILES: Cc1cc(C(CC(C)C)Nc2ncc(C(=O)NCCC(=O)O)cn2)ccc1-c1ccc(C(F)(F)F)cc1]

The title compound was prepared by a method analogous to Example 1.4, using 3-methyl-1-(2-methyl-4'-(trifluoromethyl)biphenyl-4-yl)butan-1-amine in Step A. ¹H NMR (400 MHz, CD₃OD, δ): 8.68 (s, 2H), 7.72 (d, 2H), 7.50 (d, 2H), 7.31 (s, 1H), 7.29 (d, 1H), 7.17 (d, 1H), 5.21 (m, 1H), 3.60 (m, 2H), 2.62 (m, 2H), 2.25 (s, 3H), 1.88 (m, 1H), 1.65 (m, 2H), 1.02 (d, 3H), 1.00 (d, 3H). MS (M+1): 515.7.

Example 1.27

(+/−)-3-(2-(1-(2,6-dimethyl-4'-(trifluoromethyl)biphenyl-4-yl)-3-methylbutylamino)pyrimidine-5-carboxamido)propanoic acid

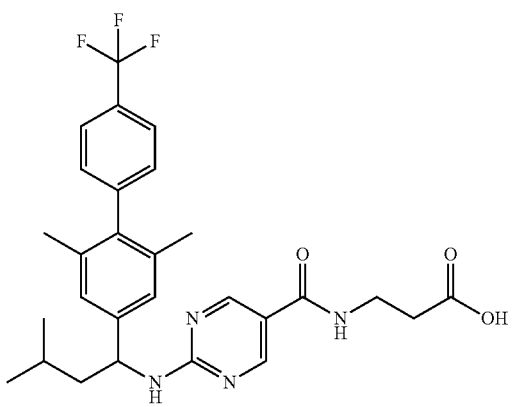 [SMILES: Cc1cc(C(CC(C)C)Nc2ncc(C(=O)NCCC(=O)O)cn2)cc(C)c1-c1ccc(C(F)(F)F)cc1]

The title compound was prepared by a method analogous to that described for Example 1.4, using 1-(2,6-dimethyl-4'-(trifluoromethyl)biphenyl-4-yl)-3-methylbutan-1-amine (prepared as in Example 1.25 steps A-B, using 4-bromo-3,5-dimethylbenzonitrile) in Step A. ¹H NMR (400 MHz, CD₃OD, δ): 8.67 (s, 2H), 7.73 (d, 2H), 7.32 (d, 2H), 7.14 (s, 2H), 5.15 (m, 1H), 3.59 (m, 2H), 2.60 (m, 2H), 1.99 (s, 6H), 1.89-1.82 (m, 1H), 1.77-1.57 (m, 2H), 0.92 (d, 3H), 0.91 (d, 3H). MS (M+1): 529.3.

Example 1.28

(+/−)-3-(6-(1-(2,6-dimethyl-4'-(trifluoromethyl)biphenyl-4-yl)-3-methylbutylamino)nicotinamido)propanoic acid

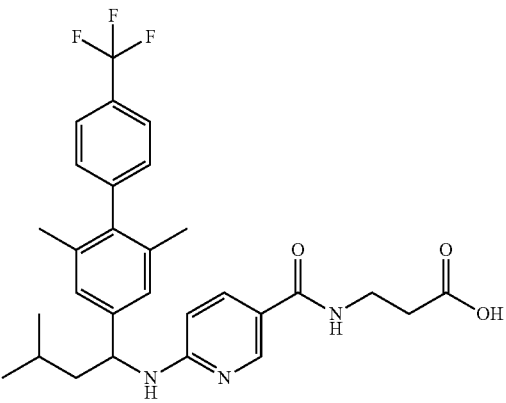 [SMILES: Cc1cc(C(CC(C)C)Nc2ccc(C(=O)NCCC(=O)O)cn2)cc(C)c1-c1ccc(C(F)(F)F)cc1]

The title compound was prepared by a method analogous to that described for Example 1.25, using 4-bromo-3,5-dimethylbenzonitrile in Step A. ¹H NMR (400 MHz, CD₃OD, δ): 8.43 (s, 1H), 7.80 (d, 1H), 7.73 (d, 2H), 7.32 (d, 2H), 7.13 (s, 2H), 6.55 (d, 1H), 4.95 (m, 1H), 3.58 (m, J=6.8 Hz, 2H), 2.60 (m, 2H), 1.98 (s, 6H), 1.86-1.72 (m, 2H), 1.66-1.57 (m, 1H), 1.02 (d, 3H), 0.99 (d, 3H). MS (M+1): 528.5.

Example 1.29

(+/−)-3-(6-(3-methyl-1-(6-(4-(trifluoromethyl)phenyl)pyridin-3-yl)butylamino)nicotinamido)propanoic acid

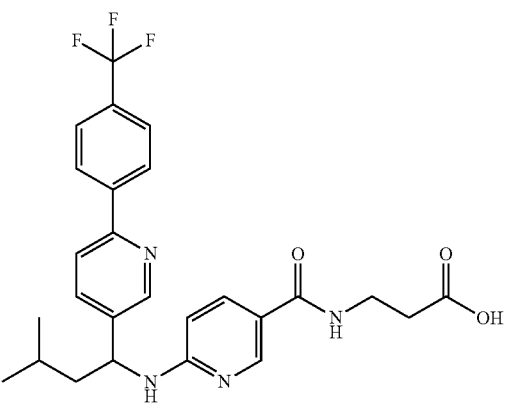

The title compound was prepared by a method analogous to that described for Example 1.25, using 6-bromonicotinonitrile in Step A. ¹H NMR (400 MHz, CD₃OD, δ): 8.62 (m, 1 H), 8.27 (m, 1 H), 8.04 (m, 2 H), 7.90-7.86 (m, 3 H), 7.69 (m, 3 H), 6.73 (m, 1 H), 5.09-5.01 (m, 1 H), 3.47 (m, 2 H), 2.49 (m, 2 H), 1.89-1.77 (m, 1 H), 1.72-1.58 (m, 2 H), 0.95 (d, 3 H), 0.92 (d, 3 H). MS (M+1): 501.3.

Example 1.30

(+/−)-3-(5-(1-(4'-(trifluoromethyl)biphenyl-4-yl)butylamino)pyrazine-2-carboxamido)propanoic acid

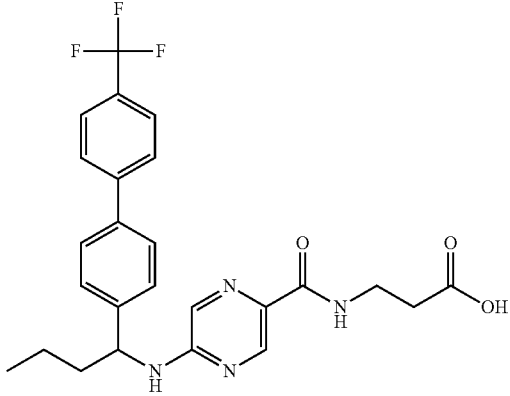 [SMILES: CCCC(Nc1cnc(C(=O)NCCC(=O)O)cn1)c1ccc(-c2ccc(C(F)(F)F)cc2)cc1]

Step A: 1-(4'-(trifluoromethyl)biphenyl-4-yl)butan-1-amine

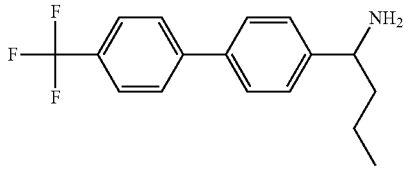 [SMILES: CCCC(N)c1ccc(-c2ccc(C(F)(F)F)cc2)cc1]

The title compound was prepared by a method analogous to that described in Example 1.25, using 4-bromobenzonitrile in Step A and n-propylmagnesium bromide in Step B. $^1$H NMR (400 MHz, CDCl$_3$, δ): 7.58 (m, 4H), 7.49 (d, 2H), 7.31 (d, 2H), 3.88 (t, 1H), 1.66-1.56 (m, 2H), 1.37-1.25 (m, 1H), 1.23-1.16 (m, 1H), 0.83 (t, 3H).

Step B: (+/−)-3-(5-(1-(4'-(trifluoromethyl)biphenyl-4-yl)butylamino)pyrazine-2-carboxamido)propanoic acid The title compound was prepared from 1-(4'-(trifluoromethyl)biphenyl-4-yl)butan-1-amine and methyl-5-chloropyrazin-2-carboxylate by a method analogous to that described for Example 1.16. $^1$H NMR (400 MHz, CD$_3$OD, δ): 8.57 (s, 1H), 7.94 (s, 1H), 7.81 (d, 2H), 7.73 (d, 2H), 7.65 (d, 2H), 7.50 (d, 2H), 5.11-5.05 (m, 1H), 3.63 (t, 2H), 2.60 (t, 2H), 1.97-1.85 (m, 2H), 1.51-1.44 (m, 1H), 1.43-1.39 (m, 1H), 1.01 (t, 3H).

Example 1.31

(+/−)-3-(5-(1-(4'-(trifluoromethyl)biphenyl-4-yl)propylamino)pyrazine-2-carboxamido)propanoic acid

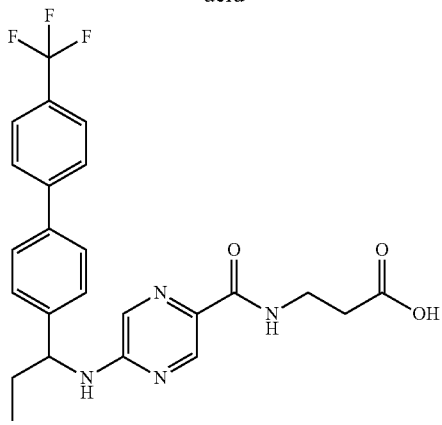

The title compound was prepared by a method analogous to that described for Example 1.30, using ethylmagnesium bromide. $^1$H NMR (400 MHz, CD$_3$OD, δ): 8.53 (s, 1H), 7.96 (s, 1H), 7.81 (d, 2H), 7.73 (d, 2H), 7.66 (d, 2H), 7.59 (d, 2H), 4.99-4.97 (m, 1H), 3.62 (t, 2H), 2.61 (t, 2H), 1.99-1.93 (m, 2H), 1.03 (t, 3H). MS (M+1): 473.2.

Example 1.32

(+/−)-3-(6-(cyclobutyl(4'-(trifluoromethyl)biphenyl-4-yl)methylamino) nicotinamido)propanoic acid

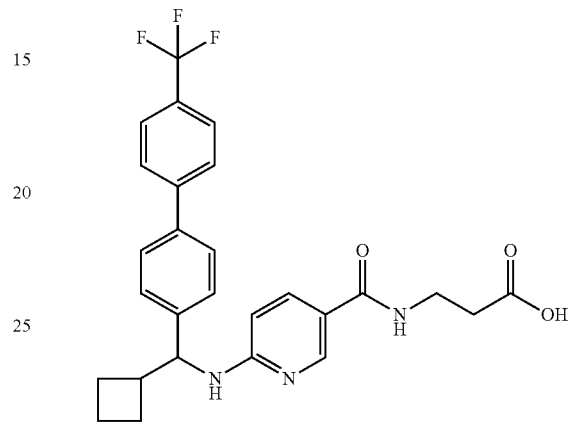

Step A: Cyclobutyl(4'-(trifluoromethyl)biphenyl-4-yl)methanamine

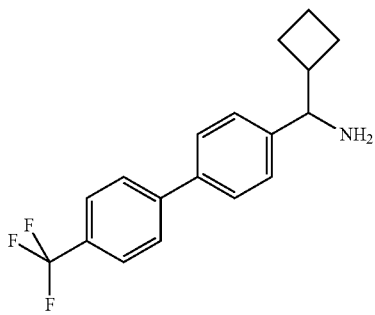 [SMILES: NC(c1ccc(-c2ccc(C(F)(F)F)cc2)cc1)C1CCC1]

Magnesium (1.86 g, 77.4 mmol) was suspended in diethyl ether (70 mL) and to the suspension was added iodine (17.8 mg, 0.07 mmol). Bromo-cyclobutane (10 g, 70 mmol) was added slowly and the mixture was refluxed for 3 h. To a solution of 4'-(trifluoromethyl)biphenyl-4-carbonitrile (300 mg, 1.21 mmol) (prepared as in Example 1.25 Step A, using 4-bromobenzonitrile) in tetrahydrofuran (3 mL) was added this prepared Grignard (334 mg, 6.06 mL in diethyl ether, 6.06 mmol) at 0° C. under nitrogen. The resulting mixture was heated in a microwave at 100° C. for 1 hr. After that time, methanol (5 mL) and sodium borohydride (91.8 mg, 2.43 mmol) were carefully added at 0° C. After stirring for 5 minutes, the reaction mixture was quenched with saturated ammonium chloride (20 mL) and extracted with ethyl acetate (3×10 mL). The combined organic layers were concentrated. Purification by column chromatography (0-6% methanol/dichloromethane) gave cyclobutyl(4'-(trifluoromethyl)biphenyl-4-yl)methanamine (0.100 g, 27%) as a yellow solid. $^1$H NMR (400 MHz, CD$_3$OD, δ): 7.84 (d, J=8.0, 2 H), 7.77

(dd, J=8.0, J=8.0, 4 H), 7.53 (d, J=8.0, 2 H), 4.27 (d, J=10.4, 1 H), 2.98-2.92 (m, 1 H), 2.08-2.06 (m, 1 H), 1.86-1.80 (m, 5 H).

Step B: (+/−)-3-(6-(cyclobutyl(4'-(trifluoromethyl)biphenyl-4-yl)methylamino) nicotinamido) propanoic acid The title compound was prepared from cyclobutyl(4'-(trifluoromethyl)biphenyl-4-yl)methanamine by a method analogous to that described for Example 1.25 steps C-D. $^1$H NMR (400 MHz, CD$_3$OD, δ): 8.31 (d, 1 H), 7.73-7.65 (m, 3 H), 7.61 (d, 2 H), 7.52 (d, 2 H), 7.38 (d, 2 H), 6.41 (d, 1 H), 4.5 (m, 1 H), 3.48 (m, 2 H), 2.78-2.51 (m, 1 H), 2.49 (m, 2 H), 2.19-2.07 (m, 1 H), 1.84-1.78 (m, 2 H). MS (M+1): 498.3.

Example 1.33

(+/−)-3-(6-(3,3-dimethyl-1-(4'-(trifluoromethyl)biphenyl-4-yl)butylamino)nicotinamido)propanoic acid

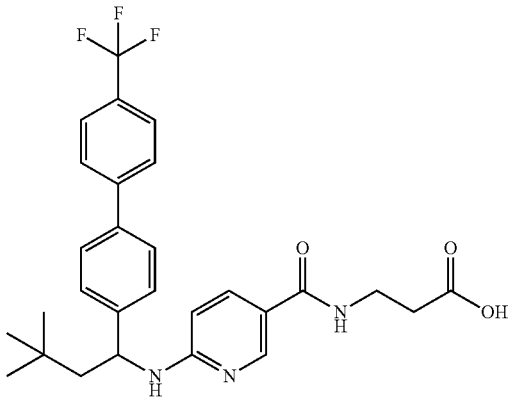 [SMILES: CC(C)(C)CC(Nc1ccc(C(=O)NCCC(=O)O)cn1)c1ccc(-c2ccc(C(F)(F)F)cc2)cc1]

The title compound was prepared by a method analogous to that described for Example 1.32, using 1-bromo-2,2-dimethylpropane. $^1$H NMR (400 MHz, CD$_3$OD, δ): 8.41 (s, 1H), 7.80 (d, 1H), 7.78 (d, 2H), 7.71 (d, 2H), 7.62 (d, 2H), 7.48 (d, 2H), 6.56 (d, 1H), 5.18 (d, 1H), 3.57 (m, 2H), 2.59 (m, 2H), 1.94-1.88 (m, 1H), 1.75-1.70 (m, 1H), 1.04 (s, 9H). MS (M+1): 514.3.

Example 1.34

(+/−)-3-(6-(cyclopropyl(4'-(trifluoromethyl)biphenyl-4-yl)methylamino)nicotinamido)propanoic acid

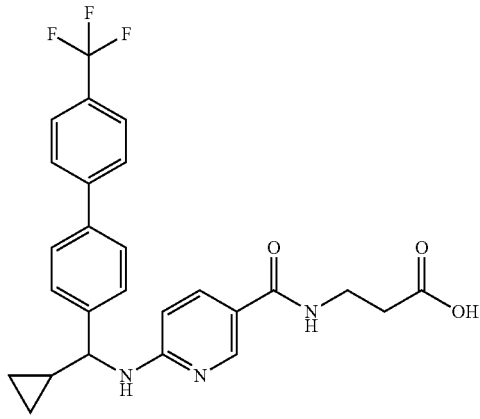 [SMILES: O=C(O)CCNC(=O)c1ccc(NC(c2ccc(-c3ccc(C(F)(F)F)cc3)cc2)C2CC2)nc1]

To a solution of 4'-(trifluoromethyl)biphenyl-4-carbaldehyde (1 g, 4 mmol), p-toluene sulfonic acid (50 mg, 0.3 mmol), and activated molecular sieves in toluene (15 mL), was added methyl 6-aminonicotinate (670 mg, 4.4 mmol). The reaction was refluxed for 12 h. The reaction was cooled to room temperature and concentrated to give the intermediate imine.

To a 0° C. solution of methyl 6-((4'-(trifluoromethyl)biphenyl-4-yl)methyleneamino)nicotinate (600 mg, 1.56 mmol) in tetrahydrofuran (10 mL) was added cyclopropylmagnesium bromide (5 mL, 2N in THF, 8 mmol). The reaction was stirred at 0° C. for 1 hr, then warmed to room temperature and left stirring for 12 h. The reaction was quenched with saturated ammonium chloride and extracted with ethyl acetate (3×15 mL). The combined organics were dried over sodium sulfate, filtered and concentrated. Purification by preparative TLC (5:1 petroleum ether:ethyl acetate) gave methyl 6-(cyclopropyl(4'-(trifluoromethyl)biphenyl-4-yl)methylamino)nicotinate (130 mg).

The title compound was prepared from methyl 6-(cyclopropyl(4'-(trifluoromethyl)biphenyl-4-yl)methylamino) nicotinate by a method analogous to that described in Example 2.1 steps F-G. $^1$H NMR (400 MHz, CD$_3$OD, δ): 8.28 (s, 1H), 7.68 (d, J=9.2 Hz, 1H), 7.67 (d, J=8.0 Hz, 2H), 7.61 (d, J=8.0 Hz, 2H), 7.52 (d, J=8.4 Hz, 2H), 7.42 (d, J=8.4 Hz, 2H), 6.41 (d, J=9.2 Hz, 1H), 4.33 (d, J=8.8 Hz, 1H), 3.46 (m, 2H), 2.46 (m, 2H), 1.38-1.12 (m, 1H), 0.69-0.49 (m, 2H), 0.37-0.36 (m, 2H). MS (M+1): 484.4.

Example 1.35

(+/−)-3-(6-(cyclopentyl(4'-(trifluoromethyl)biphenyl-4-yl)methylamino)nicotinamido)propanoic acid

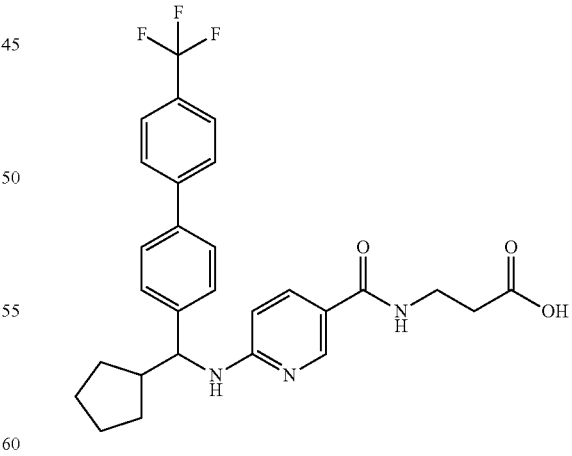

The title compound was prepared by a method analogous to that described for Example 1.34, using cyclopentylmagnesium bromide. $^1$H NMR (400 MHz, CD$_3$OD, δ): 8.57 (s, 1H), 7.94 (d, J=8.8 Hz, 1H), 7.92 (d, J=8.4 Hz, 2H), 7.97 (d, J=8.4 Hz, 2H), 7.78 (d, J=8.4 Hz, 2H), 7.67 (d, J=8.4 Hz, 2H), 6.69 (d, J=8.8 Hz, 1H), 4.88 (d, J=10.0 Hz, 1H), 3.73 (m, 2H), 2.75

(m, 2H), 2.56-2.50 (m, 1H), 2.17-2.13 (m, 1H), 1.89-1.61 (m, 6H), 1.50-1.48 (m, 1H). MS (M+1): 512.5.

Examples 1.36-1.60

Step A: N-(4-iodobenzylidene)-2-methylpropane-2-sulfinamide

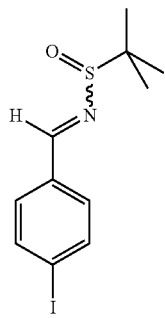

4-Iodobenzaldehyde (1.26 g, 5.43 mmol) was dissolved in dichloromethane (41.8 mL). 2-methylpropane-2-sulfinamide (0.679 g, 5.43 mmol) was added, followed by titanium(IV) ethoxide (2.25 mL, 10.9 mmol). The reaction was heated to reflux for 1 hour. The reaction was then allowed to cool to room temperature and stir for 18 hours. Methanol (8.0 mL) and saturated sodium bicarbonate (1.5 mL) were added to the reaction mixture. The resulting slurry was filtered through sodium sulfate, and rinsed with ethyl acetate. The filtrate was concentrated to yield the title compound N-(4-iodobenzylidene)-2-methylpropane-2-sulfinamide (1.69 g, 93%) as a white solid. $^1$H NMR (400 MHz, CDCl$_3$, δ): 8.51 (s, 1H), 7.80-7.84 (m, 2H), 7.53-7.57 (m, 2H), 1.25 (s, 9H). MS (M+1): 336.0.

Step B: N-(1-(4-iodophenyl)-3-methylbutyl)-2-methylpropane-2-sulfinamide

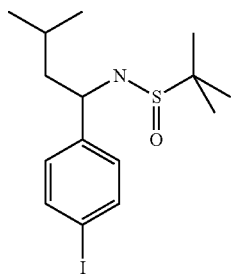 [SMILES: CC(C)CC(NS(=O)C(C)(C)C)c1ccc(I)cc1]

A solution of isobutylmagnesium bromide in diethylether (4.99 mL, 9.98 mmol) was diluted in tetrahydrofuran (11.5 mL) and cooled to 0° C. Then a solution of N-(4-iodobenzylidene)-2-methylpropane-2-sulfinamide (1.52 g, 4.54 mmol) in tetrahydrofuran (11.5 mL) was added drop-wise over 20 minutes. The resulting solution was stirred at 0° C. for 30 minutes. The ice bath was then removed and the reaction was allowed to warm to room temperature and stir for an additional 1.5 hours. The reaction was then slowly quenched by the addition of saturated ammonium chloride. This solution was diluted with water and ethyl acetate. The layers were separated, and the aqueous was extracted 2 times with ethyl acetate. The combined organics were washed with brine, dried over magnesium sulfate, filtered and concentrated. Purification by column chromatography (0-40% ethyl acetate/heptane) provided a 2:1 diastereomer mixture of N-(1-(4-iodophenyl)-3-methylbutyl)-2-methylpropane-2-sulfinamide (1.40 g, 78%) as a clear, colorless oil. $^1$H NMR (400 MHz, CDCl$_3$, δ): 7.62-7.67 (m, 2H), 7.02-7.08 (m, 2H), 4.28-4.41 (m, 1H), 3.24-3.33 (m, 1H), 1.21-1.85 (m, 3H), 1.13-1.20 (m, 9H), 0.83-0.93 (m, 6H). MS (M+1): 394.1.

Step C: 1-(4-iodophenyl)-3-methylbutan-1-amine hydrochloride

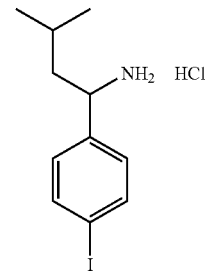

N-(1-(4-iodophenyl)-3-methylbutyl)-2-methylpropane-2-sulfinamide (1.36 g, 3.45 mmol) was dissolved in methanol (17.2 mL). 4M HCl in dioxane (4.31 mL, 17.2 mmol) was added and the reaction was stirred at room temperature for 1 hour. The reaction was concentrated and the resulting solid was triturated with ether and dried under vacuum to provide 1-(4-iodophenyl)-3-methylbutan-1-amine hydrochloride (1.1 g, 100%) as a white solid. $^1$H NMR (400 MHz, CD$_3$OD, δ): 7.80-7.84 (m, 2H), 7.20-7.24 (m, 2H), 4.25-4.31 (m, 1H), 1.83-1.92 (m, 1H), 1.71-1.79 (m, 1H), 1.34-1.42 (m, 1H), 0.92 (dd, J=12.19, 6.54 Hz, 6H).

Step D: Preparation of methyl 6-(1-(4-iodophenyl)-3-methylbutylamino)nicotinate

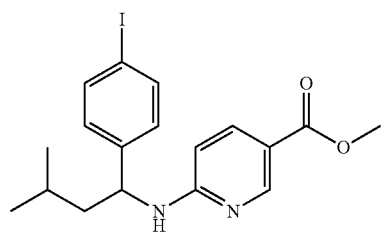 [SMILES: COC(=O)c1ccc(NC(CC(C)C)c2ccc(I)cc2)nc1]

1-(4-Iodophenyl)-3-methylbutan-1-amine hydrochloride (1.14 g, 3.49 mmol), methyl 6-fluoronicotinate (0.568 g, 3.66 mmol), and potassium carbonate (1.45 g, 10.5 mmol) were combined in N,N-dimethylformamide (11.6 mL) and heated to 100° C. for 3.5 hours. The reaction was then cooled to room temperature and diluted with water and ethyl acetate. The layers were separated and the aqueous was extracted 3 times with ethyl acetate. The combined organics were washed with brine, dried over magnesium sulfate, filtered and concentrated. Purification by column chromatography (0-30% ethyl acetate/heptane) provided methyl 6-(1-(4-iodophenyl)-3-methylbutylamino)nicotinate (0.772 g, 52%) as a white solid. $^1$H NMR (400 MHz, CDCl$_3$, δ): 8.69 (d, J=1.8 Hz, 1H), 7.89 (dd, J=8.8, 2.3 Hz, 1H), 7.60-7.64 (m, 2H), 7.04-7.08 (m, 2H), 6.16 (d, J=8.4 Hz, 1H), 5.49 (d, J=6.4 Hz, 1H), 4.62-4.69 (m, 1H), 3.82 (s, 3H), 1.54-1.76 (m, 3H), 0.90-0.97 (m, 6H). MS (M+1): 425.2.

Step E: Synthesis of Examples 1.36-1.60 in Library Format

To a mixture of the appropriate boronic acid (0.227 mmol) and polystyrene triphenylphosphine palladium(0) (0.009 mmol), was added a solution of methyl 6-(1-(4-iodophenyl)-3-methylbutylamino)nicotinate (80.0 mg, 0.19 mmol) in 1,2-dimethoxyethane (1.9 mL). Then aqueous potassium carbonate (0.95 mL, 1.9 mmol) was added. The reaction was heated for 1 hour at 100° C. in a microwave. The reaction was then filtered, the polymer was rinsed with tetrahydrofuran (3×2.0 mL), and the combined filtrates were concentrated.

The crude residue was dissolved in methanol (1.3 mL) and tetrahydrofuran (1.3 mL). 2N LiOH (1.3 mL) was added, and the reaction was heated to 60° C. for 18 hours. The reaction was then concentrated. This crude mixture was acidified by the addition of 2N HCl (5 mL) and again was concentrated.

To the crude residue was added a mixture of β-alanine t-butyl ester hydrochloride (51.8 mg, 0.285 mmol), 1-hydroxybenzotriazole hydrate (29.1 mg, 0.190 mmol), and 1-ethyl-3-(3-dimethylaminopropyl)-carbodimide hydrochloride (54.6 mg, 0.285 mmol) in tetrahydrofuran (1.9 mL). Triethylamine (106 μL, 0.760 mmol) was added and the reaction was agitated at room temperature for 18 hours. Polystyrene trisamine (250 mg, 0.95 mmol) and tetrahydrofuran (5 mL) were then added and the reaction was agitated for another 18 hours. The reaction was filtered and the polymer was rinsed with tetrahydrofuran (3×2 mL). The filtrate was concentrated.

Dichloromethane (1.0 mL) and trifluoroacetic acid (1.0 mL) were added to the crude residue. The reaction was agitated at room temperature for 1 hour. The reaction was then concentrated and purified by reversed-phase HPLC on a Waters Sunfire $C_{18}$ 19×100 mm, 0.005 mm column using a gradient of water in acetonitrile (0.05% formic acid modifier) to give the desired product.

Example 1.36

(+/−)-3-(6-(3-methyl-1-(4-(6-methylpyridin-3-yl)phenyl)butylamino) nicotinamido)propanoic acid

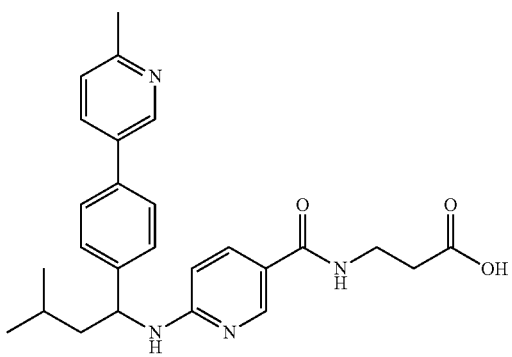 [SMILES: Cc1ccc(-c2ccc(C(CC(C)C)Nc3ccc(C(=O)NCCC(=O)O)cn3)cc2)cn1]

Analytical LCMS: retention time 0.58 minutes (Acquity HSS T3 2.1×50 mm, 1.8μ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 447.18.

Example 1.37

(+/−)-3-(641-(biphenyl-4-yl)-3-methylbutylamino) nicotinamido) propanoic acid

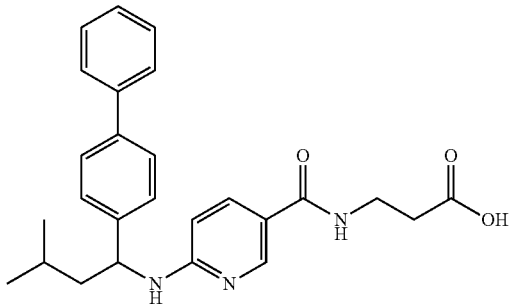 [SMILES: CC(C)CC(Nc1ccc(C(=O)NCCC(=O)O)cn1)c1ccc(-c2ccccc2)cc1]

Analytical LCMS: retention time 0.96 minutes (Acquity HSS T3 2.1×50 mm, 1.8μ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 432.22.

Example 1.38

(+/−)-3-(6-(1-(2'-fluorobiphenyl-4-yl)-3-methylbutylamino) nicotinamido)propanoic acid

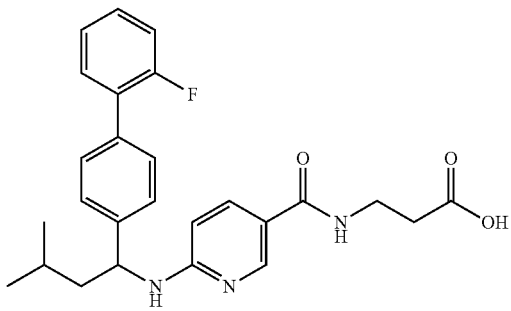 [SMILES: CC(C)CC(Nc1ccc(C(=O)NCCC(=O)O)cn1)c1ccc(-c2ccccc2F)cc1]

Analytical LCMS: retention time 0.97 minutes (Acquity HSS T3 2.1×50 mm, 1.8μ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 450.15.

Example 1.39

(+/−)-3-(6-(1-(3'-chlorobiphenyl-4-yl)-3-methylbutylamino) nicotinamido)propanoic acid

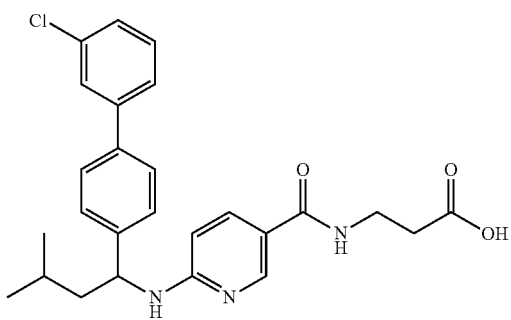 [SMILES: CC(C)CC(Nc1ccc(C(=O)NCCC(=O)O)cn1)c1ccc(-c2cccc(Cl)c2)cc1]

Analytical LCMS: retention time 1.05 minutes (Acquity HSS T3 2.1×50 mm, 1.8µ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 466.18.

Example 1.40

(+/−)-3-(6-(3-methyl-1-(4-(pyridin-3-yl)phenyl)butylamino) nicotinamido)propanoic acid

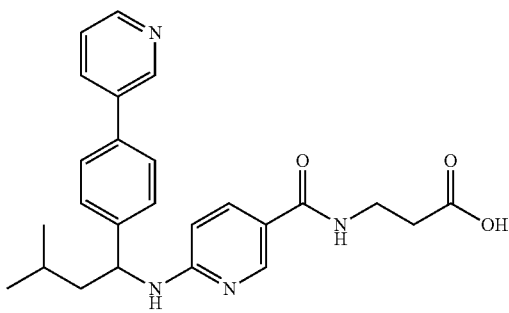 [SMILES: CC(C)CC(Nc1ccc(C(=O)NCCC(=O)O)cn1)c1ccc(-c2cccnc2)cc1]

Analytical LCMS: retention time 0.57 minutes (Acquity HSS T3 2.1×50 mm, 1.8µ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 433.21.

Example 1.41

(+/−)-3-(6-(1-(3'-fluorobiphenyl-4-yl)-3-methylbutylamino) nicotinamido)propanoic acid

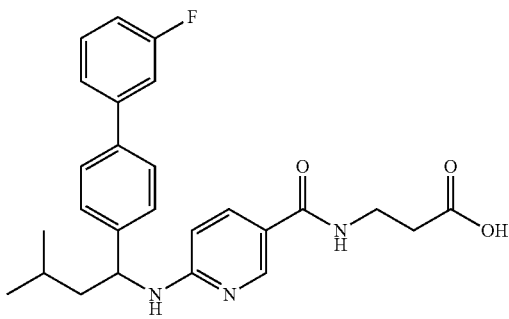 [SMILES: CC(C)CC(Nc1ccc(C(=O)NCCC(=O)O)cn1)c1ccc(-c2cccc(F)c2)cc1]

Analytical LCMS: retention time 0.98 minutes (Acquity HSS T3 2.1×50 mm, 1.8µ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 450.15.

Example 1.42

(+/−)-3-(6-(3-methyl-1-(2'-methylbiphenyl-4-yl) butylamino) nicotinamido)propanoic acid

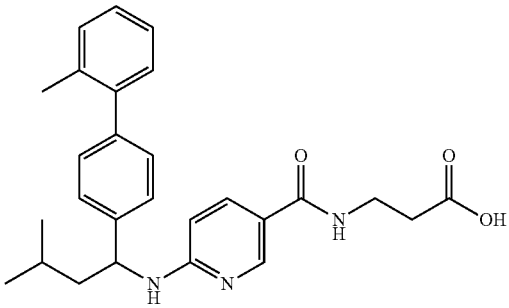 [SMILES: Cc1ccccc1-c1ccc(C(CC(C)C)Nc2ccc(C(=O)NCCC(=O)O)cn2)cc1]

Analytical LCMS: retention time 0.98 minutes (Acquity HSS T3 2.1×50 mm, 1.8µ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 450.15.

Example 1.43

(+/−)-3-(6-(1-(2'-methoxybiphenyl-4-yl)-3-methylbutylamino) nicotinamido)propanoic acid

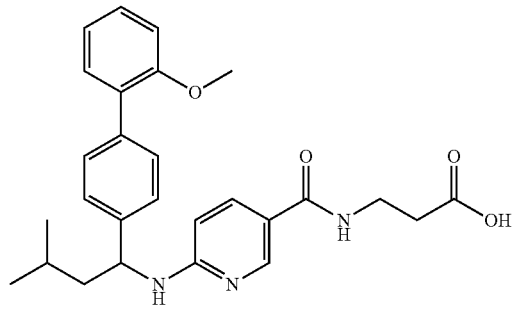 [SMILES: COc1ccccc1-c1ccc(C(CC(C)C)Nc2ccc(C(=O)NCCC(=O)O)cn2)cc1]

Analytical LCMS: retention time 0.96 minutes (Acquity HSS T3 2.1×50 mm, 1.8µ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 462.22.

Example 1.44

(+/−)-3-(6-(1-(2'-chlorobiphenyl-4-yl)-3-methylbutylamino) nicotinamido)propanoic acid

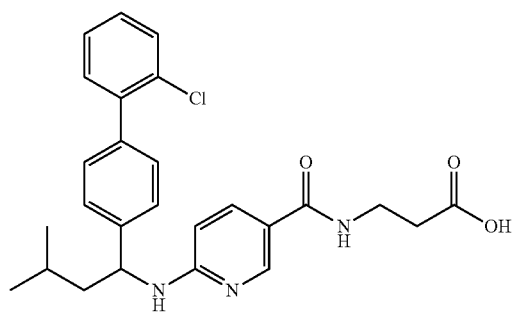 [SMILES: CC(C)CC(Nc1ccc(C(=O)NCCC(=O)O)cn1)c1ccc(-c2ccccc2Cl)cc1]

Analytical LCMS: retention time 1.00 minute (Acquity HSS T3 2.1×50 mm, 1.8μ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 466.18.

Example 1.45

(+/−)-3-(6-(1-(4'-cyanobiphenyl-4-yl)-3-methylbutylamino) nicotinamido)propanoic acid

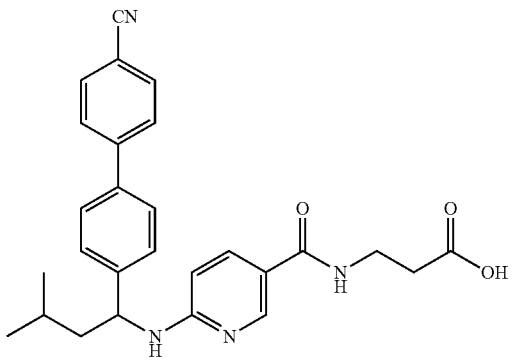 [SMILES: CC(C)CC(Nc1ccc(C(=O)NCCC(=O)O)cn1)c1ccc(-c2ccc(C#N)cc2)cc1]

Analytical LCMS: retention time 0.91 minutes (Acquity HSS T3 2.1×50 mm, 1.8μ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 457.21.

Example 1.46

(+/−)-3-(6-(1-(4'-ethoxybiphenyl-4-yl)-3-methylbutylamino) nicotinamido)propanoic acid

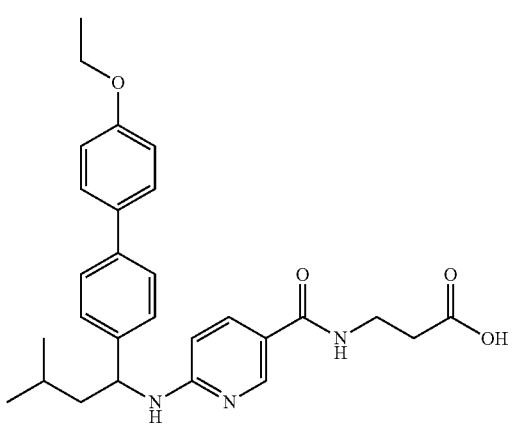 [SMILES: CCOc1ccc(-c2ccc(C(CC(C)C)Nc3ccc(C(=O)NCCC(=O)O)cn3)cc2)cc1]

Analytical LCMS: retention time 1.03 minutes (Acquity HSS T3 2.1×50 mm, 1.8μ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 476.20.

Example 1.47

(+/−)-3-(6-(1-(3'-methoxybiphenyl-4-yl)-3-methylbutylamino) nicotinamido)propanoic acid

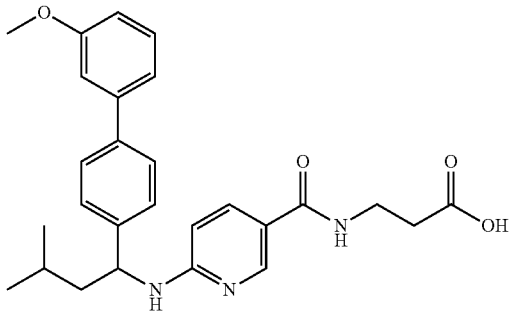 [SMILES: COc1cccc(-c2ccc(C(CC(C)C)Nc3ccc(C(=O)NCCC(=O)O)cn3)cc2)c1]

Analytical LCMS: retention time 0.96 minutes (Acquity HSS T3 2.1×50 mm, 1.8μ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 462.22.

Example 1.48

(+/−)-3-(6-(1-(2',6'-dimethylbiphenyl-4-yl)-3-methylbutylamino) nicotinamido)propanoic acid

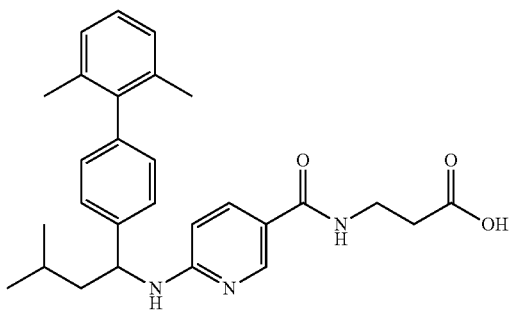 [SMILES: Cc1cccc(C)c1-c1ccc(C(CC(C)C)Nc2ccc(C(=O)NCCC(=O)O)cn2)cc1]

Analytical LCMS: retention time 1.05 minutes (Acquity HSS T3 2.1×50 mm, 1.8μ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 460.24

Example 1.49

(+/−)-3-(6-(1-(2',5'-dimethylbiphenyl-4-yl)-3-methylbutylamino) nicotinamido)propanoic acid

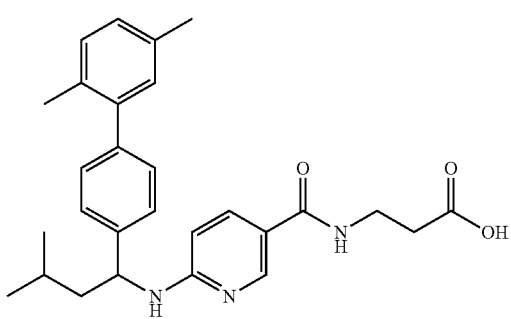 [SMILES: Cc1ccc(C)c(-c2ccc(C(CC(C)C)Nc3ccc(C(=O)NCCC(=O)O)cn3)cc2)c1]

Analytical LCMS: retention time 1.07 minutes (Acquity HSS T3 2.1×50 mm, 1.8μ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 460.24.

Example 1.50

(+/−)-3-(6-(3-methyl-1-(4'-methylbiphenyl-4-yl)butylamino) nicotinamido)propanoic acid

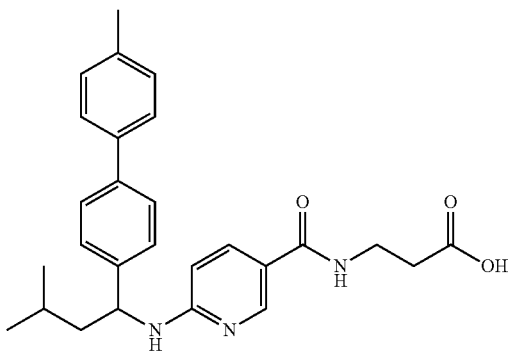 [SMILES: Cc1ccc(-c2ccc(C(CC(C)C)Nc3ccc(C(=O)NCCC(=O)O)cn3)cc2)cc1]

Analytical LCMS: retention time 1.03 minutes (Acquity HSS T3 2.1×50 mm, 1.8μ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 446.20.

Example 1.51

(+/−)-3-(6-(1-(4'-fluorobiphenyl-4-yl)-3-methylbutylamino) nicotinamido)propanoic acid

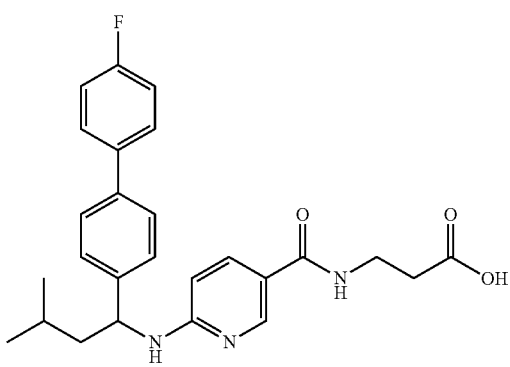 [SMILES: CC(C)CC(Nc1ccc(C(=O)NCCC(=O)O)cn1)c1ccc(-c2ccc(Cl)cc2)cc1]

Analytical LCMS: retention time 0.98 minutes (Acquity HSS T3 2.1×50 mm, 1.8μ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 450.22.

Example 1.52

(+/−)-3-(6-(1-(4'-methoxybiphenyl-4-yl)-3-methylbutylamino)nicotinamido)propanoic acid

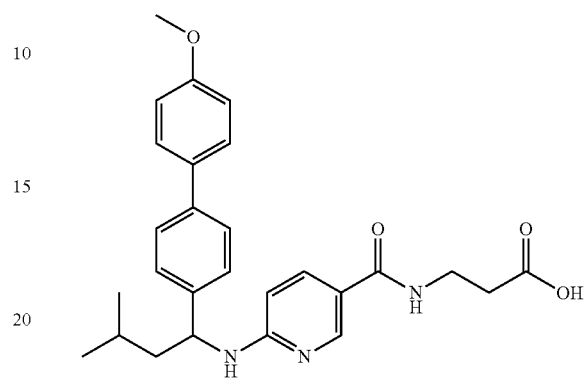

Analytical LCMS: retention time 0.96 minutes (Acquity HSS T3 2.1×50 mm, 1.8μ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 462.22.

Example 1.53

(+/−)-3-(6-(1-(4'-chlorobiphenyl-4-yl)-3-methylbutylamino) nicotinamido)propanoic acid

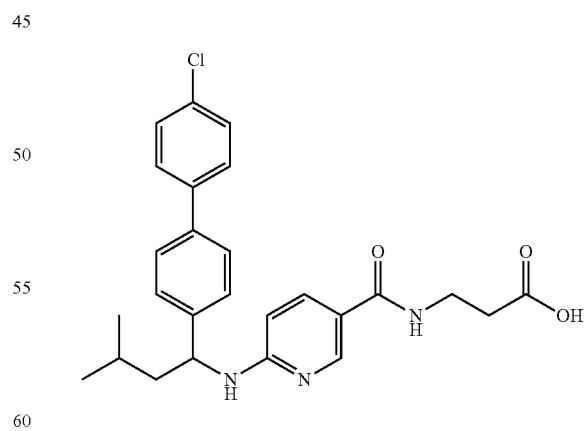

Analytical LCMS: retention time 1.05 minutes (Acquity HSS T3 2.1×50 mm, 1.8μ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 466.18.

Example 1.54

(+/−)-3-(6-(1-(4'-ethylbiphenyl-4-yl)-3-methylbutylamino) nicotinamido)propanoic acid

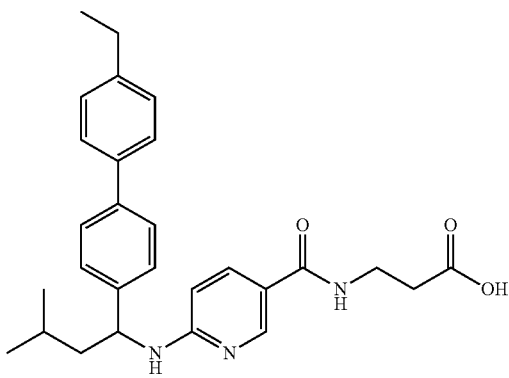 [SMILES: CCc1ccc(-c2ccc(C(CC(C)C)Nc3ccc(C(=O)NCCC(=O)O)cn3)cc2)cc1]

Analytical LCMS: retention time 1.09 minutes (Acquity HSS T3 2.1×50 mm, 1.8μ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 460.24.

Example 1.55

(+/−)-3-(6-(3-methyl-1-(4-(68yridine-2-yl)phenyl)butylamino) nicotinamido)propanoic acid

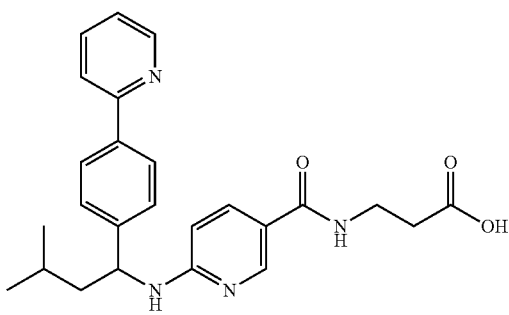 [SMILES: CC(C)CC(Nc1ccc(C(=O)NCCC(=O)O)cn1)c1ccc(-c2ccccn2)cc1]

Analytical LCMS: retention time 0.61 minutes (Acquity HSS T3 2.1×50 mm, 1.8μ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 433.21.

Example 1.56

(+/−)-3-(6-(1-(4'-(dimethylcarbamoyl)biphenyl-4-yl)-3-methylbutylamino)nicotinamido)propanoic acid

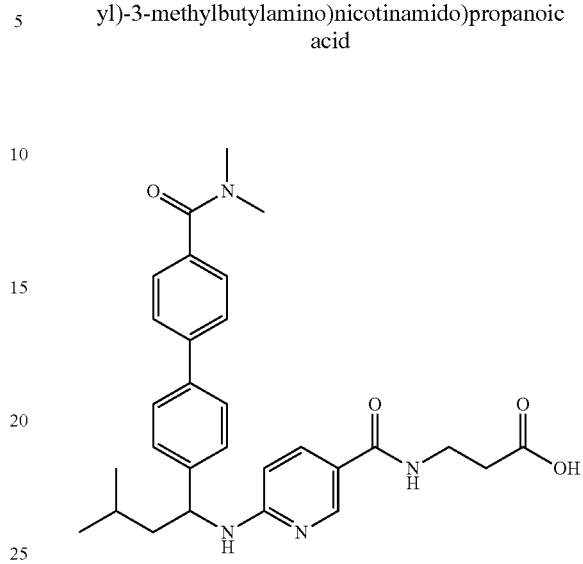

Analytical LCMS: retention time 0.81 minutes (Acquity HSS T3 2.1×50 mm, 1.8μ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 503.38.

Example 1.57

(+/−)-3-(6-(1-(4'-isopropylbiphenyl-4-yl)-3-methylbutylamino) nicotinamido)propanoic acid

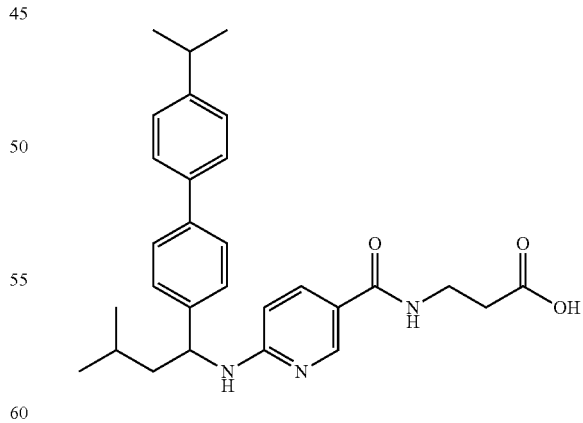

Analytical LCMS: retention time 1.14 minutes (Acquity HSS T3 2.1×50 mm, 1.8μ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 474.29.

Example 1.58

(+/−)-3-(6-(3-methyl-1-(4'-(trifluoromethoxy)biphenyl-4-yl)butylamino) nicotinamido)propanoic acid

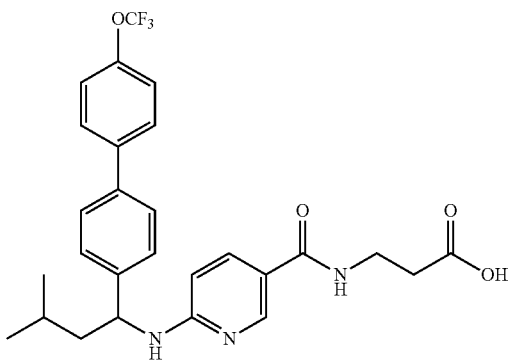 [SMILES: CC(C)CC(Nc1ccc(C(=O)NCCC(=O)O)cn1)c1ccc(-c2ccc(OC(F)(F)F)cc2)cc1]

Analytical LCMS: retention time 1.09 minutes (Acquity HSS T3 2.1×50 mm, 1.8μ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 516.23.

Example 1.59

(+/−)-3-(6-(3-methyl-1-(4'-(methylsulfonyl)biphenyl-4-yl)butylamino)nicotinamido)propanoic acid

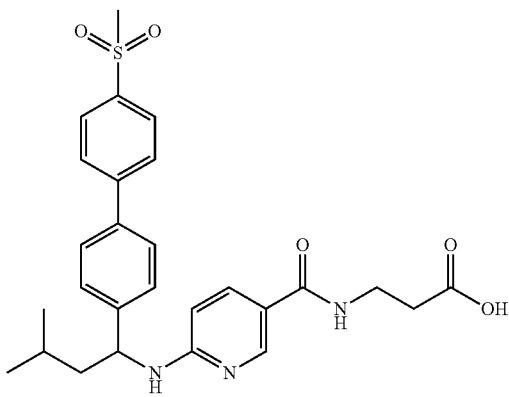 [SMILES: CC(C)CC(Nc1ccc(C(=O)NCCC(=O)O)cn1)c1ccc(-c2ccc(S(C)(=O)=O)cc2)cc1]

Analytical LCMS: retention time 0.81 minutes (Acquity HSS T3 2.1×50 mm, 1.8μ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 510.16.

Example 1.60

(+/−)-3-(6-(3-methyl-1-(4-(6-(trifluoromethyl)pyridin-3-yl)phenyl)butylamino)nicotinamido)propanoic acid

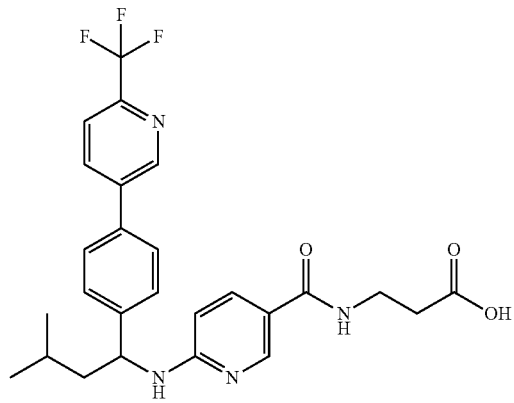 [SMILES: CC(C)CC(Nc1ccc(C(=O)NCCC(=O)O)cn1)c1ccc(-c2ccc(C(F)(F)F)nc2)cc1]

Analytical LCMS: retention time 0.95 minutes (Acquity HSS T3 2.1×50 mm, 1.8μ column; 95% water/acetonitrile linear gradient to 2% water/acetonitrile over 1.6 minutes, hold at 2% water/acetonitrile to 1.8 minutes; 0.05% trifluoroacetic acid modifier; flow rate 1.3 mL/minute); LCMS (M+1): 501.19.

Example 2.1

(+/−)-3-(6-(1-(2,6-dimethyl-4'-(trifluoromethyl)biphenyl-4-ylamino)-3-methylbutyl)nicotinamido) propanoic acid

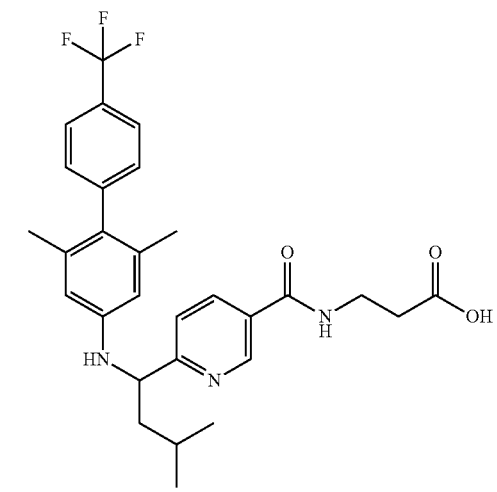 [SMILES: Cc1cc(NC(CC(C)C)c2ccc(C(=O)NCCC(=O)O)cn2)cc(C)c1-c1ccc(C(F)(F)F)cc1]

Step A: 2,6-dimethyl-4-nitrophenyl trifluoromethanesulfonate

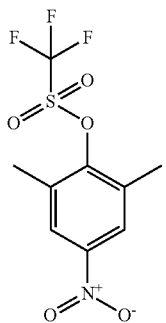 [SMILES: Cc1cc([N+](=O)[O-])cc(C)c1OS(=O)(=O)C(F)(F)F]

To a solution of 2,6-dimethyl-4-nitrophenol (6.0 g, 36 mmol) in dichloromethane (60 mL) was added pyridine (7.2 mL, 89 mmol). The solution was cooled to 0° C. and trifluoromethanesulfonic anhydride (7.2 mL, 43 mmol) was added dropwise. The reaction was stirred at 0° C. for 3 h. The reaction was diluted with saturated ammonium chloride and the layers were separated. The organic layer was washed with 1N HCl (3×50 mL), 1N NaOH (3×50 mL), and brine. The organics were dried over sodium sulfate, filtered and concentrated to give 2,6-dimethyl-4-nitrophenyl trifluoromethanesulfonate (10.0 g, 93%) as a brown solid. $^1$H NMR (400 MHz, CDCl$_3$, δ): 8.03 (s, 2H), 2.50 (s, 6H).

Step B: 2-bromo-1,3-dimethyl-5-nitrobenzene

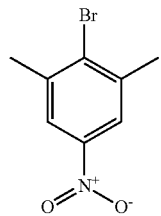

2,6-dimethyl-4-nitrophenyl trifluoromethanesulfonate (5.0 g, 17 mmol) was dissolved in N,N-dimethylformamide (40 mL). Lithium bromide monohydrate (4.7 g, 45 mmol) was added and the reaction was refluxed overnight. The reaction was diluted with saturated ammonium chloride and the layers were separated. The organics were washed with water (3×40 mL) and brine, dried over sodium sulfate, filtered and concentrated. Purification by column chromatography (2% ethyl acetate in petroleum ether) gave 2-bromo-1,3-dimethyl-5-nitrobenzene (2.7 g, 69%) as a light yellow solid. $^1$H NMR (400 MHz, CDCl$_3$, δ): 7.94 (s, 2H), 2.50 (s, 6H).

Step C: 2,6-dimethyl-4-nitro-4'-(trifluoromethyl)biphenyl

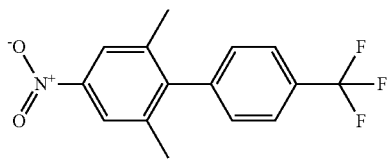

To a solution of 2-bromo-1,3-dimethyl-5-nitrobenzene (2.7 g, 11.7 mmol) in toluene (36 mL) was added tetrakis(triphenylphosphine)palladium(0) (1.36 g, 1.17 mmol), 4-(trifluoromethyl)phenylboronic acid (4.46 g, 23.5 mmol), and potassium fluoride hydrate (3.31 g, 43 mmol). The reaction was purged with nitrogen three times. Water (9 mL) was added and the reaction was refluxed overnight. The reaction was diluted with saturated ammonium chloride and the layers were separated. The organic layer was washed with water (3×40 mL) and brine, dried over sodium sulfate, filtered and concentrated. Purification by column chromatography gave 2,6-dimethyl-4-nitro-4'-(trifluoromethyl)biphenyl (1.5 g, 43%) as a yellow solid. $^1$H NMR (400 MHz, CDCl$_3$, δ): 7.99 (s, 2H), 7.75 (d, 2H), 7.26 (s, 1H), 7.25 (s, 1H), 2.10 (s, 6H).

Step D: 2,6-dimethyl-4'-(trifluoromethyl)biphenyl-4-amine

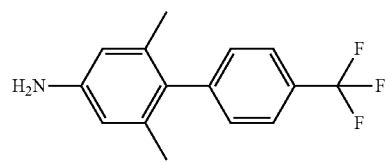 [SMILES: Cc1cc(N)cc(C)c1-c1ccc(C(F)(F)F)cc1]

To a solution of 2,6-dimethyl-4-nitro-4'-(trifluoromethyl)biphenyl (600 mg, 2.03 mmol) in ethanol (20 mL) was added 10 wt % palladium on carbon (18 mg). The reaction was pressurized to 50 psi hydrogen and stirred at room temperature overnight. The reaction was filtered onto Celite and concentrated. Purification by column chromatography gave 2,6-dimethyl-4'-(trifluoromethyl)biphenyl-4-amine (480 mg, 89%) as a light yellow solid. $^1$H NMR (400 MHz, CDCl$_3$, δ): 7.65 (d, 2H), 7.27 (s, 1H), 7.25 (s, 1H), 6.48 (s, 2H), 3.80 (s, 2H), 1.94 (s, 6H). MS (M+1): 266.1.

Step E: methyl 6-(1-(2,6-dimethyl-4'-(trifluoromethyl)biphenyl-4-ylamino)-3-methylbutyl)nicotinate

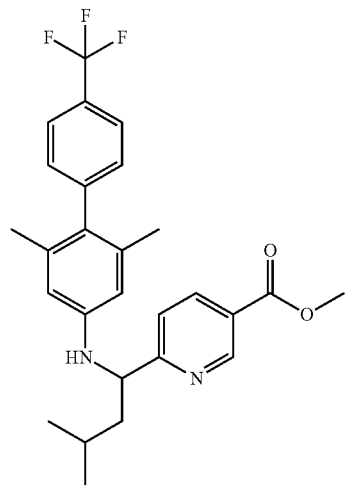

To a solution of methyl 6-formylnicotinate (200 mg, 1.21 mmol) in toluene (8 mL) containing activated molecular sieves was added 2,6-dimethyl-4'-(trifluoromethyl)biphenyl-4-amine (316 mg, 1.33 mmol). The reaction mixture was heated to 90° C. and stirred overnight. The reaction mixture was concentrated and the residue dissolved in tetrahydrofuran (8 mL). The solution was cooled to 0° C. Zinc chloride (3.64 mL of a 1.0M solution in diethyl ether, 3.64 mmol) was added, followed by isobutylmagnesium bromide (1.82 mL of a 2.0M solution in THF, 3.64 mmol). The reaction mixture was stirred at 0° C. for 2 h. The reaction was quenched with saturated aqueous ammonium chloride (5 mL). The mixture was diluted with dichloromethane (30 mL) and water (30 mL). The layers were separated and the aqueous layer was extracted with dichloromethane (30 mL) two more times. The combined organic layers were dried over sodium sulfate, filtered, and concentrated. Purification by column chromatography gave methyl 6-(1-(2,6-dimethyl-4'-(trifluoromethyl)biphenyl-4-ylamino)-3-methylbutyl)nicotinate (290 mg, 51%). $^1$H NMR (400 MHz, CDCl$_3$, δ): 9.20 (s, 1H), 8.25 (d, 1H), 7.62 (d, 4H), 7.50 (d, 2H), 7.45 (d, 1H), 7.20 (d, 2H), 6.30 (s, 2H), 4.62 (m, 1H), 3.95 (s, 3H), 3.5 (s, 3H), 1.87 (s, 6H), 1.73 (d, 3H), 1.26 (m, 3H), 1.10 (m, 6H).

Step F: methyl 3-(6-(1-(2,6-dimethyl-4'-(trifluoromethyl)biphenyl-4-ylamino)-3-methylbutyl)nicotinamido)propanoate

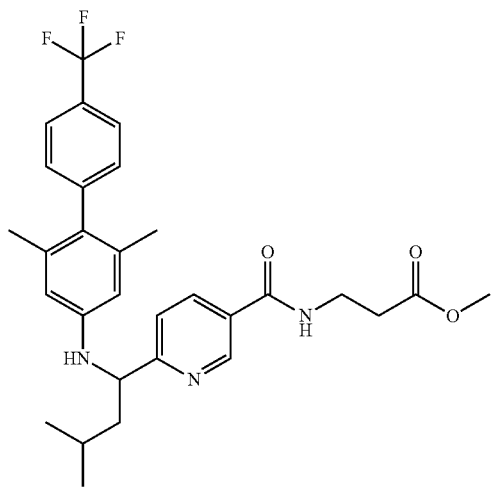

Methyl 6-(1-(2,6-dimethyl-4'-(trifluoromethyl)biphenyl-4-ylamino)-3-methylbutyl)nicotinate (290 mg, 0.62 mmol) was dissolved in H$_2$O (3 mL) and tetrahydrofuran (3 mL). The solution was cooled to 0° C. 1N LiOH (77.5 mg, 1.85 mmol) was added. The mixture was warmed to room temperature and stirred for 5 h. The mixture was then neutralized with 1N HCl and extracted with ethyl acetate. The organic layer was dried over sodium sulfate, filtered and concentrated. The residue was dissolved in N,N-dimethylformamide (5 mL). O-(7-azabenzotriazol-1-yl)-N,N,N',N'-tetramethyluronium hexafluorophosphate (338 mg, 0.888 mmol) was added and the mixture was stirred for 45 minutes. Methyl 3-aminopropanoate hydrochloride (123 mg, 0.888 mmol) and diisopropylethylamine (306 mg, 2.37 mmol) were added. The resulting mixture was stirred overnight at room temperature. The mixture was diluted with saturated ammonium chloride and extracted with ethyl acetate. The organic layer was washed with water and brine, dried over sodium sulfate, filtered and concentrated to give methyl 3-(6-(1-(2,6-dimethyl-4'-(trifluoromethyl)biphenyl-4-ylamino)-3-methylbutyl)nicotinamido)propanoate. $^1$H NMR (400 MHz, CD$_3$OD, δ): 8.88 (s, 1H), 8.10 (m, 1H), 7.64 (m, 3H), 7.23 (d, 2H), 6.31 (s, 2H), 4.55 (m, 1H), 3.65 (m, 5H), 2.65 (m, 2H), 1.82 (m, 6H), 1.60 (m, 1H), 1.0 (m, 6H).

Step G: (+/−)-3-(6-(1-(2,6-dimethyl-4'-(trifluoromethyl)biphenyl-4-ylamino)-3-methylbutyl)nicotinamido)propanoic acid Methyl 3-(6-(1-(2,6-dimethyl-4'-(trifluoromethyl) biphenyl-4-yl amino)-3-methylbutyl)nicotinamido)propanoate (400 mg, 0.74 mmol) was dissolved in H$_2$O (3 mL) and tetrahydrofuran (3 mL). Then 1N LiOH (93.0 mg, 2.2 mmol) was added. The mixture was stirred at ambient temperature for 5 hours. The mixture was neutralized with 1N HCl and extracted with ethyl acetate. The organic layer was dried over sodium sulfate, filtered and concentrated. Purification by HPLC (column: Boston Analytics Symmetrix ODS-H 150× 30 mm, 5 μm; modifier: formic acid 0.225%; gradient: 10 to 80% MeCN in water) gave (+/−)-3-(6-(1-(2,6-dimethyl-4'-(trifluoromethyl)biphenyl-4-ylamino)-3-methylbutyl)nicotinamido)propanoic acid (50.7 mg, 13%) as a yellow solid. $^1$H NMR (400 MHz, CD$_3$CN, δ): 8.85 (s, 1H), 8.02 (m, 1H), 7.64 (d, 2H), 7.46 (d, 1H), 7.22 (d, 3H), 6.32 (s, 2H), 4.59 (m, 1H), 3.54 (m, 2H), 2.55 (m, 2H), 1.93 (m, 6H), 1.78 (s, 2H), 1.72 (m, 2H), 1.60 (m, 1H), 0.96 (d, 3H), 0.91 (d, 3H). MS (M+1): 528.2.

Example 2.2

3-(6-(1-(2,6-dimethyl-4'-(trifluoromethyl)biphenyl-4-ylamino)-3-methylbutyl)nicotinamido)propanoic acid, Isomer 1

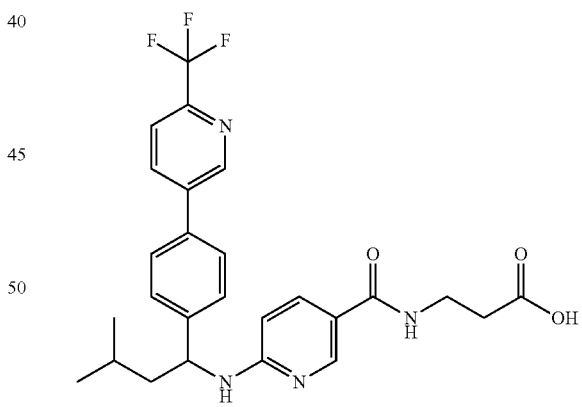

The title compound is obtained by resolving racemic 3-(6-(1-(2,6-dimethyl-4'-(trifluoromethyl)biphenyl-4-ylamino)-3-methylbutyl)nicotinamido)propanoic acid Example 2.1, by chiral SFC. Column: Chiralpak AD-H. Dimensions: 10 mm×250 cm. Mobile Phase: 75/25 CO$_2$/propanol. Flow Rate: 10.0 mL/min. Modifier: none. Retention time: 2.77 minutes.

Example 2.3

3-(6-(1-(2,6-dimethyl-4'-(trifluoromethyl)biphenyl-4-ylamino)-3-methylbutyl)nicotinamido)propanoic acid, Isomer 2

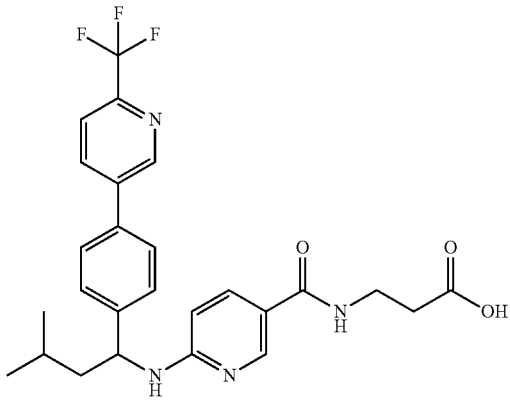 [SMILES: CC(C)CC(Nc1ccc(C(=O)NCCC(=O)O)cn1)c1ccc(-c2ccc(C(F)(F)F)nc2)cc1]

The title compound is obtained by resolving racemic 3-(6-(1-(2,6-dimethyl-4'-(trifluoromethyl)biphenyl-4-ylamino)-3-methylbutyl)nicotinamido)propanoic acid Example 2.1, by chiral SFC. Column: Chiralpak AD-H. Dimensions: 10 mm×250 cm. Mobile Phase: 75/25 CO$_2$/propanol. Flow Rate: 10.0 mL/min. Modifier: none. Retention time: 3.02 minutes.

Example 2.4

(+/−)-3-(6-(3-methyl-1-(4'-(trifluoromethyl)biphenyl-4-ylamino) butyl)nicotinamido)propanoic acid

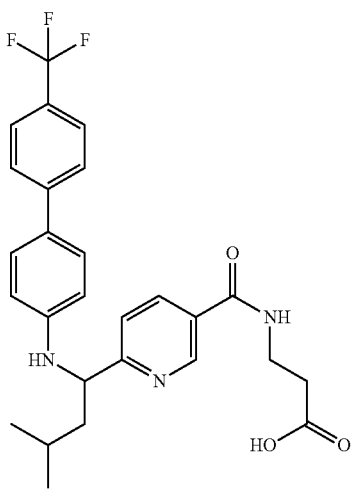 [SMILES: CC(C)CC(Nc1ccc(-c2ccc(C(F)(F)F)cc2)cc1)c1ccc(C(=O)NCCC(=O)O)cn1]

Step A: (+/−)-methyl 6-(1-hydroxy-3-methylbutyl)nicotinate

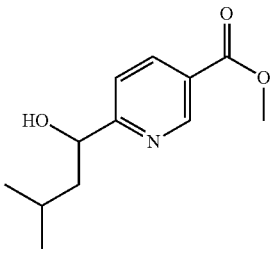 [SMILES: COC(=O)c1ccc(C(O)CC(C)C)nc1]

To a −10° C. solution of methyl 6-formylnicotinate (800 mg, 4.8 mmol) in tetrahydrofuran was added isobutylmagnesium bromide (3.6 mL, 7.2 mmol, 2.0M in THF). The resulting mixture was stirred at −10° C. After 2 hours, additional isobutylmagnesium bromide (2.4 mL, 4.8 mmol) was added and the reaction was stirred at −10° C. for another 2 hours. The reaction was quenched with water and extracted with ethyl acetate. The organic layer was dried over sodium sulfate, filtered and concentrated to a brown oil. Purification by column chromatography (0-15% ethyl acetate in petroleum ether) gave methyl 6-(1-hydroxy-3-methylbutyl)nicotinate. $^1$H NMR (400 MHz, CDCl$_3$, δ): 9.14 (s, 1H), 8.29-8.27 (d, 1H), 7.36-7.34 (d, 1H), 4.85-4.83 (m, 1H), 3.78 (s, 3H), 1.95-1.91 (m, 1H), 1.65-1.51 (m, 2H), 1.03-1.01 (d, 3H), 0.96-0.95 (d, 3H).

Step B: methyl 6-(3-methylbutanoyl)nicotinate

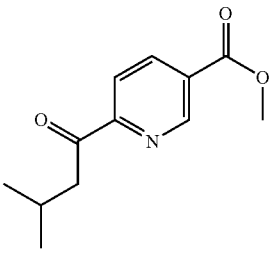 [SMILES: COC(=O)c1ccc(C(=O)CC(C)C)nc1]

To a solution of methyl 6-(1-hydroxy-3-methylbutyl)nicotinate (0.200 g, 0.896 mmol) in dichloromethane (10 mL) was added manganese dioxide (779 mg, 8.96 mmol). The reaction was stirred at room temperature overnight. The reaction was then filtered and concentration of the filtrate gave methyl 6-(3-methylbutanoyl)nicotinate (190 mg, 96%) as a yellow oil. $^1$H NMR (400 MHz, CDCl$_3$, δ): 9.25 (s, 1H), 8.40-8.42 (d, 1H), 8.07-8.09 (d, 1H), 3.98 (s, 3H), 3.11-3.12 (d, 2H), 2.27-2.34 (m, 1H), 0.99-1.00 (m, 6H).

Step C: 4'-(trifluoromethyl)biphenyl-4-amine

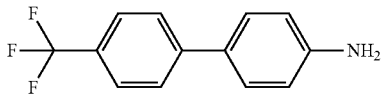

A solution of 4-bromoaniline (20 g, 116 mmol), 4-(trifluoromethyl)phenylboronic acid (15 g, 79 mmol), potassium carbonate (36.3 g, 263 mmol), and palladium(II) acetate (946 mg, 4.21 mmol) in 1,2-dimethoxyethane (80 mL) and water (80 mL) was stirred at 30° C. overnight. The reaction was then heated to 50° C. for 7 hours. The reaction was filtered through Celite and extracted with ethyl acetate (3×200 mL). The combined organics were washed with water and brine, dried over sodium sulfate, filtered and concentrated. Purification by column chromatography (0.5-1.7% petroleum ether/ethyl acetate) gave 4'-(trifluoromethyl)biphenyl-4-amine (10 g, 40%) as an off white solid. $^1$H NMR (400 MHz, (CD$_3$)$_2$SO, δ): 7.73-7.82 (m, 4H), 7.55 (dd, 2H), 6.72 (d, 2H), 5.47 (s, 2H). MS (M+1): 238.2.

Step D: methyl 6-(3-methyl-1-(4'-(trifluoromethyl) biphenyl-4-ylamino)butyl)nicotinate

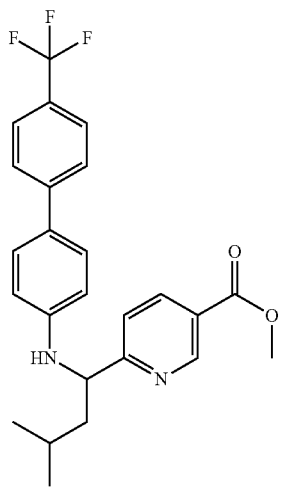 [SMILES: COC(=O)c1ccc(C(CC(C)C)Nc2ccc(-c3ccc(C(F)(F)F)cc3)cc2)nc1]

A solution of methyl 6-(3-methylbutanoyl)nicotinate (90 mg, 0.41 mmol), 4'-(trifluoromethyl)biphenyl-4-amine (145 mg, 0.610 mmol) and p-toluenesulfonic acid monohydrate (1.5 mg, 0.008 mmol) in anhydrous 1,2-dimethoxyethane (2.5 mL) was heated to 120° C. for 5 hours over activated molecular sieves in a sealed tube. The suspension was cooled to room temperature. Sodium cyanoborohydride (12.8 mg, 0.203 mmol) in methanol (1 mL) was added dropwise, immediately followed by acetic acid (0.1 mL). The resulting mixture was stirred overnight at room temperature. The reaction was concentrated and the crude residue was partitioned between ethyl acetate and saturated sodium bicarbonate. The aqueous layer was extracted again with ethyl acetate. The combined organic layers were dried over sodium sulfate, filtered and concentrated. Purification by preparative TLC (5:1 petroleum ether:ethyl acetate) gave methyl 6-(3-methyl-1-(4'-(trifluoromethyl)biphenyl-4-ylamino)butyl)nicotinate (28 mg, 15%) as a yellow solid. $^1$H NMR (400 MHz, CDCl$_3$, δ): 9.19 (s, 1H), 8.21-8.24 (d, 1H), 7.54-7.60 (m, 4H), 7.43-7.45 (d, 1H), 7.35-7.37 (d, 2H), 6.61-6.63 (d, 2H), 4.65 (s, 1H), 3.93 (s, 3H), 1.74-1.75 (d, 2H), 0.92-1.02 (m, 6H).

Step E: (+/−)-3-(6-(3-methyl-1-(4'-(trifluoromethyl) biphenyl-4-ylamino)butyl)nicotinamido)propanoic acid The title compound was prepared from methyl 6-(3-methyl-1-(4'-(trifluoromethyl)biphenyl-4-ylamino)butyl)nicotinate by a method analogous to that described in Example 2.1 steps F-G. $^1$H NMR (400 MHz, CD$_3$OD, δ): 8.90 (s, 1H), 8.05-8.15 (d, 1H), 7.52-7.69 (m, 5H), 7.35-7.38 (d, 2H), 6.60-6.65 (m, 2H) 4.69 (m, 1H) 3.57-3.62 (m, 2H), 2.58-2.63 (m, 2H), 1.70-1.90 (m, 2H), 1.59-1.66 (m, 1H), 0.98-1.03 (m, 6H). MS (M+1): 500.4.

Example 2.5

3-(6-(3-methyl-1-(4'-(trifluoromethyl)biphenyl-4-ylamino)butyl)nicotinamido)propanoic acid, Isomer 1

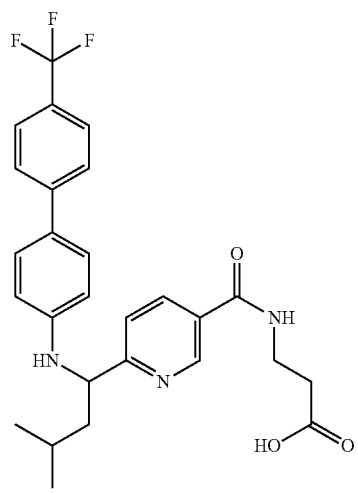 [SMILES: CC(C)CC(Nc1ccc(-c2ccc(C(F)(F)F)cc2)cc1)c1ccc(C(=O)NCCC(=O)O)cn1]

The title compound is obtained by resolving racemic 3-(6-(3-methyl-1-(4'-(trifluoromethyl)biphenyl-4-ylamino)butyl) nicotinamido)propanoic acid Example 2.4, by chiral SFC. Column: Chiralcel OJ-H. Dimensions: 10 mm×250 cm. Mobile Phase: 75/25 CO$_2$/methanol. Flow Rate: 10 mL/min. Modifier: none. Retention time: 2.94 minutes.

Example 2.6

3-(6-(3-methyl-1-(4'-(trifluoromethyl)biphenyl-4-ylamino)butyl)nicotinamido)propanoic acid, Isomer 2

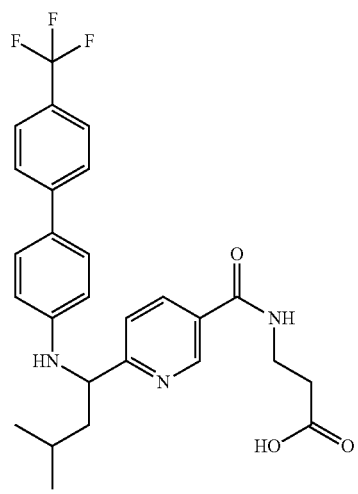 [SMILES: CC(C)CC(Nc1ccc(-c2ccc(C(F)(F)F)cc2)cc1)c1ccc(C(=O)NCCC(=O)O)cn1]

The title compound is obtained by resolving racemic 3-(6-(3-methyl-1-(4'-(trifluoromethyl)biphenyl-4-ylamino)butyl) nicotinamido)propanoic acid Example 2.4, by chiral SFC. Column: Chiralcel OJ-H. Dimensions: 10 mm×250 cm.

Mobile Phase: 75/25 CO$_2$/methanol. Flow Rate: 10 mL/min. Modifier: none. Retention time: 3.91 minutes.

Example 2.7

(+/−)-3-(6-(3-methyl-1-(6-(4-(trifluoromethyl)phenyl)pyridin-3-ylamino) butyl)nicotinamido)propanoic acid

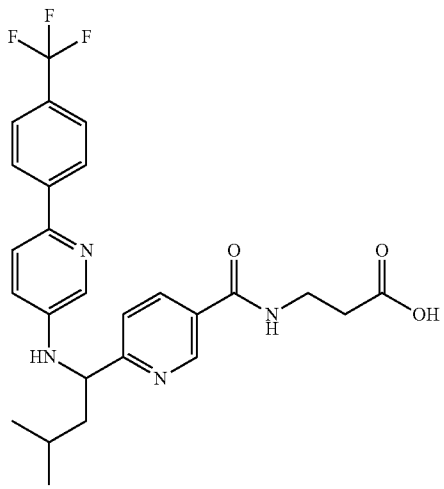 [SMILES: CC(C)CC(Nc1ccc(-c2ccc(C(F)(F)F)cc2)nc1)c1ccc(C(=O)NCCC(=O)O)cn1]

Step A:
5-nitro-2-(4-(trifluoromethyl)phenyl)pyridine

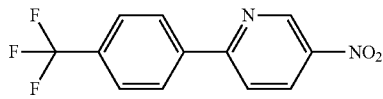

4-(trifluoromethyl)phenylboronic acid (500 mg, 2.63 mmol), 2-chloro-5-nitropyridine (417 mg, 2.63 mmol), potassium carbonate (908 mg, 6.58 mmol) and palladium(II) acetate (23.6 mg, 0.105 mmol) were combined in 1:1 dioxane:water (10 mL). The resulting mixture was stirred at 80° C. for 12 hours. The mixture was filtered and the solution was extracted with ethyl acetate. The organic layer was washed with water, then brine, dried over sodium sulfate, filtered and concentrated. Purification by column chromatography gave 5-nitro-2-(4-(trifluoromethyl)phenyl)pyridine (260 mg, 37%). $^1$H NMR (400 MHz, CDCl$_3$, δ): 9.47 (s, 1 H), 8.51 (d, 1 H), 8.14 (d, 2 H), 7.72 (d, 1 H), 7.65 (d, 2 H).

Step B:
6-(4-(trifluoromethyl)phenyl)pyridin-3-amine

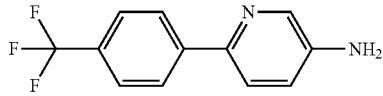

To a solution of 5-nitro-2-(4-(trifluoromethyl)phenyl)pyridine (260 mg, 0.97 mmol) in ethanol (10 mL) and tetrahydrofuran (5 mL) was added 10 wt % palladium on carbon (100 mg). The reaction was pressurized to 50 psi hydrogen and stirred at room temperature for 4 hours. The reaction was filtered through Celite and concentrated to give 6-(4-(trifluoromethyl)phenyl)pyridin-3-amine (220 mg, 95%). $^1$H NMR (400 MHz, CD$_3$OD, δ): 7.98 (s, 1 H), 7.88 (d, 2 H), 7.60 (d 2 H), 7.54 (d, 1 H), 7.09 (d, 1 H).

Step C: (+/−)-3-(6-(3-methyl-1-(6-(4-(trifluoromethyl)phenyl)pyridin-3-ylamino)butyl)nicotinamido) propanoic acid The title compound was prepared from 6-(4-(trifluoromethyl)phenyl)pyridin-3-amine and methyl 6-formylnicotinate by a method analogous to that described for Example 2.1 steps E-G. $^1$H NMR (400 MHz, CD$_3$OD, δ): 8.84 (s, 1 H), 8.06 (m, 1 H), 7.90 (s, 1 H), 7.83 (m, 2 H), 7.67 (m, 2 H), 7.65 (m, 1 H), 7.48 (m, 1 H), 7.23 (m, 1 H), 4.63-4.62 (m, 1 H), 3.53 (m, 2 H), 2.53 (m, 2 H), 1.61-1.85 (m, 3 H), 0.94 (d, 3 H), 0.89 (d, 3 H). MS (M+1): 501.1.

Example 2.8

(+/−)-3-(6-(3-methyl-1-(5-methyl-6-(4-(trifluoromethyl)phenyl)pyridin-3-ylamino)butyl)nicotinamido)propanoic acid

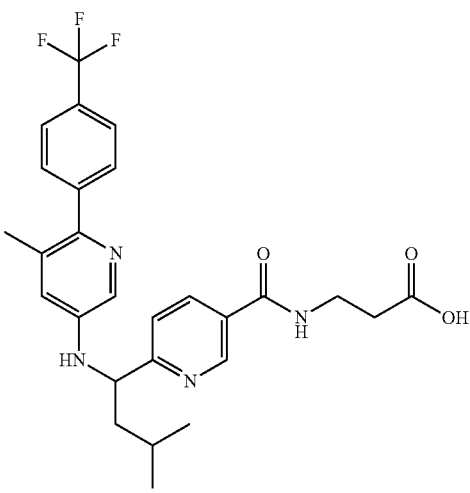

Step A: 3-methyl-5-nitro-2-(4-(trifluoromethyl)phenyl)pyridine

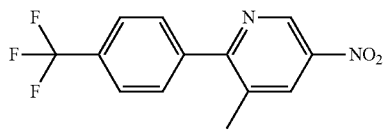

To a mixture of 4-(trifluoromethyl)phenylboronic acid (285 mg, 1.5 mmol), 2-bromo-3-methyl-5-nitropyridine (216 mg, 1.0 mmol), and potassium carbonate (345 mg, 2.5 mmol) in water (1.5 mL) and dioxane (6 mL) was added tetrakis(triphenylphosphine)palladium(0) (40 mg, 0.035 mmol). The resulting mixture was stirred at 80° C. for 4.5 hours. The mixture was cooled to room temperature. Ethyl acetate was added and the mixture was washed with water, then brine, dried over sodium sulfate, filtered and concentrated. Purification by column chromatography gave 3-methyl-5-nitro-2-(4-(trifluoromethyl)phenyl)pyridine (223 mg, 79%). $^1$H NMR (400 MHz, CDCl₃, δ): 9.35 (s, 1 H), 8.42 (s, 1 H), 7.77 (d, 2 H), 7.69 (d, 2 H), 2.51 (s, 3 H).

Step B: 5-methyl-6-(4-(trifluoromethyl)phenyl)pyridin-3-amine

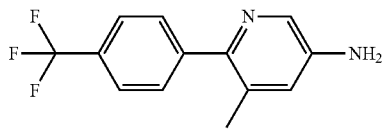 [SMILES: Cc1cc([N+](=O)[O-])cnc1-c1ccc(C(F)(F)F)cc1]

To a solution of 3-methyl-5-nitro-2-(4-(trifluoromethyl)phenyl)pyridine (223 mg, 0.79 mmol) in ethanol (30 mL) was added 10 wt % palladium on carbon (100 mg). The reaction was pressurized to 50 psi hydrogen and was stirred at room temperature for 3 hours. The reaction mixture was filtered through Celite and concentrated to give 5-methyl-6-(4-(trifluoromethyl)phenyl)pyridin-3-amine (198 mg, 99%). ¹H NMR (400 MHz, CDCl₃, δ): 8.04 (s, 1 H), 7.67 (m, 2 H), 7.60 (m, 2 H), 6.91 (s, 1 H), 3.72 (br s, 2 H), 2.30 (s, 3 H).

Step C: (+/−)-3-(6-(3-methyl-1-(5-methyl-6-(4-(trifluoromethyl)phenyl)pyridin-3-ylamino)butyl)nicotinamido)propanoic acid The title compound was prepared from methyl 6-formylnicotinate and 5-methyl-6-(4-(trifluoromethyl)phenyl)pyridin-3-amine by a method analogous to that described in Example 2.1, steps E-G. ¹H NMR (400 MHz, CD₃OD, δ): 8.95 (m, 1 H), 8.15 (m, 1 H), 7.83 (m, 1 H), 7.71 (m, 2 H), 7.59 (m, 2 H), 7.57 (m, 2 H), 6.89 (m, 1 H), 4.51 (m, 1 H), 3.64 (m, 2 H), 2.65 (m, 2 H), 2.19 (s, 3 H), 1.51-1.89 (m, 3 H), 1.05 (d, 3 H), 1.02 (d, 3 H). MS (M+1): 515.7.

Example 2.9

(+/−)-3-(6-(1-(5-methyl-6-(4-(trifluoromethyl)phenyl)pyridin-3-ylamino) butyl)nicotinamido)propanoic acid

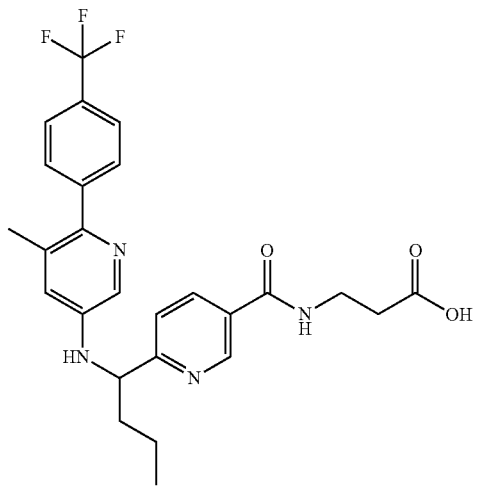 [SMILES: CCCC(Nc1cnc(-c2ccc(C(F)(F)F)cc2)c(C)c1)c1ccc(C(=O)NCCC(=O)O)cn1]

The title compound was prepared from methyl 6-formylnicotinate and 5-methyl-6-(4-(trifluoromethyl)phenyl)pyridin-3-amine by a method analogous to that described in Example 2.1 steps E-G, using n-propylmagnesium bromide. ¹H NMR (400 MHz, CD₃OD, δ): 8.84 (d, 1H), 8.05 (dd, 1H), 7.71 (d, 1H), 7.59 (d, 2H), 7.50-7.41 (m, 3H), 6.776 (d, 1H), 4.48 (t, 1H), 3.53 (t, 2H), 2.53 (t, 2H), 2.07 (s, 3H), 1.82-1.75 (m, 2H), 1.52-1.42 (m, 1H), 1.40-1.29 (m, 1H), 0.89 (t, 3H). MS (M+1): 501.

Example 2.10

(+/−)-3-(6-(1-(4'-(trifluoromethyl)biphenyl-4-ylamino)ethyl)nicotinamido)propanoic acid

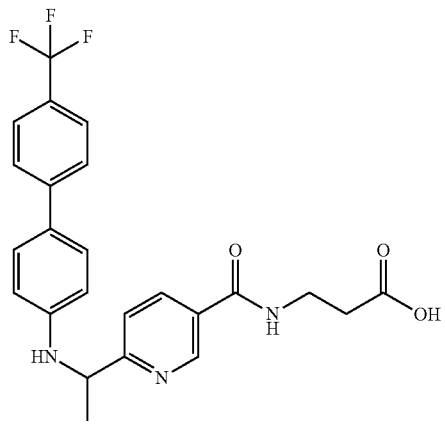 [SMILES: CC(Nc1ccc(-c2ccc(C(F)(F)F)cc2)cc1)c1ccc(C(=O)NCCC(=O)O)cn1]

The title compound was prepared from 4'-(trifluoromethyl)biphenyl-4-amine and methyl 6-formylnicotinate by a method analogous to that described in Example 2.1 steps E-G, using methylmagnesium bromide. ¹H NMR (400 MHz, CD₃OD, δ): 8.92 (s, 1 H), 8.12 (d, 1 H), 7.60 (m, 5 H), 7.37 (d, 2 H), 6.59 (d, 2 H), 4.65 (m, 1 H), 3.62 (m, 2 H), 2.62 (m, 2 H), 1.56 (d, 3 H). MS (M+1): 458.5.

Example 2.11

(+/−)-3-(6-(1-(5-methyl-6-(4-(trifluoromethyl)phenyl)pyridin-3-ylamino)propyl)nicotinamido)propanoic acid

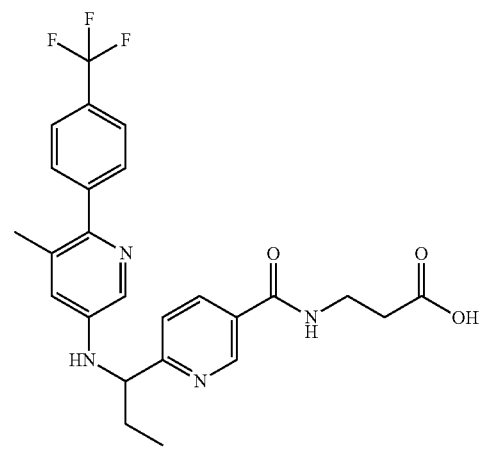 [SMILES: CCC(Nc1cnc(-c2ccc(C(F)(F)F)cc2)c(C)c1)c1ccc(C(=O)NCCC(=O)O)cn1]

The title compound was prepared from methyl 6-formylnicotinate and 5-methyl-6-(4-(trifluoromethyl)phenyl)pyridin-3-amine in a manner analogous to Example 2.1, steps E-G, using ethylmagnesium bromide. ¹H NMR (400 MHz, CD₃OD, δ): 8.84 (d, 1H), 8.06 (dd, 1H), 8.71 (d, 1H), 7.59 (d, 2H), 7.50-7.41 (m, 3H), 6.76 (d, 1H), 4.40 (t, 1H), 3.53 (t, 2H), 2.53 (t, 2H), 2.07 (s, 3H), 1.90-1.82 (m, 2H), 0.94 (t, 3H). MS (M+1): 487.

Example 2.12

(+/−)-N-((1H-tetrazol-5-yl)methyl)-6-(3-methyl-1-(4'-(trifluoromethyl) biphenyl-4-ylamino)butyl)nicotinamide

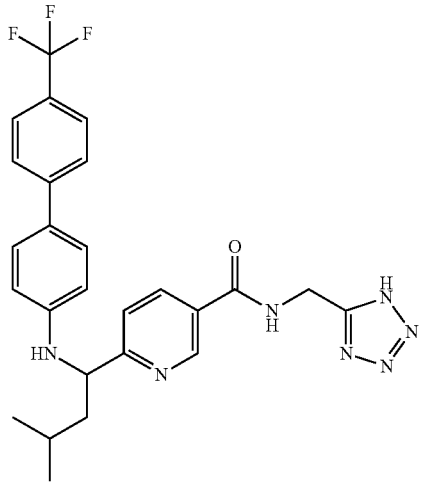 [SMILES: CC(C)CC(Nc1ccc(-c2ccc(C(F)(F)F)cc2)cc1)c1ccc(C(=O)NCc2nnn[nH]2)cn1]

Step A: methyl 6-(3-methyl-1-(4'-(trifluoromethyl) biphenyl-4-ylamino)butyl)nicotinate

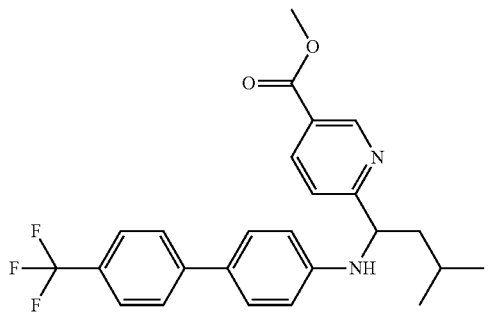 [SMILES: COC(=O)c1ccc(C(CC(C)C)Nc2ccc(-c3ccc(C(F)(F)F)cc3)cc2)nc1]

To a solution of methyl 6-formylnicotinate (0.200 g, 1.21 mmol) in tetrahydrofuran (8 mL) containing activated molecular sieves was added 4'-(trifluoromethyl)biphenyl-4-amine (316 mg, 1.33 mmol). The reaction was heated to 90° C. and stirred overnight. The reaction was concentrated to dryness and the residue was dissolved in tetrahydrofuran (8 mL). The solution was cooled to 0° C. Zinc chloride (3.52 mL, 1M in diethyl ether, 3.52 mmol) was added, followed by isobutylmagnesium bromide (1.47 mL, 2.0M in THF, 3.52 mmol). The reaction was stirred at 0° C. for 2 hours. The reaction was quenched with saturated ammonium chloride. The mixture was diluted with dichloromethane and water. The layers were separated and the aqueous was extracted again with dichloromethane. The combined organic layers were dried over sodium sulfate, filtered and concentrated. Purification by column chromatography gave methyl 6-(3-methyl-1-(4'-(trifluoromethyl)biphenyl-4-ylamino)butyl)nicotinate (210 mg, 39%) as a yellow oil. $^1$H NMR (400 MHz, CD$_3$OD, δ): 9.09 (s, 1H), 8.31 (d, 1H), 7.72-7.57 (m, 5H), 7.41 (d, 2H), 6.65 (d, 2H), 4.61-4.52 (m, 1H), 3.94 (s, 3H), 1.92-1.73 (m, 2H), 1.1.72-1.61 (m, 1H), 1.05 (d, 3H), 0.91 (d, 3H).

Step B: 6-(3-methyl-1-(4'-(trifluoromethyl)biphenyl-4-ylamino)butyl)nicotinic acid

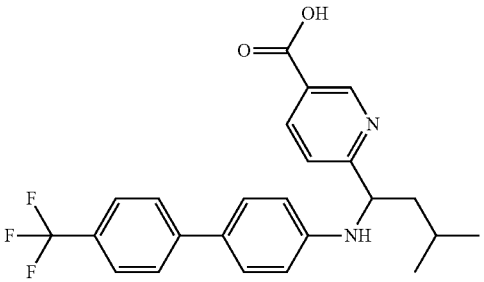 [SMILES: CC(C)CC(Nc1ccc(-c2ccc(C(F)(F)F)cc2)cc1)c1ccc(C(=O)O)cn1]

Methyl 6-(3-methyl-1-(4'-(trifluoromethyl)biphenyl-4-ylamino)butyl)nicotinate (190 mg, 0.429 mmol) was dissolved in water (3 mL) and tetrahydrofuran (3 mL). 1N LiOH (54.0 mg, 1.29 mmol) was added. The reaction was stirred at room temperature for 2 hours. The reaction was neutralized with 1N HCl and extracted with ethyl acetate. The organic layer was dried over sodium sulfate, filtered and concentrated to give 6-(3-methyl-1-(4'-(trifluoromethyl)biphenyl-4-ylamino)butyl)nicotinic acid (180 mg, 98%) as a yellow solid. 1H NMR (400 MHz, CD$_3$OD, δ): 9.08 (s, 1H), 8.25 (d, 1H), 7.59-7.63 (m, 5H), 7.38 (d, 2H), 6.63 (d, 2H), 4.65 (m, 1H), 1.85 (m, 2H), 1.65 (m, 1H), 1.00 (m, 6H).

Step C: (+/−)-N-((1H-tetrazol-5-yl)methyl)-6-(3-methyl-1-(4'-(trifluoromethyl)biphenyl-4-ylamino)butyl)nicotinamide To a solution of 6-(3-methyl-1-(4'-(trifluoromethyl)biphenyl-4-ylamino) butyl)nicotinic acid (0.100 g, 0.233 mmol) in N,N-dimethylformamide (3.0 mL) was added 1,1'-carbonyldiimidazole (75.6 mg, 0.466 mmol) and N,N-diisopropylethylamine (181 mg, 1.40 mmol). The reaction was stirred for 30 minutes at 80° C. (1H-tetrazol-5-yl)methanamine (80.2 mg, 0.466 mmol) was added and the reaction continued to stir at 80° C. overnight. The reaction was diluted with saturated ammonium chloride and extracted with ethyl acetate. The organic layer was washed with brine, dried over sodium sulfate, filtered and concentrated. Purification by preparative HPLC (column: Boston Analytics Symmetrix ODS-H 150× 30 mm, 5 μm; modifier: formic acid 0.225%; gradient: 10 to 80% MeCN in water) gave N-((1H-tetrazol-5-yl)methyl)-6-(3-methyl-1-(4'-(trifluoromethyl)biphenyl-4-ylamino)butyl) nicotinamide (15.7 mg, 13%) as a light yellow solid. $^1$H NMR (400 MHz, CD$_3$OD, δ): 9.35 (m, 1H), 8.98 (s, 1H), 8.15 (d, 1H), 7.72 (d, 4H), 7.50 (d, 1H), 7.35 (d, 2H), 6.64 (m, 3H), 4.75 (d, 2H), 4.55 (m, 1H), 1.75 (m, 2H), 1.55 (m, 1H), 0.95 (d, 3H), 0.85 (d, 3H). MS (M+1): 510.4.

Example 2.13

(+/−)-6-(3-methyl-1-(4'-(trifluoromethyl)biphenyl-4-ylamino)butyl)-N-(2H-tetrazol-5-yl)nicotinamide

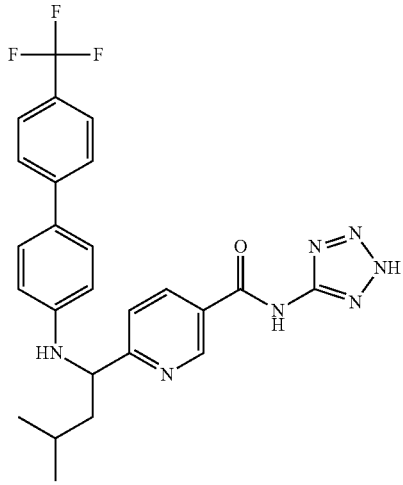 [SMILES: CC(C)CC(Nc1ccc(-c2ccc(C(F)(F)F)cc2)cc1)c1ccc(C(=O)Nc2nn[nH]n2)cn1]

To a solution of 6-(3-methyl-1-(4'-(trifluoromethyl)biphenyl-4-ylamino)butyl)nicotinic acid (0.100 g, 0.233 mmol) in N,N-dimethylformamide (1.5 mL) was added 1,1'-carbonyldiimidazole (49.1 mg, 0.303 mmol) and N,N-diisopropylethylamine (45.2 mg, 0.350 mmol). The mixture was stirred for 30 minutes at 80° C. 5-Aminotetrazole (59.5 mg, 0.699 mmol) was then added. The resulting mixture was stirred overnight at 80° C. The reaction was concentrated and purification by preparative HPLC gave 6-(3-methyl-1-(4'-(trifluoromethyl)biphenyl-4-ylamino)butyl)-N-(2H-tetrazol-5-yl)nicotinamide (50.0 mg, 43%) as a light yellow solid. $^1$H NMR (400 MHz, CD$_3$OD, δ): 8.90 (s, 1H), 8.05-8.15 (d, 1H), 7.52-7.69 (m, 5H), 7.35-7.38 (m, 2H), 6.61-6.69 (m, 2H), 4.69 (m, 1H), 1.76-1.88 (m, 2H), 1.60-1.70 (m, 1H), 0.98-1.03 (m, 6H). MS (M+1): 496.3.

Example 2.14

(+/−)-3-(4-(1-(6-(4-(trifluoromethyl)phenyl)pyridazin-3-ylamino)butyl)benzamido)propanoic acid

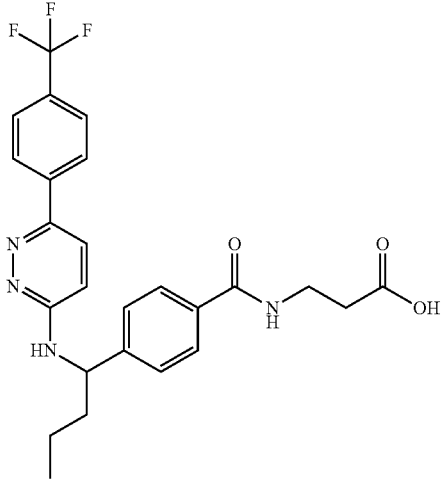 [SMILES: CCCC(Nc1ccc(-c2ccc(C(F)(F)F)cc2)nn1)c1ccc(C(=O)NCCC(=O)O)cc1]

Step A:
6-(4-(trifluoromethyl)phenyl)pyridazin-3-amine

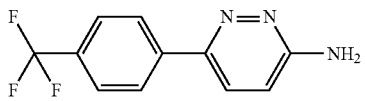

A flask containing 4-trifluorophenylboronic acid (1.300 g, 6.845 mmol), 6-chloropyridazin-3-amine (887 mg, 6.84 mmol), sodium carbonate (1.450 g, 13.7 mmol) and 1,1'-bis(diphenylphosphino)ferrocene palladium(II) dichloride (0.250 g, 0.342 mmol) was evacuated and back filled with nitrogen three times. Dimethoxyethane (8 mL) and water (2 mL) were then added. The mixture was heated to 70° C. overnight. The reaction was diluted with water and extracted with ethyl acetate three times. The combined organic layers were dried over sodium sulfate, filtered and concentrated. Purification by column chromatography (0-100% ethyl acetate in heptane) gave 6-(4-(trifluoromethyl)phenyl)pyridazin-3-amine (1.637 g, 53%). $^1$H NMR (400 MHz, CDCl$_3$, δ): 8.07 (d, J=8.19 Hz, 2 H), 7.71 (d, J=8.19 Hz, 2 H), 7.65 (d, J=9.17 Hz, 1 H), 6.84 (d, J=9.17 Hz, 1 H), 4.90 (br. s., 2 H). MS (M+1): 240.2.

Step B: ethyl 4-(1-(methylsulfonyloxy)butyl)benzoate

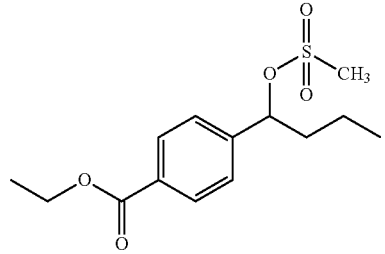 [SMILES: CCCC(OS(C)(=O)=O)c1ccc(C(=O)OCC)cc1]

Methanesulfonyl chloride (341 mg, 2.97 mmol) was added dropwise to a solution of ethyl 4-(1-hydroxybutyl)benzoate (504 mg, 2.27 mmol) and triethylamine (477 mg, 4.58 mmol) in dichloromethane (5 mL) at 0° C. The reaction was stirred at 0° C. for 2 hours. The reaction was diluted with ethyl acetate and washed with saturated ammonium chloride, saturated sodium bicarbonate, and brine. The organics were dried over sodium sulfate, filtered and concentrated to give ethyl 4-(1-(methylsulfonyloxy)butyl)benzoate. $^1$H NMR (400 MHz, CDCl$_3$, δ): 8.02-8.10 (d, J=8.19 Hz, 2 H), 7.44 (d, J=8.19 Hz, 2 H), 5.50-5.61 (m, 1 H), 4.37 (q, J=7.22 Hz, 2 H), 1.97-2.11 (m, 1 H), 1.78-1.88 (m, 1 H), 1.39 (t, J=7.22 Hz, 3 H), 1.28-1.52 (m, 2 H), 0.94 (t, J=7.41 Hz, 3 H).

Step C: ethyl 4-(1-(6-(4-(trifluoromethyl)phenyl) pyridazin-3-ylamino)butyl)benzoate

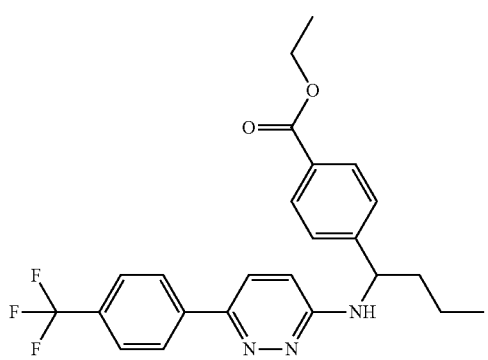 [SMILES: CCCC(Nc1ccc(-c2ccc(C(F)(F)F)cc2)nn1)c1ccc(C(=O)OCC)cc1]

A solution of 6-(4-(trifluoromethyl)phenyl)pyridazin-3-amine (140 mg, 0.585 mmol) in N,N-dimethylformamide (2 mL) was added to a suspension of 60% sodium hydride (27.2 mg, 0.679 mmol) in N,N-dimethylformamide (2 mL) at 0° C. The mixture was stirred at room temperature for 30 minutes. A mixture of ethyl 4-(1-(methylsulfonyloxy)butyl)benzoate (0.170 g, 0.566 mmol) in N,N-dimethylformamide (3 mL) was then added at room temperature. The reaction was stirred for 2 hours. The reaction was diluted with ethyl acetate and washed with water and brine. The organics were dried over sodium sulfate, filtered and concentrated. Purification by column chromatography (0-15% ethyl acetate in heptanes) gave ethyl 4-(1-(6-(4-(trifluoromethyl)phenyl)pyridazin-3-ylamino)butyl)benzoate (25.0 mg, 10%) as an oil. $^1$H NMR (400 MHz, CDCl$_3$, δ): 7.98-8.05 (m, 4 H), 7.67 (d, J=8.19 Hz, 2 H), 7.53 (d, J=9.36 Hz, 1 H), 7.44 (d, J=8.19 Hz, 2 H), 6.57 (d, J=9.36 Hz, 1 H), 5.56-5.67 (m, 1 H), 4.82-4.93 (m, 1 H), 4.34 (q, J=7.22 Hz, 2 H), 1.79-2.01 (m, 2 H), 1.36 (t, J=7.22 Hz, 3 H), 1.28-1.54 (m, 2 H), 0.96 (t, J=7.32 Hz, 3 H). MS (M+1): 444.1.

Step D: (+/−)-3-(4-(1-(6-(4-(trifluoromethyl)phenyl) pyridazin-3-ylamino)butyl)benzamido)propanoic acid Ethyl 4-(1-(6-(4-(trifluoromethyl)phenyl)pyridazin-3-ylamino)butyl)benzoate was hydrolyzed to the corresponding carboxylic acid using a method analogous to that described in Example 2.12 step B. The title compound was then prepared from 4-(1-(6-(4-(trifluoromethyl)phenyl)pyridazin-3-ylamino)butyl)benzoic acid using a method analogous to that described in Example 1.23 step B, using tert-butyl 3-aminopropanoate. Purification by preparative HPLC gave the title compound. Column: Waters Atlantis dC18 4.6×50 mm, 5 um. Modifier: TFA 0.05%. Gradient: 95% H$_2$O/5% MeCN linear to 5% H$_2$0/95% MeCN over 4.0 minutes, HOLD at 5% H$_2$0/95% MeCN to 5.0 minutes. Flow: 2.0 mL/min. Retention time: 2.45 minutes. MS (M+1): 487.1.

Example 2.15

(+/−)-3-(4-(1-(2-(4-(trifluoromethyl)phenyl)pyrimidin-5-ylamino)butyl)benzamido)propanoic acid

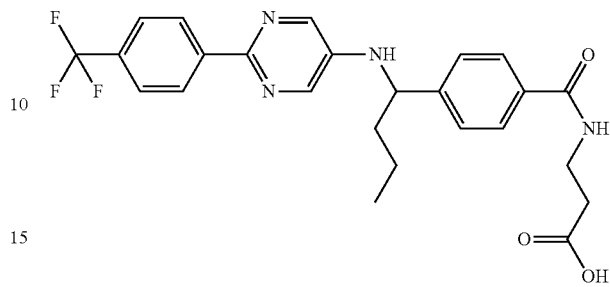

Step A:
2-(4-(trifluoromethyl)phenyl)pyrimidin-5-amine

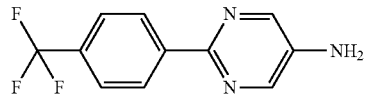

The title compound was prepared by a method analogous to the described in Example 2.14 step A, using 2-chloropyrimidin-5-amine. $^1$H NMR (400 MHz, CDCl$_3$, δ): 8.41 (d, J=8.00 Hz, 2 H), 8.30 (s, 2 H), 7.68 (d, J=8.19 Hz, 2 H), 3.81 (br.s, 2 H). MS (M+1): 240.1.

Step B: Ethyl 4-butyrylbenzoate

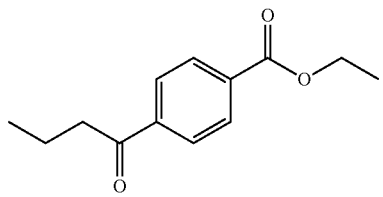 [SMILES: CCCC(=O)c1ccc(C(=O)OCC)cc1]

At −40° C., isopropylmagnesium chloride lithium chloride (15.3 mL, 1.3M in THF, 19.9 mmol) was added dropwise to a solution of ethyl 4-iodobenzoate (5.00 g, 18.11 mmol) in tetrahydrofuran (30 mL). The solution was stirred at −40° C. for 40 minutes. Butyraldehyde (1830 mg, 25.4 mmol) was added. The reaction was allowed to warm to room temperature over 3 hours. The reaction was quenched with 1N HCl and extracted with ethyl acetate three times. The combined organic layers were dried over sodium sulfate, filtered and concentrated. The crude residue (1.0 g, 4.5 mmol) was combined with dichloromethane (16.7 mL), dimethylsulfoxide (4.79 mL), and triethylamine (2.28 g, 22.5 mmol) and cooled to 0° C. Sulfur trioxide pyridine complex (2.15 g, 13.5 mmol) was added in portions and the mixture was stirred at 0° C. for 1 hour. The reaction was allowed to gradually warm to room temperature and stir over 2 hours. The reaction was quenched with brine and diluted with dichloromethane. The layers were separated and the aqueous layer was extracted again with dichloromethane (20 mL). The combined organic layers were dried over sodium sulfate, filtered and concentrated. Purification by column chromatography (0-30% ethyl acetate in heptane) gave ethyl 4-butyrylbenzoate. ¹H NMR (400 MHz, CDCl₃, δ): 8.05-8.17 (m, 2 H), 7.92-8.04 (m, 2 H), 4.40 (q, J=7.15 Hz, 2 H), 2.96 (t, J=7.22 Hz, 2 H), 1.69-1.86 (m, 2 H), 1.40 (t, J=7.12 Hz, 3 H), 1.00 (t, J=7.22 Hz, 3 H).

Step C: ethyl 4-(1-(2-(4-(trifluoromethyl)phenyl)pyrimidin-5-ylamino)butyl)benzoate

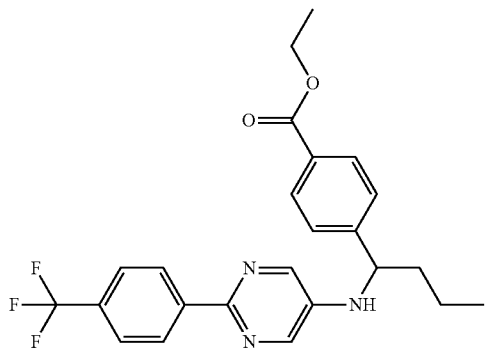 [SMILES: CCCC(Nc1cnc(-c2ccc(C(F)(F)F)cc2)nc1)c1ccc(C(=O)OCC)cc1]

Methanol (0.70 mL) was added to a flask containing ethyl 4-butyrylbenzoate (82.8 mg, 0.376 mmol), 2-(4-(trifluoromethyl)phenyl)pyrimidin-5-amine (90.0 mg, 0.376 mmol) and decaborane (46.0 mg, 0.376 mmol) at room temperature under nitrogen. The resulting solution was stirred at room temperature overnight. The mixture was diluted with 1N HCl and extracted with ethyl acetate twice. The combined organic layers were dried over sodium sulfate, filtered and concentrated. Purification by column chromatography (0-35% ethyl acetate in heptane) gave ethyl 4-(1-(2-(4-(trifluoromethyl)phenyl)pyrimidin-5-ylamino)butyl)benzoate (40.0 mg, 24%). ¹H NMR (400 MHz, CDCl₃, δ): 8.32 (d, J=8.19 Hz, 2 H), 8.07 (s, 2 H), 7.98-8.04 (m, 2 H), 7.63 (d, J=8.19 Hz, 2 H), 7.36-7.41 (m, 2 H), 4.38-4.43 (m, 2 H), 4.35 (q, J=7.02 Hz, 2 H), 1.75-1.91 (m, 2 H), 1.36 (t, J=7.02 Hz, 3 H), 1.20-1.52 (m, 2 H), 0.94 (t, J=7.32 Hz, 2 H). MS (M+1): 444.3.

Step D: (+/−)-3-(4-(1-(2-(4-(trifluoromethyl)phenyl)pyrimidin-5-ylamino)butyl)benzamido)propanoic acid The title compound was prepared from ethyl 4-(1-(2-(4-(trifluoromethyl)phenyl)pyrimidin-5-ylamino)butyl)benzoate using a method analogous to that described in Example 2.14 step D. ¹H NMR (400 MHz, CDCl₃, δ): 8.49 (s, 2 H), 8.20 (d, J=8.39 Hz, 2 H), 7.70 (d, J=8.19 Hz, 4 H), 7.38 (d, J=8.19 Hz, 2 H), 7.11-7.20 (m, 1 H), 4.40-4.49 (m, 1 H), 3.62-3.75 (m, 2 H), 2.62-2.72 (m, 2 H), 1.71-1.96 (m, 2 H), 1.29-1.53 (m, 2 H), 0.92 (t, J=7.32 Hz, 3 H). MS (M+1): 487.3.

Example 2.16

3-(4-(1-(2-(4-(trifluoromethyl)phenyl)pyrimidin-5-ylamino)butyl)benzamido)propanoic acid, Isomer 1

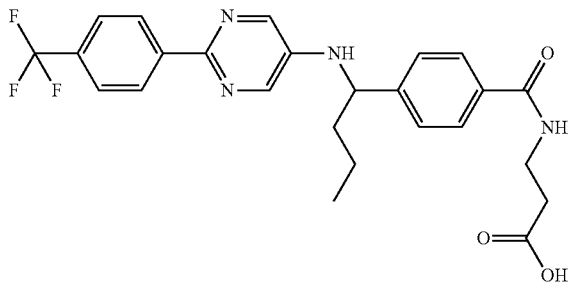 [SMILES: CCCC(Nc1cnc(-c2ccc(C(F)(F)F)cc2)nc1)c1ccc(C(=O)NCCC(=O)O)cc1]

The title compound is obtained by resolving racemic 3-(4-(1-(2-(4-(trifluoromethyl)phenyl)pyrimidin-5-ylamino)butyl)benzamido)propanoic acid Example 2.15, by chiral SFC. Column: Chiralcel OJ-H. Dimensions: 10 mm×250 mm. Mobile Phase: 65/35 CO₂/methanol. Flow Rate: 10 mL/min. Modifier: none. Retention time: 2.78 minutes.

Example 2.17

3-(4-(1-(2-(4-(trifluoromethyl)phenyl)pyrimidin-5-ylamino)butyl)benzamido)propanoic acid, Isomer 2

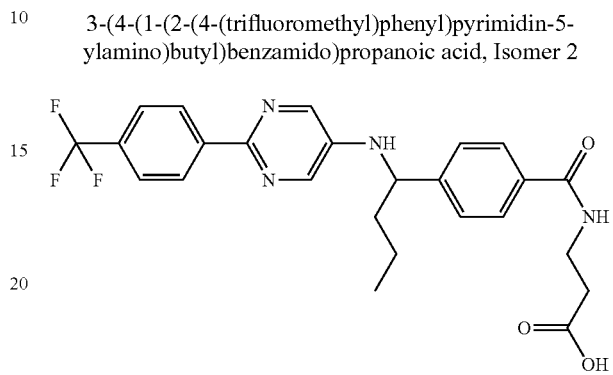

The title compound is obtained by resolving racemic 3-(4-(1-(2-(4-(trifluoromethyl)phenyl)pyrimidin-5-ylamino)butyl)benzamido)propanoic acid Example 2.15, by chiral SFC. Column: Chiralcel OJ-H. Dimensions: 10 mm×250 mm. Mobile Phase: 65/35 CO₂/methanol. Flow Rate: 10 mL/min. Modifier: none. Retention time: 3.29 minutes.

Example 3.1

(+/−)-3-(6-(3-methyl-1-(4'-(trifluoromethyl)biphenyl-4-Yloxy)butyl)nicotinamido)propanoic acid

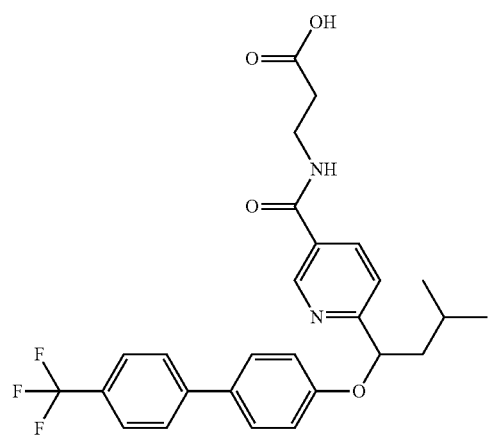 [SMILES: CC(C)CC(Oc1ccc(-c2ccc(C(F)(F)F)cc2)cc1)c1ccc(C(=O)NCCC(=O)O)cn1]

Step A: 4'-(trifluoromethyl)biphenyl-4-ol

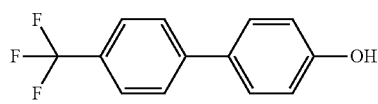

4-(trifluoromethyl)phenylboronic acid (263 mg, 1.39 mmol) was suspended in water (2 mL). 4-bromophenol (0.200 g, 1.16 mmol), potassium carbonate (484 mg, 3.47 mmol), and palladium(II) acetate (13.3 mg, 0.0580 mmol) were added. The reaction was allowed to stir open to ambient atmosphere for 60 hours. The reaction was filtered through Celite and extracted three times with ethyl acetate. The combined organics were washed with 1N HCl, water, and brine, dried over magnesium sulfate, filtered and concentrated. Purification by column chromatography (0-20% ethyl acetate in heptanes) gave 4'-(trifluoromethyl) biphenyl-4-ol (150 mg, 55%) as a white solid. $^1$H NMR (400 MHz, CDCl$_3$, δ): 7.63-7.70 (m, 4H), 7.50-7.54 (m, 2H), 6.95 (d, J=8.8 Hz, 2H), 4.81 (s, 1H). MS (M-1): 237.0.

Step B: methyl 6-(3-methyl-1-(4'-(trifluoromethyl)biphenyl-4-yloxy)butyl)nicotinate

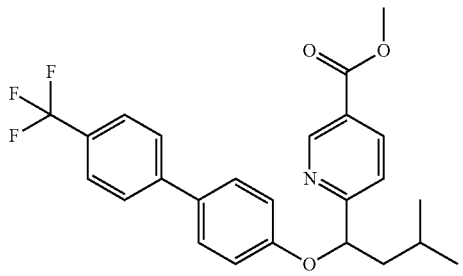 [SMILES: COC(=O)c1ccc(C(CC(C)C)Oc2ccc(-c3ccc(C(F)(F)F)cc3)cc2)nc1]

To a 0° C. solution of 4'-(trifluoromethyl)biphenyl-4-ol (133 mg, 0.56 mmol), methyl 6-(1-hydroxy-3-methylbutyl)nicotinate (150 mg, 0.67 mmol) and triphenylphosphine (147 mg, 0.56 mmol) in tetrahydrofuran (2 mL) was added diisopropyl azodicarboxylate (113 mg, 0.56 mmol). The reaction was stirred at room temperature overnight. The reaction was washed with brine (10 mL), dried over sodium sulfate, filtered and concentrated. Purification by column chromatography gave methyl 6-(3-methyl-1-(4'-(trifluoromethyl)biphenyl-4-yloxy)butyl)nicotinate. $^1$H NMR (400 MHz, CDCl$_3$, δ): 9.19 (s, 1H), 8.25-8.23 (d, 1H), 7.63-7.61 (d, 2H), 7.58-7.56 (d, 2H), 7.49-7.47 (d, 1H), 7.44-7.43 (d, 2H), 6.93-6.90 (d, 2H), 5.40-5.37 (m, 1H), 3.93 (s, 3H), 2.00-1.93 (m, 2H), 1.75-1.70 (m, 1H), 1.03-0.96 (m, 6H).

Step C: 6-(3-methyl-1-(4'-(trifluoromethyl)biphenyl-4-yloxy)butyl)nicotinic acid

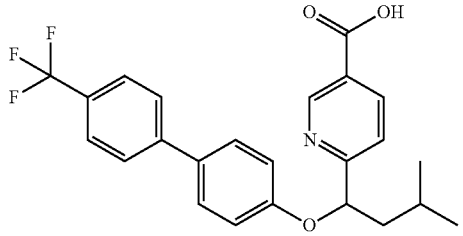 [SMILES: CC(C)CC(Oc1ccc(-c2ccc(C(F)(F)F)cc2)cc1)c1ccc(C(=O)O)cn1]

To a solution of methyl 4-(1-(4'-(trifluoromethyl)biphenyl-4-yloxy)butyl)nicotinate (150 mg, 0.34 mmol) in tetrahydrofuran (10 mL) was added 2N LiOH (10 mL). The reaction was stirred for 2 hours at 30° C. The reaction was acidified to pH=5 by addition of 1N HCl and extracted with ethyl acetate. The organic layer was dried over sodium sulfate, filtered and concentrated to give 6-(3-methyl-1-(4'-(trifluoromethyl)biphenyl-4-yloxy)butyl)nicotinic acid as a yellow gum. $^1$H NMR (400 MHz, CDCl$_3$, δ): 9.25 (s, 1H), 8.30-8.28 (d, 1H), 7.64-7.61 (d, 2H), 7.58-7.56 (d, 2H), 7.54-7.52 (d, 1H), 7.44-7.42 (d, 2H), 6.94-6.91 (d, 2H), 5.43-5.40 (m, 1H), 1.98-1.95 (m, 2H), 1.80-1.74 (m, 1H), 1.04-0.97 (m, 6H).

Step D: (+/−)-3-(6-(3-methyl-1-(4'-(trifluoromethyl)biphenyl-4-yloxy)butyl)nicotinamido)propanoic acid To a solution of 6-(3-methyl-1-(4'-(trifluoromethyl)biphenyl-4-yloxy)butyl)nicotinic acid (150 mg, 0.35 mmol) in N,N-dimethylformamide (2 mL) were added O-(7-azabenzotriazol-1-yl)-N,N,N',N'-tetramethyl uronium hexafluorophosphate (358 mg, 0.94 mmol) and N-methylmorpholine (212 mg, 2.1 mmol). After stirring for 15 min, methyl 3-aminopropionate hydrochloride (73.0 mg, 0.52 mmol) was added. The resulting mixture was stirred overnight at room temperature. The mixture was poured into water and extracted with ethyl acetate. The combined organic layers were washed with brine, dried over sodium sulfate, filtered and concentrated.

The crude residue was dissolved in tetrahydrofuran (10 mL) and 2N LiOH (10 mL) was added. The reaction mixture was stirred for 2 h at 30° C. The reaction was acidified to pH=5 by addition of 1N HCl, and extracted with ethyl acetate. The organic layer was dried over sodium sulfate and concentrated. Purification by HPLC (column: Boston Analytics Symmetrix ODS-H 150×30 mm, 5 μm; modifier: formic acid 0.225%; gradient: 60 to 80% MeCN in water) gave (+/−)-3-(6-(3-methyl-1-(4'-(trifluoromethyl)biphenyl-4-yloxy)butyl)nicotinamido)propanoic acid (46.1 mg, 27.2%) as a white solid. $^1$H NMR (400 MHz, CD$_3$OD, δ): 8.94 (s, 1H), 8.15-8.12 (d, 1H), 7.66-7.61 (m, 4H), 7.55-7.53 (d, 1H), 7.50-7.47 (d, 2H), 6.94-6.92 (d, 2H), 5.43-5.40 (m, 1H), 3.63-3.59 (m, 2H), 2.63-2.60 (m, 2H), 1.97-1.99 (m, 2H), 1.70-1.69 (m, 1H), 1.01-0.97 (m, 6H). MS (M+1): 501.4.

Example 3.2

(+/−)-3-(6-(3-methyl-1-(4'-(trifluoromethyl)biphenyl-4-yl)butoxy)nicotinamido)propanoic acid

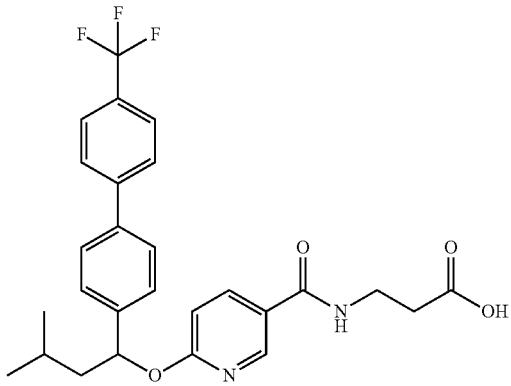 [SMILES: CC(C)CC(Oc1ccc(C(=O)NCCC(=O)O)cn1)c1ccc(-c2ccc(C(F)(F)F)cc2)cc1]

Step A: 3-methyl-1-(4'-(trifluoromethyl)biphenyl-4-yl)butan-1-ol

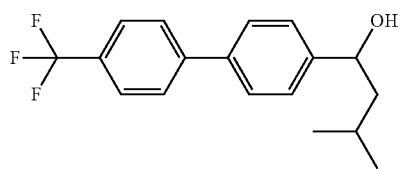

To a solution of 4'-(trifluoromethyl)biphenyl-4-carbaldehyde (7.0 g, 28 mmol) in tetrahydrofuran (280 mL) was added isobutylmagnesium bromide (21 mL, 2M in THF, 42 mmol)

dropwise at −15° C. The reaction was stirred at −10° C. for 2 hours. The reaction was quenched with 1N HCl (10 mL) and extracted with ethyl acetate (3×20 mL). The combined organics were dried over sodium sulfate, filtered and concentrated. Purification by column chromatography gave 3-methyl-1-(4'-(trifluoromethyl)biphenyl-4-yl)butan-1-ol (3.9 g, 45%) as a solid. $^1$H NMR (400 MHz, CDCl$_3$, δ): 7.62 (s, 4H), 7.52-7.50 (m, 2H), 7.40-7.38 (m, 2H), 4.77-4.73 (m, 1H), 1.75-1.67 (m, 1H), 1.50-1.46 (m, 2H), 0.92-0.90 (m, 6H).

Step B: methyl 6-(3-methyl-1-(4'-(trifluoromethyl)biphenyl-4-yl)butoxy)nicotinate

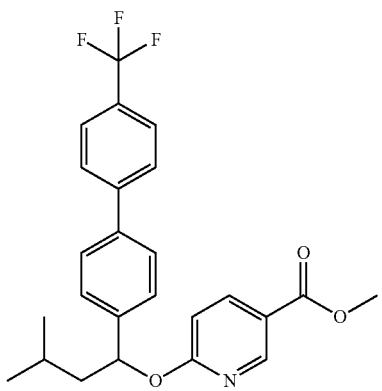 [SMILES: COC(=O)c1ccc(OC(CC(C)C)c2ccc(-c3ccc(C(F)(F)F)cc3)cc2)nc1]

A mixture of triphenylphosphine (1.34 g, 5.09 mmol), 3-methyl-1-(4'-(trifluoromethyl)biphenyl-4-yl)butan-1-ol (942 mg, 3.06 mmol), and methyl 6-hydroxynicotinate (0.390 g, 2.55 mmol) in tetrahydrofuran (30 mL) was stirred at room temperature for 0.5 hours. Diisopropyl azodicarboxylate (1.02 g, 5.09 mmol) was added dropwise. After consumption of the starting material, as indicated by TLC, the mixture was concentrated. Purification by column chromatography gave methyl 6-(3-methyl-1-(4'-(trifluoromethyl)biphenyl-4-yl)butoxy)nicotinate (400.0 mg, 36%). $^1$H NMR (400 MHz, CDCl$_3$, δ): 8.69 (d, 1H), 8.04-8.06 (m, 1H), 7.56-7.61 (m, 4H), 7.42-7.48 (m, 4H), 6.72 (d, 1H), 6.20-6.24 (m, 1H), 3.78 (s, 3H), 1.94-2.01 (m, 1H), 1.58-1.72 9 (m, 2H), 0.89-0.94 (m, 6H).

Step C: Preparation of methyl 3-(6-(3-methyl-1-(4'-(trifluoromethyl)biphenyl-4-yl)butoxy)nicotinamido) propanoate

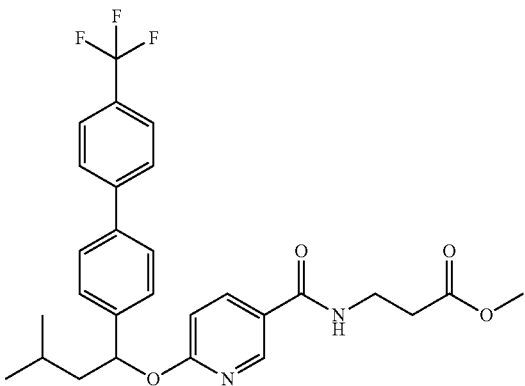 [SMILES: COC(=O)CCNC(=O)c1ccc(OC(CC(C)C)c2ccc(-c3ccc(C(F)(F)F)cc3)cc2)nc1]

To a solution of methyl 6-(3-methyl-1-(4'-(trifluoromethyl)biphenyl-4-yl)butoxy)nicotinate (400.0 mg, 0.46 mmol) in tetrahydrofuran (5 mL) was added a solution of LiOH monohydrate (378 mg, 9.02 mmol) in water (5 mL) dropwise at 0° C. After the addition, the mixture was stirred at room temperature for 48 hours. Tetrahydrofuran was removed under reduced pressure and the remaining aqueous residue was acidified to pH=3 by addition of 1N HCl. The mixture was extracted with ethyl acetate. The organic layer was washed with water and brine, dried over sodium sulfate, filtered and concentrated. The residue was dissolved in N,N-dimethylformamide (5 mL) and O-(7-azabenzotriazol-1-yl)-N,N,N',N'-tetramethyl uronium hexafluorophosphate (637 mg, 1.68 mmol) was added. The mixture was stirred for 15 minutes at ambient temperature. Methyl 3-aminopropanoate hydrochloride (150 mg, 1.10 mmol) and diisopropylethylamine (540 mg, 4.2 mmol) were added to the reaction mixture. The resulting mixture was stirred at room temperature for 1 hour. The mixture was poured into saturated NaCl (20 mL) and was extracted with ethyl acetate (30 mL). The organic layer was washed with water (20 mL) and brine (20 mL), dried over sodium sulfate and concentrated. Purification by preparative TLC gave methyl 3-(6-(3-methyl-1-(4'-(trifluoromethyl)biphenyl-4-yl)butoxy)nicotinamido)propanoate (400 mg) as a white solid. $^1$H NMR (400 MHz, CDCl$_3$, δ): 8.40 (m, 1H), 7.87-7.90 (m, 1H), 7.56-7.61 (m, 4H), 7.41-7.48 (m, 4H), 6.74 (d, 1H), 6.62-6.65 (m, 1H), 6.15-6.19 (m, 1H), 3.59-3.54 (m, 5H), 2.53-2.56 (m, 2H), 1.94-2.01 (m, 1H), 1.57-1.73 (m, 2H), 0.89-0.94 (m, 6H).

Step D: (+/−)-3-(6-(3-methyl-1-(4'-(trifluoromethyl)biphenyl-4-yl)butoxy)nicotinamido) propanoic acid To a solution of methyl 3-(6-(3-methyl-1-(4'-(trifluoromethyl)biphenyl-4-yl)butoxy)nicotinamido)propanoate (0.40 g, 0.77 mmol) in tetrahydrofuran (5 mL) was added a solution of LiOH monohydrate (326 mg, 7.77 mmol) in water (5 mL). The mixture was stirred at room temperature overnight. Tetrahydrofuran was removed under reduced pressure and the aqueous residue was acidified to pH=3 by addition of 1N HCl. The mixture was extracted with ethyl acetate. The organic layer was washed with water and brine, dried over sodium sulfate, filtered and concentrated. Purification by HPLC (column: Phenomenex Gemini 200×21.2 mm, 10 μm; modifier: ammonium hydroxide (to pH 10); gradient: 28 to 50% acetonitrile in water) gave (+/−)-3-(6-(3-methyl-1-(4'-(trifluoromethyl)biphenyl-4-yl)butoxy)nicotinamido)propanoic acid (30 mg) as a white solid. $^1$H NMR (400 MHz, CD$_3$OD, δ): 8.49-8.53 (m, 1H), 8.0-8.05 (m, 1H), 7.77 (d, 2H), 7.72 (d, 2H), 7.61 (d, 2H), 7.49 (d, 2H), 6.88 (d, 1H), 6.25-6.20 (m, 1H), 3.50-3.55 (m, 2H), 2.50-2.40 (m, 2H), 2.08-2.02 (m, 1H), 1.80-1.63 (m, 2H), 1.01-0.96 (m, 6H). MS (M+Na): 523.5.

Example 3.3

(+/−)-3-(6-(1-(4'-(trifluoromethyl)biphenyl-4-yloxy)ethyl)nicotinamido) propanoic acid

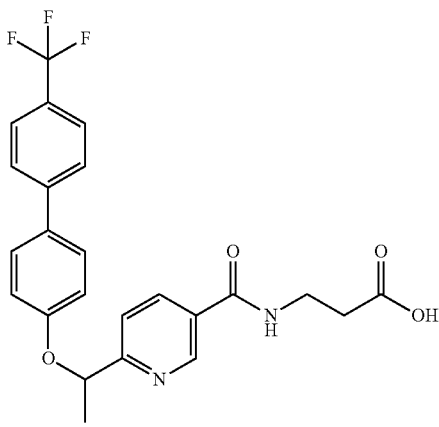 [SMILES: CC(Oc1ccc(-c2ccc(C(F)(F)F)cc2)cc1)c1ccc(C(=O)NCCC(=O)O)cn1]

Step A: Preparation of methyl 6-(1-hydroxyethyl)nicotinate

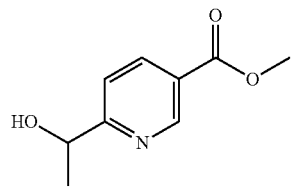

To a −78° C. solution of methyl 6-formylnicotinate (0.300 g, 1.82 mmol) in tetrahydrofuran (6 mL) was added methylmagnesium bromide (0.787 mL, 3M in THF, 2.36 mmol) over 20 minutes. The solution was warmed to 0° C. and stirred for 2 hours. The mixture was quenched with saturated ammonium chloride, extracted with ethyl acetate, dried over sodium sulfate, filtered and concentrated. Purification by preparative TLC gave methyl 6-(1-hydroxyethyl)nicotinate (230 mg, 70%) as a red oil. $^1$H NMR (400 MHz, CD$_3$OD, δ): 8.93 (m, 1H), 8.26-8.29 (m, 1H), 7.59 (d, 1H), 4.73-4.83 (m, 1H), 3.84 (s, 3H), 1.37 (d, 3H).

Step B: 6-(1-(4'-(trifluoromethyl)biphenyl-4-yloxy)ethyl)nicotinic acid

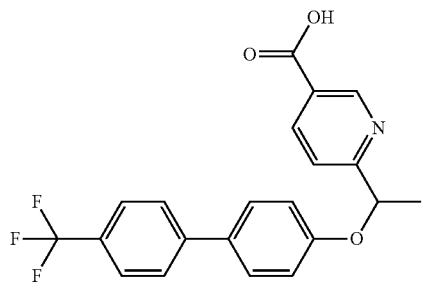 [SMILES: CC(Oc1ccc(-c2ccc(C(F)(F)F)cc2)cc1)c1ccc(C(=O)O)cn1]

To a 0° C. solution of methyl 6-(1-hydroxyethyl)nicotinate (0.100 g, 0.552 mmol) and 4-dimethylaminopyridine (152 mg, 1.32 mmol) in dichloromethane (10 mL) was added methanesulfonyl chloride (75.9 mg, 0.662 mmol) dropwise. The resulting mixture was stirred at room temperature for 1 hour. Additional methanesulfonyl chloride (75.9 mg, 0.662 mmol) was added and the mixture stirred at room temperature for an additional 2 hours. The mixture was quenched with water and extracted with dichloromethane. The organic layer was dried over sodium sulfate, filtered and concentrated to give crude methyl 641-(methylsulfonyloxy)ethyl)nicotinate (134 mg) as an oil which was used in the next step directly.

To a 0° C. solution of 4'-(trifluoromethyl)biphenyl-4-ol (263 mg, 1.1 mmol) in tetrahydrofuran (6 mL) was added sodium hydride (44.2 mg, 60 wt % in mineral oil, 1.1 mmol). The reaction mixture was stirred at 0° C. for 30 minutes. A solution of the crude methyl 641-(methylsulfonyloxy)ethyl)nicotinate prepared above in DMSO (6 mL) was added. The mixture was heated to 60° C. for 48 hours. The mixture was quenched with water and extracted with dichloromethane. The organic layer was dried over sodium sulfate, filtered and concentrated to give 6-(1-(4'-(trifluoromethyl)biphenyl-4-yloxy)ethyl)nicotinic acid (60 mg). $^1$H NMR (400 MHz, CD$_3$OD, δ): 8.98 (m, 1H), 8.19-8.21 (m, 1H), 7.54-7.61 (m, 4H), 7.42-7.44 (m, 3H), 6.86-6.89 (m, 1H), 5.42-4.43 (q, 1H), 1.58 (d, 9H).

Step C: (+/−)-3-(6-(1-(4'-(trifluoromethyl)biphenyl-4-yloxy)ethyl)nicotinamido) propanoic acid To a room temperature solution of 6-(1-(4'-(trifluoromethyl)biphenyl-4-yloxy)ethyl)nicotinic acid (60.0 mg, 0.16 mmol) in N,N-dimethylformamide (3 mL) was added O-(7-azabenzotriazol-1-yl)-N,N,N',N'-tetramethyl uronium hexafluorophosphate (118 mg, 0.310 mmol). Methyl 3-aminopropionate hydrochloride (32.4 mg, 0.232 mmol) and N-methylmorpholine (93.9 mg, 0.930 mmol) were added. The resulting mixture was stirred at room temperature for 12 hours. The reaction was diluted with saturated ammonium chloride and extracted with ethyl acetate. The combined organic layers were dried over sodium sulfate, filtered and concentrated. The residue was dissolved in tetrahydrofuran (5 mL). 2N LiOH (5 mL) was added. The mixture was stirred at room temperature for 2 hours. The reaction was acidified to pH ~3 with 1N HCl and extracted with ethyl acetate. The organic layer was dried over sodium sulfate, filtered and concentrated. Purification by HPLC (column: Kromasil Eternity-5-C18 150×30 mm, 5 μm; modifier: formic acid 0.225%; gradient: 46 to 66% MeCN in water) gave 3-(6-(1-(4'-(trifluoromethyl)biphenyl-4-yloxy)ethyl)nicotinamido)propanoic acid (25.3 mg, 34%). $^1$H NMR (400 MHz, CD$_3$OD, δ): 8.95 (m, 1H), 8.16-8.19 (m, 1H), 7.66-7.72 (m, 4H), 7.60-7.62 (m, 1H), 7.54-7.56 (m, 2H), 6.98-7.00 (m, 2H), 5.55-5.57 (q, 1H), 3.62-3.65 (m, 2H), 2.62-2.64 (m, 2H), 1.70 (d, 3H). MS (M+1): 459.4.

Example 4.1

(S)—N-({6-[(3-methyl-1-{4-[5-(trifluoromethyl)pyridin-2-yl]phenyl}butyl)amino]pyridin-3-yl}carbonyl)-beta-alanine

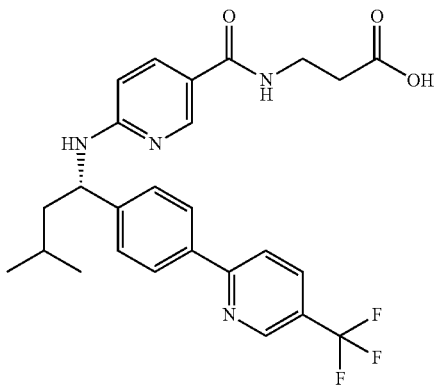 [SMILES: CC(C)C[C@H](Nc1ccc(C(=O)NCCC(=O)O)cn1)c1ccc(-c2ccc(C(F)(F)F)cn2)cc1]

Step A:
4-[5-(trifluoromethyl)pyridin-2-yl]benzaldehyde

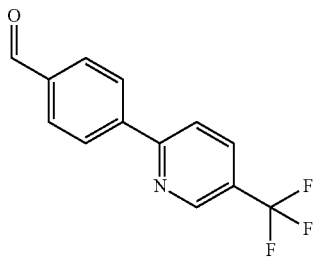 [SMILES: O=Cc1ccc(-c2ccc(C(F)(F)F)cn2)cc1]

To a solution of 4-formylphenylboronic acid (100 g, 0.67 mol) and 2-chloro-5-(trifluoromethyl)pyridine-2 (121 g, 0.67 mol) in acetonitrile (900 mL) was added Pd(dppf)Cl$_2$ (24 g, 33.5 mmol) and 2M aqueous Na$_2$CO$_3$ (837 mL). The resulting mixture was heated at reflux for 3 h under nitrogen atmosphere. The reaction mixture was extracted with ethyl acetate (3*500 mL). The combined organic layers were dried over Na$_2$SO$_4$, filtered and concentrated under reduced pressure. The crude material was purified by silica gel chromatography to give 4-(5-(trifluoromethyl)pyridin-2-yl)benzaldehyde (115 g) as a light yellow solid. $^1$H NMR (400 MHz CDCl$_3$) δ10.04 (s, 1H), 8.92 (s, 1H), 8.15 (d, J=8.0 Hz, 2H), 7.98 (d, J=8.0 Hz, 1H), 7.96 (d, J=8.0 Hz, 2H), 7.86 (d, J=8.0 Hz, 1H). MS (M+1)=252.0.

Step B: (S)-2-methyl-N-[(1E)-{4-[5-(trifluoromethyl)pyridin-2-yl]phenyl}methylene]propane-2-sulfinamide

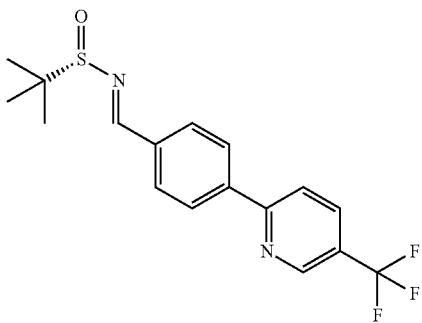 [SMILES: CC(C)(C)[S@](=O)/N=C/c1ccc(-c2ccc(C(F)(F)F)cn2)cc1]

A three-neck two liter flask equipped with dropping funnel, reflux condenser, and mechanical stirrer was charged with 4-[5-(trifluoromethyl)pyridin-2-yl]benzaldehyde (69.00 g, 274.7 mmol) and (S)-(−)-2-methyl-2-propanesulfinamide (33.66 g, 277.7 mmol). The apparatus was purged with dry nitrogen and warmed with a heat gun. The solids were suspended in dichloromethane (1.0 L) whereupon titanium(IV) ethoxide (115 ml, 549 mmol) was added dropwise over 30 minutes during which time the solids dissolved affording a yellow solution. No increase in temperature was observed. The reaction was heated to reflux for 12 hours. The reaction was quenched with a dropwise addition of MeOH (400 mL) followed by saturated aqueous sodium bicarbonate (150 mL). The resulting precipitate was removed by filtration through a pad of 1:1 celite:florisil and the filter cake was washed with ethyl acetate (3×200 ml). The resulting mixture was partially concentrated under vacuum (50% volume) and then dried over magnesium sulfate. The resulting solution was filtered through a Buchner funnel, the salts were washed with ethyl acetate (3×200 ml) and the resulting filtrate was concentrated in vacuo. The crude solid was suspended in heptane (250 ml) and heated to boiling with a heat gun whereupon ethyl acetate was added in aliquots to dissolve the solids. The mixture was then cooled slowly to affect crystallization (slowly to ambient temperature, then with ice). The solids were collected by vacuum filtration, and the process was repeated once more to yield the final product (78.78 g, 81%) as an off-white crystalline solid. $^1$H NMR (400 MHz, CDCl$_3$, δ): 9.01 (s, 1H), 8.67 (s, 1H), 8.19 (d, J=8.4 Hz, 2H), 8.07 (dd, J=8.4, 2.0 Hz, 1H), 8.01 (d, J=8.4 Hz, 2H), 7.94 (d, J=8.2 Hz, 1H), 1.30 (s, 9H). MS (M+1) 355.1.

Step C: (S,S)-2-methyl-N-(3-methyl-1-{4-[5-(trifluoromethyl)pyridin-2-yl]phenyl}butyl)propane-2-sulfinamide

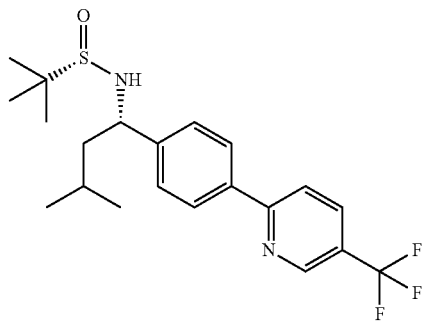 [SMILES: CC(C)C[C@H](N[S@@](=O)C(C)(C)C)c1ccc(-c2ccc(C(F)(F)F)cn2)cc1]

A three-neck three liter flask equipped with a mechanical stirred, internal thermometer, and dropping funnel was evacuated, heated with a heatgun, and backfilled with dry nitrogen three times. The apparatus was then charged with anhydrous zinc chloride (667 ml, 333 mmol, 0.5M in tetrahydrofuran) and the solution was cooled to 0° C. A solution of isobutylmagnesium bromide (511 ml, 1.02 mol, 2.0M in diethylether) was added dropwise to the well-stirred solution over approximately 1.5 hours, resulting in an exothermic reaction and the formation of a precipitate. The temperature was maintained below 15° C. through the course of the addition. At the conclusion, the dropping funnel was washed with tetrahydrofuran (3×20 ml) and the reaction was slowly warmed to ambient temperature and stirred for approximately 1.5 h. The reaction was cooled to −78° C., whereupon a solution of the (S)-2-methyl-N-[(1E)-{4-[5-(trifluoromethyl)pyridin-2-yl]phenyl}methylene]propane-2-sulfinamide (78.78 g, 222.3 mmol) in tetrahydrofuran (250 ml) was added dropwise over approximately 30 minutes. At this point, the reaction was quenched carefully with saturated aqueous ammonium chloride, the cold bath was removed, water was added and the reaction allowed to warm to ambient temperature. The contents were transferred to a separatory funnel, along with methyl tert-butylether and some additional water. The layers were separated and the aqueous layer was extracted with methyl tert-butylether (3×500 ml). The combined organic extracts were dried over magnesium sulfate, filtered, and concentrated in vacuo. The crude material was purified via ISCO MPLC (SiO$_2$, 0-80% ethyl acetate in heptane) to yield the product (74.0 g, 81%) as a gum. $^1$H NMR (400 MHz, CDCl$_3$, δ): 8.94 (s, 1H), 7.96-8.05 (m, 3H), 7.84 (d, J=8.2 Hz, 1H), 7.49 (d, J=8.2 Hz, 2H), 4.43-4.52 (m, 1H), 3.40-3.50 (m, 1H), 1.85-1.94 (m, 1H), 1.62-1.75 (m, 1H), 1.47-1.57 (m, 1H), 1.24 (s, 9H), 0.95 (d, J=6.4 Hz, 3H), 0.90 (d, J=6.6 Hz, 3H). MS (M-C4H10NOS): 292.1.

Step D: (S)-3-methyl-1-{4-[6-(trifluoromethyl)pyridin-2-yl]phenyl}butan-1-amine

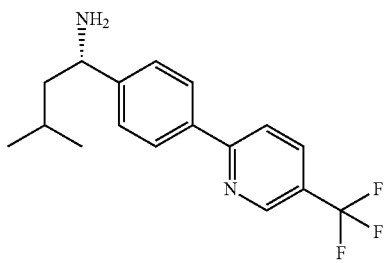 [SMILES: CC(C)C[C@H](N)c1ccc(-c2ccc(C(F)(F)F)cn2)cc1]

A cooled solution (0° C. by internal thermometer) of (S,S)-2-methyl-N-(3-methyl-1-{4-[5-(trifluoromethyl)pyridin-2-yl]phenyl}butyl)propane-2-sulfinamide (74.0 g, 179 mmol) in methanol (0.90 L) was treated with 2.0M hydrochloric acid in diethylether (233 ml, 466 mmol) dropwise while maintaining the reaction temperature below 15° C. Following 1 hour, the solvent was removed in vacuo and the resulting oil was treated with diethylether to precipitate the product as a fine white solid. The solid was collected via filtration, and washed with diethylether (3×100 ml). The remaining solid was dried in vacuo. The crude material was used for further transformations.

Step E: (S)-methyl 6-[(3-methyl-1-{4-[5-(trifluoromethyl)pyridin-2-yl]phenyl}butyl)amino]nicotinate

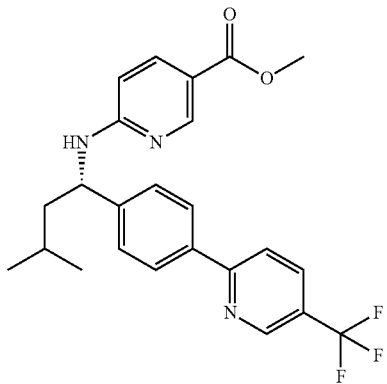 [SMILES: COC(=O)c1ccc(N[C@@H](CC(C)C)c2ccc(-c3ccc(C(F)(F)F)cn3)cc2)nc1]

A mixture of crude (S)-3-methyl-1-{4-[5-(trifluoromethyl)pyridin-2-yl]phenyl}butan-1-amine (66.34 g, 192.4 mmol), methyl 6-fluoronicotinate (32.8 g, 212 mmol), and freshly pulverized and dried (150 C, vacuum oven, 12 h) tripotassium phosphate (75.6 g, 356 mmol) was purged with dry nitrogen then diluted with N,N-dimethylacetamide (320 ml). The mixture was heated to 110° C. (107-108° C. internal temperature) for 24 hours. The reaction was diluted with water (~1.5 L) and the resulting mixture was stirred vigorously for 15 minutes. The aqueous portion was decanted, leaving behind a thick amorphous solid. This material was washed with water (2×1 L). The resulting solid was dissolved in ethyl acetate and the remaining water was removed via azeotropic distillation (rotary evaporator, approximately 2×1 L ethyl acetate). The combined aqueous layers were stirred vigorously for 12 hours resulting in the precipitation of an additional aliquot (approximately 500 mg) of the crude product that was combined with the originally recovered material. The crude material was purified via ISCO MPLC (SiO$_2$, 0-75% ethyl acetate in heptane) to yield the product (53.0 g, 62%) as a white foam. $^1$H NMR (400 MHz, CDCl$_3$, δ): 8.93 (s, 1H), 8.72 (d, J=2.0 Hz, 1H), 8.00 (d, J=8.2 Hz, 2H), 7.97 (dd, J=8.5, 2.1 Hz, 1H), 7.92 (dd, J=8.9, 2.2 Hz, 1H), 7.81 (d, J=8.4 Hz, 1H), 7.47 (d, J=8.2 Hz, 2H), 6.25 (d, J=8.8 Hz, 1H), 5.79 (d, J=6.5 Hz, 1H), 4.73-4.85 (m, 1H), 3.84 (s, 3H), 1.77-1.86 (m, 1H), 1.65-1.77 (m, 2H), 1.01 (d, J=6.1 Hz, 3H), 0.97 (d, J=6.1 Hz, 3H). MS (M+1): 444.5.

Step F: (S)-6-[(3-methyl-1-{4-[5-(trifluoromethyl)pyridin-2-yl]phenyl}butyl)amino]nicotinic acid

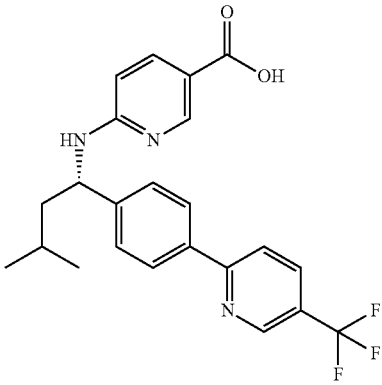 [SMILES: CC(C)C[C@H](Nc1ccc(C(=O)O)cn1)c1ccc(-c2ccc(C(F)(F)F)cn2)cc1]

A mixture of (S)-methyl 6-[(3-methyl-1-{4-[5-(trifluoromethyl)pyridin-2-yl]phenyl}butyl)amino]nicotinate (53.0 g, 119.5 mmol) was dissolved in methanol (239 ml) and tetrahydrofuran (120 ml) and treated with aqueous lithium hydroxide (120 ml, 239 mmol, 2.0M). An additional aliquot of methanol was added to homogenize the mixture (110 ml, ~2 ml/g). The reaction was heated to 50° C. for 12 h. The reaction was concentrated in vacuo, and the crude residue was diluted with water (500 ml). The solution was vigorously stirred and slowly acidified with aqueous 1.0M hydrochloric acid (240 ml, to approximately pH 5.0). The precipitated solid was collected by filtration and the remaining solid was dissolved with ethyl acetate and transferred into a separate flask. The crude solid was dried in vacuo and used directly for further transformations.

Step G: (S)-ethyl N-({6-[(3-methyl-1-{4-[5-(trifluoromethyl)pyridin-2-yl]phenyl}butyl)amino]pyridin-3-yl}carbonyl)-beta-alaninate

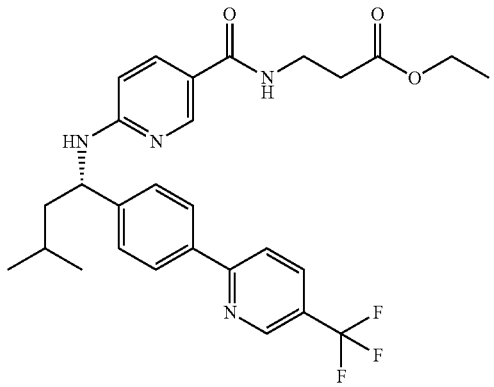 [SMILES: CCOC(=O)CCNC(=O)c1ccc(N[C@@H](CC(C)C)c2ccc(-c3ccc(C(F)(F)F)cn3)cc2)nc1]

To a mixture of ethyl 3-aminopropionate hydrochloride (41.1 g, 268 mmol), (S)-6-[(3-methyl-1-{4-[5-(trifluoromethyl)pyridin-2-yl]phenyl}butyl)amino]nicotinic acid (57.51 g, 133.9 mmol), hydroxybenzotriazole hydrate (20.5 g, 134 mmol), and triethylamine (103 ml, 737 mmol) in dichloromethane (1.34 L) was added 1-ethyl-3-(3-dimethylaminopropyl)carbodimide hydrochloride (38.9 g, 201 mmol) at ambient temperature. The reaction was heated to 40° C. for 12 hours. The reaction was diluted with saturated aqueous sodium bicarbonate (1.5 L) and the organic layer was separated. The aqueous layer was extracted with dichloromethane (2×500 ml) and the combined organic layers were washed with brine (1 L), then dried over sodium sulfate, filtered, and concentrated in vacuo. The crude material was purified via ISCO MPLC (SiO$_2$, 0-100% ethyl acetate in heptane) to yield the product (60.9 g, 86%) as a white foam. $^1$H NMR (400 MHz, CDCl$_3$, δ): 8.93 (s, 1H), 8.51 (d, J=2.0 Hz, 1H), 7.95-8.02 (m, 3H), 7.81 (d, J=8.6 Hz, 1H), 7.78 (dd, J=9.1, 2.4 Hz, 1H), 7.47 (d, J=8.2 Hz, 2H), 6.73 (t, J=5.7 Hz, 1H), 6.29 (d, J=8.8 Hz, 1H), 5.81-5.91 (m, 1H), 4.76 (q, J=6.8 Hz, 1H), 4.10-4.16 (m, 2H), 3.67 (q, J=6.1 Hz, 2H), 2.60 (t, J=5.9 Hz, 2H), 1.77-1.87 (m, 1H), 1.65-1.77 (m, 2H), 1.23-1.28 (m, 3H), 1.01 (d, J=6.1 Hz, 3H), 0.97 (d, J=6.1 Hz, 3H). MS (M+1): 529.3.

Step H: (S)—N-({6-[(3-methyl-1-{4-[5-(trifluoromethyl)pyridin-2-yl]phenyl}butyl)amino]pyridin-3-yl}carbonyl)-beta-alanine

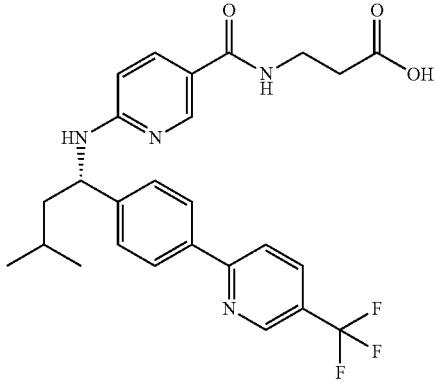 [SMILES: CC(C)C[C@H](Nc1ccc(C(=O)NCCC(=O)O)cn1)c1ccc(-c2ccc(C(F)(F)F)cn2)cc1]

A mixture of (S)-ethyl N-({6-[(3-methyl-1-{4-[5-(trifluoromethyl)pyridin-2-yl]phenyl}butyl)amino]pyridin-3-yl}carbonyl)beta-alaninate (60.9 g, 115 mmol) was dissolved in methanol (230 ml) and tetrahydrofuran (115 ml) and treated with aqueous lithium hydroxide (115 ml, 0.230 mol, 2.0M). The reaction was heated to 50° C. for 30 minutes. The solution was concentrated in vacuo, and the resulting residue was diluted with water (approximately 500 ml). The mixture was then acidified with aqueous 1.0M hydrochloric acid (230 ml, to approximately pH 4.0). The precipitated solid was collected by filtration and washed with water (2×100 ml). Air was pulled through the filter cake over 12 hours to affect drying of the product. The crude solid was transferred into a 2-liter flask with a stirbar and the solid was suspended in ethyl acetate (approximately 1.5 L). Sodium sulfate (approximately 500 g) was added and the mixture was stirred vigorously for a further 1 hour. The cloudy mixture was filtered through a plug of celite, resulting in a clear solution. The solution was concentrated in vacuo and the remaining solid was suspended in diethyl ether (1 L) and concentrated in vacuo (the process was repeated twice). The resulting solid was pulverized with a mortar and pestle, and dried in a vacuum oven for 12 hours at 60° C. The final product (50.1 g, 87%) was obtained as a off-white solid. $^1$H NMR (400 MHz, DMSO-d$_6$, δ): 9.01 (s, 1H), 8.39 (d, J=1.2 Hz, 1H), 8.26 (dd, J=8.4, 2.0 Hz, 2H), 8.15 (d, J=8.4 Hz, 1H), 8.10 (d, J=8.2 Hz, 2H), 7.84 (d, J=6.7 Hz, 1H), 7.55 (d, J=8.2 Hz, 2H), 6.66 (br. s., 1H), 5.15 (br. s., 1H), 3.33-3.43 (m, 2H), 2.45 (t, J=7.0 Hz, 2H), 1.74-1.86 (m, 1H), 1.62-1.72 (m, 1H), 1.51-1.62 (m, 1H), 0.95 (d, J=6.5 Hz, 3H), 0.92 (d, J=6.5 Hz, 3H). MS (M+1): 501.4.

Example 4.2

(+/−)-N-({6-[(cyclohexyl{2-[4-(trifluoromethyl)phenyl]pyrimidin-5-yl}methyl)amino]pyridin-3-yl}carbonyl)-beta-alanine

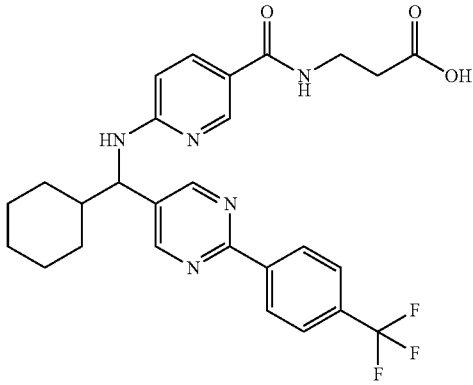 [SMILES: O=C(O)CCNC(=O)c1ccc(NC(c2cnc(-c3ccc(C(F)(F)F)cc3)nc2)C2CCCCC2)nc1]

Step A: 2-Dimethylaminormethylene-1,3-bis(dimethylimmonio)proqane bis(tetrafluoroborate

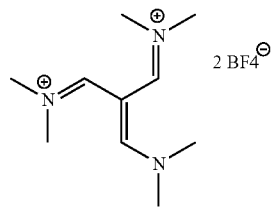

To a 3-neck flask equipped with a reflux condenser was added bromoacetic acid (25 g, 0.18 mol) and POCl$_3$ (50 mL, 0.54 mol). The solution was cooled to 0° C. and DMF (84 mL, 1.1 mol) was added dropwise over 30 min. The resulting solution was heated to 110° C. for 3 h. As the mixture was heated, it began to exotherm and evolve gas. The mixture was cooled to 0° C. and a solution of aqueous 40% HBF$_4$ (63 g, 0.36 mol) in methanol (100 mL) was added slowly over 1 h, via an addition funnel. Isopropanol (100 mL) was added. The resulting slurry was stirred at 0° C. for 2 h. The solids were collected by filtration to provide 2-Dimethylaminormethylene-1,3-bis(dimethylimmonio)propane bis(tetrafluoroborate (50 g) as a pale yellow solid. $^1$H NMR (400 MHz, DMSO-d$_6$) δ 8.42 (s, 3H), 3.54 (s, 9H), 3.39 (s, 9H).

4-(trifluoromethyl)benzimidamide hydrochloride

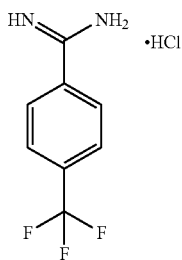 [SMILES: N=C(N)c1ccc(C(F)(F)F)cc1 ; Cl]

To a 3-neck flask equipped with a reflux condenser was added 4-(trifluoromethyl)benzonitrile (80 g, 0.468 mol), NaNH$_2$ (27.4 g, 0.701 mol), 18-Crown-6 (1.2 g) and toluene (350 mL). The solution was heated to reflux for 4 h. The mixture was cooled to 0° C. and concentrated aqueous HCl (140 mL) was added slowly. The precipitated solid was collected by filtration and washed with 1:2 methanol:dichloromethane (1:2, 250 mL) to provide 4-(trifluoromethyl)benzimidamide hydrochloride (53 g) as a yellow solid. $^1$H NMR (400 MHz, DMSO-d$_6$) δ 9.83 (s, 2H), 9.62(s, 2H), 8.09 (d, J=8.0 Hz, 2H), 7.90 (d, J=8.0 Hz, 2H).

2-(4-(trifluoromethyl)phenyl)pyrimidine-5-carbaldehyde

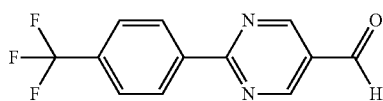

To a solution of containing 4-(trifluoromethyl)benzimidamide hydrochloride (50 g, 0.22 mol) and 2-dimethylaminomethylene-1,3-bis(dimethylammonio)propane bis(tetrafluoroborate (50 g, 0.27 mol) in ethanol (500 mL) was added sodium methoxide (36 g, 0.67 mol). The mixture was stirred for 1 h at 90° C. then cooled to room temperature. The mixture was extracted with ethyl acetate (200 mL*3). The organic layer was dried over Na$_2$SO$_4$, filtered and concentrated under reduced pressure. The crude product was purified via silica gel chromatography to give 2-(4-(trifluoromethyl)phenyl)pyrimidine-5-carbaldehyde (25 g) as a colorless solid. $^1$H NMR (400 MHz, CDCl$_3$) δ 10.12 (s, 1H), 9.19 (s, 2H), 8.61 (d, J=8.0 Hz, 2H), 7.72 (d, J=8 Hz, 2H).

Step B: (+/−)-cyclohexyl{2-[4-(trifluoromethyl)phenyl]pyrimidin-5-yl}methanol

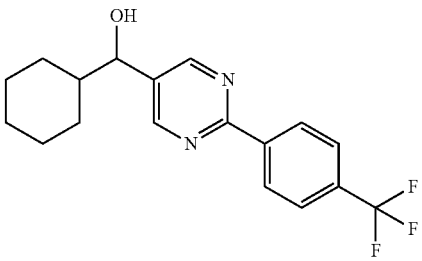 [SMILES: OC(c1cnc(-c2ccc(C(F)(F)F)cc2)nc1)C1CCCCC1]

To a solution of 4-[5-(trifluoromethyl)pyrimidin-2-yl]carbaldehyde (1.00 g, 3.97 mmol) in tetrahydrofuran (19.8 ml) was added cyclohexylmagnesium bromide (2.58 ml, 5.15 mmol, 2.0M in diethyl ether) at −78° C. The solution turned a deep red color that shifted to blue as the Grignard reagent was added. The reaction was stirred at −78° C. for 1 hour then quenched with saturated aqueous ammonium chloride. The reaction was warmed to ambient temperature, then diluted with diethylether. The organic layer was separated and the aqueous layer was extracted with diethyl ether (3×). The combined organic extracts were dried over sodium sulfate, filtered, and concentrated in vacuo. The crude material was purified via ISCO MPLC (SiO$_2$, 0-100% ethyl acetate in heptane) to yield the product (0.440 g, 33%) as a solid. $^1$H NMR (400 MHz, CDCl$_3$, δ): 8.78 (s, 2H), 8.58 (d, J=8.0 Hz, 2H), 7.76 (d, J=8.4 Hz, 2H), 4.56 (dd, J=6.3, 3.3 Hz, 1H), 1.99 (d, J=3.5 Hz, 1H), 1.94 (d, J=12.3 Hz, 1H), 1.65-1.86 (m, 4H), 1.52-1.58 (m, 1H), 0.97-1.31 (m, 5H). MS (M+1): 337.2.

Step C: cyclohexyl{2-[4-(trifluoromethyl)phenyl]pyrimidin-5-yl}methanone

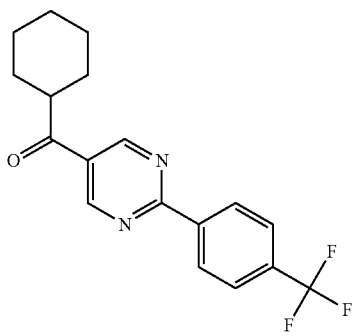 [SMILES: O=C(c1cnc(-c2ccc(C(F)(F)F)cc2)nc1)C1CCCCC1]

A mixture of (+/−)-cyclohexyl{2-[4-(trifluoromethyl)phenyl]pyrimidin-5-yl}methanol (0.440 g, 1.31 mmol) in dichloromethane (4.8 ml), dimethyl sulfoxide (3.7 ml) and triethylamine (0.911 ml, 6.54 mmol) was cooled to 0° C. Sulfur trioxide pyridine complex (0.625 g, 3.92 mmol) was added in portions and the mixture stirred at 0° C. for 1 hour then slowly raised to ambient temperature over 12 hours. The reaction was quenched with water and diluted with diethylether. The aqueous layer was extracted with diethylether and the combined organic layers were washed with brine. The combined organic extracts were dried over magnesium sulfate, filtered and concentrated in vacuo, affording a crude solid. This material was used without further purification.

Step D: (+/−)-1-cyclohexyl-1-{2-[4-(trifluoromethyl)phenyl]pyrimidin-5-yl}methanamine

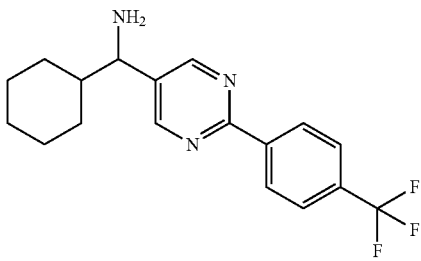 [SMILES: NC(c1cnc(-c2ccc(C(F)(F)F)cc2)nc1)C1CCCCC1]

To a solution of crude cyclohexyl{2-[4-(trifluoromethyl)phenyl]pyrimidin-5-yl}methanone (505 mg, 1.51 mmol), and ammonium acetate (1.19 g, 15.1 mmol) in methanol (7.6 ml) was added sodium cyanoborohydride (0.150 g, 2.26 mmol). The flask was fitted with a reflux condenser and heated to reflux for 12 hours. The reaction was concentrated in vacuo, then diluted with dichloromethane and aqueous 1.0M sodium hydroxide. The mixture was stirred for 30 minutes, whereupon the aqueous layer was extracted with dichloromethane (3×). The combined organic layers were dried over sodium sulfate, filtered, and concentrated in vacuo. The crude material was diluted in dichloromethane, passed through a plug of SiO2 with 20% methanol in dichloromethane and was concentrated in vacuo. The crude product was used without further purification.

Step E: (+/−)-methyl 6-[(cyclohexyl{2-[4-(trifluoromethyl)phenyl]pyrimidin-5-yl}methyl)amino]nicotinate

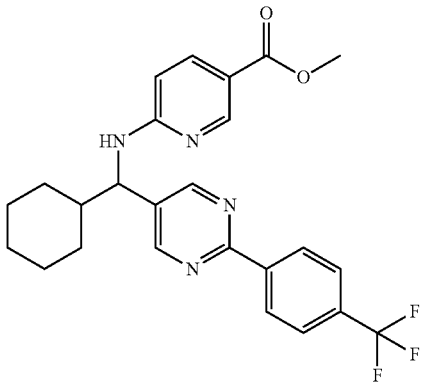 [SMILES: COC(=O)c1ccc(NC(c2cnc(-c3ccc(C(F)(F)F)cc3)nc2)C2CCCCC2)nc1]

A mixture of crude (+/−)-1-cyclohexyl-1-{2-[4-(trifluoromethyl)phenyl]pyrimidin-5-yl}methanamine (405 mg, 1.21 mmol), methyl 6-fluoronicotinate (225 mg, 1.45 mmol), and potassium carbonate (501 mg, 3.62 mmol) in N,N-dimethylformamide (4.2 ml) was heated to 120° C. for 12 hours. The reaction mixture was diluted with water to precipitate a crude solid that was collected by filtration. The crude material was purified via ISCO MPLC (SiO2, 0-50% ethyl acetate in heptane) to yield the product (0.486 g, 86%) as a solid. $^1$H NMR (400 MHz, CDCl$_3$, δ): 8.78 (s, 2H), 8.70 (d, J=1.6 Hz, 1H), 8.55 (d, J=8.2 Hz, 2H), 7.94 (dd, J=8.8, 2.0 Hz, 1H), 7.74 (d, J=8.2 Hz, 2H), 6.31 (d, J=8.8 Hz, 1H), 5.38 (d, J=7.0 Hz, 1H), 4.76 (t, J=6.9 Hz, 1H), 3.84 (s, 3H), 1.97 (d, J=12.5 Hz, 1H), 1.59-1.88 (m, 5H), 1.04-1.34 (m, 5H). MS (M+1): 471.2.

Step F: (+/−)-6-[(cyclohexyl{2-[4-(trifluoromethyl)phenyl]pyrimidin-5-yl}methyl)amino]nicotinic acid

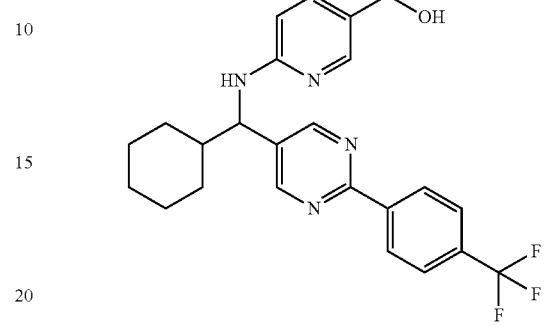

A mixture of the (+/−)-methyl 6-[(cyclohexyl{2-[4-(trifluoromethyl)phenyl]pyrimidin-5-yl}methyl)amino]nicotinate (486 mg, 1.03 mmol) was dissolved in methanol (2.1 ml) and tetrahydrofuran (1.0 ml) and treated with aqueous lithium hydroxide (1.0 ml, 2.1 mmol, 2.0M). The reaction was heated to 50° C. for 12 hours. The mixture was concentrated in vacuo, and the residue was diluted with water and acidified with aqueous 1.0M hydrochloric acid. The mixture was then concentrated in vacuo a second time, and the crude residue was used directly for further transformations.

Step G: (+/−)-ethyl N-({6-[(cyclohexyl{2-[4-(trifluoromethyl)phenyl]pyrimidin-5-yl}methyl)amino]pyridin-3-yl}carbonyl)-beta-alaninate

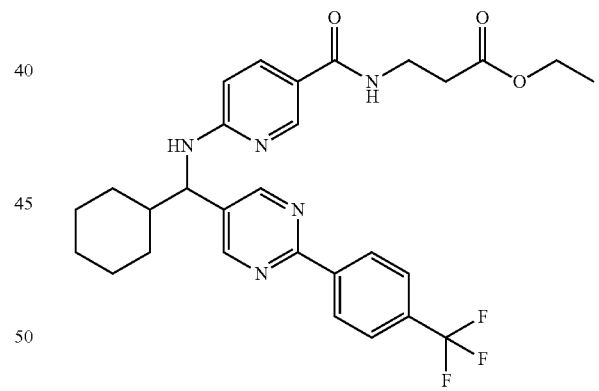

To a mixture of ethyl 3-aminopropionate hydrochloride (487 mg, 4.15 mmol), crude (+/−)-6-[(cyclohexyl{2-[4-(trifluoromethyl)phenyl]pyrimidin-5-yl}methyl)amino]nicotinic acid (948 mg, 2.08 mmol), hydroxybenzotriazole hydrate (318 mg, 2.08 mmol), and triethylamine (1.16 ml, 8.31 mmol) in dichloromethane (21 ml) was added 1-ethyl-3-(3-dimethylaminopropyl)carbodiimide hydrochloride (442 mg, 2.28 mmol). The reaction was stirred for 12 hours at ambient temperature. The reaction was diluted with water and the organic layer was separated. The aqueous layer was extracted with dichloromethane (2×) and the combined organic layers were dried over sodium sulfate, filtered, and concentrated in vacuo. The crude material was purified via ISCO MPLC (SiO2, 0-100% ethyl acetate in heptane) to yield the product. The enantiomers were separated by chiral SFC to afford the two products (Isomer 1=50 mg, 5% and isomer 2=50 mg, 5%) as solids. Column: Chiralcel OJ-H. Dimensions: 10 mm×250 cm. Mobile Phase: 70/30 $CO_2$/methanol. Flow Rate: 10 mL/min. Modifier: none. Isomer 1: Retention time: 2.37 minutes. Isomer 2: Retention time: 2.95 minutes. $^1$H NMR (400 MHz, $CDCl_3$, δ): 8.76 (s, 2H), 8.53 (d, J=8.2 Hz, 2H), 8.43 (d, J=2.0 Hz, 1H), 7.78 (dd, J=8.7, 2.2 Hz, 1H), 7.71 (d, J=8.2 Hz, 2H), 6.71 (t, J=5.8 Hz, 1H), 6.30-6.36 (m, 1H), 5.84 (br. s., 1H), 4.68 (t, J=6.9 Hz, 1H), 4.13 (q, J=6.9 Hz, 2H), 3.65 (q, J=5.9 Hz, 2H), 2.58 (t, J=5.8 Hz, 2H), 1.95 (d, J=12.3 Hz, 1H), 1.56-1.85 (m, 6H), 1.23 (t, J=7.0 Hz, 3H), 1.04-1.20 (m, 4H). MS (M+1): 556.4.

Step H: (+/−)-N-({6-[(cyclohexyl{2-[4-(trifluoromethyl)phenyl]pyrimidin-5-yl}methyl)amino]pyridin-3-yl}carbonyl)-beta-alanine

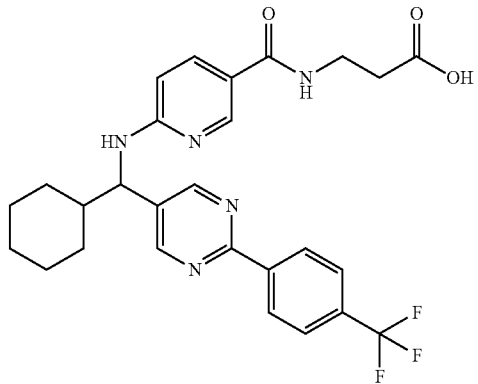 [SMILES: O=C(O)CCNC(=O)c1ccc(NC(c2cnc(-c3ccc(C(F)(F)F)cc3)nc2)C2CCCCC2)nc1]

In two separate reaction vessels, (+) and (−)-ethyl N-({6-[(cyclohexyl{2-[4-(trifluoromethyl)phenyl]pyrimidin-5-yl}methyl)amino]pyridin-3-yl}carbonyl)-beta-alaninate (0.050 g, 0.090 mmol) were separately dissolved in methanol (0.2 ml) and tetrahydrofuran (0.10) and treated with aqueous lithium hydroxide (0.090 ml, 0.36 mmol, 2.0M aq.). The reactions were heated to 50° C. for 12 hours. The reactions were concentrated in vacuo, then diluted with water and acidified with aqueous 1.0M hydrochloric acid. The precipitated solids were collected for both acids and dried in vacuo to give the products as single enantiomers. $^1$H NMR (400 MHz, $CD_3OD$, δ): 8.91 (s, 2H), 8.60 (d, J=8.2 Hz, 2H), 8.34 (s, 1H), 8.18 (d, J=8.0 Hz, 1H), 7.80 (d, J=8.2 Hz, 2H), 7.10 (d, J=9.4 Hz, 1H), 4.79 (d, J=8.0 Hz, 2H), 3.58 (t, J=6.7 Hz, 2H), 2.60 (t, J=6.7 Hz, 2H), 1.92-2.09 (m, 2H), 1.66-1.90 (m, 3H), 1.53 (d, J=12.3 Hz, 1H), 1.05-1.43 (m, 7H). MS (M+1): 528.4.

5-(4-(trifluoromethyl)phenyl)pyrazin-2-amine

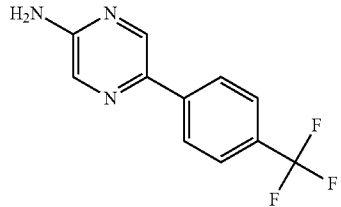 [SMILES: Nc1cnc(-c2ccc(C(F)(F)F)cc2)cn1]

A 100 mL round bottom flask was charged with 2-amino-5-iodopyrimidine (3.66 g, 21.1 mmol), (4-(trifluoromethyl)phenyl)boronic acid (4.00 g, 21.1 mmol) and MeCN (84 mL). Stirred 15 minutes at room temperature until a nice clear solution is obtained. The resulting solution is then treated with 1,1'-Bis(diphenylphosphino)ferrocene-palladium(11) dichloride dichloromethane complex (508 mg, 695 μmol) was added followed by the sodium carbonate 1M aq. (52.7 mL, 52.7 mmol). Reaction refluxed for 2 hours. Reaction cooled down to room temperature and dissolved with ammonium chloride solution (aq. sat.). Aqueous layer extracted with ethyl acetate (3×). Combined organic layers washed with brine (1×), dried over sodium sulfate, filtered and concentrated to give the crude material. Purification by silica gel flash chromatography (Ethyl Acetate/DCM) provide the title compound as a light yellow solid (4.4 g, 87%). $^1$H NMR (400 MHz, DMSO-$d_6$) δ 6.76 (s, 2 H) 7.76 (d, J=8.41 Hz, 2 H) 7.99 (d, J=1.57 Hz, 1 H) 8.14 (d, J=8.22 Hz, 2 H) 8.62 (d, J=1.37 Hz, 1 H). MS (M+1): 240.2.

tert-butyl (5-(4-(trifluoromethyl)phenyl)pyrazin-2-yl)carbamate

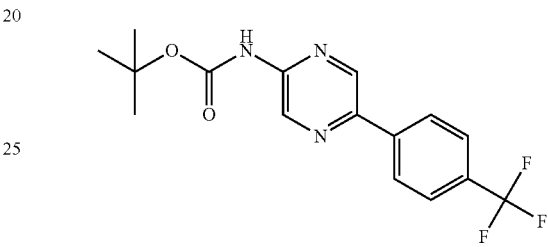

5-(4-(trifluoromethyl)phenyl)pyrazin-2-amine (4.40 g, 18.4 mmol) was suspended in acetonitrile (92 mL) and dimethylaminopyridine (116 mg, 920 μmol) was added in one portion. di-tert-butyl dicarbonate (4.01 g, 18.4 mmol) was then added and the reaction mixture was stirred overnight at room temperature. Reaction mixture diluted with citric acid solution (10% aq.)/water (1/1). After stirring for 5 minutes the reaction mixture was transferred to an extraction funnel and extracted with DCM (3×). Combined organic layers washed with water (1×), with brine (1×), dried over sodium sulfate, filtered and concentrated to provide the crude material. Purification by silica gel flash chromatography (Ethyl Acetate/DCM) provide the title compound as a white solid (3.14 g, 50.3%) $^1$H NMR (400 MHz, CHLOROFORM-d) δ 1.57-1.61 (m, 9 H) 7.74 (d, J=8.22 Hz, 2 H) 8.09 (d, J=8.02 Hz, 2 H) 8.13 (s, 1 H) 8.71 (d, J=1.56 Hz, 1 H) 9.40 (d, J=1.17 Hz, 1 H); MS (M+1): 340.1.

(±)-Ethyl 4-(1-((tert-butoxycarbonyl)(5-(4-(trifluoromethyl)phenyl)pyrazin-2-yl)amino)butyl)benzoate

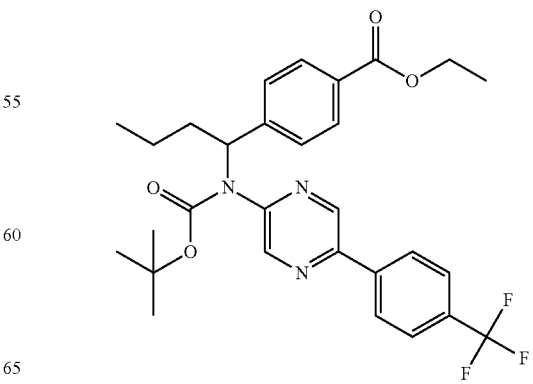

A round bottom flask was charged with triphenylphosphine (2.64 g, 10.0 mmol), diisopropylazodicarboxylate (1.99 mL, 10.0 mmol) and THF (23 mL) at 0° C. After the ylid crashed out of solution (less than 10 minutes), tert-butyl (5-(4-(trifluoromethyl)phenyl)pyrazin-2-yl)carbamate (3.10 g, 9.10 mmol) and (±)-ethyl 4-(1-hydroxybutyl)benzoate (2.03 g, 9.14 mmol) followed by THF (10 mL). Reaction stirred at room temperature overnight. Reaction diluted with DCM and ammonium chloride solution (aq. sat.) and transferred to an extraction funnel. Aqueous extracted twice with DCM. Combined organic layers washed with brine (1×), dried over sodium sulfate, filtered and concentrated to provide the crude material. Purification by silica gel flash chromatography (MeOH/DCM) provide the title compound as a yellow gum (4.86 g, 98.0%). $^1$H NMR (400 MHz, CHLOROFORM-d) δ 0.96 (t, 3 H) 1.36 (s, 9 H) 1.37-1.54 (m, 5 H) 2.06-2.18 (m, 1 H) 2.23-2.35 (m, 1 H) 4.38 (q, J=7.24 Hz, 2 H) 5.77 (dd, J=9.10, 6.55 Hz, 1 H) 7.51 (d, J=8.61 Hz, 2H) 7.76 (d, J=8.61 Hz, 2H) 7.95-8.02 (m, 2H) 8.12 (d, J=8.22 Hz, 2H) 8.74 (d, J=1.37 Hz, 1 H) 8.83 (d, J=1.56 Hz, 1 H); MS (M+1): 544.5.

(±)-4-(1-((5-(4-(trifluoromethyl)phenyl)pyrazin-2-yl)amino)butyl)benzoic acid

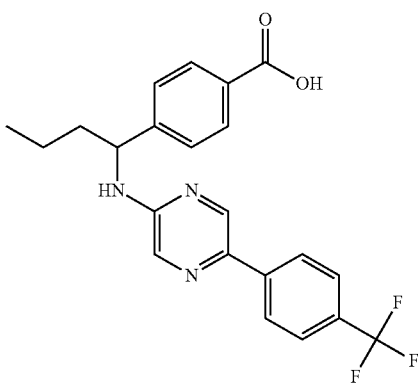 [SMILES: CCCC(Nc1cnc(-c2ccc(C(F)(F)F)cc2)cn1)c1ccc(C(=O)O)cc1]

Part A: A round bottom flask was charged with (±)-ethyl 4-(1-((tert-butoxycarbonyl)(5-(4-(trifluoromethyl)phenyl)pyrazin-2-yl)amino)butyl)benzoate (4.85 g, 8.92 mmol), DCM (60 mL) and TFA (15 mL). Reaction mixture stirred at room temperature for 3 hours. Sodium bicarbonate (sat. aq.) used to quench the excess TFA and the aqueous layer is extracted with DCM (3×). Combined organics washed with water (1×), brine (1×), dried over sodium sulfate filtered and concentrated to provide (±)-ethyl 4-(1-((5-(4-(trifluoromethyl)phenyl)pyrazin-2-yl)amino)butyl)benzoate as a crude orange gum (4.01 g, quant.). No further purification before next step. MS (M+1): 444.3.

Part B: A round bottom flask was charged with (±)-ethyl 4-(1-((5-(4-(trifluoromethyl)phenyl)pyrazin-2-yl)amino)butyl)benzoate (3.96 g, 8.93 mmol), MeOH (70 mL) and THF (70 mL). NaOH aq. 1M (44.6 mL) was then added in one portion and reaction stirred at room temperature for 1 hour and at 50° C. for 2 hours. Reaction mixture was cooled down to room temperature and organic solvents removed under reduced pressure. Water added to dissolve the crude solid and pH adjusted to ca. 4.5 with HCl (aq. 1N). The yellow solid formed was then recovered by filtration with a buchner funnel and dried under high vacuum to provide (±)-4-(1-((5-(4-(trifluoromethyl)phenyl)pyrazin-2-yl)amino)butyl)benzoic acid as a yellow solid (3.23 g, 87.1%). MS (M+1): 416.3.

(±)-ethyl 3-(4-(1-((5-(4-(trifluoromethyl)phenyl)pyrazin-2-yl)amino)butyl)benzamido) propanoate

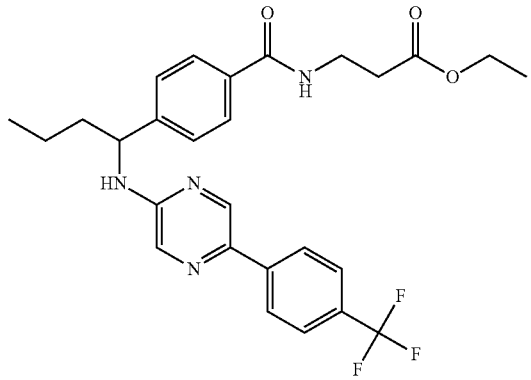 [SMILES: CCCC(Nc1cnc(-c2ccc(C(F)(F)F)cc2)cn1)c1ccc(C(=O)NCCC(=O)OCC)cc1]

The title compound is obtained by a method analogous to the one described for example 1.1 (step G) using (±)-4-(1-((5-(4-(trifluoromethyl)phenyl)pyrazin-2-yl)amino)butyl)benzoic acid for starting material to provide (±)-ethyl 3-(4-(1-((5-(4-(trifluoromethyl)phenyl)pyrazin-2-yl)amino)butyl)benzamido)propanoate (3.34 g, 84.0%) as a light yellow solid. $^1$H NMR (400 MHz, DMSO-d$_6$) δ 0.87 (t, 3 H) 1.12 (t, J=7.24 Hz, 3 H) 1.22-1.44 (m, 2 H) 1.63-1.86 (m, 2 H) 2.51 (t, J=6.94 Hz, 2 H) 3.38-3.47 (m, 2 H) 4.02 (q, J=7.11 Hz, 2 H) 4.92-5.01 (m, 1 H) 7.41 (d, J=8.22 Hz, 2 H) 7.71 (t, J=8.31 Hz, 4 H) 7.91 (d, J=7.63 Hz, 1 H) 8.02-8.11 (m, 3 H) 8.42 (t, J=5.48 Hz, 1 H) 8.54 (s, 1 H); MS (M+1): 515.4.

Example 4.3

(±)-3-(4-(1-((5-(4-(trifluoromethyl)phenyl)pyrazin-2-yl)amino)butyl)benzamido)propanoic acid

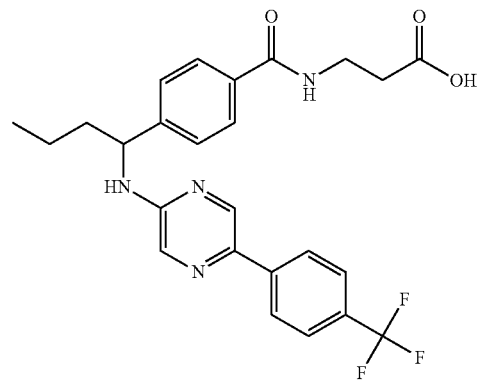

The title compound is obtained by a method analogous to the one described for example 1.1 (step H) using (±)-ethyl 3-(4-(1-((5-(4-(trifluoromethyl)phenyl)pyrazin-2-yl)amino)butyl)benzamido)propanoate for starting material. Filtration of the solid formed after acidification to pH 4 with 1N HCl provide (±)-3-(4-(1-((5-(4-(trifluoromethyl)phenyl)pyrazin-2-yl)amino)butyl)benzamido) propanoic acid (178 mg, 73.5%) as a white solid. $^1$H NMR (400 MHz, DMSO-d$_6$) δ 0.90 (t, J=7.34 Hz, 3 H) 1.24-1.49 (m, 2 H) 1.66-1.88 (m, 2 H) 2.45-2.48 (m, 2 H) 3.39-3.46 (m, 2 H) 4.96-5.04 (m, 1 H) 7.44 (d, J=8.22 Hz, 2 H) 7.70-7.78 (m, 4 H) 7.94 (d, J=8.02 Hz, 1

H) 8.06-8.14 (m, 3 H) 8.43 (t, J=5.67 Hz, 1 H) 8.57 (d, J=1.37 Hz, 1 H) 12.17 (br. s., 1 H); MS (M+1): 487.3.

Examples 4.4 and 4.5

(S)-3-(4-(1-((5-(4-(trifluoromethyl)phenyl)pyrazin-2-yl)amino)butyl)benzamido)propanoic acid and (R)-3-(4-(1-((5-(4-(trifluoromethyl)phenyl)pyrazin-2-yl)amino)butyl)benzamido)propanoic acid

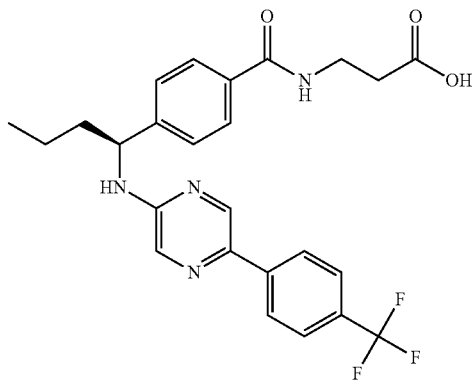

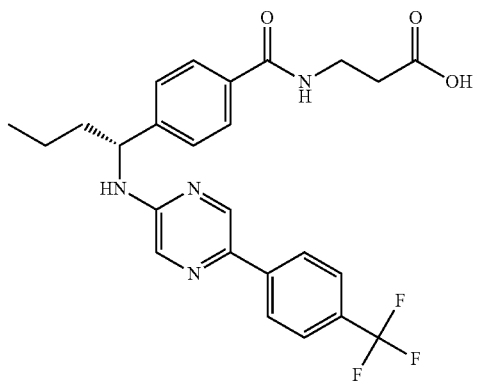 [SMILES: CCCC(Nc1cnc(-c2ccc(C(F)(F)F)cc2)cn1)c1ccc(C(=O)NCCC(=O)O)cc1]

Enantiopure starting material was provided by resolving the enantiomers of (±)-ethyl 3-(4-(1-((5-(4-(trifluoromethyl)phenyl)pyrazin-2-yl)amino)butyl)benzamido) propanoate using chiral preparative SFC. Column: Chiralpak IC. Dimensions: 21 mm×250 cm. Mobile Phase: 65/35 $CO_2$/methanol. Flow Rate: 65 mL/min. Modifier: 0.2% isopropylamine. Retention time: 3.85 min (peak 1), 4.48 min. (peak 2). Subsequent saponification of (+ and −)-ethyl 3-(4-(1-((5-(4-(trifluoromethyl)phenyl)pyrazin-2-yl)amino)butyl)benzamido) propanoate by a method analogous to the one described for example 1.1 (step H) to provide (+ and −)-3-(4-(1-((5-(4-(trifluoromethyl)phenyl)pyrazin-2-yl)amino)butyl)benzamido) propanoic acid (678 mg, 99.8%; from peak 1) and (643 mg, 94.5%; from peak 2). $^1H$ NMR (400 MHz, DMSO-$d_6$) δ 0.90 (t, J=7.34 Hz, 3 H) 1.24-1.49 (m, 2 H) 1.66-1.88 (m, 2 H) 2.45-2.48 (m, 2H) 3.39-3.46 (m, 2 H) 4.96-5.04 (m, 1 H) 7.44 (d, J=8.22 Hz, 2 H) 7.70-7.78 (m, 4 H) 7.94 (d, J=8.02 Hz, 1 H) 8.06-8.14 (m, 3 H) 8.43 (t, J=5.67 Hz, 1 H) 8.57 (d, J=1.37 Hz, 1 H) 12.17 (br. s., 1 H); MS (M+1): 487.3.

Example 4.6

3-(N-methyl-6-((3-methyl-1-(4'-(trifluoromethyl)-[1,1'-biphenyl]-4-yl)butyl)amino)nicotinamido)propanoic acid (single enantiomer)

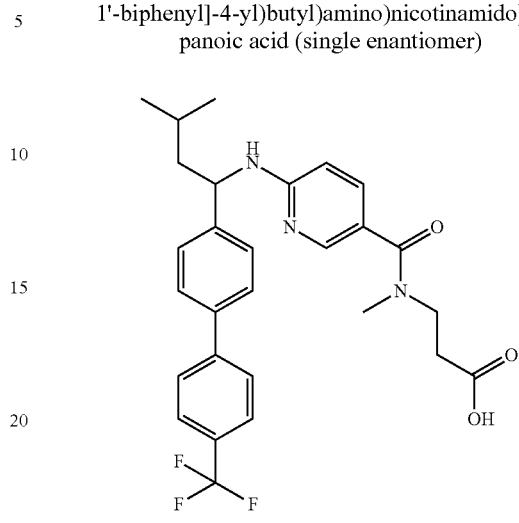

The title compound is obtained by a method analogous to the one described for example 1.23 except tert-butyl 3-(N-methyl-6-((3-methyl-1-(4'-(trifluoromethyl)-[1,1'-biphenyl]-4-yl)butyl)amino)nicotinamido)propanoate used in the synthesis was resolved by chiral chromatography; Column: Chiralpak AD-H. Dimensions: 10 mm×250 cm. Mobile Phase: 65/35 $CO_2$/methanol. Flow Rate: 10 mL/min. Modifier: none. Retention time: 4.23 min (peak 1), 6.81 min. (peak 2; >99% ee). Peak 2 (1.15 g, 2.02 mmol) was then deprotected under the TFA/DCM previously reported. Concentration of the reaction mixture under reduced pressure provide a crude orange gum. Water (150 mL) added to the gum and NaOH 1M aq. added slowly until reaching pH 11 to obtain a clear solution of the crude. Acidification to pH4 with 1N HCl followed by filtration of the solid formed (washed with plenty of water) provide 3-(N-methyl-6-((3-methyl-1-(4'-(trifluoromethyl)-[1,1'-biphenyl]-4-yl)butyl)amino)nicotinamido)propanoic acid (915 mg, 88.2%) as a white solid. $^1H$ NMR (400 MHz, DMSO-$d_6$) δ 0.91 (d, 3 H) 0.95 (d, J=6.46 Hz, 3 H) 1.49-1.59 (m, 1 H) 1.61-1.71 (m, 1 H) 1.71-1.82 (m, 1 H) 2.52-2.55 (m, 2 H) 2.92 (s, 3 H) 3.53 (t, J=7.24 Hz, 2 H) 5.09 (br. s., 1 H) 6.56 (d, J=1.17 Hz, 1 H) 7.44 (d, J=9.39 Hz, 1 H) 7.50 (d, J=8.22 Hz, 2 H) 7.54-7.65 (m, 1 H) 7.67 (d, J=8.02 Hz, 2 H) 7.75-7.82 (m, 2 H) 7.83-7.89 (m, 2 H) 8.00 (d, J=2.15 Hz, 1 H) 12.27 (br. s., 1 H); MS (M+1): 514.4.

(±)-(tetrahydro-2H-pyran-4-yl)(4'-(trifluoromethyl)-[1,1'-biphenyl]-4-yl)methanol

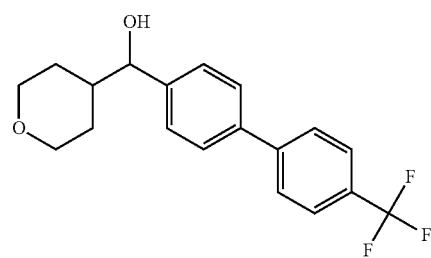 [SMILES: OC(c1ccc(-c2ccc(C(F)(F)F)cc2)cc1)C1CCOCC1]

A round bottom flask at −78° C. was charged with 4-bromo-4'-(trifluoromethyl)-1,1'-biphenyl (192 mg, 0.638 mmol) and THF (2.1 mL). nBuLi 2.5M in Hexane (281 µL, 702 mmol) was then added dropwise. The mixture stirred for one hour at −78° C. after which time, tetrahydro-2H-pyran-4-carbaldehyde (86 µL, 0.83 mmol) was added in one portion and mixture stirred for 30 minutes. Reaction mixture warmed up to 0° C. and stirred for an additional hour. Reaction quenched with ammonium chloride solution (aq. sat.) and extracted twice with ethyl acetate. Combined organic layers washed with brine, dried over sodium sulfate, filtered and concentrated to provide the crude oil. Purification by silica gel flash chromatography (MeOH/DCM) to give the title compound as a colorless oil (118 mg, 55.0%). MS (M): 336.

Example 4.7

(±)-3-(6-(((tetrahydro-2H-pyran-4-yl)(4'-(trifluoromethyl)-[1,1'-biphenyl]-4-yl)methyl)amino)nicotinamido)propanoic acid

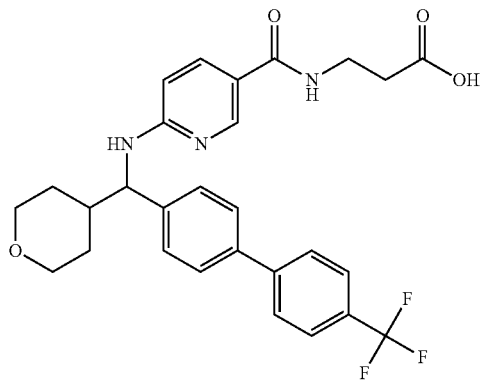 [SMILES: O=C(O)CCNC(=O)c1ccc(NC(c2ccc(-c3ccc(C(F)(F)F)cc3)cc2)C2CCOCC2)nc1]

The title compound was synthesized by a method analogous to the one described for Example 4.2 using (±)-(tetrahydro-2H-pyran-4-yl)(4'-(trifluoromethyl)-[1,1'-biphenyl]-4-yl)methanol for starting material. Filtration of the solid formed after acidification to pH4 with 1N HCl provide (±)-3-(6-(((tetrahydro-2H-pyran-4-yl)(4'-(trifluoromethyl)-[1,1'-biphenyl]-4-yl)methyl)amino)nicotinamido)propanoic acid (14.8 mg, 77.9%) as a white solid. $^1$H NMR (400 MHz, DMSO-$d_6$) δ 1.14-1.41 (m, 4 H) 1.76-1.84 (m, 1 H) 2.44 (t, J=7.04 Hz, 2 H) 3.14-3.29 (m, 2 H) 3.36 (q, J=6.46 Hz, 2 H) 3.75-3.83 (m, 1 H) 3.85-3.93 (m, 1 H) 4.87 (br. s., 1 H) 6.55 (d, J=8.61 Hz, 1 H) 7.49 (d, J=8.02 Hz, 2 H) 7.60-7.64 (m, 1 H) 7.67 (d, J=8.41 Hz, 2 H) 7.74 (dd, J=8.90, 2.45 Hz, 1 H) 7.78 (d, J=8.41 Hz, 2 H) 7.83-7.89 (m, 2 H) 8.14 (t, J=5.67 Hz, 1 H) 8.39 (d, J=2.35 Hz, 1 H) 12.15 (s, 1 H); MS (M+1): 528.4.

(±)-2-bromo-5-(1-hydroxybutyl)benzonitrile

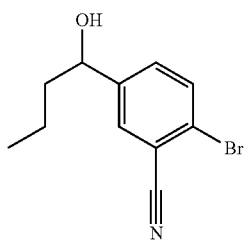

A round bottom flask was charged with the 2-bromo-5-iodobenzonitrile (2.00 g, 6.49 mmol) and THF (9 mL). Solution cooled down to −8° C. (ice/brine bath). Turbo Grignard 1.3M in THF (5.50 mL, 7.14 mmol) is then added in one portion and the reaction stirred for 15 minutes at −8° C. Butyraldehyde (0.698 µL, 7.79 mmol) is then charged in another flask and the preformed anion is added over the aldehyde/THF (4 mL) via canula and then, reaction allowed to warmed at room temperature overnight under magnetic stirring. Ammonium chloride (sat. aq.) added to the mixture. Extracted 3× with Ethyl Acetate. Combined organic layers washed with water (1×), with brine (1×), dried over sodium sulfate, filtered and concentrated to afford the crude material. Purification by silica gel flash chromatography (Ethyl Acetate/Heptane) provide the title compound as a yellow oil (1.33 g, 80.6%). $^1$H NMR (400 MHz, DMSO-$d_6$) δ 0.83 (t, J=7.41 Hz, 3 H) 1.18-1.34 (m, 2 H) 1.46-1.57 (m, 2 H) 4.52-4.58 (m, 1 H) 5.37 (d, J=4.88 Hz, 1 H) 7.56 (dd, J=8.58, 1.95 Hz, 1 H) 7.79 (d, J=8.39 Hz, 1 H) 7.81 (d, J=2.15 Hz, 1 H); MS (M): 255.

(±)-4-(1-hydroxybutyl)-4'-(trifluoromethyl)-[1,1'-biphenyl]-2-carbonitrile

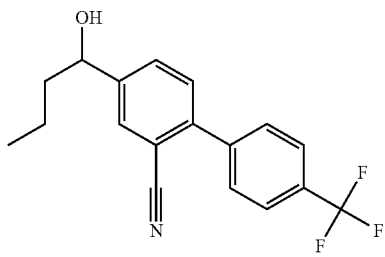 [SMILES: CCCC(O)c1ccc(-c2ccc(C(F)(F)F)cc2)c(C#N)c1]

A sealed flask was charged with the (4-(trifluoromethyl)phenyl)boronic acid (1.09 g, 5.76 mmol), 2-bromo-5-(1-hydroxybutyl)benzonitrile (1.33 g, 5.23 mmol) and acetonitrile (17 mL). Once everything get into solution, 1,1'-Bis(diphenylphosphino)ferrocene-palladium(II)dichloride dichloromethane complex (115 mg, 157 µmol) was added followed by the sodium carbonate 2M aq. (6.54 mL, 13.1 mmol). Flask sealed and heated at 140° C. for 1 hour. Organic solvent removed under reduced pressure and ethyl acetate added. Organics washed with water (1×), with brine (1×), dried over sodium sulfate, filtered and concentrated to provide the crude material. Purification by silica gel flash chromatography (Ethyl Acetate/Heptane) provide the title compound as a colorless oil (1.39 g, 83.2%). $^1$H NMR (400 MHz, DMSO-d6) δ 0.87-0.93 (m, 3 H) 1.25-1.45 (m, 2 H) 1.57-1.67 (m, 2 H) 4.64-4.70 (m, 1 H) 5.41 (d, J=4.68 Hz, 1 H) 7.64 (d, J=8.00 Hz, 1 H) 7.75-7.79 (m, 1 H) 7.82 (d, J=8.00 Hz, 2 H) 7.88-7.94 (m, 3 H).

Example 4.8

(±)-3-(6-((1-(2-cyano-4'-(trifluoromethyl)-[1,1'-biphenyl]-4-yl)butyl)amino) nicotinamido)propanoic acid

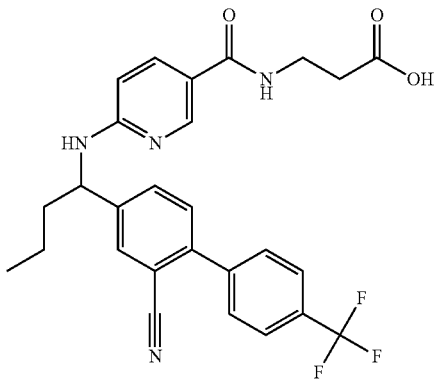 [SMILES: CCCC(Nc1ccc(C(=O)NCCC(=O)O)cn1)c1ccc(-c2ccc(C(F)(F)F)cc2)c(C#N)c1]

The title compound is obtained by a method analogous to the one described for Example 4.2 using (±)-4-(1-hydroxybutyl)-4'-(trifluoromethyl)-[1,1'-biphenyl]-2-carbonitrile for starting material. Filtration of the solid formed after acidification to pH4 with 1N HCl (±)-3-(6-((1-(2-cyano-4'-(trifluoromethyl)-[1,1'-biphenyl]-4-yl)butyl)amino)nicotinamido) propanoic acid as a white solid (526 mg, 99.9%). $^1$H NMR (400 MHz, DMSO-d6) δ 0.91 (t, 3 H) 1.26-1.51 (m, 2 H) 1.66-1.89 (m, 2 H) 2.45 (t, J=7.02 Hz, 2 H) 3.36-3.43 (m, 2 H) 5.11 (br. s., 1 H) 6.58 (d, J=8.78 Hz, 1 H) 7.59-7.70 (m, 2 H) 7.76-7.84 (m, 4 H) 7.85-7.92 (m, 2 H) 7.97 (d, J=1.56 Hz, 1 H) 8.19 (t, J=5.46 Hz, 1 H) 8.40 (d, J=2.34 Hz, 1 H) 12.16 (br. s., 1 H); MS (M+1): 511.3.

Example 4.9

(+/−)-3-({5-[3-methyl-1-(4'-trifluoromethyl-biphenyl-4-yl)-butylamino]-pyrimidine-2-carbonyl}-amino)-propionic acid

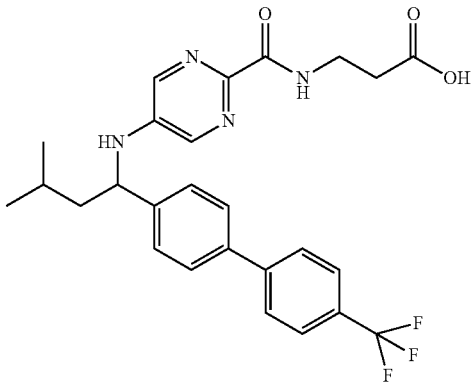 [SMILES: CC(C)CC(Nc1cnc(C(=O)NCCC(=O)O)nc1)c1ccc(-c2ccc(C(F)(F)F)cc2)cc1]

Step A:
5-(benzhydrylidene-amino)-pyrimidine-2-carboxylic acid methyl ester

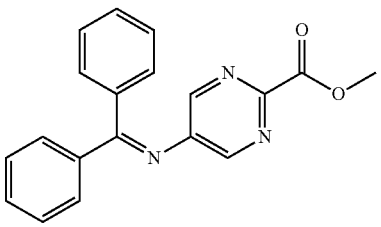 [SMILES: COC(=O)c1ncc(N=C(c2ccccc2)c2ccccc2)cn1]

To a round bottom was added 5-bromo-pyrimidine-2-carboxylic acid methyl ester (14.50 g, 66.81 mmol), (+/−)-BINAP (4.16 g, 6.68 mmol), Pd(OAc)$_2$ (750 mg, 3.34 mmol), and Cs$_2$CO$_3$ (26.1 g, 80.2 mmol). Toluene (100 mL) and benzophenone imine (12.3 mL, 73.5 mmol) were added and the mixture heated to 105° C. as an orange mixture. At 17 h, the reaction was cooled and partitioned between ethyl acetate and 1N NaOH. The aqueous layer was extracted with ethyl acetate and the combined organics dried over MgSO$_4$. Purification by silica gel flash chromatography (ethyl acetate/heptane) gave 5-(benzhydrylidene-amino)-pyrimidine-2-carboxylic acid methyl ester (9.83 g, 46%) as a bright yellow solid. $^1$H NMR (400 MHz, DMSO-d$_6$, δ): 8.42 (s, 2 H) 7.74 (d, J=6.8 Hz, 2 H) 7.61 (m, 1 H) 7.54 (m, 2 H) 7.38 (br. s., 3 H) 7.26 (br. s., 2 H) 3.83 (s, 3 H); MS (M+1): 318.2.

Step B: 5-amino-pyrimidine-2-carboxylic acid methyl ester

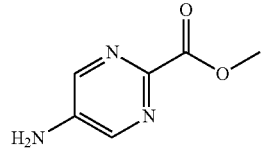

5-(Benzhydrylidene-amino)-pyrimidine-2-carboxylic acid methyl ester (9.83 g, 31.0 mmol) was dissolved in methanol (100 mL) and sodium acetate (12.2 g, 149 mmol) was added followed by hydroxylamine hydrochloride (7.75 g, 112 mmol). This was stirred at room temperature as a pale yellow mixture. At 3 h another 7.75 g of hydroxylamine hydrochloride and 12.2 g of sodium acetate were added. At 4 d, silica gel was added directly to the reaction mixture for dry loading purposes. Purification by silica gel flash chromatography (methanol/ethyl acetate) gave 5-amino-pyrimidine-2-carboxylic acid methyl ester impure with acetic acid (6.074 g, 79%) as a white solid. After placing in a vacuum oven for 6 d, some of the acetic acid was removed. The material was carried on as is. $^1$H NMR (400 MHz, DMSO-d$_6$, δ): 8.15 (s, 2 H) 6.35 (s, 2 H) 3.79 (s, 3 H); MS (M+1): 154.8.

Step C:
5-tert-butoxycarbonylamino-pyrimidine-2-carboxylic acid methyl ester

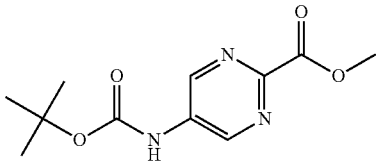 [SMILES: COC(=O)c1ncc(NC(=O)OC(C)(C)C)cn1]

5-amino-pyrimidine-2-carboxylic acid methyl ester (2.000 g, 13.06 mmol) was suspended in acetonitrile (20 mL). 4-Dimethylaminopyridine (1.600 g, 13.1 mmol) was added and the reaction placed in an ice bath. Di-tert-butyl dicarbonate (4.700 g, 21.5 mmol) was then added and the reaction was stirred at reflux. At 2.5 h, the reaction was concentrated, sat. $NH_4Cl$ and ethyl acetate were added, and with stirring the pH was carefully adjusted to ~4 with 1 N HCl. The layers were separated and the aqueous was extracted with ethyl acetate. The combined organics were dried over $MgSO_4$. Purification by silica gel flash chromatography (ethyl acetate/heptane) gave 5-tert-butoxycarbonylamino-pyrimidine-2-carboxylic acid methyl ester impure with ethyl acetate (2.583 g, 74%) as a white solid. $^1$H NMR (400 MHz, DMSO-$d_6$, δ): 10.17 (s, 1 H) 8.98 (s, 2 H) 3.87 (s, 3 H) 1.50 (s, 9 H); MS (M+1): 254.2.

Step D: (+/−)-5-{tert-butoxycarbonyl-[3-methyl-1-(4'-trifluoromethyl-biphenyl-4-yl)-butyl]-amino}-pyrimidine-2-carboxylic acid methyl ester

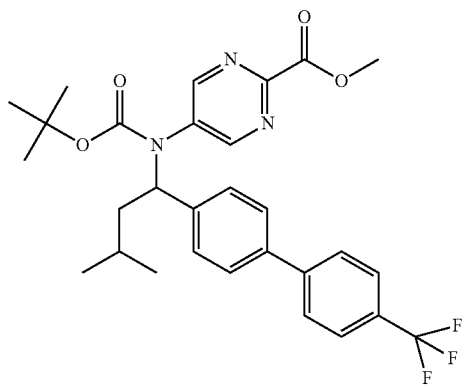 [SMILES: COC(=O)c1ncc(N(C(=O)OC(C)(C)C)C(CC(C)C)c2ccc(-c3ccc(C(F)(F)F)cc3)cc2)cn1]

3-methyl-1-(4'-(trifluoromethyl)biphenyl-4-yl)butan-1-ol (1.120 g, 3.630 mmol) (prepared as in Example 3.2 Step A) was combined with 5-tert-butoxycarbonylamino-pyrimidine-2-carboxylic acid methyl ester (0.920 g, 3.63 mmol) and dissolved in anhydrous tetrahydrofuran (20 mL). Triphenylphosphine (1.43 g, 5.45 mmol) was added and the reaction was brought to 0° C. Diisopropyl azodicarboxylate (1.43 mL, 6.90 mmol) was added dropwise over 5 min. The reaction was stirred as a yellow solution, allowing the bath to warm to room temperature. At 3 d, the reaction was concentrated. Purification by silica gel flash chromatography (ethyl acetate/heptane) gave impure (+/−)-5-{tert-butoxycarbonyl-[3-methyl-1-(4'-trifluoromethyl-biphenyl-4-yl)-butyl]-amino}-pyrimidine-2-carboxylic acid methyl ester (1.501 g) as a pale yellow oil. MS (M+1): 544.4.

Step E: (+/−)-5-[3-methyl-1-(4'-trifluoromethyl-biphenyl-4-yl)-butylamino]-pyrimidine-2-carboxylic acid methyl ester

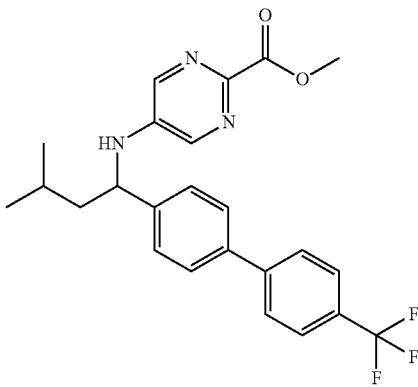 [SMILES: COC(=O)c1ncc(NC(CC(C)C)c2ccc(-c3ccc(C(F)(F)F)cc3)cc2)cn1]

(+/−)-5-{tert-Butoxycarbonyl-[3-methyl-1-(4'-trifluoromethyl-biphenyl-4-yl)-butyl]-amino}-pyrimidine-2-carboxylic acid methyl ester (1.498 g impure) was dissolved in dichloromethane (10 mL) and trifluoroacetic acid (3 mL) was added. This was stirred at room temperature. At 70 min, another 3 mL of trifluoroacetic acid was added. At 90 min, the reaction was concentrated and the material was partitioned between ethyl acetate and sat. $NaHCO_3$. The aqueous layer was extracted with ethyl acetate and the combined organics dried over $MgSO_4$. Purification by silica gel flash chromatography (ethyl acetate/heptane) gave (+/−)-5-[3-methyl-1-(4'-trifluoromethyl-biphenyl-4-yl)-butylamino]-pyrimidine-2-carboxylic acid methyl ester (0.620 g) as a white foam. $^1$H NMR (400 MHz, $CDCl_3$, δ): 8.16 (s, 2 H) 7.67-7.73 (m, 2 H) 7.61-7.66 (m, 2 H) 7.56 (d, J=8.2 Hz, 2 H) 7.39 (d, J=8.2 Hz, 2 H) 4.68 (d, J=5.7 Hz, 1 H) 4.46-4.57 (m, 1 H) 3.98 (s, 3 H) 1.79-1.92 (m, 1 H) 1.64-1.79 (m, 2 H) 1.05 (d, J=6.2 Hz, 3 H) 0.99 (d, J=6.2 Hz, 3 H); MS (M+1): 444.3.

Step F: (+/−)-5-[3-methyl-1-(4'-trifluoromethyl-biphenyl-4-yl)-butylamino]-pyrimidine-2-carboxylic acid

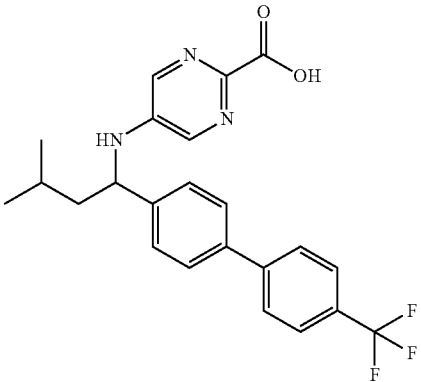 [SMILES: CC(C)CC(Nc1cnc(C(=O)O)nc1)c1ccc(-c2ccc(C(F)(F)F)cc2)cc1]

(+/−)-5-[3-Methyl-1-(4'-trifluoromethyl-biphenyl-4-yl)-butylamino]-pyrimidine-2-carboxylic acid methyl ester (617 mg, 1.39 mmol) was dissolved in tetrahydrofuran (6 mL) and methanol (2 mL), and 1.0 M NaOH (6 mL, 6 mmol) was added. This was stirred at 50° C. for 2.5 h before cooling and bringing to pH 3 with 1 N HCl. This was extracted three times with ethyl acetate. The combined organics were dried over $MgSO_4$ and concentrated in vacuo to give (+/−)-5-[3-methyl-1-(4'-trifluoromet hyl-biphenyl-4-yl)-butylamino]-pyrimidine-2-carboxylic acid with ethyl acetate (0.636 g) as clear foam. $^1$H NMR (400 MHz, DMSO-$d_6$, δ): 8.18 (s, 2 H) 7.84-7.91 (m, 2 H) 7.75-7.81 (m, 2 H) 7.71 (d, J=8.2 Hz, 2 H) 7.55 (d, J=8.2 Hz, 2 H) 7.42 (d, J=7.8 Hz, 1 H) 4.63-4.74 (m, 1 H) 1.74-1.85 (m, 1 H) 1.67 (dt, J=13.1, 6.5 Hz, 1 H) 1.51-1.61 (m, 1 H) 0.98 (d, J=6.4 Hz, 3 H) 0.93 (d, J=6.4 Hz, 3 H); MS (M+1): 430.3.

Step G: (+/−)-3-({5-[3-methyl-1-(4'-trifluoromethyl-biphenyl-4-yl)-butylamino]-pyrimidine-2-carbonyl}-amino)-propionic acid ethyl ester

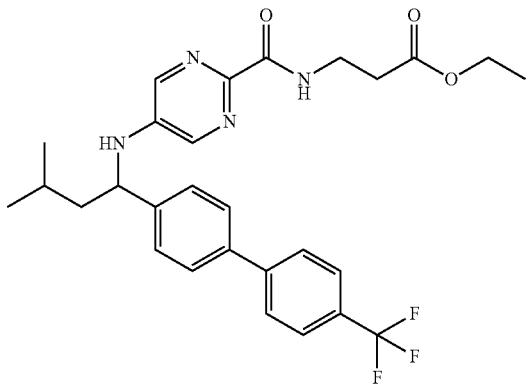 [SMILES: CCOC(=O)CCNC(=O)c1ncc(NC(CC(C)C)c2ccc(-c3ccc(C(F)(F)F)cc3)cc2)cn1]

(+/−)-5-[3-Methyl-1-(4'-trifluoromethyl-biphenyl-4-yl)-butylamino]-pyrimidine-2-carboxylic acid (636 mg, theoretical 596 mg, 1.39 mmol) was combined with N-(3-dimethylaminopropyl)-N'-ethylcarbodimide hydrochloride (399 mg, 2.08 mmol), 1-hydroxybenzotriazole hydrate (319 mg, 2.08 mmol), and anhydrous dichloromethane (10 mL). Beta-alanine ethyl ester hydrochloride (256 mg, 1.67 mmol) was added followed by triethylamine (0.386 mL, 2.78 mmol). This was stirred at room temperature as a solution for 17 h before the reaction was partitioned between ethyl acetate and sat. NH$_4$Cl. The aqueous layer was extracted with ethyl acetate and the combined organics dried over MgSO$_4$. Purification by silica gel flash chromatography (ethyl acetate/heptanes followed by methanol/ethyl acetate) gave impure material. The residue was partitioned between ethyl acetate and sat. NaHCO$_3$. The aqueous layer was extracted with ethyl acetate and the combined organics dried over MgSO$_4$ and concentrated in vacuo to give (+/−)-3-({5-[3-methyl-1-(4'-trifluoromethyl-biphenyl-4-yl)-butylamino]-pyrimidine-2-carbonyl}-amino)-propionic acid ethyl ester (0.687 g, 94%) as a clear oil. $^1$H NMR (400 MHz, CDCl$_3$, δ): 8.17 (t, J=6.2 Hz, 1 H) 8.09 (s, 2 H) 7.62-7.73 (m, 4 H) 7.56 (d, J=8.2 Hz, 2 H) 7.40 (d, J=8.2 Hz, 2 H) 4.53-4.58 (m, 1 H) 4.44-4.52 (m, 1 H) 4.11-4.19 (m, 2 H) 3.72 (q, J=6.2 Hz, 2 H) 2.61 (t, J=6.0 Hz, 2 H) 1.66-1.87 (m, 3 H) 1.21-1.29 (m, 3 H) 1.04 (d, J=6.0 Hz, 3 H) 0.99 (d, J=5.9 Hz, 3 H); MS (M+1): 529.7.

Step H: (+/−)-3-({5-[3-methyl-1-(4'-trifluoromethyl-biphenyl-4-yl)-butylamino]-pyrimidine-2-carbonyl}-amino)-propionic acid

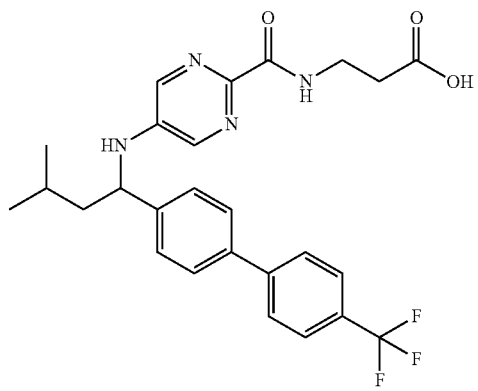 [SMILES: CC(C)CC(Nc1cnc(C(=O)NCCC(=O)O)nc1)c1ccc(-c2ccc(C(F)(F)F)cc2)cc1]

(+/−)-3-({5-[3-Methyl-1-(4'-trifluoromethyl-biphenyl-4-yl)-butylamino]-pyrimidine-2-carbonyl}-amino)-propionic acid ethyl ester (14.6 mg, 28.0 mmol) was dissolved in tetrahydrofuran (3 mL) and methanol (1 mL), and 1.0 M NaOH (1 mL, 1 mmol) was added. This was stirred at room temperature for 10 min. The reaction brought to pH 3 with 1 N HCl. The methanol was concentrated in vacuo and the residue was extracted twice with ethyl acetate. The combined organics were dried over MgSO$_4$ and concentrated in vacuo to give crude product. Purification by reversed-phase HPLC gave (+/−)-3-({5-[3-methyl-1-(4'-trifluoromethyl-biphenyl-4-yl)-butylamino]-pyrimidine-2-carbonyl}-amino)-propionic acid (13.8 mg). Analytical LCMS: retention time 3.40 minutes (Waters Atlantic dC$_{18}$ 4.6×50 mm, 5 μm column; 5% acetonitrile/water (0.05% trifluoroacetic acid modifier) linear gradient to 95% acetonitrile/water over 4.0 minutes, hold at 95% acetonitrile/water for 1.0 minute; flow rate 2.0 mL/minute); MS (M+1): 501.3.

Examples 4.10 and 4.11

3-({5-[(R)-3-methyl-1-(4'-trifluoromethyl-biphenyl-4-yl)-butylamino]-pyrimidine-2-carbonyl}-amino)-propionic acid and 3-({5-[(S)-3-methyl-1-(4'-trifluoromethyl-biphenyl-4-yl)-butylamino]-pyrimidine-2-carbonyl}-amino)-propionic acid

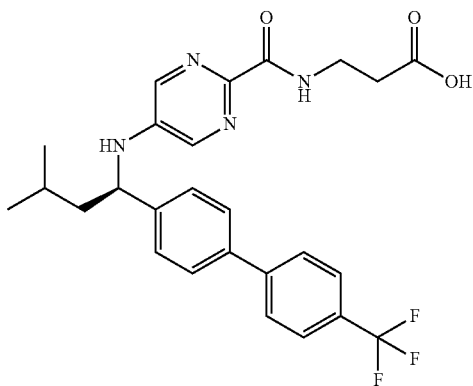

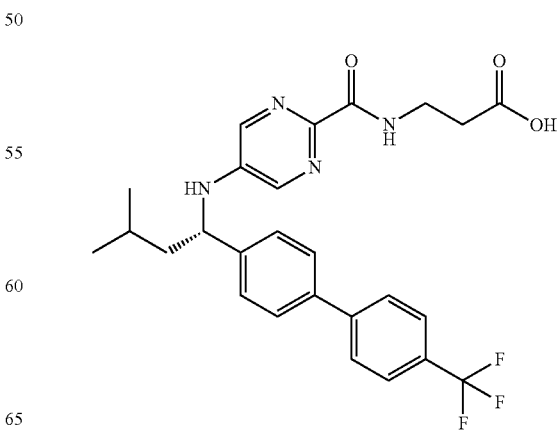

Step A: 3-({5-[(R)-3-methyl-1-(4'-trifluoromethyl-biphenyl-4-yl)-butylamino]-pyrimidine-2-carbonyl}-amino)-propionic acid ethyl ester and 3-({5-[(S)-3-methyl-1-(4'-trifluoromethyl-biphenyl-4-yl)-butylamino]-pyrimidine-2-carbonyl}-amino)-propionic acid ethyl ester Step B: 3-({5-[(R)-3-methyl-1-(4'-trifluoromethyl-biphenyl-4-yl)-butylamino]-pyrimidine-2-carbonyl}-amino)-propionic acid and 3-({5-[(S)-3-methyl-1-(4'-trifluoromethyl-biphenyl-4-yl)-butylamino]-pyrimidine-2-carbonyl}-amino)-propionic acid

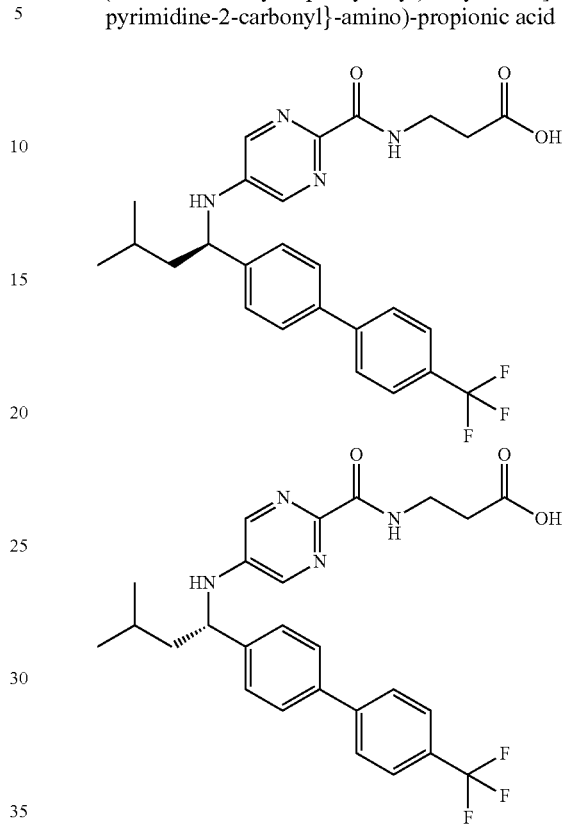

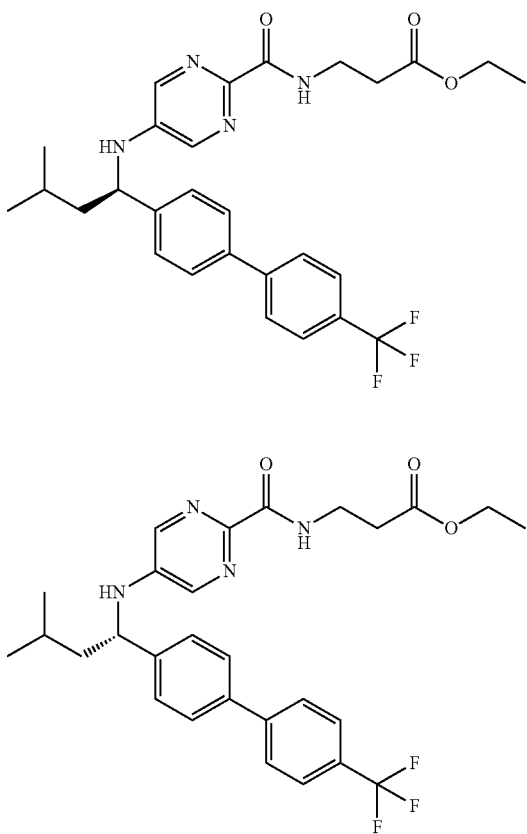

(+/−)-3-({5-[3-Methyl-1-(4'-trifluoromethyl-biphenyl-4-yl)-butylamino]-pyrimidine-2-carbonyl}-amino)-propionic acid ethyl ester was purified by chiral SFC. Column: Chiralpak AD-H. Dimensions: 10 mm×250 mm. Mobile Phase: 70/30 CO$_2$/ethanol. Flow Rate: 10.0 ml/min. The early eluting peak (Peak 1) was concentrated in vacuo to give one enantiomer of 100% ee (289 mg). Analytical chiral SFC: Column—Chiralpak AD-H. Dimensions: 4.6 mm×25 cm. Mobile Phase: 70/30 CO$_2$/ethanol. Flow Rate: 2.5 mL/min. Retention time: 3.29 minutes. MS (M+1): 529.7. The late eluting peak (Peak 2) was concentrated in vacuo to give one enantiomer of 100% ee (124 mg). Analytical chiral SFC: Column—Chiralpak AD-H. Dimensions: 4.6 mm×25 cm. Mobile Phase: 70/30 CO$_2$/ethanol. Flow Rate: 2.5 mL/min. Retention time: 4.29 minutes. MS (M+1): 529.7.

3-({5-[3-methyl-1-(4'-trifluoromethyl-biphenyl-4-yl)-butylamino]-pyrimidine-2-carbonyl}-amino)-propionic acid ethyl ester Peak 1 (286.4 mg, 0.542 mmol) was dissolved in tetrahydrofuran (3 mL) and methanol (1 mL), and 1.0 M NaOH (2 mL, 2 mmol) was added. This was stirred at room temperature for 10 min. The reaction brought to pH 3 with 1 N HCl. This was extracted twice with ethyl acetate. The combined organics were dried over MgSO$_4$ and concentrated in vacuo to give an oil. The material was triturated with four portions of diethylether to give one enantiomer of 3-({5-[3-methyl-1-(4'-trifluoromethyl-biphenyl-4-yl)-butylamino]-pyrimidine-2-carbonyl}-amino)-propionic acid (266 mg, 97%) as a white solid. $^1$H NMR (400 MHz, DMSO-d$_6$, δ): 12.21 (br. s., 1 H) 8.39 (t, J=6.0 Hz, 1 H) 8.16 (s, 2 H) 7.83-7.91 (m, 2 H) 7.75-7.81 (m, 2 H) 7.70 (d, J=8.2 Hz, 2 H) 7.54 (d, J=8.2 Hz, 2 H) 7.27 (d, J=7.6 Hz, 1 H) 4.60-4.72 (m, 1 H) 3.36-3.46 (m, 2 H) 2.44 (t, J=6.9 Hz, 2 H) 1.74-1.85 (m, 1 H) 1.67 (m, 1 H) 1.51-1.60 (m, 1 H) 0.98 (d, J=6.4 Hz, 3 H) 0.92 (d, J=6.4 Hz, 3 H); MS (M+1): 501.6.

3-({5-[3-methyl-1-(4'-trifluoromethyl-biphenyl-4-yl)-butylamino]-pyrimidine-2-carbonyl}-amino)-propionic acid ethyl ester Peak 2 (150 mg, 0.284 mmol) was dissolved in tetrahydrofuran (3 mL) and methanol (1 mL), and 1.0 M NaOH (1 mL) was added. This was stirred at room temperature for 10 min. The reaction brought to pH 4 with 1 N HCl. This was extracted twice with ethyl acetate. The combined organics were dried over MgSO$_4$ and concentrated in vacuo to give an oil. The material was triturated with four portions of diethylether to give the opposite enantiomer of 3-({5-[3-methyl-1-(4'-trifluoromethyl-biphenyl-4-yl)-butylamino]-pyrimidine-2-carbonyl}-amino)-propionic acid (111 mg, 78%) as a white solid. $^1$H NMR (400 MHz, DMSO-d$_6$, δ): 12.21 (br. s., 1 H) 8.39 (t, J=6.0 Hz, 1 H) 8.16 (s, 2 H) 7.83-7.91 (m, 2 H) 7.75-7.81 (m, 2 H) 7.70 (d, J=8.2 Hz, 2 H) 7.54 (d, J=8.2 Hz, 2 H) 7.27 (d, J=7.6 Hz, 1 H) 4.61-4.72 (m, 1 H) 3.36-3.45 (m, 2 H) 2.44 (t, J=6.9 Hz, 2 H) 1.74-1.85 (m, 1 H) 1.62-1.72 (m, 1 H) 1.50-1.61 (m, 1 H) 0.98 (d, J=6.4 Hz, 3 H) 0.92 (d, J=6.4 Hz, 3 H); MS (M+1): 501.6.

Example 4.12

3-[(6-{(S)-3-methyl-1-[2-(4-trifluoromethyl-phenyl)-pyrimidin-5-yl]-butylamino}-pyridine-3-carbonyl)-amino]-propionic acid

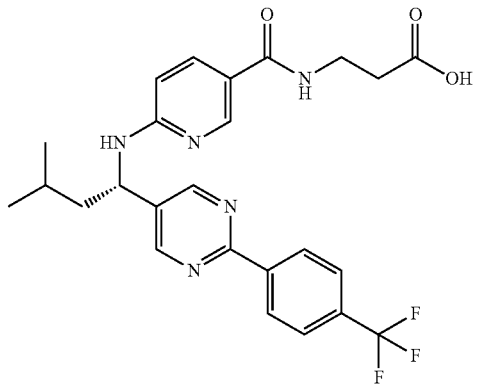 [SMILES: CC(C)C[C@H](Nc1ccc(C(=O)NCCC(=O)O)cn1)c1cnc(-c2ccc(C(F)(F)F)cc2)nc1]

Steps A-C are the preparation of 2-(4-trifluoromethyl-phenyl)-pyrimidine-5-carbaldehyde as previously described Step D: (S)-2-methyl-propane-2-sulfinic acid 1-[2-(4-trifluoromethyl-phenyl)-pyrimidin-5-yl]-meth-(E)-ylideneamine

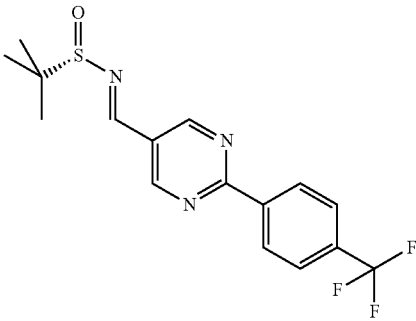 [SMILES: CC(C)(C)[S@](=O)/N=C/c1cnc(-c2ccc(C(F)(F)F)cc2)nc1]

2-(4-trifluoromethyl-phenyl)-pyrimidine-5-carbaldehyde (35.25 g, 138.9 mmol) was suspended in anhydrous dichloromethane (470 mL) in a 3-necked 1 L flask with overhead stirrer, condenser and internal temperature. (S)-(−)-2-methyl-2-propanesulfinamide (17.13 g, 141.3 mmol) was added followed by titanium(IV) ethoxide (37.3 mL, 178 mmol). This gave a yellow solution which was heated to reflux for 3 h. The heating was discontinued and the reaction placed in an ice bath. When the internal temperature was ~10° C., anhydrous methanol (246 mL) was added followed by sat. aq. NaHCO$_3$ (71 mL). Solid crashed out which was stirred for 2 h. The solids were filtered off with a Buchner funnel using ethyl acetate to aid in transfer. Several portions of ethyl acetate were used to rinse the solid. The solid was added back into the 3-necked flask and mechanically stirred for 20 min with ethyl acetate. This was refiltered. This process was repeated to remove most of the product. The filtrate was dried over Na$_2$SO$_4$ and concentrated in vacuo to give (S)-2-methyl-propane-2-sulfinic acid 1-[2-(4-trifluoromethyl-phenyl)-pyrimidin-5-yl]-meth-(E)-ylideneamine (49.00 g, 99%) as a white solid. $^1$H NMR (400 MHz, CDCl$_3$, δ): 9.25 (s, 2 H) 8.70 (s, 1 H) 8.66 (d, J=8.2 Hz, 2 H) 7.79 (d, J=8.2 Hz, 2 H) 1.31 (s, 9 H); MS (M+1): 356.1.

Step E: (S)-2-methyl-propane-2-sulfinic acid {(S)-3-methyl-1-[2-(4-trifluoromethyl-phenyl)-pyrimidin-5-yl]-butyl}-amide

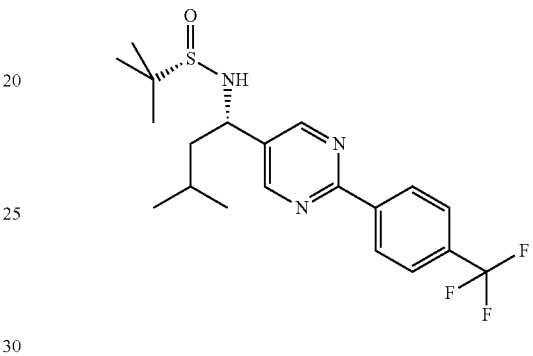

Dimethyl zinc (117 mL, 2.0 M in toluene, 234 mmol) was added to an oven-dried and nitrogen-purged 500 mL round bottom flask with stir bar. Isobutylmagnesium bromide (103 mL, 2.0 M in ether, 206 mmol) was added over 5 min with stirring and the solution was allowed to stir at room temperature for 30 minutes. (S)-2-Methyl-propane-2-sulfinic acid 1-[2-(4-trifluoromethyl-phenyl)-pyrimidin-5-yl]-meth-(E)-ylideneamine (48.83 g, 137.4 mmol) was placed in an oven dried nitrogen-purged 2 L 3-necked flask with addition funnel, overhead stirring, and internal temperature. The solid was dissolved in anhydrous THF (690 mL) and cooled to −78° C. where it was a white suspension. The zincate solution was cannulated into the addition funnel and then added dropwise over 75 min to the sulfinyl imine, maintaining an internal temperature of less than −72° C. The reaction was then allowed to stir at −78° C. as a yellow solution. At 75 min, the reaction was quenched with saturated NH$_4$Cl, adding 100 mL over 45 min, keeping the internal temperature below-70° C. A second 400 mL was then added more quickly (~20 min), keeping the internal temperature below −47° C. Gas evolution was observed at these higher temperatures indicating perhaps a latency period. Upon adding a final 100 mL, no gas evolution was observed indicating the reaction was quenched. The cold bath was removed, another 300 mL of water was added and the reaction allowed to warm to 5° C. at which point the contents were added to an addition funnel, along with ethyl acetate and some additional water. The layers were separated and the aqueous layer extracted with three additional portions of ethyl acetate. The combined organics were dried over MgSO$_4$. Purification was done on half the material in two batches by silica gel flash chromatography (ethyl acetate/heptane) to give (S)-2-methyl-propane-2-sulfinic acid {(S)-3-methyl-1-[2-(4-trifluoromethyl-phenyl)-pyrimidin-5-yl]-butyl}-amide (38.83 g, 68%) as a yellow solid. $^1$H NMR (400 MHz, CDCl$_3$, δ): 8.82 (s, 2 H) 8.57 (d, J=8.2 Hz, 2 H) 7.75 (d, J=8.4 Hz, 2 H) 4.49 (q, J=7.2 Hz, 1 H) 3.44 (d, J=5.7 Hz, 1 H)

1.99 (dt, J=13.9, 7.3 Hz, 1 H) 1.51-1.77 (m, 2 H) 1.24 (s, 9 H) 0.99 (d, J=6.6 Hz, 3 H) 0.95 (d, J=6.4 Hz, 3 H); MS (M+1): 414.3.

Step F: (S)-3-methyl-1-[2-(4-trifluoromethyl-phenyl)-pyrimidin-5-yl]-butylamine hydrochloride

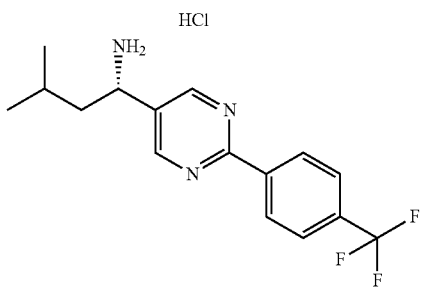 [SMILES: Cl ; CC(C)C[C@H](N)c1cnc(-c2ccc(C(F)(F)F)cc2)nc1]

(S)-2-methyl-propane-2-sulfinic acid {(S)-3-methyl-1-[2-(4-trifluoromethyl-phenyl)-pyrimidin-5-yl]-butyl}-amide (38.83 g, 93.90 mmol) was dissolved in methanol and transferred to a 3-necked 1 L flask with overhead stirring and internal temperature. A total of 210 mL methanol was added to give a yellow solution. This was placed in an ice bath and at an internal temperature of 8° C., HCl in ether (188 mL, 2.0 M, 376 mmol) was added over 2 min. The temperature went up to 14° C. The ice bath was removed and the reaction stirred for ~5 min as a yellow solution than as a white slurry. At 30 min, the reaction was rotovapped to dryness and the solid slurried in diethylether (200 mL) for 1 h. The solid was collected by Buchner filtration, washing with additional diethylether. This was suction dried for ~1 h and then placed on the vacuum pump to give (S)-3-methyl-1-[2-(4-trifluoromethyl-phenyl)-pyrimidin-5-yl]-butylamine hydrochloride (31.58 g, 97%) as a white solid. $^1$H NMR (400 MHz, DMSO-d$_6$, δ): 9.19 (s, 2 H) 8.78 (br. s., 3 H) 8.61 (d, J=8.2 Hz, 2 H) 7.93 (d, J=8.4 Hz, 2 H) 4.47 (br. s., 1 H) 1.84-2.03 (m, 2 H) 1.41 (m, 1 H) 0.83-0.96 (m, 6 H).

Step G: 6-fluoro-nicotinic acid methyl ester

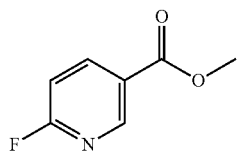

A round bottom flask was charged with K$_2$CO$_3$ (191 g, 1380 mmol), 6-fluoronicotinic acid (77.8 g, 551 mmol) and dimethylformamide (551 mL). Methyl iodide (51.5 mL, 827 mmol) was then added in one portion at room temperature and mixture stirred overnight at room temperature. The reaction mixture was partitioned between ethyl acetate and water. The organic layer was washed three times with water and once with brine, and then dried over Na$_2$SO$_4$. Purification by silica gel flash chromatography (ethyl acetate/dichloromethane) gave 6-fluoro-nicotinic acid methyl ester (71.8 g, 84%) as a white solid. $^1$H NMR (400 MHz, CDCl$_3$, δ): 3.96 (s, 3 H) 7.01 (dd, J=8.58, 2.93 Hz, 1 H) 8.41 (ddd, J=8.49, 7.61, 2.44 Hz, 1 H) 8.89 (d, J=2.34 Hz, 1 H); MS (M+1): 156.1.

Step H: 6-{(S)-3-methyl-1-[2-(4-trifluoromethyl-phenyl)-pyrimidin-5-yl]-butylamino}-nicotinic acid methyl ester

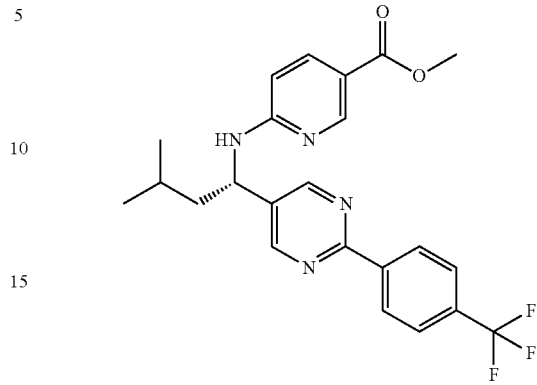

(S)-3-methyl-1-[2-(4-trifluoromethyl-phenyl)-pyrimidin-5-yl]-butylamine hydrochloride (31.33 g, 90.60 mmol) was combined with 6-fluoro-nicotinic acid methyl ester (16.9 g, 109 mmol) and K$_2$CO$_3$ (37.6 g, 272 mmol, 325 mesh) in a 500 mL N$_2$-purged round bottom. Anhydrous dimethylformamide (115 mL) was added. The reaction was heated to 100° C. as a suspension. At 35 min another 3.00 g of 6-fluoro-nicotinic acid methyl ester was added. At 20 h, the reaction was placed in an ice bath and when the internal temperature was below room temperature sat. NH$_4$Cl (500 mL) was added. This was stirred for a couple minutes in the bath and then the bath was removed and stirred at room temperature. Ethyl acetate (600 mL) and a small amount of water were added and the layers separated. The aqueous was extracted with ethyl acetate (150 mL) and the combined organics were washed with additional sat. NH$_4$Cl (125 mL). The aqueous was back extracted with ethyl acetate (50 mL). The combined organics were dried over MgSO$_4$. Purification was done by silica gel flash chromatography (ethyl acetate/heptane) to give impure 6-{(S)-3-methyl-1-[2-(4-trifluoromethyl-phenyl)-pyrimidin-5-yl]butylamino}-nicotinic acid methyl ester (38.07 g) as a pale yellow solid. $^1$H NMR (400 MHz, CDCl$_3$, δ): 8.85 (s, 2 H) 8.69 (d, J=1.6 Hz, 1 H) 8.55 (d, J=8.2 Hz, 2 H) 8.01 (dd, J=8.8, 2.1 Hz, 1 H) 7.74 (d, J=8.4 Hz, 2 H) 6.39 (d, J=8.8 Hz, 1 H) 5.01 (q, J=6.9 Hz, 1 H) 3.86 (s, 3 H) 1.85-1.98 (m, 1 H) 1.70-1.82 (m, 2 H) 1.05 (d, J=6.2 Hz, 3 H) 1.01 (d, J=6.0 Hz, 3 H); MS (M+1): 445.3.

Step I: 6-{(S)-3-methyl-1-[2-(4-trifluoromethyl-phenyl)-pyrimidin-5-yl]-butylamino}-nicotinic acid

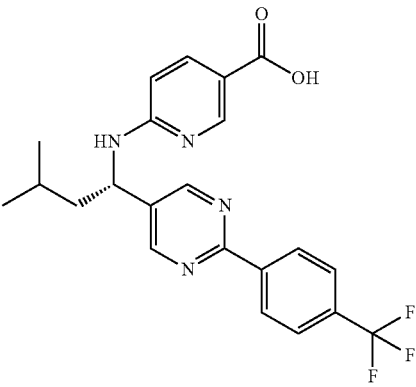 [SMILES: CC(C)C[C@H](Nc1ccc(C(=O)O)cn1)c1cnc(-c2ccc(C(F)(F)F)cc2)nc1]

6-{(S)-3-methyl-1-[2-(4-trifluoromethyl-phenyl)-pyrimidin-5-yl]-butylamino}-nicotinic acid methyl ester (38.07 g impure) was dissolved in tetrahydrofuran (200 mL) and methanol (65 mL), and 1.0 M NaOH (200 mL) was added. This was stirred in a 50° C. bath at first as a suspension and then a clear solution. At 2 h the bath temperature was raised to 60° C. At 5 h most of the organics were concentrated in vacuo. A small amount of tetrahydrofuran was added and the contents stirred in an ice bath. 1 N HCl was added until pH 5 (190 mL). Ethyl acetate (300 mL) was added and stirred for several minutes to ensure constant pH. The layers were separated. The aqueous layer was back extracted with additional ethyl acetate (100 mL) and the combined organics were dried over MgSO$_4$. This was concentrated in vacuo to give 6-{(S)-3-methyl-1-[2-(4-trifluoromethyl-phenyl)-pyrimidin-5-yl]-butylamino}-nicotinic acid with ethyl acetate (31.09 g, 68% yield over two steps) as a white solid. $^1$H NMR (400 MHz, DMSO-d$_6$, δ): 12.34 (br. s., 1 H) 8.94 (s, 2 H) 8.52 (d, J=8.2 Hz, 2 H) 8.46 (d, J=2.1 Hz, 1 H) 7.90 (d, J=8.0 Hz, 1 H) 7.85 (d, J=8.4 Hz, 2 H) 7.78 (dd, J=8.9, 2.2 Hz, 1 H) 6.58 (d, J=8.8 Hz, 1 H) 5.18 (br. s., 1 H) 1.77-1.91 (m, 1 H) 1.55-1.75 (m, 2 H) 0.93 (d, J=6.2 Hz, 3 H) 0.89 (d, J=6.0 Hz, 3 H); MS (M+1): 431.2.

Step J: 3-[(6-{(S)-3-methyl-1-[2-(4-trifluoromethyl-phenyl)-pyrimidin-5-yl]-butylamino}-pyridine-3-carbonyl)-amino]-propionic acid ethyl ester

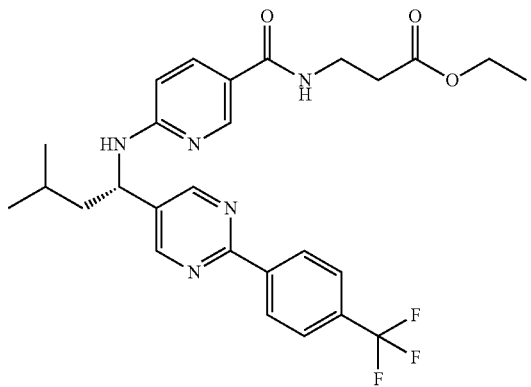 [SMILES: CCOC(=O)CCNC(=O)c1ccc(N[C@@H](CC(C)C)c2cnc(-c3ccc(C(F)(F)F)cc3)nc2)nc1]

6-{(S)-3-Methyl-1-[2-(4-trifluoromethyl-phenyl)-pyrimidin-5-yl]-butylamino}-nicotinic acid (31.1 g wet with ethyl acetate, theoretical 65.8 mmol) was dissolved in dichloromethane (270 mL). 1-Hydroxybenotriazole hydrate (15.1 g, 98.7 mmol) was added followed by N-(3-dimethylaminopropyl)-N'-ethylcarbodiimide hydrochloride (18.9 g, 98.7 mmol). beta-Alanine ethyl ester hydrochloride (12.1 g, 79.0 mmol) was added and the reaction was placed in an ice bath. When only slightly cool, triethylamine (18.3 mL, 132 mmol) was added over 3 min. The bath was then removed and the reaction was stirred at room temperature as a solution. At 16 h, most of the dichloromethane was rotovapped off. The residue was partitioned between ethyl acetate and sat. NH$_4$Cl. The aqueous was extracted with additional ethyl acetate and the combined organics were washed with sat. NaHCO$_3$ two times. The first aqueous was back extracted with ethyl acetate to remove a small amount of product. The combined organics were washed with brine and dried over MgSO$_4$. The material was purified by silica gel flash chromatography (ethyl acetate/heptane) and then further purified by chiral SFC. Column: Chiralcel OJ-H. Dimensions: 21 mm×250 mm. Mobile Phase: 80/20 CO$_2$/ethanol. Flow Rate: 65 ml/min. The purified material was taken up in ethyl acetate, filtered through a course frit and concentrated in vacuo to give 3-[(6-{(S)-3-methyl-1-[2-(4-trifluoromethyl-phenyl)-pyrimidin-5-yl]-butylamino}-pyridine-3-carbonyl)-amino]-propionic acid ethyl ester with ethyl acetate (29.2 g) as a white foam. $^1$H NMR (400 MHz, CDCl$_3$, δ): 8.83 (s, 2 H) 8.54 (d, J=8.0 Hz, 2 H) 8.46 (d, J=2.0 Hz, 1 H) 7.81 (dd, J=8.7, 2.2 Hz, 1 H) 7.73 (d, J=8.4 Hz, 2 H) 6.64 (t, J=5.8 Hz, 1 H) 6.36 (d, J=8.6 Hz, 1 H) 5.13 (d, J=6.7 Hz, 1 H) 4.97-5.08 (m, 1 H) 4.09-4.21 (m, 2 H) 3.68 (q, J=5.9 Hz, 2 H) 2.60 (t, J=5.9 Hz, 2 H) 1.81-1.95 (m, 1 H) 1.67-1.81 (m, 2 H) 1.26 (t, J=7.1 Hz, 3 H) 1.03 (d, J=6.1 Hz, 3 H) 1.00 (d, J=6.1 Hz, 3 H); MS (M+1): 530.2. Analytical chiral SFC: Column—Chiralcel OJ-H. Dimensions: 4.6 mm×25 cm. Mobile Phase: 80/20 CO$_2$/ethanol. Flow Rate: 2.5 mL/min. Retention time: 5.18 minutes.

Step K: 3-[(6-{(S)-3-methyl-1-[2-(4-trifluoromethyl-phenyl)-pyrimidin-5-yl]-butylamino}-pyridine-3-carbonyl)-amino]-propionic acid

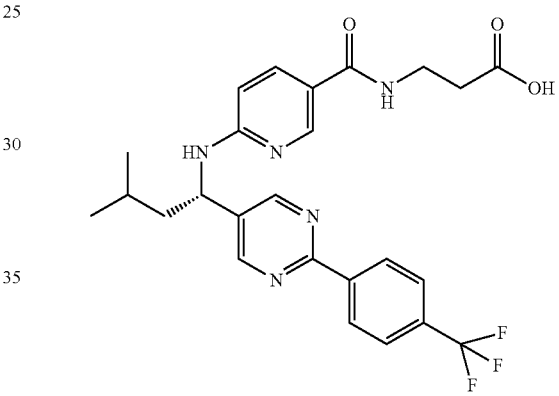

3-[(6-{(S)-3-Methyl-1-[2-(4-trifluoromethyl-phenyl)-pyrimidin-5-yl]-butylamino}-pyridine-3-carbonyl)-amino]-propionic acid ethyl ester (29.2 g wet with ethyl acetate, theoretically 54.0 mmol) was dissolved in tetrahydrofuran (135 mL) and methanol (45 mL), and 1.0 M sodium hydroxide (135 mL) was added. This was stirred at room temperature for 20 min before most of the organics were rotovapped off. A small amount of tetrahydrofuran was added and the mostly aqueous contents were stirred in an ice bath. 1 N HCl (130 mL) was added until pH 5. Ethyl acetate was added and stirred for ~20 min to ensure constant pH. The material was added to a sep funnel and the layers separated. The aqueous was back extracted with additional ethyl acetate and the combined organics were washed with brine and dried over MgSO$_4$. This was concentrated and the solid was placed in a vacuum oven for two days to give 3-[(6-{(S)-3-methyl-1-[2-(4-trifluoromethyl-phenyl)-pyrimidin-5-yl]-butylamino}-pyridine-3-carbonyl)-amino]-propionic acid as a white foam. $^1$H NMR (400 MHz, DMSO-d$_6$, δ): 12.16 (s, 1 H) 8.97 (s, 2 H) 8.54 (d, J=8.2 Hz, 2 H) 8.41 (d, J=2.0 Hz, 1 H) 8.19 (t, J=5.4 Hz, 1 H) 7.87 (d, J=8.4 Hz, 2 H) 7.78 (dd, J=8.8, 2.3 Hz, 1 H) 7.68 (d, J=8.0 Hz, 1 H) 6.58 (d, J=8.6 Hz, 1 H) 5.09-5.26 (m, 1 H) 3.38 (q, J=6.7 Hz, 2 H) 2.44 (t, J=7.0 Hz, 2 H) 1.80-1.94 (m, 1 H) 1.57-1.77 (m, 2 H) 0.96 (d, J=6.1 Hz, 3 H) 0.92 (d, J=6.3 Hz, 3 H); MS (M+1): 502.3.

Example 4.13

(+/−)-3-(6-(4,4,4-trifluoro-1-(4'-(trifluoromethyl)biphenyl-4-yl)butylamino)nicotinamido)propanoic acid

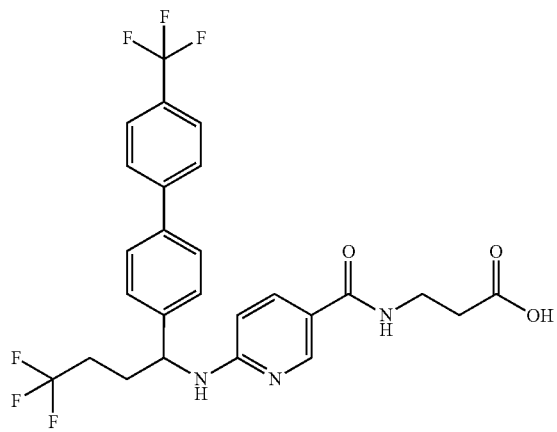 [SMILES: O=C(O)CCNC(=O)c1ccc(NC(CCC(F)(F)F)c2ccc(-c3ccc(C(F)(F)F)cc3)cc2)nc1]

Step A: 4-bromo-4'-(trifluoromethyl)biphenyl

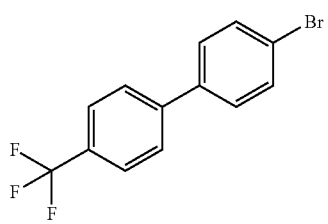 [SMILES: FC(F)(F)c1ccc(-c2ccc(Br)cc2)cc1]

A 250 mL flask was charged with 4-(trifluoromethyl)phenylboronic acid (4.85 g, 25.5 mmol), 4-bromoiodobenzene (7.22 g, 25.5 mmol), Pd(OAc)$_2$ (57.2 mg, 0.255 mmol) and sodium carbonate (5.41 g, 51.0 mmol). The flask was flushed with nitrogen, then n-propanol (40 mL) and water (8 mL) were added. The mixture was stirred at 100° C. overnight. The reaction mixture was cooled to room temperature and diluted with water. The mixture was extracted with ethyl acetate. The organic layer was washed with brine, dried over Na$_2$SO$_4$, and concentrated under reduced pressure. The crude residue was purified by silica gel chromatography to provide 4-bromo-4'-(trifluoromethyl)biphenyl (5.4 g, 70%) as a colorless solid. $^1$H NMR (400 MHz, CDCl$_3$) δ 7.62-7.73 (m, 4H), 7.57-7.61 (m, 2H), 7.43-7.47 (m, 2H).

Step B: 4,4,4-trifluoro-1-(4'-(trifluoromethyl)biphenyl-4-yl)butan-1-ol

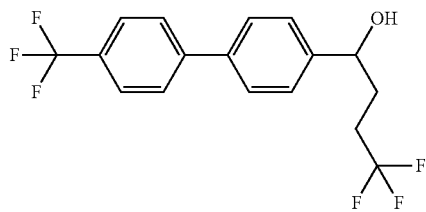 [SMILES: OC(CCC(F)(F)F)c1ccc(-c2ccc(C(F)(F)F)cc2)cc1]

n-Butyllithium (150 uL of a 2.5M solution in hexanes, 0.38 mmol) was added dropwise to a −78° C. solution of 4-bromo-4'-(trifluoromethyl)biphenyl (113 mg, 0.375 mmol) in 3 mL THF. The resulting solution was stirred at −78° C. 15 min. 4,4,4-trifluorobutyraldehyde (98 mg, 0.78 mmol) was added neat. The resulting colorless solution was stirred at −78° C. 20 min. 1 mL sat. aqueous NH$_4$Cl was added, and the mixture warmed to room temperature. The reaction mixture was partitioned between Et$_2$O and water. The organic layer was dried over MgSO$_4$ and concentrated to give a colorless oil. The crude material was purified by silica gel chromatography to provide 4,4,4-trifluoro-1-(4'-(trifluoromethyl)biphenyl-4-yl)butan-1-ol (87 mg, 67%). $^1$H NMR (400 MHz, CDCl$_3$) δ 7.64-7.71 (m, 4H), 7.57-7.62) m, 2H), 7.41-7.47 (m, 2H), 4.78-4.87 (m, 1H), 2.10-2.39 (m, 3H), 1.96-2.09 (m, 1H).

Step C: methyl 6-(tert-butoxycarbonylamino)nicotinate

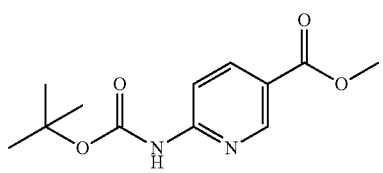 [SMILES: COC(=O)c1ccc(NC(=O)OC(C)(C)C)nc1]

Di-t-butyl dicarbonate (5.0 g, 23 mmol) was added to a room temperature suspension of methyl 6-aminonicotinate (2.65 g, 17.4 mmol) and 4-(dimethylamino)pyridine (109 mg, 0.86 mmol) in 40 mL acetonitrile. The resulting orange reaction mixture was stirred at room temperature overnight. The suspended solid was collected by filtration, washed with acetonitrile, and air dried to give methyl 6-(tert-butoxycarbonylamino)nicotinate (2.64 g, 60%) as a colorless solid. The filtrate was concentrated. The residue was dissolved in dichloromethane and passed through a plug of silica gel (~75 g) eluting with 3:1 heptane:EtOAc (400 mL). Concentration of the eluent provided an additional 1.5 g methyl 6-(tert-butoxycarbonylamino)nicotinate. $^1$H NMR (400 MHz, CDCl$_3$) δ 8.89-8.92 (m, 1H), 8.49-8.58 (br s, 1H), 8.22-8.26 (m, 1H), 8.02-8.07 (m, 1H), 3.89 (s, 3H), 1.54 (s, 9H).

Step D: methyl 6-(tert-butoxycarbonyl(4,4,4-trifluoro-1-(4'-(trifluoromethyl)biphenyl-4-yl)butyl)amino)nicotinate

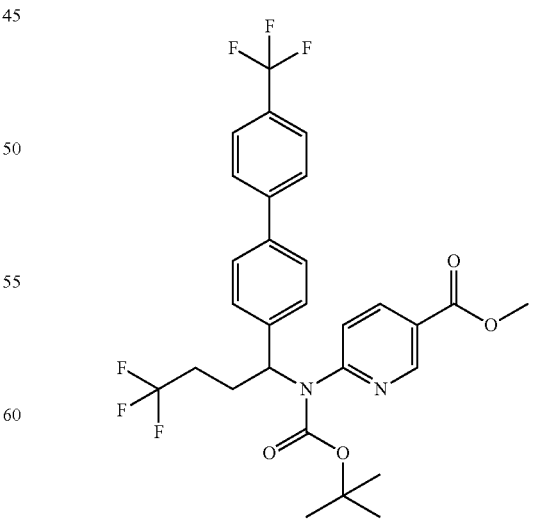

Diisopropyl azodicarboxylate (50 μL, 0.25 mmol) was added to a room temperature solution of 4,4,4-trifluoro-1-(4'-

(trifluoromethyl)biphenyl-4-yl)butan-1-ol (84 mg, 0.24 mmol), methyl 6-(tert-butoxycarbonylamino)nicotinate (74 mg, 0.29 mmol), and triphenylphosphine (65 mg, 0.25 mmol) in 1.5 mL THF. The resulting solution was stirred overnight at room temperature. The solution was partitioned between dichloromethane and water. The organic layer was dried over MgSO$_4$ and concentrated to give a colorless solid. Purification by silica gel chromatography provided methyl 6-(tert-butoxycarbonyl(4,4,4-trifluoro-1-(4'-(trifluoromethyl)biphenyl-4-yl)butyl)amino)nicotinate (30 mg, 21%) as a colorless solid. $^1$H NMR (400 MHz, CDCl$_3$) δ 8.99-9.01 (m, 1H), 8.17-8.21 (m, 1H), 7.63-7.69 (m, 4H), 7.49-7.54 (m, 3H), 7.39-7.44 (m, 2H), 5.98-6.08 (m, 1H), 3.92 (s, 3H), 2.61-2.74 (m, 1H), 2.39-2.54 (m, 1H), 2.17-2.36 (m, 2H), 1.31 (s, 9H).

Step F: methyl 3-(6-(4,4,4-trifluoro-1-(4'-(trifluoromethyl)biphenyl-4-yl)butylamino) nicotinamido) propanoate

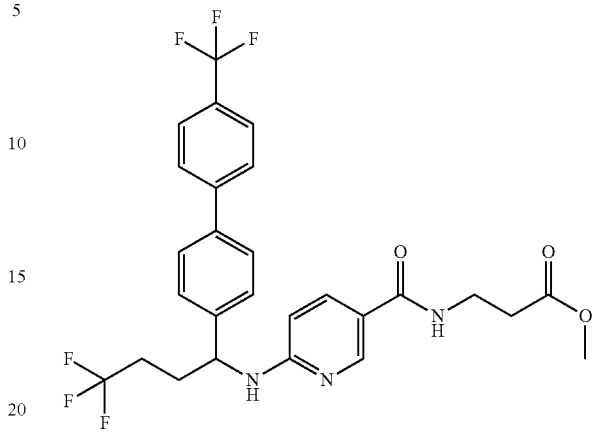

Methyl 6-(4,4,4-trifluoro-1-(4'-(trifluoromethyl)biphenyl-4-yl)butylamino)nicotinate (18 mg, 0.037 mmol) was dissolved in 1 mL methanol. 500 μL 1N aqueous sodium hydroxide was added. The resulting solution was stirred overnight at room temperature then at 50° C. for 1 h. The solution was concentrated under reduced pressure and the residue partitioned between dichloromethane and 1N aqueous HCl. The organic layer was dried over MgSO$_4$ and concentrated under reduced pressure. The residue was dissolved in 2 mL dichloromethane. Triethylamine (20 μL, 0.14 mmol), HOAt (10 mg, 0.073 mmol), and methyl 3-aminopropionate hydrochloride (10 mg, 0.072 mmol) were added. EDCI (10 mg, 0.052 mmol) was added and the resulting solution stirred 72 h at room temperature. The reaction solution was washed with water and the aqueous layer extracted with dichloromethane. The combined organic layers were dried over MgSO$_4$ and concentrated to give a pale yellow oil. Purification by silica gel chromatography provided methyl 3-(6-(4,4,4-trifluoro-1-(4'-(trifluoromethyl)biphenyl-4-yl)butylamino)nicotinamido) propanoate (13 mg, 63%) as a colorless film. $^1$H NMR (400 MHz, CDCl$_3$) δ 8.49 (d, J=2.1 Hz, 1H), 7.77 (dd, J=8.6 Hz, 2.4 Hz, 1H), 7.61-7.69 (m, 4H), 7.54-7.59 (m, 2H), 7.39-7.43 (m, 2H), 6.56-6.63 (m, 1H), 6.30 (d, J=8.6 Hz, 1H), 5.14 (d, J=7.8 Hz, 1H), 4.91-4.99 (m, 1H), 3.62-3.70 (m, 5H), 2.57-2.63 (m, 2H), 2.07-2.32 (m, 4H).

Step E: methyl 6-(4,4,4-trifluoro-1-(4'-(trifluoromethyl)biphenyl-4-yl)butylamino)nicotinate

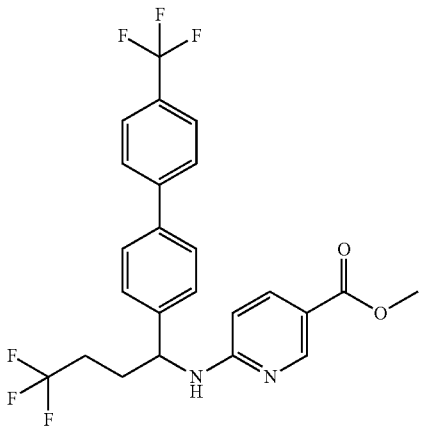 [SMILES: COC(=O)c1ccc(NC(CCC(F)(F)F)c2ccc(-c3ccc(C(F)(F)F)cc3)cc2)nc1]

A 2M solution of HCl in diethyl ether (1 mL, 2 mmol) was added to a room temperature solution of methyl 6-(tert-butoxycarbonyl(4,4,4-trifluoro-1-(4'-(trifluoromethyl)biphenyl-4-yl)butyl)amino)nicotinate (30 mg, 0.051 mmol) in 1 mL dichloromethane. After 18 h, the solution was concentrated and the residue redissolved in 2 mL trifluoroacetic acid. After 2 h, the solution was concentrated under reduced pressure. The residue was dissolved in ethyl acetate and washed with saturated aqueous sodium bicarbonate. The organic layer was dried over MgSO$_4$ and concentrated to give methyl 6-(4,4,4-trifluoro-1-(4'-(trifluoromethyl)biphenyl-4-yl)butylamino)nicotinate (18 mg, 73%) as a colorless film. $^1$H NMR (400 MHz, CDCl$_3$) 8.72-8.74 (m, 1H), 7.94 (dd, J=8 Hz, 2.5 Hz, 2H), 7.61-7.70 (m, 4H), 7.57 (d, J=8.2 Hz, 2H), 7.42 (d, J=8.2 Hz, 2H), 6.29 (d, J=8.8 Hz, 1H), 5.40 (d, J=7.6 Hz, 1H), 4.90-5.01 (m, 1H), 3.83 (s, 3H), 2.06-2.36 (m, 4H).

Step G: 3-(6-(4,4,4-trifluoro-1-(4'-(trifluoromethyl)biphenyl-4-yl)butylamino)nicotinamido) propanoic acid Methyl 3-(6-(4,4,4-trifluoro-1-(4'-(trifluoromethyl)biphenyl-4-yl)butylamino) nicotinamido)propanoate (13 mg, 0.023 mmol) was dissolved in 1 mL methanol. 100 μL 1N aqueous sodium hydroxide was added. The resulting solution was stirred at room temperature overnight. The reaction solution was concentrated under reduced pressure. The residue was dissolved in 5 mL water and the solution adjusted to pH 3 by addition of 1N aqueous HCl. The resulting mixture was extracted with ethyl acetate. The organic extract was dried over MgSO$_4$ and concentrated to give a colorless film. Residual solvent was removed under a stream of nitrogen to give 3-(6-(4,4,4-trifluoro-1-(4'-(trifluoromethyl)biphenyl-4- yl)butylamino)nicotinamido)propanoic acid (7.6 mg, 64%) as a colorless solid. $^1$H NMR (400 MHz, CDCl$_3$) δ 9.24 (br s, 1H), 8.06-8.14 (m, 2H), 7.55-7.65 (m, 4H), 7.52 (d, J=8.2 Hz, 2H), 7.38 (d, J=8.2 Hz, 2H). 6.40 (d, J=9.8 Hz, 1H), 4.46-4.55 (m, 1H), 3.64-3.72 (m, 2H), 2.52-2.59 (m, 2H), 2.04-2.32 (m, 4H). MS (M+H) 540.4.

Example 4.14

3-(6-(2-cyclopropyl-1-(4'-(trifluoromethyl)biphenyl-4-yl)ethylamino)nicotinamido)propanoic acid

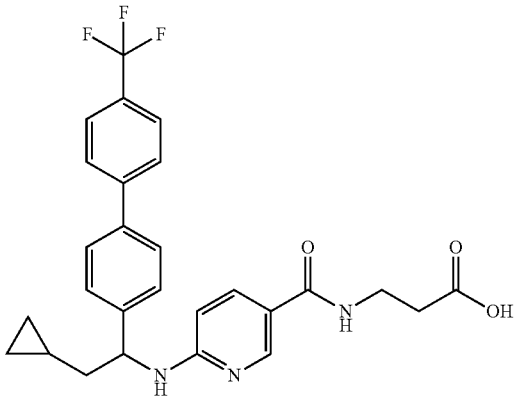 [SMILES: O=C(O)CCNC(=O)c1ccc(NC(CC2CC2)c2ccc(-c3ccc(C(F)(F)F)cc3)cc2)nc1]

Step A: 1-bromo-4-(nitromethyl)benzene

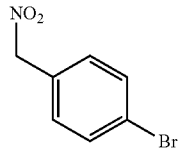 [SMILES: O=[N+]([O-])Cc1ccc(Br)cc1]

1-bromo-4-(bromomethyl)benzene (16.2 g, 65.0 mmol) was dissolved in diethyl ether (150 ml) and cooled to 0° C. Silver (I) nitrite (20 g, 130 mmol) was added in portions at 0° C. The mixture was stirred overnight at room temperature. The reaction mixture was filtered and the filtrate concentrated under reduced pressure. Purified by silica gel chromatography provided 1-bromo-4-(nitromethyl)benzene (9.5 g) as a colorless solid. $^1$H NMR (400 MHz, CDCl$_3$) δ 7.58 (d, J=8.4 Hz, 2H), 7.34 (d, J=8.4 Hz, 2H), 5.40 (s, 2H).

Step B: 4-(nitromethyl)-4'-(trifluoromethyl)biphenyl

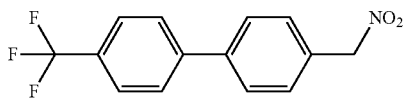

To a solution of 1-bromo-4-(nitromethyl)benzene (5.00 g, 20 mmol) in toluene (40 mL) was added palladium tetrakis (triphenylphosphine) (2.67 g, 2.31 mmol), 4-(trifluoromethyl)phenylboronic acid (5.28 g, 27.8 mmol) and potassium fluoride (4.0 g, 69 mmol). The reaction mixture was purged with nitrogen and heated to reflux. Water (10 mL) was added and the mixture was refluxed overnight. The mixture was diluted with saturated aqueous NH$_4$Cl and the phases separated. The aqueous layer was extracted with ethyl acetate (20 mL *3). The combined organic layers were washed with water (50 mL*3), brine, dried over Na$_2$SO$_4$ and concentrated.

The crude residue was purified by silica gel chromatography to give 4-(nitromethyl)-4'-(trifluoromethyl)biphenyl (2.0 g) as a yellow solid. $^1$H NMR (400 MHz, CDCl$_3$): δ 7.75-7.66 (m, 6H), 7.57 (d, J=8.0 Hz, 2H), 5.51 (s, 2H).

Step C: 2-cyclopropyl-1-(4'-(trifluoromethyl)biphenyl-4-yl)ethanamine

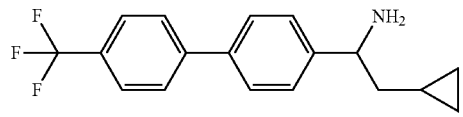 [SMILES: NC(CC1CC1)c1ccc(-c2ccc(C(F)(F)F)cc2)cc1]

To a room temperature solution of 4-(nitromethyl)-4'-(trifluoromethyl)biphenyl (200 mg, 0.711 mmol) and DBU (54.4 mg, 0.355 mmol) in DMF (3 ml) was added cyclopropanecarbaldehyde (99.7 mg, 1.42 mmol). The reaction mixture was stirred at room temperature overnight. The resulting mixture was diluted with water and extracted with ethyl acetate (10 mL*3). The combined organic layers were dried over Na$_2$SO$_4$ and concentrated under reduced pressure. The crude product was purified by preparative TLC to give impure (Z)-4-(2-cyclopropyl-1-nitrovinyl)-4'-(trifluoromethyl)biphenyl (110 mg) as a colorless solid. To a solution of the impure (Z)-4-(2-cyclopropyl-1-nitrovinyl)-4'-(trifluoromethyl)biphenyl (55 mg, 0.16 mmol) in THF (3 mL) was added Raney nickel. The reaction mixture was stirred at room temperature under an atmosphere of hydrogen (40 psi) overnight. The reaction mixture was purified by preparative TLC to give 2-cyclopropyl-1-(4'-(trifluoromethyl)biphenyl-4-yl)ethanamine (20 mg) as a colorless solid. $^1$H NMR (400 MHz, CDCl$_3$) δ 7.62-7.60 (m, 4H), 7.49 (d, J=8.0 Hz, 2H), 7.39 (d, J=8.0 Hz, 2H), 4.04-4.08 (m, 1H), 1.70-1.56 (m, 1H), 1.54-1.49 (m, 1H), 0.65-0.50 (m, 1H), 0.45-0.30 (m, 2H), 0.15-0.00 (m, 2H).

Step D: methyl 6-(2-cyclopropyl-1-(4'-(trifluoromethyl)biphenyl-4-yl)ethylamino)nicotinate

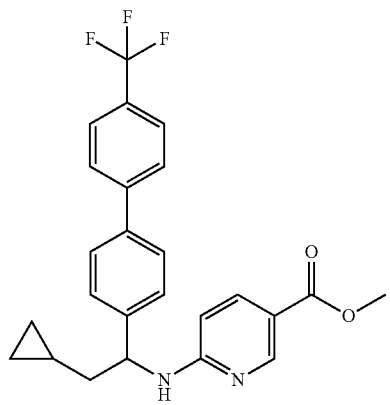 [SMILES: COC(=O)c1ccc(NC(CC2CC2)c2ccc(-c3ccc(C(F)(F)F)cc3)cc2)nc1]

A mixture of 2-cyclopropyl-1-(4'-(trifluoromethyl)biphenyl-4-yl)ethanamine (90 mg, 0.30 mmol), methyl 6-fluoronicotinate (68.7 mg, 0.443 mmol) and potassium carbonate (122 mg, 0.885 mmol) in DMF (5 mL) was stirred for 12 h at 120° C. The reaction mixture was concentrated to dryness under reduced pressure. The crude residue was purified by preparative TLC to give methyl 6-(2-cyclopropyl-1-(4'-(trifluoromethyl)biphenyl-4-yl)ethylamino)nicotinate (60 mg) as a yellow oil. $^1$H NMR (400 MHz, CDCl$_3$) δ 8.66 (s, 1H), 7.85-7.88 (m, 1H), 7.62-7.60 (m, 4H), 7.49 (d, J=8.0 Hz, 2H), 7.37 (d, J=8.0 Hz, 2H), 6.18 (d, J=8.8 Hz, 1H), 5.80 (br, 1H), 4.74-4.72 (m, 1H), 3.78 (s, 3H), 1.83-1.56 (m, 2H), 0.71-0.60 (m, 1H), 0.50-0.33 (m, 2H), 0.18-0.05 (m, 2H).

Step E: 3-(6-(2-cyclopropyl-1-(4'-(trifluoromethyl)biphenyl-4-yl)ethylamino)nicotinamido) propanoic acid To a solution of methyl 6-(2-cyclopropyl-1-(4'-(trifluoromethyl)biphenyl-4-yl)ethylamino)nicotinate (60 mg, 0.14 mmol) in THF (3.0 mL) was added 170 μL of a 2M aqueous solution of sodium hydroxide (0.34 mL). The reaction solution was stirred at 60° C. overnight. The mixture was acidified to pH 3 by addition of 1N aqueous HCl. The mixture was extracted with ethyl acetate (5 mL×3). The combined organic layers were washed with water, brine, then dried over $Na_2SO_4$ and concentrated under reduced pressure. The residue was dissolved in DMF (3 mL). methyl 3-aminopropionate hydrochloride (32.7 mg, 0.234 mmol) was added. HATU (134 mg, 0.351 mmol) was added. The mixture was stirred for 15 mins. Diisopropylethylamine (60.5 mg, 0.468 mmol) was added. The resulting mixture was stirred 2 h at room temperature. The reaction mixture was poured into water and the phases separated. The aqueous layer was extracted with ethyl acetate (3 mL×3). The combined organic layers were washed with water, dried over $Na_2SO_4$ and concentrated under reduced pressure to give a yellow solid. This solid was dissolved in THF (1.5 mL). A solution of lithium hydroxide dihydrate (14.7 mg, 0.351 mmol) in water (1.5 mL) was added. The reaction mixture was stirred for 1 h at room temperature. The mixture was acidified to pH 3 by addition of 1N aqueous HCl. The mixture was extracted with ethyl acetate (5 mL*3), and the combined organic layers were washed with water, brine, dried over $Na_2SO_4$ and concentrated to dryness. Purification by HPLC (column: Kromasil Eternity-5-$C_{18}$ 150×30 mm×5 μm; modifier 0.0685% TFA; gradient 10 to 80% acetonitrile in water) gave 3-(6-(2-cyclopropyl-1-(4'-(trifluoromethyl)biphenyl-4-yl)ethylamino)nicotinamido)propanoic acid (7.00 mg) as a colorless solid. $^1$H NMR (400 MHz, Methanol-$d_4$) δ 8.32 (s, 1H), 7.72-7.67 (m, 3H), 7.60 (d, J=8.4 Hz, 2H), 7.53 (d, J=8.4 Hz, 2H), 7.40 (d, J=8.4 Hz, 2H), 6.43 (d, J=8.8 Hz, 1H), 4.90-5.00 (m, 1H), 3.40-3.48 (m, 2H), 2.40-2.45 (m, 2H), 1.83-1.74 (m, 1H), 1.65-1.55 (m, 1H), 0.75-0.60 (m, 1H), 0.45-0.28 (m, 2H), 0.18-0.00 (m, 2H). MS (M+1)=498.3.

Example 4.15

3-(6-(3-methyl-1-(5-methyl-6-(4-(trifluoromethyl)phenyl)pyridin-3-yl)butylamino)nicotinamido)propanoic acid

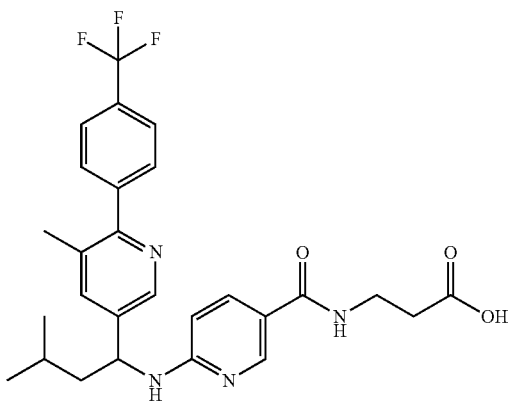 [SMILES: Cc1cc(C(CC(C)C)Nc2ccc(C(=O)NCCC(=O)O)cn2)cnc1-c1ccc(C(F)(F)F)cc1]

The title compound was prepared by a method analogous to that described for Example 1.25, using 6-chloro-5-methylnicotinonitrile in Step A. $^1$H NMR (400 MHz, $CD_3OD$) δ 8.53 (s, 1H), 8.43 (s, 1H), 7.95 (s, 1), 7.90-7.89 (m, 1H), 7.83 (d, J=8.0 Hz, 2H), 7.71 (d, J=8.0 Hz, 2H), 6.70-6.68 (m, 1H), 3.61-3.58 (m, 2H), 2.63-2.60 (m, 2H), 2.37 (s, 3H), 1.96-1.89 (m, 1H), 1.82-1.77 (m, 1H), 1.71-1.67 (m, 1H), 1.07-1.02 (m, 6H). MS (M+1)=515.4.

Example 4.16

3-(6-(1-(6-(4-chlorophenyl)-5-methylpyridin-3-ylamino)-3-methylbutyl)nicotinamido)propanoic acid, Isomer 1

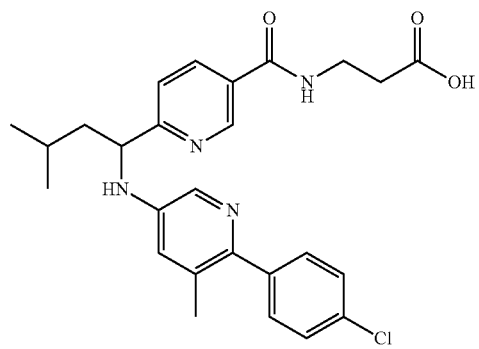 [SMILES: Cc1cc(NC(CC(C)C)c2ccc(C(=O)NCCC(=O)O)cn2)cnc1-c1ccc(Cl)cc1]

Step A: 6-(4-chlorophenol)-5-methylpyridin-3-amine

To a solution of 6-chloro-5-methylpyridin-3-amine (3 g, 20 mmol) in 1,2-dimethoxyethane (30 mL) was added $PdCl_2$(dppf) (770 mg, 1.16 mmol), 4-chlorophenylboronic acid (4.94 g, 31.6 mmol), and $K_3PO_4$ (8.93 g, 42.1 mmol). The reaction mixture was purged with nitrogen and heated to reflux. Water (20 mL) was added and the reaction mixture was stirred at reflux for 48 h. The reaction mixture was extracted with ethyl acetate (30 mL*3). The combined organic layers were concentrated under reduced pressure. Purification by silica gel chromatography provided 6-(4-chlorophenyl)-5-methylpyridin-3-amine (2.5 g) as a yellow solid. $^1$HNMR (400 MHz, $CDCl_3$) δ 7.96 (s, 1 H), 7.30-7.36 (m, 4H), 6.83 (s, 1H), 2.21 (s, 3H).

Step B: 3-(6-(1-(6-(4-chlorophenyl)-5-methylpyridin-3-ylamino)-3-methylbutyl)nicotinamido)propanoic acid, Isomer 1

(+/−)-methyl 3-(6-(1-(6-(4-chlorophenyl)-5-methylpyridin-3-yl)-3-methylbutylamino)nicotinamido)propanoate was prepared using a procedure analogous to that described in Example 2.1, Steps E-F, using 6-(4-chlorophenyl)-5-methylpyridin-3-amine in step E. The racemate was resolved by SFC using a Chiralcel OD-3 50×4.6 mm×3 μm column, eluting with a 5% to 40% methanol in $CO_2$ gradient (0.05% diethylamine modifier, flow rate 4 ml/min) to provide methyl 3-(6-(1-(6-(4-chlorophenyl)-5-methylpyridin-3-yl)-3-methylbutylamino)nicotinamido) propanoate, Isomer 1 (retention time: 1.33 min) and methyl 3-(6-(1-(6-(4-chlorophenyl)-5-methylpyridin-3-yl)-3-methylbutylamino)nicotinamido) propanoate, Isomer 2 (retention time: 1.53 min). methyl 3-(6-(1-(6-(4-chlorophenyl)-5-methylpyridin-3-yl)-3-methylbutylamino)nicotinamido) propanoate, Isomer 1 (450 mg, 0.909 mmol) was dissolved in THF (8 mL). 8 mL 2N aqueous lithium hydroxide was added. The mixture was stirred at room temperature for 1 h. The mixture was adjusted to pH=5-6 by addition of 1N aqueous HCl and extracted with ethyl acetate (5 mL*3). The combined organic layers were dried over Na$_2$SO$_4$ and concentrated under reduced pressure. Residual solvent was removed by lyophilization to give 3-(6-(1-(6-(4-chlorophenyl)-5-methylpyridin-3-ylamino)-3-methylbutyl)nicotinamido)propanoic acid, Isomer 1 (238.0 mg) as a colorless solid. $^1$H NMR (400 MHz, CD$_3$OD) δ 8.82 (d, J=2 Hz, 1H), 8.02-8.04 (m, 1H), 7.67 (d, J=2.4 Hz, 1H), 7.46 (d, J=8.4 Hz, 1H), 7.21-7.30 (m, 4H), 6.73 (d, J=2.4 Hz, 1H), 4.49-4.52 (m, 1H), 3.50-3.54 (m, 2H), 2.46-2.49 (m, 2H), 2.04 (s, 3H), 1.65-1.75 (m, 2H), 1.50-1.51 (m, 1H), 0.93 (d, J=6.0 Hz, 3H), 0.88 (d, J=6.0 Hz, 3H). MS (M+1)=481.3.

Example 4.17

3-(2-(1-(4'-(trifluoromethyl)biphenyl-4-yl)butylamino)pyrimidine-5-carboxamido)propanoic acid

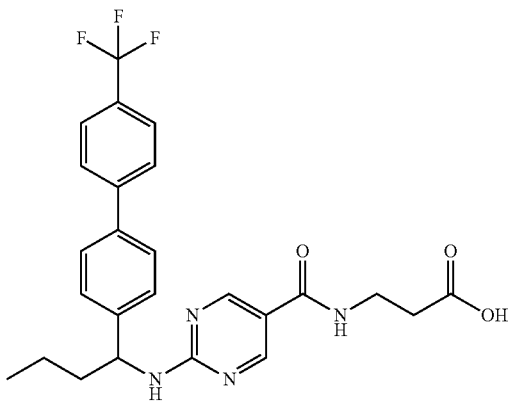 [SMILES: CCCC(Nc1ncc(C(=O)NCCC(=O)O)cn1)c1ccc(-c2ccc(C(F)(F)F)cc2)cc1]

The title compound was prepared using a method analogous to that described in Example 1.4, starting from methyl 2-chloropyrimidine-5-carboxylate and 1-(4'-(trifluoromethyl)biphenyl-4-yl)butan-1-amine (prepared in a manner analogous to that described in Example 1.25 Steps A-B starting from 4-bromobenzonitrile). $^1$H NMR (400 MHz, MeOD) δ 8.55 (s, 2H), 7.69 (d, J=8.4 Hz, 2H), 7.61 (d, J=8.4 Hz, 2H), 7.53 (d, J=8.0 Hz, 2H), 7.39 (d, J=8.4 Hz, 2H), 5.01-5.05 (m, 1H), 3.45-3.48 (m, 2H), 2.46-2.50 (m, 2H), 1.86-1.70 (m, 2H), 1.42-1.25 (m, 2H), 0.88 (t, J=7.4 Hz, 3H).MS (M+1)= 487.3.

Example 4.18

3-(4-(1-(6-(4-(trifluoromethyl)phenyl)pyridin-3-ylamino)butyl)benzamido)propanoic acid

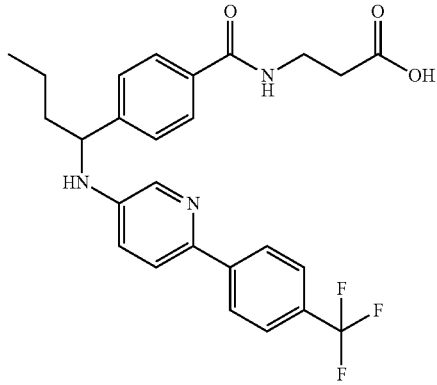 [SMILES: CCCC(Nc1ccc(-c2ccc(C(F)(F)F)cc2)nc1)c1ccc(C(=O)NCCC(=O)O)cc1]

Step A: Methyl 4-(1-hydroxybutyl)benzoate

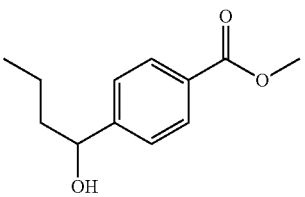

A solution of methyl 4-formylbenzoate (2.09 g, 12.7 mmol) in tetrahydrofuran (50 mL) was cooled to 0° C. To this solution was added n-propylmagnesium bromide (6.4 mL, 2.0M in THF) dropwise over 20 minutes. The reaction was stirred at 0° C. for 2 h. The reaction was then quenched by addition of saturated aqueous ammonium chloride. This mixture was extracted with ethyl acetate. The organic layer was dried over magnesium sulfate, filtered and concentrated. Purification by silica gel chromatography gave methyl 4-(1-hydroxybutyl)benzoate (1.25 g, 47%) as a colorless oil. $^1$H NMR (400 MHz, CDCl$_3$, δ) 7.97-8.02 (m, 2H), 7.40 (d, J=8.4 Hz, 2H), 4.74 (dd, J=7.8, 5.7 Hz, 1H), 3.90 (s, 3H), 1.61-1.82 (m, 2H), 1.23-1.49 (m, 2H), 0.92 (t, J=7.32 Hz, 3H).

Step B: Methyl 4-butyrylbenzoate

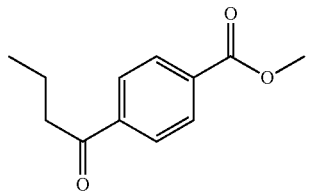

Pyridinium chlorochromate (1.25 g, 5.80 mmol) was added to a 0° C. solution of methyl 4-(1-hydroxybutyl)benzoate (602.5 mg, 2.89 mmol) in 9.6 mL dichloromethane. The reaction mixture was allowed to warm to room temperature and stirred for 3 h. MgSO$_4$ was added, and the solids removed by filtration. The filtrate was concentrated to give a brown solid. Purification by silica gel chromatography provided methyl 4-butyrylbenzoate (491.2 mg) as a colorless solid. $^1$H NMR (400 MHz, CDCl₃, δ): 8.08-8.13 (m, 2H), 7.97-8.01 (m, 2H), 3.94 (s, 3H), 2.96 (t, J=7.3 Hz, 2H), 1.77 (m, 2H), 1.00 (t, J=7.41 Hz, 3H).

Step C: 4-Butyrylbenzoic acid

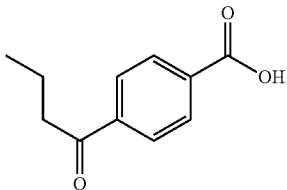

Methyl 4-butyrylbenzoate (256.1 mg, 1.242 mmol) was dissolved in tetrahydrofuran (3 mL) and methanol (3.0 mL). 1N aqueous sodium hydroxide (3.73 mL) was added and the reaction mixture was heated to 50° C. for 3 h. The reaction mixture was then cooled to room temperature and concentrated. The crude residue was taken up in water and acidified to pH 5 by addition of 1N aqueous HCl. A colorless precipitate formed. The solids were filtered off and dried under vacuum to give 4-butyrylbenzoic acid (155.4 mg, 65%) as a colorless solid. ¹H NMR (400 MHz, CDCl₃, δ) 8.16-8.21 (m, 2H), 8.01-8.05 (m, 2H), 2.98 (t, J=7.2 Hz, 2H), 1.78 (m, 2H), 1.01 (t, J=7.41 Hz, 3H).

Step D: Methyl 3-(4-butyrylbenzamido)propanoate

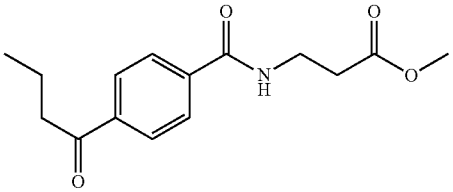 [SMILES: CCCC(=O)c1ccc(C(=O)NCCC(=O)OC)cc1]

1-ethyl-3-(3-dimethylaminopropyl)carbodimide hydrochloride (154 mg, 0.801 mmol) was added to a solution of 4-butyrylbenzoic acid (154 mg, 0.801 mmol), methyl 3-aminopropanoate hydrochloride (90.8 mg, 0.881 mmol), 1-hydroxy-7-azabenzotriazole (109 mg, 0.801 mmol), and triethylamine (120 μL, 0.86 mmol) in dichloromethane (8.0 mL). The reaction was stirred at room temperature for 19 h. The reaction was diluted with dichloromethane and washed with water and brine. The organic layer was dried over magnesium sulfate, filtered, and concentrated. Purification by silica gel chromatography gave methyl 3-(4-butyrylbenzamido)propanoate (124.1 mg, 56%) as a colorless solid. ¹H NMR (400 MHz, CDCl₃) δ 7.99 (d, J=8.4 Hz, 2H), 7.83 (d, J=8.2 Hz, 2H), 6.89 (br. s., 1H), 3.69-3.77 (m, 5H), 2.95 (t, J=7.2 Hz, 2H), 2.66 (t, J=5.8 Hz, 2H), 1.71-1.82 (m, 2H), 1.00 (t, J=7.43 Hz, 3H. MS (M+1): 278.2.

Step E: 3-(4-(1-(6-(4-(trifluoromethyl)phenyl)pyridin-3-ylamino)butyl)benzamido)propanoic acid To a solution of methyl 3-(4-butyrylbenzamido)propanoate (128 mg, 0.46 mmol) and 6-(4-(trifluoromethyl)phenyl)pyridin-3-amine (100 mg, 0.42 mmol, prepared as in Example 2.7, StepB) in dry methanol (4.8 mL) was added decaborane (31 mg, 0.25 mmol). The resulting mixture was stirred at 30° C. overnight. The solvent was removed under reduced pressure and the residue was purified by preparative TLC to provide impure methyl 3-(4-(1-(6-(4-(trifluoromethyl)phenyl)pyridin-3-ylamino)butyl)benzamido)propanoate. This material was dissolved in THF (3 mL) and water (3 mL). Aqueous lithium hydroxide (1.00 mmol) was added. The resulting mixture was stirred at 20° C. for 1 h. The solvent was removed under reduced pressure. The residue dissolved in water and the solution brought to pH 3-4 by addition of 1N aqueous HCl. The mixture was extracted with dichloromethane (10 mL*2). The combined organic layers were concentrated. Purified by preparative HPLC (column: Phenomenex Gemini C₁₈ 250×21.2 mm×10 μm; modifier: 0.225% formic acid; gradient: 10 to 30% acetonitrile in water) to give 3-(4-(1-(6-(4-(trifluoromethyl)phenyl)pyridin-3-ylamino)butyl)benzamido)propanoic acid (20 mg) as a colorless solid. ¹H NMR (400 MHz, CD₃OD) δ 7.90-7.95 (m, 3H), 7.86-7.79 (m, 5H), 7.52 (d, J=8.0 Hz, 2H), 7.43-7.47 (m, 1H), 4.57-4.60 (m, 1H), 3.60-3.64 (m, 2H), 2.62-2.65 (m, 2H), 1.94-1.96 (m, 1H), 1.82-1.86 (m, 1H), 1.57-1.43 (m, 2H), 1.01 (t, J=7.2 Hz, 3H). MS (M+1)=486.3.

Example 4.19

(+/−)-3-(6-(3-methyl-1-(2-(4-(trifluoromethyl)phenyl)pyrimidin-5-yl)butylamino)nicotinamido)propanoic acid

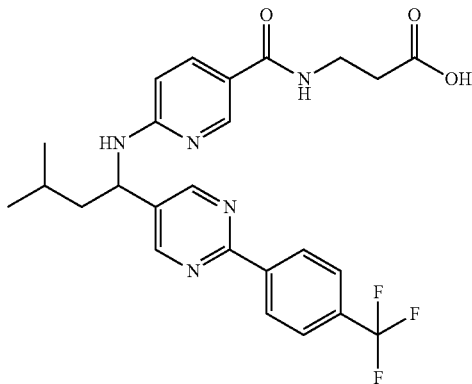 [SMILES: CC(C)CC(Nc1ccc(C(=O)NCCC(=O)O)cn1)c1cnc(-c2ccc(C(F)(F)F)cc2)nc1]

Step A:
1-(2-chloropyrimidin-5-yl)-3-methylbutan-1-ol

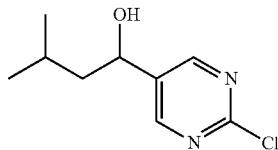

To a solution of 5-bromo-2-chloropyrimidine (5.0 g, 25.8 mmol) in diethyl ether (129 mL) and THF (129 mL) was added isovaleraldehyde (4.45 g, 51.7 mmol). The reaction mixture was cooled to −78° C., and n-butyllithium (15.4 mL of a 1.6 M solution in hexanes, 24.6 mmol) was added. The mixture was stirred for 30 m at −78° C. The reaction mixture was quenched by addition of saturated aqueous NH₄Cl, and extracted with ethyl acetate (300 mL×3). The combined organic layers were dried over Na₂SO₄ and concentrated under reduced pressure to give 1-(2-chloropyrimidin-5-yl)-3-methylbutan-1-ol (1.98 g) as yellow oil. ¹HNMR (400 MHz, CDCl₃) δ 8.54 (s, 2H), 4.76-4.80 (m, 1H), 1.75-1.66 (m, 2H), 1.45-1.37 (m, 1H), 0.89 (d, J=6.35 Hz, 6H).

Step B: 3-methyl-1-(2-(4-(trifluoromethyl)phenyl)pyrimidin-5-yl)butan-1-ol

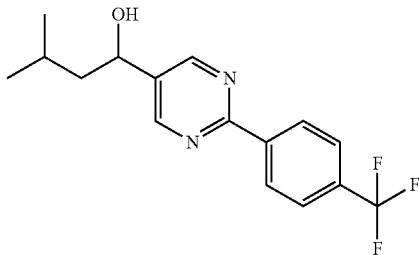 [SMILES: CC(C)CC(O)c1cnc(-c2ccc(C(F)(F)F)cc2)nc1]

To a solution of the 1-(2-chloropyrimidin-5-yl)-3-methylbutan-1-ol (600 mg, 2.99 mmol) in toluene (15.0 mL) was added Pd(PPh$_3$)$_4$ (346 mg, 0.299 mmol), 4-(trifluoromethyl)phenyl boronic acid (682 mg, 3.59 mmol), potassium fluoride (521 mg, 8.97 mmol) and water (3.7 mL). The reaction mixture was purged with nitrogen and heated to reflux for 5 h. The phases were separated and the aqueous layer was extracted with ethyl acetate (3×200 mL). The combined organic layers were concentrated under reduced pressure. The crude solid was purified by silics gel chromatography to give 3-methyl-1-(2-(4-(trifluoromethyl)phenyl)pyrimidin-5-yl)butan-1-ol (138 mg) as a yellow solid. $^1$HNMR (400 MHz, CDCl$_3$) δ 8.77 (s, 2H), 8.55 (d, J=8.4 Hz, 2H), 7.68 (d, J=8.4 Hz, 2H), 4.81-4.84 (m, 1H), 1.92-1.65 (m, 2H), 1.53-1.47 (m, 1H), 0.94 (d, J=6.4 Hz, 6H).

Step C: (+/−)-3-(6-(3-methyl-1-(2-(4-(trifluoromethyl)phenyl)pyrimidin-5-yl)butylamino)nicotinamido)propanoic acid The title compound was prepared using a method analogous to that described in Example 4.13, Steps D-G, starting from 3-methyl-1-(2-(4-(trifluoromethyl)phenyl)pyrimidin-5-yl)butan-1-ol. Colorless solid. $^1$HNMR (400 MHz, CD$_3$OD) δ 8.89 (s, 2H), 8.56 (d, J=8.4 Hz, 2H), 8.44 (d, J=2.0 Hz, 1H), 7.78-7.84 (m, 3H), 6.63 (d, J=8.8 Hz, 1H), 5.21-5.25 (m, 1H), 3.56-3.59 (m, 2H), 2.59-2.61 (m, 2H), 1.97-1.90 (m, 1H), 1.86-1.77 (m, 1H), 1.73-1.66 (m, 1H), 1.01-1.06 (m, 6H). MS (M+1)=502.3.

Example 4.20

3-(6-(3-methyl-1-(6-(4-(trifluoromethyl)phenyl)pyridin-3-yl)butylamino)nicotinamido)propanoic acid, Isomer 1 and Example 4.21: 3-(6-(3-methyl-1-(6-(4-(trifluoromethyl)phenyl)pyridin-3-yl)butylamino) nicotinamido) propanoic acid, Isomer 2

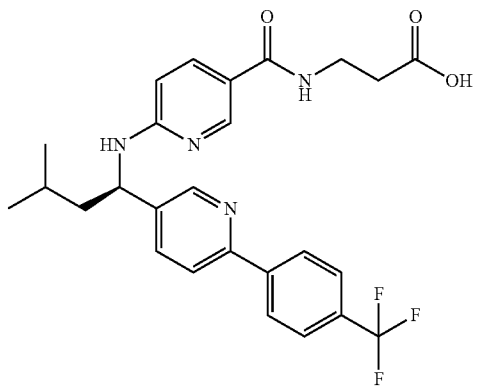

Step A: methyl 3-(6-(3-methyl-1-(6-(4-(trifluoromethyl)phenyl)pyridin-3-yl)butylamino)nicotinamido)propanoate, Isomer 1 and methyl 3-(6-(3-methyl-1-(6-(4-(trifluoromethyl)phenyl)pyridin-3-yl)butylamino)nicotinamido)propanoate, Isomer 2

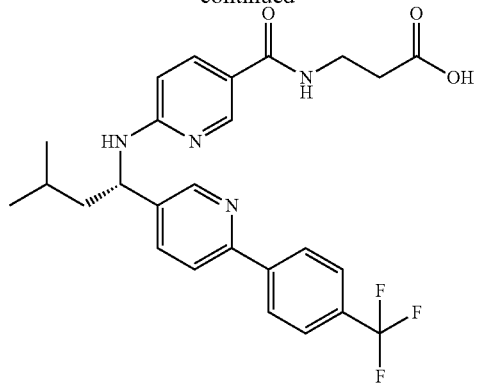

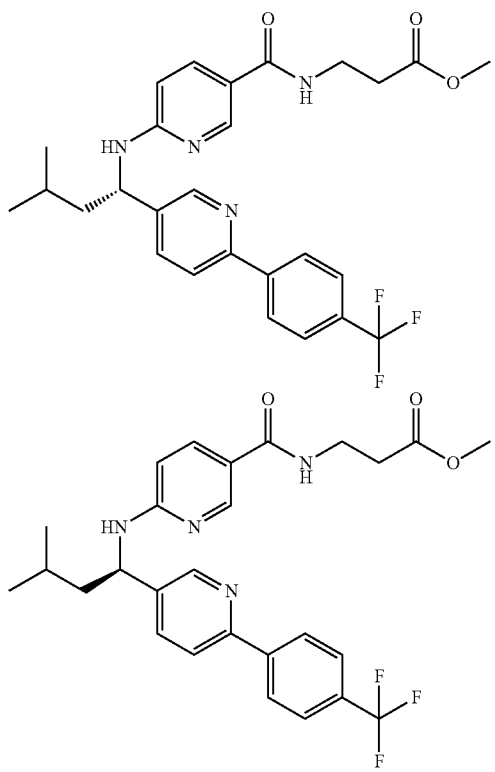

(+/−)-methyl 3-(6-(3-methyl-1-(6-(4-(trifluoromethyl)phenyl)pyridin-3-yl)butylamino)nicotinamido)propanoate (prepared as described in Example 1.29) was resolved via SFC (Column: Chiralcel OJ-H 250×4.6 mm×5 μm, Mobile phase: 5 to 40% methanol in CO$_2$, modifier: 0.05% diethylamine, flow rate: 2.5 mL/min) to give methyl 3-(6-(3-methyl-1-(6-(4-(trifluoromethyl)phenyl)pyridin-3-yl)butylamino)nicotinamido)propanoate, Isomer 1 (retention time: 7.36 min) and methyl 3-(6-(3-methyl-1-(6-(4-(trifluoromethyl)phenyl)pyridin-3-yl)butylamino) nicotinamido)propanoate, Isomer 2 (retention time: 8.85 min).

Step B: 3-(6-(3-methyl-1-(6-(4-(trifluoromethyl)phenyl)pyridin-3-yl)butylamino)nicotinamido)propanoic acid, Isomer 1

Methyl 3-(6-(3-methyl-1-(6-(4-(trifluoromethyl)phenyl)pyridin-3-yl)butylamino) nicotinamido)propanoate, Isomer 1 (950 mg, 1.85 mmol) was dissolved in water (5 mL) and THF (5 mL). Then LiOH (2.3 mL of a 2N aqueous solution, 5.6 mmol) was added. The mixture was stirred at room temperature for 2 h. The mixture was acidified to pH 5 with 1N aqueous HCl and extracted with EtOAc (5 mL*3). The combined organic layers were dried over Na$_2$SO$_4$ and concentrated to dryness to give 3-(6-(3-methyl-1-(6-(4-(trifluoromethyl)phenyl)pyridin-3-yl)butylamino)nicotinamido)propanoic acid, Isomer 1 (604.2 mg) as a colorless solid. $^1$H NMR (400 MHz, CD$_3$OD) δ 8.62 (s, 1H), 8.27 (m, 1H), 8.04 (m, 2H), 7.90-7.86 (m, 3H), 7.69 (m, 3H), 6.73 (m, 1H), 5.09-5.01 (m, 1H), 3.47 (m, 2H), 2.49 (m, 2H), 1.89-1.77 (m, 1H), 1.72-1.58 (m, 2H), 0.95 (d, J=6.4 Hz, 3H), 0.92 (d, J=6.4 Hz, 3H). MS (M+1)=501.3.

Step C: 3-(6-(3-methyl-1-(6-(4-(trifluoromethyl)phenyl)pyridin-3-yl)butylamino)nicotinamido)propanoic acid, Isomer 2

Methyl 3-(6-(3-methyl-1-(6-(4-(trifluoromethyl)phenyl)pyridin-3-yl)butylamino)nicotinamido)propanoate, Isomer 2 (980 mg, 1.90 mmol) was dissolved in water (5 mL) and THF (5 mL). Then LiOH (2.35 mL of a 2N aqueous solution, 5.70 mmol) was added. The mixture was stirred at room temperature for 2 h. The mixture was acidified to pH 5 with 1N aqueous HCl and extracted with EtOAc (5 mL*3). The combined organic layers were dried over Na$_2$SO$_4$ and concentrated to dryness to give 3-(6-(3-methyl-1-(6-(4-(trifluoromethyl)phenyl)pyridin-3-yl)butylamino)nicotinamido)propanoic acid, Isomer 2 (604.2 mg) as a colorless solid. $^1$H NMR (400 MHz, CD$_3$OD) δ 8.62 (s, 1H), 8.27 (m, 1H), 8.04 (m, 2H), 7.90-7.86 (m, 3H), 7.69 (m, 3H), 6.73 (m, 1H), 5.09-5.01 (m, 1H), 3.47 (m, 2H), 2.49 (m, 2H), 1.89-1.77 (m, 1H), 1.72-1.58 (m, 2H), 0.95 (d, J=6.4 Hz, 3H), 0.92 (d, J=6.4 Hz, 3H). MS (M+1)=501.3.

Example 4.22

(+/−)-3-(6-(3-methyl-1-(4-(5-(trifluoromethyl)pyridin-2-yl)phenyl)butylamino)nicotinamido)propanoic acid

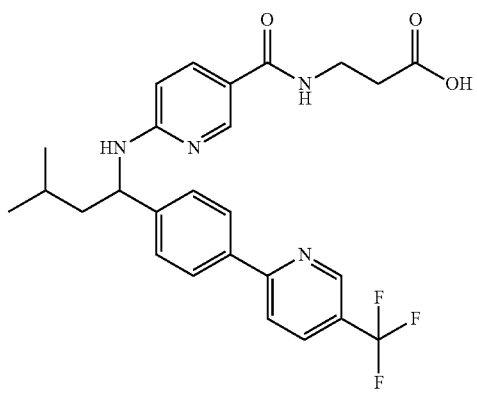 [SMILES: CC(C)CC(Nc1ccc(C(=O)NCCC(=O)O)cn1)c1ccc(-c2ccc(C(F)(F)F)cn2)cc1]

The title compound was prepared using a method analogous to that described in Example 1.25, using 4-cyanophenylboronic acid and 2-chloro-5-(trifluoromethyl)pyridine in Step A. Colorless solid. $^1$HNMR (400 MHz, CD$_3$OD) δ 8.78 (s, 1H), 8.29 (s, 1H), 8.03 (dd, J=8.8 Hz, J=2.4 Hz, 1H), 7.92-7.94 (m, 3H), 7.69 (dd, J=8.8 Hz, J=2.4 Hz, 1H), 7.42 (d, J=8.0 Hz, 2H), 6.47 (d, J=8.8 Hz, 1H), 4.97-4.99 (m, 1H), 3.44-3.47 (m, 2H), 2.46-2.49 (m, 2H), 1.77-1.67 (m, 2H), 1.64-1.50 (m, 1H), 0.87-0.92 (m, 6H). MS (M+1)=501.3.

Example 4.23

3-(6-(1-(2-methoxy-4'-(trifluoromethyl)biphenyl-4-yl)butylamino)nicotinamido)propanoic acid

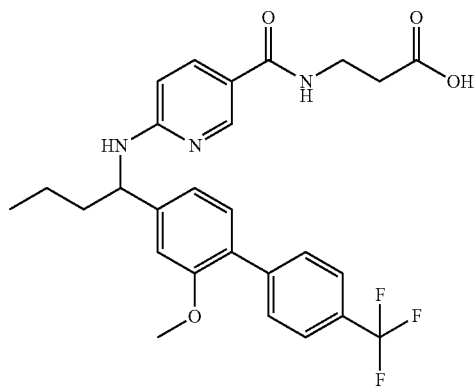 [SMILES: CCCC(Nc1ccc(C(=O)NCCC(=O)O)cn1)c1ccc(-c2ccc(C(F)(F)F)cc2)c(OC)c1]

Step A: 4-bromo-3-methoxybenzonitrile

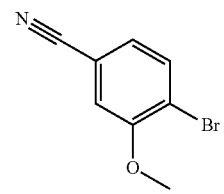

To a solution of 4-bromo-3-methoxyaniline (4 g, 19.8 mmol) in water (22 mL) was added concentrated HCl (7 mL). After cooling to 0° C., a solution of sodium nitrite (1.5 g, 22 mmol) in water (5 mL) was added dropwise. The resulting mixture was stirred at 0° C. for 30 min. After neutralizing with solid potassium carbonate, the reaction mixture was added to a mixture of copper (I) cyanide (2.13 g, 23.8 mmol) and potassium cyanide (3.2 g, 50 mmol) in water (22 mL) at 70° C. The reaction mixture was stirred at 70° C. for 1 h. After cooling to room temperature, the reaction was extracted with toluene (100 mL*4). The combined extracts were dried over Na$_2$SO$_4$, filtered, and concentrated under reduced pressure. The residue was purified by silica gel chromatography to give 4-bromo-3-methoxybenzonitrile (1.7 g) as a yellow solid. $^1$HNMR (400 MHz, CDCl$_3$) δ 7.64 (d, J=8.4 Hz, 1H), 7.14 (dd, J=8.0, 1.6 Hz, 1H), 7.09-7.10 (m, 1H), 3.87 (s, 3H).

Step B: 2-methoxy-4'-(trifluoromethyl)biphenyl-4-carbonitrile

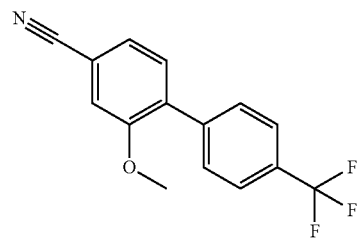 [SMILES: COc1cc(C#N)ccc1-c1ccc(C(F)(F)F)cc1]

A mixture of 4-bromo-3-methoxybenzonitrile (500 mg, 2.36 mmol), 4-(trifluoromethyl)phenyl boronic acid (671.9 mg, 3.54 mmol) and potassium fluoride (411 mg, 7.08 mmol) in toluene (11 mL) and water (3 mL) was purged with nitrogen. Pd(PPh$_3$)$_4$ (272.7 mg, 0.236 mmol) was added. The resulting mixture was heated at reflux overnight. The reaction mixture was washed with water (200 ml) and extracted with ethyl acetate (150 mL*4). The combined organic extracts were dried over Na$_2$SO$_4$, filtered, and concentrated under reduced pressure. The residue was purified by silica gel chromatography to give 2-methoxy-4'-(trifluoromethyl)biphenyl-4-carbonitrile (620 mg) as a colorless solid. $^1$HNMR (400 MHz, CDCl$_3$) δ 7.68 (d, J=8.4 Hz, 2H), 7.60 (d, J=8.4 Hz, 2H), 7.36-7.40 (m, 2H), 7.22 (s, 1H), 3.87 (s, 3H).

Step C: 3-(6-(1-(2-methoxy-4'-(trifluoromethyl)biphenyl-4-yl)butylamino)nicotinamido)propanoic acid The title compound was prepared using a method analogous to that described in Example 1.25, Steps B-D, using 2-methoxy-4'-(trifluoromethyl)biphenyl-4-carbonitrile and n-propylmagnesium bromide in Step B. Colorless solid. $^1$HNMR (400 MHz, CD$_3$OD) δ 8.44 (d, J=2.0 Hz, 1H), 7.83 (dd, J=9.2, 2.0 Hz, 1H), 7.66 (s, 4H), 7.29 (d, J=8.0 Hz, 1H), 7.14 (s, 1H), 7.08 (d, J=8.0 Hz, 1H), 6.59 (d, J=8.8 Hz, 1H), 3.83 (s, 3H), 3.57-3.60 (m, 2H), 2.59-2.63 (m, 2H), 1.94-1.84 (m, 2H), 1.57-1.54 (m, 1H), 1.48-1.44 (m, 1H), 1.02 (t, J=7.4 Hz, 3H). MS (M+1)=516.3.

Example 4.24

3-(6-(1-(3-methoxy-4'-(trifluoromethyl)biphenyl-4-yl)butylamino)nicotinamido)propanoic acid

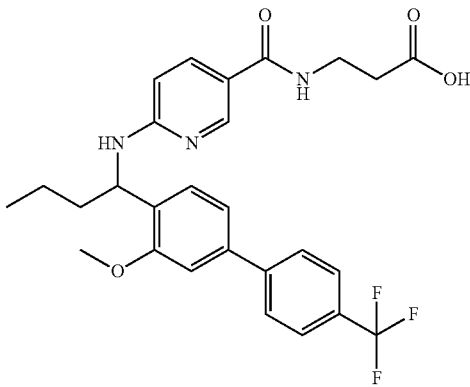 [SMILES: CCCC(Nc1ccc(C(=O)NCCC(=O)O)cn1)c1ccc(-c2ccc(C(F)(F)F)cc2)cc1OC]

Step A: 4-bromo-2-methoxybenzonitrile

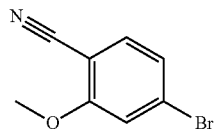

To a solution of 4-bromo-2-hydroxybenzonitrile (2 g, 10 mmol) in DMF (15 mL) and was added iodomethanel (2.87 g, 20.2 mmol) and potassium carbonate (2.79 g, 20.2 mmol) at room temperature. The mixture was stirred at room temperature for 12 h. The reaction mixture was diluted with water and extracted with ethyl acetate (10 mL*3). The combined organic layers were dried over anhydrous Na$_2$SO$_4$ and concentrated under reduced pressure to give 4-bromo-2-methoxybenzonitrile (2.08 g) as a yellow solid. $^1$H NMR (400 MHz, CDCl$_3$) δ 7.34 (d, J=8.0 Hz, 1H), 7.10 (dd, J=8.4, 1.6 Hz, 1H), 7.06 (d, J=1.6 Hz, 1H), 3.87 (s, 3H).

Step B: 3-methoxy-4'-(trifluoromethyl)biphenyl-4-carbonitrile

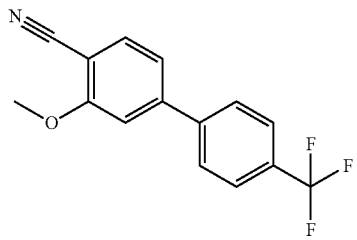 [SMILES: COc1cc(-c2ccc(C(F)(F)F)cc2)ccc1C#N]

To a solution of 4-bromo-2-methoxybenzonitrile (2.08 g, 9.81 mmol) and 4-(trifluoromethyl)phenylboronic acid (2.80 g, 14.7 mmol), potassium fluoride (1.71 g, 29.4 mmol) and Pd(PPh$_3$)$_4$ (1.13 g, 0.98 mmol) in toluene (40 mL) added water (10 mL). The mixture was stirred at 110° C. for 12 h. The reaction mixture was diluted with water and extracted with ethyl acetate (20 mL×3). The combined organic layers were dried over anhydrous Na$_2$SO$_4$ and concentrated under reduced pressure. Purification by silica gel chromatography gave 3-methoxy-4'-(trifluoromethyl)biphenyl-4-carbonitrile (2.66 g) as a colorless solid. $^1$H NMR (400 MHz, CDCl$_3$) δ 7.67 (d, J=8.4 Hz, 2H), 7.63-7.56 (m, 3H), 7.15 (dd, J=8.0, 1.2 Hz, 1H), 7.06 (s, 1H), 3.95 (s, 3H).

Step C: 3-(6-(1-(3-methoxy-4'-(trifluoromethyl)biphenyl-4-yl)butylamino) nicotinamido)propanoic acid The title compound was prepared using a procedure analogous to that described in Example 1.25, Steps B-D, using 3-methoxy-4'-(trifluoromethyl)biphenyl-4-carbonitrile and n-propylmagnesium bromide in Step B. Colorless solid. $^1$H NMR (400 MHz, CD$_3$OD) δ 8.37 (d, J=2.0 Hz, 1H), 8.00 (dd, J=9.2, 2.4 Hz, 1H), 7.83 (d, J=8.0 Hz, 2H), 7.74 (d, J=8.0 Hz, 2H), 7.40 (d, J=8.0 Hz, 1H), 7.29 (d, J=1.2 Hz, 1H), 7.25 (dd, J=8.0, 2.4 Hz, 1H), 6.77 (d, J=8.8 Hz, 1H), 5.22-5.17 (m, 1H), 4.02 (s, 1H), 3.57-3.61 (m, 2H), 2.59-2.63 (m, 2H), 1.97-1.87 (m, 2H), 1.56-1.41 (m, 2H), 1.02 (t, J=7.4 Hz, 3H). MS (M+1)=516.3.

Example 4.25

3-(6-(1-(2-(4-(trifluoromethoxy)phenyl)pyrimidin-5-yl) butylamino)nicotinamido)propanoic acid

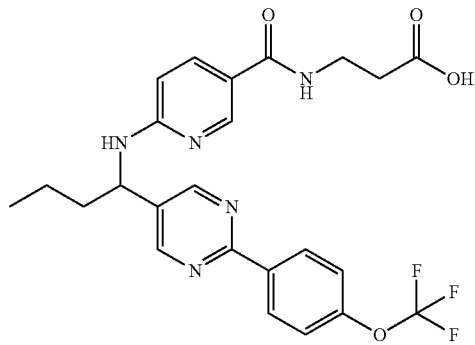 [SMILES: CCCC(Nc1ccc(C(=O)NCCC(=O)O)cn1)c1cnc(-c2ccc(OC(F)(F)F)cc2)nc1]

The title compound was prepared using a procedure analogous to that described in Example 4.19, using n-butenaldehyde and 5-bromo-2-chloropyrimidine in Step A, and 4-(trifluoromethoxy)phenylboronic acid in Step B. Colorless solid. $^1$H NMR (400 MHz, CD$_3$OD) δ 8.85 (s, 2H), 8.48 (d, J=8.8 Hz, 2H), 8.38 (d, J=2 Hz, 1H), 7.92 (d, J=8.4 Hz, 1H), 7.38 (d, J=8.8 Hz, 2H), 6.75 (d, J=8.4 Hz, 1H), 5.04-5.08 (m 1H), 3.54-3.58 (m, 2H), 2.57-2.60 (m, 2H), 1.99-1.89 (m, 2H), 1.57-1.44 (m, 2H), 1.01 (t, J=7.2 Hz, 3H). MS (M+1)=504.2.

Example 4.26

3-(6-(cyclopentyl(4'-fluorobiphenyl-4-yl)methylamino)nicotinamido) propanoic acid, Isomer 1 and Example 4.27: 3-(6-(cyclopentyl(4'-fluorobiphenyl-4-yl)methylamino)nicotinamido)propanoic acid, Isomer 2

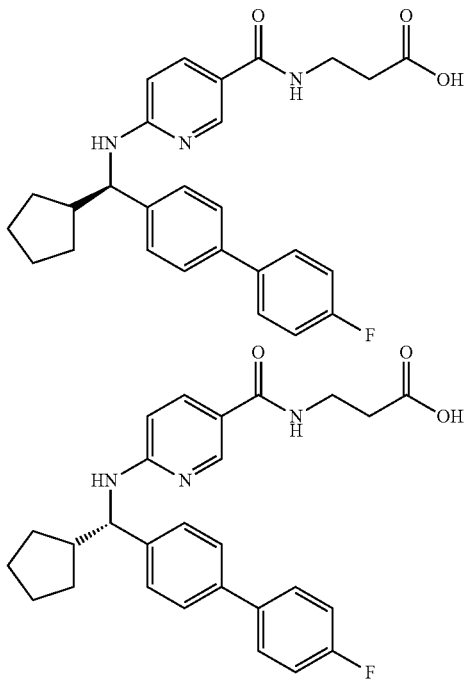

Step A: 4'-fluorobiphenyl-4-carbonitrile

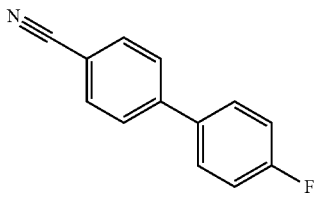 [SMILES: N#Cc1ccc(-c2ccc(F)cc2)cc1]

To a solution of 4-bromobenzonitrile (4.0 g, 22 mmol) and 4-fluorophenylboronic acid (4.6 g, 32 mmol) in 4:1 toluene:water (100 mL) were added potassium fluoride (3.8 g, 66 mmol) and Pd(PPh$_3$)$_4$ (2.5 g, 2.2 mmol). The resulting mixture was stirred at reflux for 12 h. The mixture was cooled to room temperature and extracted with ethyl acetate (30 mL*3). The combined organic layers were washed with water, brine, dried over anhydrous Na$_2$SO$_4$ and concentrated under reduced pressure. Purification of the crude residue by silica gel chromatography gave 4'-fluorobiphenyl-4-carbonitrile (4.2 g) as a colorless solid. $^1$H NMR (400 MHz, CD$_3$OD) δ 7.69 (s, 4H), 7.63-7.60 (m, 2H), 7.15-7.10 (m, 2H).

Step B: (+/−)-methyl 3-(6-(cyclopentyl(4'-fluorobiphenyl-4-yl)methylamino)nicotinamido)propanoate

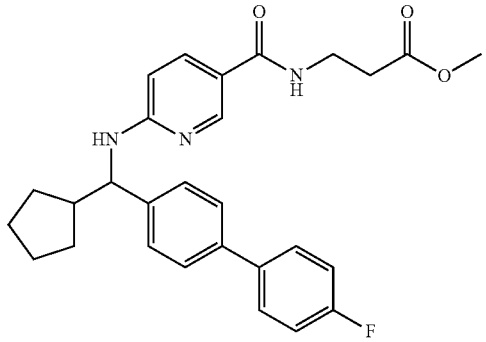 [SMILES: COC(=O)CCNC(=O)c1ccc(NC(c2ccc(-c3ccc(F)cc3)cc2)C2CCCC2)nc1]

(+/−)-methyl 3-(6-(cyclopentyl(4'-fluorobiphenyl-4-yl)methylamino)nicotinamido) propanoate was prepared using a procedure analogous to that described in Example 1.25, Steps B-D, using 4'-fluorobiphenyl-4-carbonitrile and cyclopentylmagnesium bromide in Step B.

Step C: Methyl 3-(6-(cyclopentyl(4'-fluorobiphenyl-4-yl)methylamino)nicotinamido) propanoate, Isomer 1 and Methyl 3-(6-(cyclopentyl(4'-fluorobiphenyl-4-yl)methylamino)nicotinamido)propanoate, Isomer 2

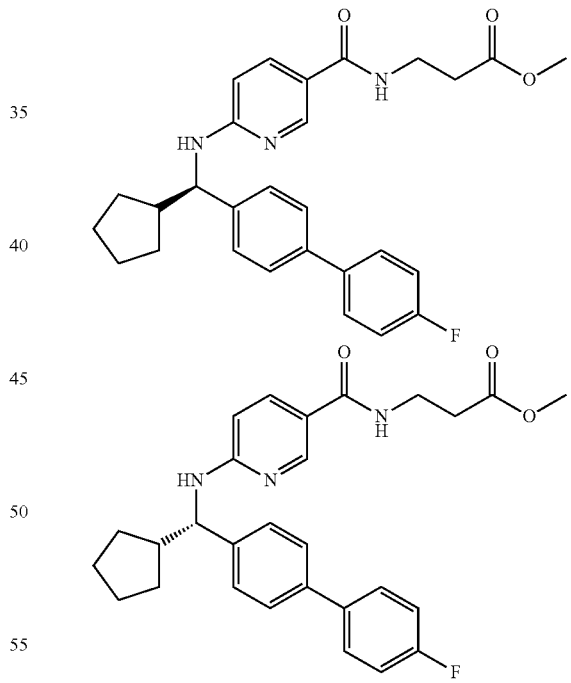

(+/−)-methyl 3-(6-(cyclopentyl(4'-fluorobiphenyl-4-yl)methylamino)nicotinamido) propanoate was resolved by SFC (Column: Chiralpak AS-H 150×4.6 mm×5 μm; Mobile phase: 5 to 40% ethanol in CO$_2$, modifier: 0.05% diethylamine, flow rate: 3 mL/min) to give methyl 3-(6-(cyclopentyl(4'-fluorobiphenyl-4-yl)methylamino) nicotinamido)propanoate, Isomer 1 (retention time: 3.89 min) and methyl 3-(6-(cyclopentyl(4'-fluorobiphenyl-4-yl)methylamino) nicotinamido)propanoate, Isomer 2 (retention time: 4.08 min).

Step D: 3-(6-(cyclopentyl(4'-fluorobiphenyl-4-yl) methylamino)nicotinamido) propanoic acid, Isomer 1

To a solution of methyl 3-(6-(cyclopentyl(4'-fluorobiphenyl-4-yl)methylamino)nicotinamido)propanoate, Isomer 1 (540 mg, 1.14 mmol) in THF (15 mL) was 15 mL 2N aquous lithium hydroxide. The mixture was stirred at 30° C. for 2 h. The mixture was neutralized with 1N aqueous HCl and extracted with ethyl acetate (20 mL*3). The combined organic layers were dried over Na$_2$SO$_4$ and concentrated under reduced pressure to give 3-(6-(cyclopentyl(4'-fluorobiphenyl-4-yl)methylamino)nicotinamido)propanoic acid, Isomer 1 (290.1 mg) as a colorless solid. $^1$H NMR (400 MHz, CD$_3$OD) δ8.18 (s, 1H), 8.07 (dd, J=9.6, 2.0 Hz, 1H), 7.48-7.51 (m, 4H), 7.39 (d, J=8.0 Hz, 2H), 7.02-7.07 (m, 2H), 6.98 (d, J=9.6 Hz, 1H), 4.48 (d, J=9.2 Hz, 1H), 3.45-3.48 (m, 2H), 2.47-2.50 (m, 2H), 2.37-2.31 (m, 1H), 1.94-1.90 (m, 1H), 1.65-1.35 (m, 6H), 1.29-1.26 (m, 1H). MS (M+1)=461.9.

Step E: 3-(6-(cyclopentyl(4'-fluorobiphenyl-4-yl) methylamino)nicotinamido) propanoic acid, Isomer 2

To a solution of methyl 3-(6-(cyclopentyl(4'-fluorobiphenyl-4-yl)methylamino)nicotinamido)propanoate, Isomer 2 (480 mg, 1.01 mmol) in THF (15 mL) was added 15 mL 2N aqueous lithium hydroxide. The mixture was stirred at 30° C. for 2 h. The mixture was neutralized with 1N aqueous HCl and extracted with ethyl acetate (20 mL*3). The combined organic layers were dried over Na$_2$SO$_4$ and concentrated to dryness to give 3-(6-(cyclopentyl(4'-fluorobiphenyl-4-yl)methylamino)nicotinamido)propanoic acid, Isomer 2 (273.2 mg) as a colorless solid. $^1$H NMR (400 MHz, CD$_3$OD) δ8.18 (s, 1H), 8.07 (dd, J=9.6, 2.0 Hz, 1H), 7.48-7.51 (m, 4H), 7.39 (d, J=8.0 Hz, 2H), 7.02-7.07 (m, 2H), 6.98 (d, J=9.6 Hz, 1H), 4.48 (d, J=9.2 Hz, 1H), 3.45-3.48 (m, 2H), 2.47-2.50 (m, 2H), 2.37-2.31 (m, 1H), 1.94-1.90 (m, 1H), 1.65-1.35 (m, 6H), 1.29-1.26 (m, 1H). MS (M+1)=462.0.

Example 4.28

3-(6-(cyclopentyl(2-(4-(trifluoromethyl)phenyl)pyrimidin-5-yl)methylamino)nicotinamido)propanoic acid

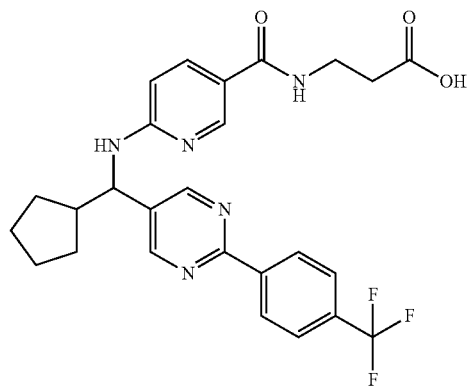 [SMILES: O=C(O)CCNC(=O)c1ccc(NC(c2cnc(-c3ccc(C(F)(F)F)cc3)nc2)C2CCCC2)nc1]

The title compound was prepared using a procedure analogous to that described in Example 4.19, using cyclopentanecarbaldehyde and 5-bromo-2-chloropyrimidine in Step A, and 4-(trifluoromethyl)phenylboronic acid in Step B. Colorless solid. $^1$H NMR (400 MHz, CD$_3$OD) δ 9.03 (s, 2H), 8.68 (d, J=8.0 Hz, 2H), 8.45 (d, J=1.6 Hz 1H), 8.16-8.18 (m, 1H), 7.89 (d, J=8.4 Hz, 2H), 7.04-7.06 (m, 1H), 4.89 (d, J=10.0 Hz, 1H), 3.65-3.68 (m, 2H), 2.67-2.70 (m, 2H), 2.62-2.56 (m, 1H), 2.16-2.13 (m, 1H), 1.86-1.58 (m, 6H), 1.43-1.38 (m, 1H). MS (M+1)=514.2.

Example 4.29

3-(6-((tetrahydro-2H-pyran-4-yl)(4'-(trifluoromethyl) biphenyl-4-yl) methylamino)nicotinamido)propanoic acid, Isomer 1 and Example 4.30

3-(6-((tetrahydro-2H-pyran-4-yl)(4'-(trifluoromethyl) biphenyl-4-yl)methylamino)nicotinamido)propanoic acid, Isomer 2

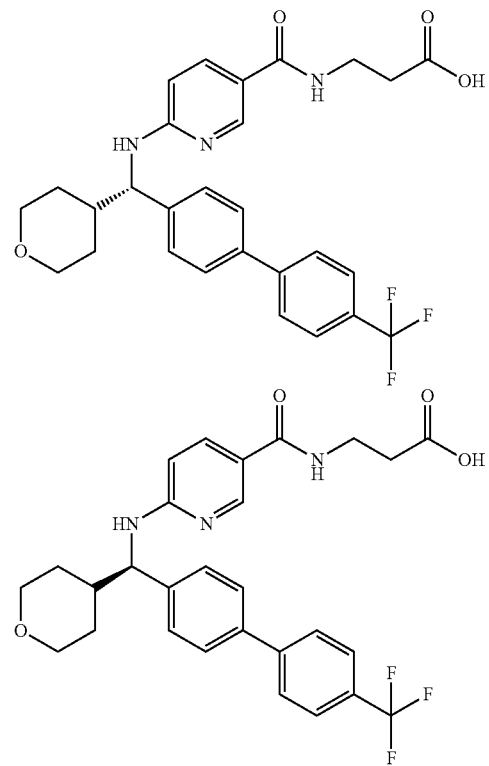

Step A: (+/−)-methyl 3-(6-((tetrahydro-2H-pyran-4-yl)(4'-(trifluoromethyl)biphenyl-4-yl)methylamino) nicotinamido)propanoate

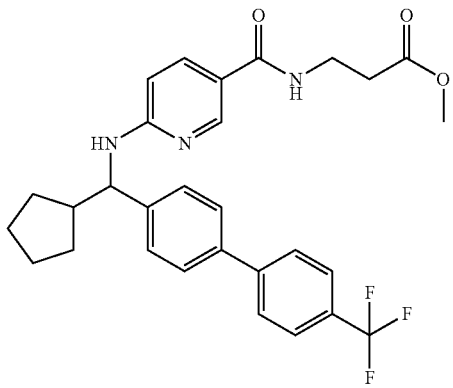 [SMILES: COC(=O)CCNC(=O)c1ccc(NC(c2ccc(-c3ccc(C(F)(F)F)cc3)cc2)C2CCCC2)nc1]

(+/−)-methyl 3-(6-((tetrahydro-2H-pyran-4-yl)(4'-(trifluoromethyl)biphenyl-4-yl)methylamino)nicotinamido)propanoate was prepared using a method analogous to the described in Example 4.13, Steps B-F, using tetrahydro-2H-pyran-4-carbaldehyde and 4-bromo-4'-(trifluoromethyl)biphenyl in Step B. Colorless solid. $^1$H NMR (400 MHz, CDCl$_3$) δ 8.45 (d, J=1.95 Hz, 1H), 7.75 (dd, J=8.8, 2.3 Hz, 1H), 7.61-7.68 (m, 4H), 7.53 (d, J=8.2 Hz, 2H), 7.36 (d, J=8.2 Hz, 2H), 6.53-6.62 (m, 1H), 6.27 (d, J=8.6 Hz, 1H), 5.62-5.74 (m, 1H), 4.49-4.58 (m, 1H), 3.90-4.07 (m, 2H), 3.59-3.72 (m, 5H), 3.26-3.42 (m, 2H), 2.56-2.62 (m, 2H), 1.92-2.05 (m, 1H), 1.80-1.90 (m, 1H), 1.31-1.58 (m, 3H).

Step B: methyl 3-(6-((tetrahydro-2H-pyran-4-yl)(4'-(trifluoromethyl)biphenyl-4-yl)methylamino)nicotinamido)propanoate, Isomer 1 and methyl 3-(6-((tetrahydro-2H-pyran-4-yl)(4'-(trifluoromethyl)biphenyl-4-yl)methylamino)nicotinamido)propanoate, Isomer 2

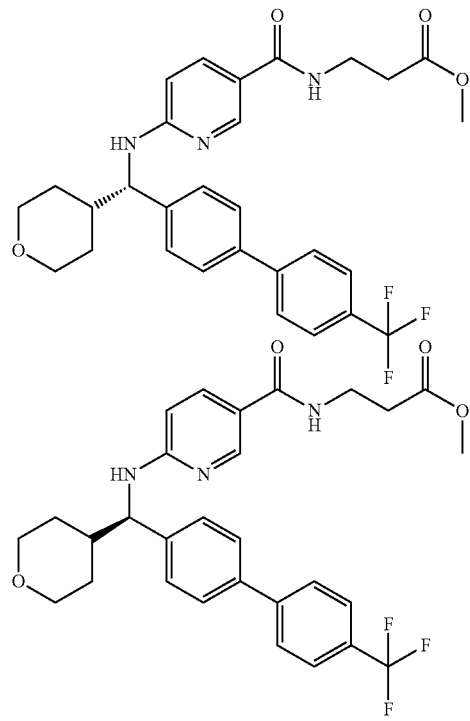

(+/−)-Methyl 3-(6-((tetrahydro-2H-pyran-4-yl)(4'-(trifluoromethyl)biphenyl-4-yl)methylamino)nicotinamido)propanoate was resolved by SFC (Column: Chiralpak AD-H 10×250 mm; Mobile phase: 50% methanol in CO$_2$; modifier: none; flow rate: 10 mL/min)) to give methyl 3-(6-((tetrahydro-2H-pyran-4-yl)(4'-(trifluoromethyl)biphenyl-4-yl)methylamino)nicotinamido)propanoate, Isomer 1 (retention time 6.55 min) and methyl 3-(6-((tetrahydro-2H-pyran-4-yl)(4'-(trifluoromethyl)biphenyl-4-yl)methylamino)nicotinamido)propanoate, Isomer 2 (retention time: 14.45 min).

Step C: 3-(6-((tetrahydro-2H-pyran-4-yl)(4'-(trifluoromethyl)biphenyl-4-yl)methylamino)nicotinamido)propanoic acid, Isomer 1

Methyl 3-(6-((tetrahydro-2H-pyran-4-yl)(4'-(trifluoromethyl)biphenyl-4-yl)methylamino)nicotinamido)propanoate, Isomer 1 (165 mg, 0.30 mmol) was dissolved in methanol (3 mL). 3 mL 1N aqueous sodium hydroxide was added and the mixture stirred 1 h at room temperature. The reaction mixture was concentrated under reduced pressure. The residue was dissolved in 5 mL water and the solution adjusted to pH 3 by addition of 1N aqueous HCl. The resulting mixture was extracted with ethyl acetate. The organic layer was dried over MgSO$_4$ and concentrated to give a colorless solid. The solid was stored in a 70° C. vacuum oven overnight to give 3-(6-((tetrahydro-2H-pyran-4-yl)(4'-(trifluoromethyl)biphenyl-4-yl)methylamino)nicotinamido)propanoic acid, Isomer 1 as a colorless solid. $^1$H NMR (400 MHz, CDCl$_3$) δ 9.55 (d, J=5.0 Hz, 1H), 8.16-8.24 (m, 2H), 7.91 (br, s, 1H), 7.59-7.70 (m, 4H), 7.55 (d, J=8.19 Hz, 2H), 7.39 (d, J=8.19 Hz, 2H), 6.52 (d, J=9.56 Hz, 1H), 4.23-4.32 (m, 1H), 3.93-4.11 (m, 2H), 3.63-3.82 (m, 2H), 3.28-3.48 (m, 2H), 2.58-2.68 (m, 2H), 2.04-2.18 (m, 1H), 1.84-1.96 (m, 1H), 1.44-1.65 (m, 2H), 1.32-1.43 (m, 1H). MS (M+1)=528.6.

Step D: 3-(6-((tetrahydro-2H-pyran-4-yl)(4'-(trifluoromethyl)biphenyl-4-yl)methylamino)nicotinamido)propanoic acid, Isomer 2

Methyl 3-(6-((tetrahydro-2H-pyran-4-yl)(4'-(trifluoromethyl)biphenyl-4-yl)methylamino)nicotinamido)propanoate, Isomer 2 (170 mg, 0.31 mmol) was dissolved in methanol (3 mL). 3 mL 1N aqueous sodium hydroxide was added and the mixture stirred 1 h at room temperature. The reaction mixture was concentrated under reduced pressure. The residue was dissolved in 10 mL water and the solution adjusted to pH 3 by addition of 1N aqueous HCl. The resulting mixture was extracted with ethyl acetate. The organic layer was dried over MgSO$_4$ and concentrated to give a colorless solid. The solid was stored in a 70° C. vacuum oven overnight to give 3-(6-((tetrahydro-2H-pyran-4-yl)(4'-(trifluoromethyl)biphenyl-4-yl)methylamino)nicotinamido)propanoic acid, Isomer 2 as a colorless solid. $^1$H NMR (400 MHz, CDCl$_3$) δ 9.55 (d, J=5.0 Hz, 1H), 8.16-8.24 (m, 2H), 7.91 (br, s, 1H), 7.59-7.70 (m, 4H), 7.55 (d, J=8.19 Hz, 2H), 7.39 (d, J=8.19 Hz, 2H), 6.52 (d, J=9.56 Hz, 1H), 4.23-4.32 (m, 1H), 3.93-4.11 (m, 2H), 3.63-3.82 (m, 2H), 3.28-3.48 (m, 2H), 2.58-2.68 (m, 2H), 2.04-2.18 (m, 1H), 1.84-1.96 (m, 1H), 1.44-1.65 (m, 2H), 1.32-1.43 (m, 1H). MS (M+1)=528.6.

Example 4.31

3-(4-(3-methyl-1-(2-(4-(trifluoromethyl)phenyl)pyrimidin-5-ylamino)butyl)benzamido)propanoic acid

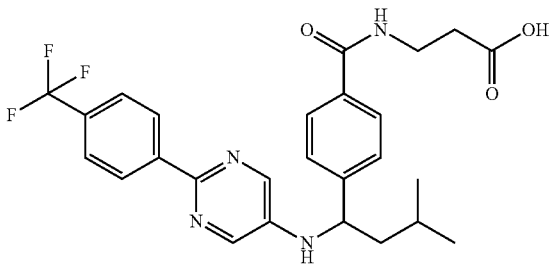 [SMILES: CC(C)CC(Nc1cnc(-c2ccc(C(F)(F)F)cc2)nc1)c1ccc(C(=O)NCCC(=O)O)cc1]

The title compound was prepared by a decaborane reductive amination reaction of the 4-trifluoromethylphenylpyrimidine-5-carbaldehyde with the corresponding appropriate amine. $^1$H NMR (400 MHz, CHLOROFORM-d) δ ppm 0.93 (d, J=6.24 Hz, 3 H) 0.98 (d, J=6.24 Hz, 3 H) 1.53-1.85 (m, 3 H) 2.66 (t, J=5.76 Hz, 2 H) 3.69 (d, J=5.85 Hz, 2 H) 4.47 (dd, J=7.90, 5.95 Hz, 1 H) 6.96-7.05 (m, 1 H) 7.38 (d, J=8.19 Hz, 2 H) 7.69 (m, 4 H) 8.22 (d, J=8.19 Hz, 2 H) 8.33 (s, 2 H). LCMS: m/z=501.2 [M+H].

Example 4.32

3-(3-(3-methyl-1-(2-(4-(trifluoromethyl)phenyl)pyrimidin-5-yl)amino)butyl)picolinamido)propanoic acid

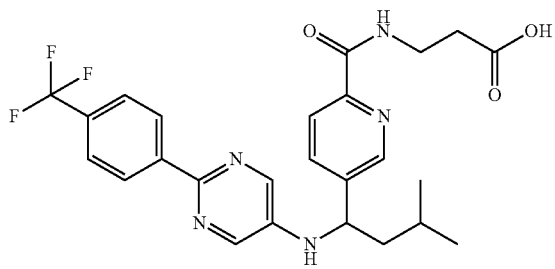 [SMILES: CC(C)CC(Nc1cnc(-c2ccc(C(F)(F)F)cc2)nc1)c1ccc(C(=O)NCCC(=O)O)nc1]

The title compound was prepared by a decaborane reductive amination reaction of the 4-trifluoromethylphenylpyrimidine-5-carbaldehyde with the corresponding appropriate amine. LCMS: Instrument: Minnie, RT=3.63 min, m/z=502.4 MH+ N,3-dimethoxy-N-methylcyclobutanecarboxamide

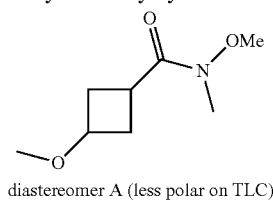

diastereomer A (less polar on TLC)

Dichloromethane (20 mL) was added to the vial containing 3-methoxycyclobutanecarboxylic acid (1:1 isomers, 1500 mg, 11.53 mmol), N-methoxymethanamine.HCl (1514 mg, 15.53 mmol) and HATU (6570 mg, 17.3 mmol). Hunig's base (8.03 mL, 46.1 mmol) was then added. The mixture was stirred at room temperature overnight. The mixture was diluted with H2O and extracted with EtOAc three times. Insoluble solids were observed in the aqueous layer. The combined organic layers were washed with brined, dried over Na$_2$SO$_4$ and concentrated. The crude was dissolved in EtOAc and loaded to the column and purified by CombiFlash (40 g silica gel, EtOAc/heptane: 0->50%), leading to less polar diastereomer A and slightly more polar diastereomer B. Diastereomer A: $^1$H NMR (400 MHz, CHLOROFORM-d) δ ppm 2.09-2.25 (m, 2 H) 2.43-2.57 (m, 2 H) 3.17 (s, 3 H) 3.23 (s, 3 H) 3.43 (m, 1 H) 3.63 (s, 3 H) 3.98-4.09 (m, 1 H). GCMS: observed 173 for C8H15NO3.

(3-methoxycyclobutyl)(4'-(trifluoromethyl)biphenyl-4-yl)methanol

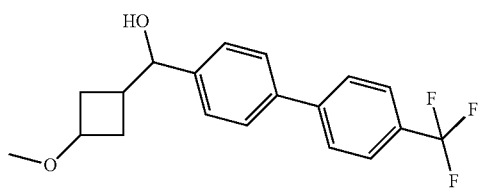 [SMILES: COC1CC(C(O)c2ccc(-c3ccc(C(F)(F)F)cc3)cc2)C1]

nBuLi (1.27 mL, 1.6 M, 2.03 mmol) was added to the biphenyl bromide (610 mg, 2.03 mmol) in THF (4 mL) at −78° C. The resulting greenish solution was stirred for 1 h. The less polar diastereomer A made above in THF (2 mL) was added at −78° C. and stirred at 0° C. for 30 minutes and room temperature for 2 h. Quenched with 1 N HCl and extracted with EtOAc three times. The combined organic layers were washed with brined, dried over Na$_2$SO$_4$ and concentrated. The crude was purified by CombiFlash (4 g silica gel, EtOAc/heptane: 0->40%), leading to the desired product. $^1$H NMR (400 MHz, CHLOROFORM-d) δ ppm 2.38 (m, 2 H) 2.67 (m, 2 H) 3.30 (s, 3 H) 3.96-4.10 (m, 2 H) 6.93-6.97 (m, 2 H) 7.47-7.51 (m, 2 H) 7.66-7.69 (m, 2 H) 7.97-8.02 (m, 2 H)

Sodium borohydride (56.5 mg, 1.50 mmol) was added to the solution of the ketone (200 mg, 0.598 mmol) made above in methanol (5 mL) at 0° C. The mixture was stirred at room temperature for 20 minutes and quenched with 1 N HCl. The mixture was extracted with EtOAc three times. The combined organic layers were washed with brine, dried over sodium sulfate and concentrated. The crude was purified by CombiFlash (4 g silica gel, EtOAc/heptane: 0->50%), leading to the desired product. $^1$H NMR (400 MHz, CHLOROFORM-d) δ ppm 1.97 (br.s., 1 H), 2.03 (m, 3 H) 2.27-2.44 (m, 1 H) 2.53-2.73 (m, 1 H) 3.22 (s, 3 H) 3.89-4.04 (m, 1 H) 4.63-4.74 (m, 1 H) 7.42 (d, J=8.19 Hz, 2 H) 7.57 (d, J=8.39 Hz, 2 H) 7.67 (s, 4 H). LCMS: m/z=319.1 [M—OH].

Example 4.33

3-(6-((3-methoxycyclobutyl)(4'-(trifluoromethyl)biphenyl-4-yl)methylamino)nicotinamido)propanoic acid

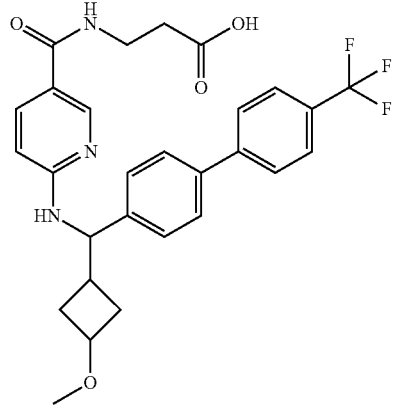 [SMILES: COC1CC(C(Nc2ccc(C(=O)NCCC(=O)O)cn2)c2ccc(-c3ccc(C(F)(F)F)cc3)cc2)C1]

$^1$H NMR (400 MHz, CHLOROFORM-d) δ ppm 2.05 (m, 2 H) 2.14-2.33 (m, 2 H) 2.71 (m, 2 H) 2.89 (m, 1 H) 3.64 (m, 2 H) 3.95 (m, 1 H) 4.31-4.51 (m, 1 H) 6.65 (m, 1 H) 7.40 (d, J=7.80 Hz, 2 H) 7.58 (d, J=7.61 Hz, 2 H) 7.60-7.71 (m, 4 H) 7.71-7.86 (m, 1 H) 8.32 (d, J=9.36 Hz, 1 H) 8.82-9.06 (m, 1 H) 9.40-9.61 (m, 1 H). LCMS: m/z=528.1 [M+H].

(tetrahydro-2H-pyran-3-yl)(4'-(trifluoromethyl)biphenyl-4-yl)methanol

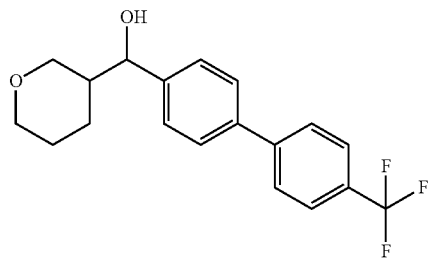

diastereomer A

A solution of the corresponding bromide (1000 mg, 3.32 mmol) in tetrahydrofuran (30 mL) was cooled to −78° C. n-BuLi (2.08 mL, 1.6 M in hexane, 3.32 mmol) was added and the mixture was stirred at −78° C. for 30 min. Pyran-3-carbaldehyde (379 mg, 3.32 mmol) in tetrahydrofuran (2 mL) was added via syringe. The mixture was stirred at −78° C. for 30 min and then warmed to room temperature. Ammonium chloride (5 mL, saturated aq) was added and the mixture was extracted with ethyl acetate. The organic layer was dried over sodium sulfate and concentrated. The crude was purified by chromatography. 12 g silica gel column eluting with 0-50% EtOAc in heptanes, leading to two diastereomers: more polar diastereomer A (192 mg, 17.2%) and less polar diastereomer B (487 mg, 43.6%). For more polar diastereomer A (192 mg, 17.2%) $^1$H NMR (400 MHz, CHLOROFORM-d) δ ppm 1.20 (m, 1 H) 1.38-1.62 (m, 3 H) 1.85-1.99 (m, 1 H) 3.40 (m, 1 H) 3.73-3.86 (m, 2 H) 4.06-4.20 (m, 1 H) 4.45 (d, J=8.39 Hz, 1 H) 7.38 (d, J=8.19 Hz, 2 H) 7.50-7.61 (m, 2 H) 7.66 (s, 4 H). LCMS: m/z=319.2 for [M—OH].

Example 4.34

3-(6-((tetrahydro-2H-pyran-3-yl)(4'-(trifluoromethyl)biphenyl-4-yl)methylamino)nicotinamido)propanoic acid

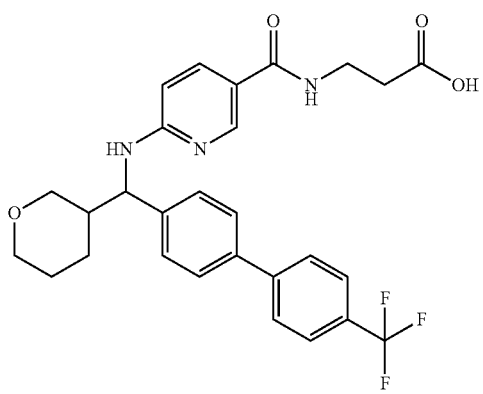 [SMILES: O=C(O)CCNC(=O)c1ccc(NC(c2ccc(-c3ccc(C(F)(F)F)cc3)cc2)C2CCCOC2)nc1]

The compound was prepared from the more polar diastereomeric alcohol A using a Mitsunobu coupling reaction with the appropriate amine. $^1$H NMR (400 MHz, CHLOROFORM-d) δ ppm 1.69 (m, 3 H) 2.13 (m, 2 H) 2.54-2.65 (m, 2 H) 3.27 (dd, J=11.41, 8.29 Hz, 1 H) 3.45-3.64 (m, 2 H) 3.71 (m, 3 H) 4.36-4.51 (m, 1 H) 6.53 (d, J=9.95 Hz, 1 H) 7.41 (d, J=8.19 Hz, 2 H) 7.55 (d, J=8.19 Hz, 2 H) 7.58-7.75 (m, 5H) 8.10-8.21 (m, 2 H) 9.35 (m, 1 H). LCMS: m/z=528.3 [M+H].

Example 4.35

3-(6-(cyclopentyl(2-(4-(trifluoromethyl)phenyl)pyrimidin-5-yl)methylamino)nicotinamido)propanoic acid, Isomer and Example 4.36: 3-(6-(cyclopentyl(2-(4-(trifluoromethyl)phenyl)pyrimidin-5-yl)methylamino)nicotinamido)propanoic acid, Isomer 2

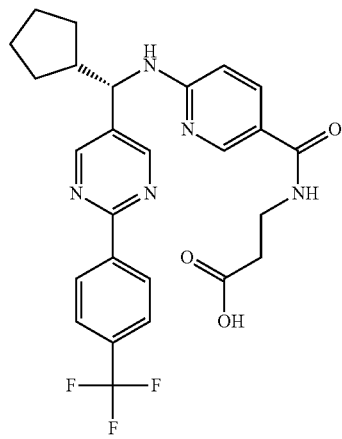

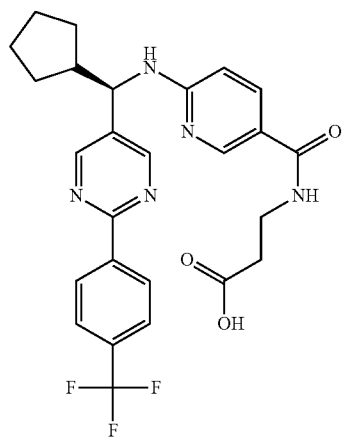

Step A: (+/−)-cyclopentyl(2-(4-(trifluoromethyl)phenyl)pyrimidin-5-yl)methanol

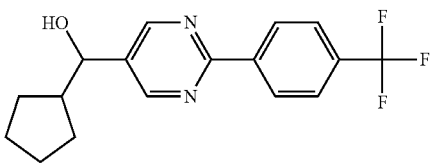 [SMILES: OC(c1cnc(-c2ccc(C(F)(F)F)cc2)nc1)C1CCCC1]

To a −78° C. solution of 2-(4-(trifluoromethyl)phenyl)pyrimidine-5-carbaldehyde (1.0 g, 3.96 mmol) in THF (6 mL) was added cyclopentylmagnesium bromide (2.97 mL of a 2.0M solution in THF, 5.95 mmol). The solution was stirred at 0° C. for two hours. The mixture was quenched with saturated aqueous NH₄Cl, dried over anhydrous Na₂SO₄, filtered and concentrated under reduced pressure. The crude residue was purified by silica gel chromatography to give cyclopentyl(2-(4-(trifluoromethyl)phenyl)pyrimidin-5-yl)methanol (1.0 g) as a red oil.

¹H NMR (400 MHz, CDCl₃) δ 8.20 (s, 2H), 8.57 (d, J=8.0 Hz, 2H), 7.75 (d, J=8.0 Hz, 2H), 4.62-4.51 (m, 1H), 2.30-2.22 (m, 1H), 2.21-2.17 (m, 1H), 1.93-1.82 (m, 1H), 1.72-1.49 (m, 6H), 1.37-1.13 (m, 1H).

Step B: (+/−)-methyl 6-(cyclopentyl(2-(4-(trifluoromethyl)phenyl)pyrimidin-5-yl)methylamino)nicotinate

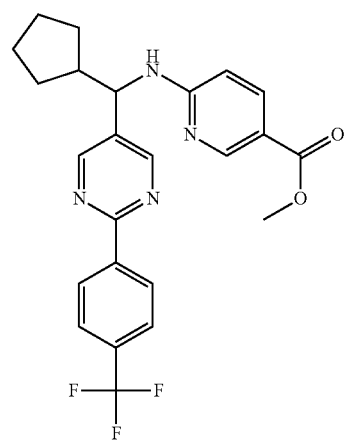 [SMILES: COC(=O)c1ccc(NC(c2cnc(-c3ccc(C(F)(F)F)cc3)nc2)C2CCCC2)nc1]

Step C: methyl 3-(6-(cyclopentyl(2-(4-(trifluoromethyl)phenyl)pyrimidin-5-yl)methylamino)nicotinamido)propanoate, Isomer 1 and Methyl 3-(6-(cyclopentyl(2-(4-(trifluoromethyl)phenyl)pyrimidin-5-yl)methylamino) nicotinamido)propanoate, Isomer 2

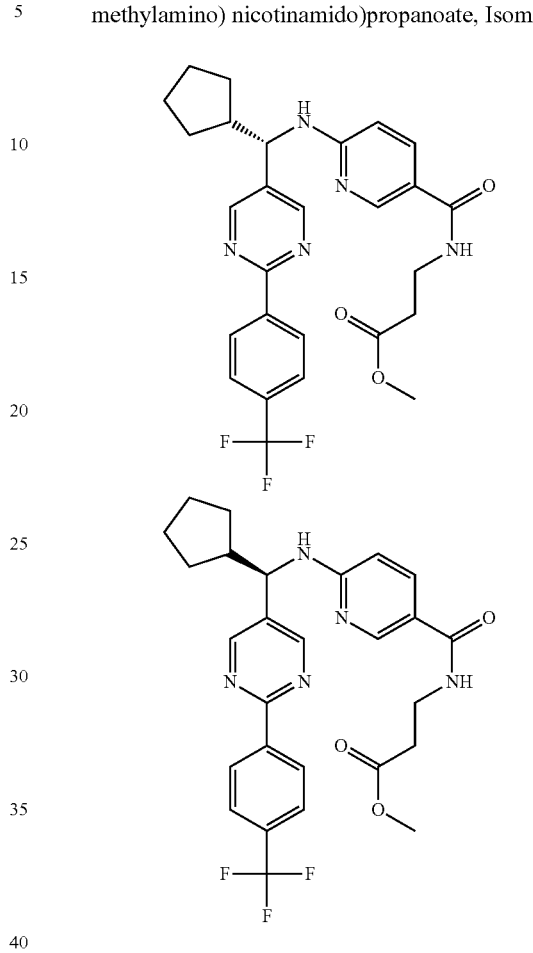

To a 0° C. mixture of cyclopentyl(2-(4-(trifluoromethyl)phenyl)pyrimidin-5-yl)methanol compound 3 (1.0 g, 3.1 mmol) and methyl 6-(tert-butoxycarbonylamino)nicotinate (1.17 g, 4.65 mmol) in THF (20 mL) was added triphenylphosphine (2.03 g, 7.75 mmol) followed by diethyl azodicarboxylate (1.35 mg, 7.75 mmol). The mixture was stirred at 40° C. overnight. The reaction mixture was diluted with water and extracted with ethyl acetate. The combined organic layers were dried over Na₂SO₄ and concentrated under reduced pressure. Purification by silica gel chromatography gave 900 mg of the t-butylcarbamate, which was dissolved in dichloromethane (30 mL). The solution was cooled to 0° C. Trifluoroacetic acid (3 ml) was added. The mixture was stirred for 2 h at room temperature. The mixture was diluted with saturated aqueous NaHCO₃ and extracted with ethyl acetate. The organic layer was washed with water, dried over Na₂SO₄, and concentrated to dryness under reduced pressure. The crude residue was purified by silica gel chromatography to give (+/−)-methyl 6-(cyclopentyl(2-(4-(trifluoromethyl)phenyl)pyrimidin-5-yl)methylamino)nicotinate (723.3 mg) as a colorless solid. ¹H NMR (400 MHz, CDCl₃) δ 9.09 (s, 2H), 9.05 (s, 1H), 8.57 (d, J=8.0 Hz, 2H), 8.22 (d, J=8.0 Hz, 1H), 7.74 (d, J=8.0 Hz, 2H), 7.51 (d, J=8.0 Hz, 1H), 5.54-5.51(m, 1H), 3.95 (s, 3H), 3.22-3.10 (m, 1H), 1.81-1.69 (m, 1H), 1.68-1.52 (m, 5H), 1.42 (s, 9H), 1.31-1.12 (m, 2H).

To a solution of (+/−)-methyl 6-(cyclopentyl(2-(4-(trifluoromethyl)phenyl)pyrimidin-5-yl)methylamino)nicotinate (972 mg, 2.13 mmol) in THF (10 mL) was added 2N aqueous LiOH (10.7 mL, 21.4 mmol). The mixture was stirred at 50° C. overnight. The mixture was neutralized by addition of 1N aqueous HCl and extracted with ethyl acetate. The combined organic layers were dried over Na₂SO₄ and concentrated under reduced pressure. The residue was dissolved in DMF (5 mL). HATU (1.19 g, 3.15 mmol) was added. The mixture was stirred for 45 min. Methyl 3-aminopropanoate hydrochloride (435 mg, 3.15 mmol) and N,N-diisopropylethylamine (1.08 g, 8.4 mmol) were added. The resulting mixture was stirred at room temperature for 2 h. The mixture was diluted with aqueous NH₄Cl. The organic layer was washed with water, dried over Na₂SO₄, and concentrated under reduced pressure to give crude (+/−)-methyl 3-(6-(cyclopentyl(2-(4-(trifluoromethyl)phenyl)pyrimidin-5-yl)methylamino)nicotinamido)propanoate (1.2 g). Resolution by SFC (Column: AD 250 mm*20 mm*5 μm, Mobile phase: 45:55 CO₂:methanol, Flow rate: 80 mL/min, Modifier: 0.1% diethylamine) to give methyl 3-(6-(cyclopentyl(2-(4-(trifluoromethyl)phenyl)pyrimidin-5-yl)methylamino)nicotinamido)propanoate, Isomer 1 (Retention time 1.36 min, 450 mg) and methyl 3-(6-(cyclopentyl(2-(4-(trifluoromethyl)phenyl)pyrimidin-5-yl)methylamino)nicotinamido)propanoate, Isomer 2 (Retention time 3.50 min, 460 mg).

Step D: 3-(6-(cyclopentyl(2-(4-(trifluoromethyl) phenyl)pyrimidin-5-yl)methylamino)nicotinamido) propanoic acid, Isomer 1

Methyl 3-(6-(cyclopentyl(2-(4-(trifluoromethyl)phenyl) pyrimidin-5-yl)methylamino)nicotinamido)propanoate, Isomer 1 (450 mg, 0.853 mmol) was dissolved in water (5 mL) and THF (5 mL).2N aqueous LiOH (4.3 mL, 8.53 mmol) was added. The mixture was stirred at room temperature for 2 h. The mixture was neutralized by addition of 1N aqueous HCl and extracted with ethyl acetate. The combined organic layers were dried over $Na_2SO_4$ and concentrated to dryness to give methyl 3-(6-(cyclopentyl(2-(4-(trifluoromethyl)phenyl)pyrimidin-5-yl)methylamino)nicotinamido)propanoate, Isomer 1 (303.1 mg) as a colorless solid.

$^1$H NMR (400 MHz, Methanol-$d_4$) δ 8.92 (s, 2H), 8.57 (d, J=8.0 Hz, 1H), 8.37 (s, 1H), 7.97 (d, J=8.0 Hz, 2H), 7.78 (d, J=8.0 Hz, 1H), 6.83 (d, J=8.0 Hz, 1H), 4.81-4.70 (m, 1H), 3.54 (t, J=7.2 Hz, 2H), 2.58 (t, J=7.2 Hz, 2H), 2.52-2.49 (m, 1H), 2.09-2.01 (m, 1H), 1.78-1.47 (m, 6H), 1.35-1.22 (m, 1H). MS (M+1)=514.13.

Step E: 3-(6-(cyclopentyl(2-(4-(trifluoromethyl)phenyl)pyrimidin-5-yl)methylamino)nicotinamido)propanoic acid, Isomer 2

Methyl 3-(6-(cyclopentyl(2-(4-(trifluoromethyl)phenyl) pyrimidin-5-yl)methylamino)nicotinamido)propanoate, Isomer 2 (460 mg, 0.872 mmol) was dissolved in water (5 mL) and THF (5 mL).2N aqueous LiOH (4.4 mL, 8.72 mmol) was added. The mixture was stirred at room temperature for 2 h. The mixture was neutralized by addition of 1N aqueous HCl and extracted with ethyl acetate. The combined organic layers were dried over $Na_2SO_4$ and concentrated to dryness to give methyl 3-(6-(cyclopentyl(2-(4-(trifluoromethyl)phenyl)pyrimidin-5-yl)methylamino)nicotinamido)propanoate, Isomer 1 (308.9 mg) as a colorless solid.

$^1$H NMR (400 MHz, Methanol-$d_4$) δ 8.92 (s, 2H), 8.57 (d, J=8.0 Hz, 1H), 8.37 (s, 1H), 7.97 (d, J=8.0 Hz, 2H), 7.78 (d, J=8.0 Hz, 1H), 6.83 (d, J=8.0 Hz, 1H), 4.81-4.70 (m, 1H), 3.54 (t, J=7.2 Hz, 2H), 2.58 (t, J=7.2 Hz, 2H), 2.52-2.49 (m, 1H), 2.09-2.01 (m, 1H), 1.78-1.47 (m, 6H), 1.35-1.22 (m, 1H). MS (M+1)=514.13.

Example 4.37

3-(6-(1-(2-(4-(trifluoromethyl)phenyl)pyrimidin-5-yl)butylamino)nicotinamido)propanoic acid, Isomer 1 and Example 4.38: 3-(6-(1-(2-(4-(trifluoromethyl) phenyl)pyrimidin-5-yl)butylamino)nicotinamido) propanoic acid, Isomer 2

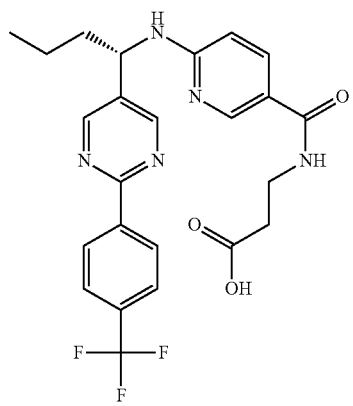

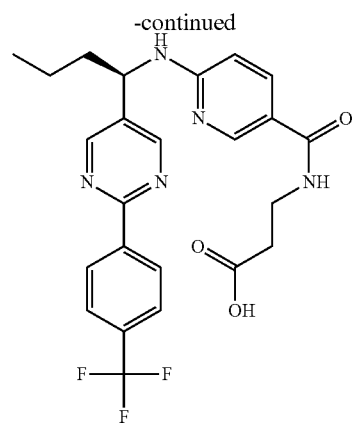

Step A: (+/−)-1-(2-(4-(trifluoromethyl)phenyl)pyrimidin-5-yl)butan-1-ol

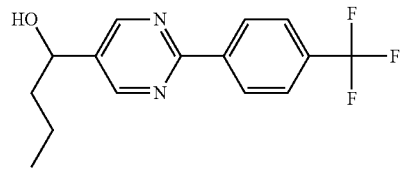 [SMILES: CCCC(O)c1cnc(-c2ccc(C(F)(F)F)cc2)nc1]

To a −78° C. solution of 2-(4-(trifluoromethyl)phenyl)pyrimidine-5-carbaldehyde (1.0 g, 3.96 mmol) in THF (20 mL) was added n-propylmagnesium bromide (2.97 mL of a 2.0M solution in THF, 5.95 mmol). The solution was stirred at 0° C. for two hours. The mixture was quenched with saturated aqueous $NH_4Cl$, dried over anhydrous $Na_2SO_4$, filtered and concentrated under reduced pressure. The crude residue was purified by silica gel chromatography to give (+/−)-1-(2-(4-(trifluoromethyl)phenyl)pyrimidin-5-yl)butan-1-ol (1.1 g) as a red oil. $^1$H NMR (400 MHz, CDCl$_3$) δ 8.75 (s, 2H), 8.50 (d, J=8.0 Hz, 2H), 7.68 (d, J=8.0 Hz, 2H), 4.79-4.68 (m, 1H), 1.98-1.91 (m, 1H), 1.85-1.63 (m, 2H), 1.47-1.29 (m, 2H), 0.92 (t, J=7.2 Hz, 3H).

Step B: (+/−)-methyl 6-(1-(2-(4-(trifluoromethyl) phenyl)pyrimidin-5-yl)butylamino)nicotinate

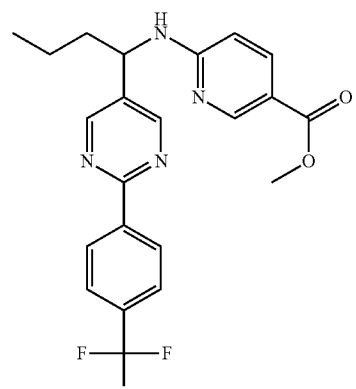

To a 0° C. mixture of (+/−)-1-(2-(4-(trifluoromethyl)phenyl)pyrimidin-5-yl)butan-1-ol (1.1 g, 3.7 mmol) and methyl 6-(tert-butoxycarbonylamino)nicotinate (1.40 g, 9.25 mmol) in THF (20 mL) was added triphenylphosphine (2.42 g, 9.25 mmol) followed by diethyl azodicarboxylate (1.61 mg, 9.25 mmol). The mixture was stirred at 40° C. overnight. The reaction mixture was diluted with water and extracted with ethyl acetate. The combined organic layers were dried over Na$_2$SO$_4$ and concentrated under reduced pressure. Purification by silica gel chromatography gave the t-butylcarbamate, which was dissolved in dichloromethane (30 mL). The solution was cooled to 0° C. Trifluoroacetic acid (3 ml) was added. The mixture was stirred for 2 h at room temperature. The mixture was diluted with saturated aqueous NaHCO$_3$ and extracted with ethyl acetate. The organic layer was washed with water, dried over Na$_2$SO$_4$, and concentrated to dryness under reduced pressure. The crude residue was purified by silica gel chromatography to give (+/−)-methyl 6-(1-(2-(4-(trifluoromethyl)phenyl)pyrimidin-5-yl)butylamino)nicotinate (796 mg) as a colorless solid. $^1$H NMR (400 MHz, CDCl$_3$) δ 8.97 (s, 1H), 8.94 (s, 2H), 8.53 (d, J=8.0 Hz, 2H), 8.19 (s, 1H), 7.71 (d, J=8.0 Hz, 2H), 7.56 (d, J=8.0 Hz, 1H), 5.90-5.81 (m, 1H), 3.91 (s, 3H), 2.32-2.09 (m, 2H), 1.35 (s, 9H), 0.89 (t, J=7.2 Hz, 3H), 0.82-0.80 (m, 2 H).

Step C: methyl 3-(6-(1-(2-(4-(trifluoromethyl)phenyl)pyrimidin-5-yl)butylamino)nicotinamido)propanoate, Isomer 1 and methyl 3-(6-(1-(2-(4-(trifluoromethyl)phenyl)pyrimidin-5-yl)butylamino)nicotinamido)propanoate, Isomer 2

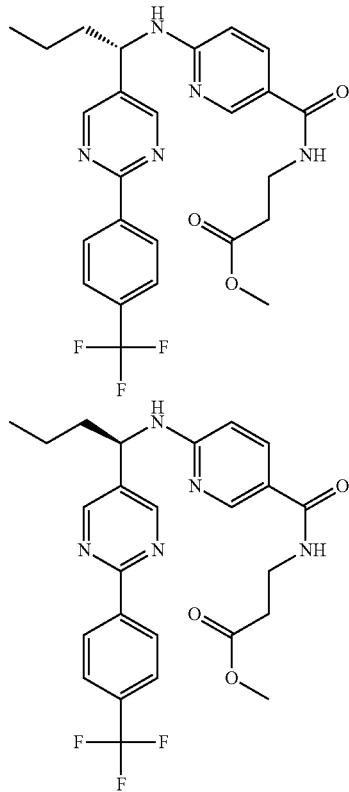

To a solution of (+/−)-methyl 6-(1-(2-(4-(trifluoromethyl)phenyl)pyrimidin-5-yl)butylamino)nicotinate (796 mg, 1.85 mmol) in THF (10 mL) was added 2N aqueous LiOH (8 mL, 16 mmol). The mixture was stirred at 50° C. overnight. The mixture was neutralized by addition of 1N aqueous HCl and extracted with ethyl acetate. The combined organic layers were dried over Na$_2$SO$_4$ and concentrated under reduced pressure. The residue was dissolved in DMF (5 mL). HATU (1.026 g, 2.7 mmol) was added. The mixture was stirred for 45 min. Methyl 3-aminopropanoate hydrochloride (373 mg, 2.7 mmol) and N,N-diisopropylethylamine (930 mg, 7.2 mmol) were added. The resulting mixture was stirred at room temperature for 2 h. The mixture was diluted with aqueous NH$_4$Cl. The organic layer was washed with water, dried over Na$_2$SO$_4$, and concentrated under reduced pressure to give crude (+/−)-methyl 3-(6-(1-(2-(4-(trifluoromethyl)phenyl)pyrimidin-5-yl)butylamino)nicotinamido)propanoate (1.0 g). Resolution by SFC (Column: OJ 250 mm*20 mm*20 μm, Mobile phase: 75:25 CO$_2$:methanol, Flow rate: 80 mL/min, Modifier: 0.1% diethylamine) to give methyl 3-(6-(1-(2-(4-(trifluoromethyl)phenyl)pyrimidin-5-yl)butylamino)nicotinamido)propanoate, Isomer 1 (Retention time 0.959 min, 390 mg) and methyl 3-(6-(1-(2-(4-(trifluoromethyl)phenyl)pyrimidin-5-yl)butylamino)nicotinamido)propanoate, Isomer 2 (Retention time 1.87 min, 400 mg).

Step D: 3-(6-(1-(2-(4-(trifluoromethyl)phenyl)pyrimidin-5-yl)butylamino)nicotinamido) propanoic acid, Isomer 1

The methyl 3-(6-(1-(2-(4-(trifluoromethyl)phenyl)pyrimidin-5-yl)butylamino)nicotinamido)propanoate, Isomer 1 (390 mg, 0.778 mmol) was dissolved in water (5 mL) and THF (5 mL). Aqueous 2N LiOH (4.7 mL, 9.4 mmol) was added. The mixture was stirred at room temperature for 2 h. The mixture was neutralized by addition of 1N aqueous HCl and extracted with ethyl acetate. The combined organic layers were dried over Na$_2$SO$_4$ and concentrated to dryness, to give 3-(6-(1-(2-(4-(trifluoromethyl)phenyl)pyrimidin-5-yl)butylamino)nicotinamido) propanoic acid, Isomer 1 (261 mg) as a colorless solid. $^1$H NMR (400 MHz, Methanol-d$_4$) δ 8.87 (s, 2H), 8.50 (d, J=8.0 Hz, 2H), 8.39 (s, 1H), 7.82 (d, J=8.8 Hz, 1H), 7.77 (d, J=8.8 Hz, 2H), 6.63 (d, J=8.8 Hz, 1H), 5.11-5.07 (m, 1H), 3.55 (t, J=6.8 Hz, 2 H), 2.57 (t, J=6.8 Hz, 2H), 1.98-1.71 (m, 2H), 1.43-1.62 (m, 2H), 1.00 (t, J=7.2 Hz, 2H). MS (M+1)=488.1.

Step E: 3-(6-(1-(2-(4-(trifluoromethyl)phenyl)pyrimidin-5-yl)butylamino)nicotinamido) propanoic acid, Isomer 2

The methyl 3-(6-(1-(2-(4-(trifluoromethyl)phenyl)pyrimidin-5-yl)butylamino)nicotinamido)propanoate, Isomer 2 (400 mg, 0.80 mmol) was dissolved in water (5 mL) and THF (5 mL). Aqueous 2N LiOH (4.0 mL, 8.0 mmol) was added. The mixture was stirred at room temperature for 2 h. The mixture was neutralized by addition of 1N aqueous HCl and extracted with ethyl acetate. The combined organic layers were dried over Na$_2$SO$_4$ and concentrated to dryness, to give 3-(6-(1-(2-(4-(trifluoromethyl)phenyl)pyrimidin-5-yl)butylamino)nicotinamido) propanoic acid, Isomer 2 (277 mg) as a colorless solid. $^1$H NMR (400 MHz, Methanol-d$_4$) δ 8.87 (s, 2H), 8.50 (d, J=8.0 Hz, 2H), 8.39 (s, 1H), 7.82 (d, J=8.8 Hz, 1H), 7.77 (d, J=8.8 Hz, 2H), 6.63 (d, J=8.8 Hz, 1H), 5.11-5.07 (m, 1H), 3.55 (t, J=6.8 Hz, 2 H), 2.57 (t, J=6.8 Hz, 2H), 1.98-1.71 (m, 2H), 1.43-1.62 (m, 2H), 1.00 (t, J=7.2 Hz, 2H). MS (M+1)=488.1.

Biological Data
Glucagon cAMP Assay

The Cisbio cAMP detection assay is used to determine the ability of punitive glucagon antagonist to block glucagon induced cAMP production. Potential glucagon antagonists are re-suspended and diluted in 100% DMSO. Prior to use in the Glucagon cAMP assay 100×DMSO compound stocks are diluted 20× with DMEM-F12 media (Invitrogen) containing either 0.1% or 4% BSA. 2 uls of 5× compound stocks are spotted into the appropriate wells of low binding white solid bottom 384 well plates (Corning). 2 uls of 5% DMSO or known glucagon antagonist are added to each plate to define the assay window. CHOK1 cells stably transfected with the human glucagon receptor are removed from culture flasks with cell dissociation buffer. Cell pellets are re-suspended, at a concentration of $8.3e^5$ cells/ml in DMEM-F12 with or without 4% BSA and 200 uM IBMX. 6 uls of cell suspensions are added to the assay plates. Plates are incubated for 20 min at room temperature prior to the addition of a 100 pM challenge dose of glucagon. On a separate plate glucagon dose response curves are run to determine the $EC_{50}$ of glucagon. After a 30 min room temperature incubation the reaction is terminated by the addition of lysis buffer containing the cAMP detection reagents. Plates are incubated for an additional 60 min at room temperature prior to being read on the Perkin Elmer fluorescent plate reader. Raw is converted to nM of cAMP produced based on a cAMP standard curve. Converted data is then analyzed using the Pfizer data analysis program. $IC_{50}$ values are determined from the generated sigmoidal dose response curves. Kb values are the calculated using a modified Cheng-Prusoff equation. The data is provided below in Table 1.

TABLE 1 cAMP Data

| Example Number | N (number of times assayed) | cAMP kb (nm) |
|---|---|---|
| 1.1 | 23 | 1700 |
| 1.2 | 8 | 140 |
| 1.3 | 23 | 73 |
| 1.4 | 10 | 560 |
| 1.5 | 8 | 2900 |
| 1.6 | 16 | 210 |
| 1.7 | 8 | 170 |
| 1.8 | 6 | 1000 |
| 1.9 | 14 | 130 |
| 1.10 | 12 | 180 |
| 1.11 | 14 | 280 |
| 1.12 | 18 | 560 |
| 1.13 | 30 | 150 |
| 1.14 | 6 | 990 |
| 1.15 | 10 | 78 |
| 1.16 | 2 | 150 |
| 1.17 | 16 | 1100 |
| 1.18 | 18 | 120 |
| 1.19 | 4 | 890 |
| 1.20 | 1 | 1000 |
| 1.21 | 1 | 520 |
| 1.22 | 1 | 6700 |
| 1.23 | 6 | 300 |
| 1.24 | 2 | 1600 |
| 1.25 | 4 | 95 |
| 1.26 | 4 | 390 |
| 1.27 | 4 | 260 |
| 1.28 | 4 | 83 |
| 1.29 | 10 | 160 |
| 1.30 | 4 | 540 |
| 1.31 | 4 | 540 |
| 1.32 | 1 | 610 |
| 1.33 | 4 | 120 |
| 1.34 | 4 | 550 |
| 1.35 | 10 | 50 |
| 1.36 | 8 | 870 |
| 1.37 | 8 | 220 |
| 1.38 | 2 | 600 |
| 1.39 | 8 | 110 |
| 1.40 | 2 | 4600 |
| 1.41 | 2 | 450 |
| 1.42 | 2 | 780 |
| 1.43 | 8 | 190 |
| 1.44 | 2 | 580 |
| 1.45 | 2 | 620 |
| 1.46 | 10 | 92 |
| 1.47 | 10 | 180 |
| 1.48 | 2 | 1200 |
| 1.49 | 2 | 750 |
| 1.50 | 10 | 70 |
| 1.51 | 10 | 160 |
| 1.52 | 10 | 120 |
| 1.53 | 10 | 46 |
| 1.54 | 2 | 230 |
| 1.55 | 2 | 4800 |
| 1.56 | 2 | 5000 |
| 1.57 | 7 | 120 |
| 1.58 | 10 | 120 |
| 1.59 | 2 | 1500 |
| 1.60 | 4 | 280 |
| 2.1 | 4 | 38 |
| 2.2 | 14 | 54 |
| 2.3 | 5 | 310 |
| 2.4 | 2 | 300 |
| 2.5 | 7 | 760 |
| 2.6 | 7 | 500 |
| 2.7 | 10 | 280 |
| 2.8 | 13 | 130 |
| 2.9 | 4 | 820 |
| 2.10 | 6 | 1700 |
| 2.11 | 4 | 1800 |
| 2.12 | 8 | 730 |
| 2.13 | 8 | 1900 |
| 2.14 | 4 | 290 |
| 2.15 | 4 | 120 |
| 2.16 | 4 | 120 |
| 2.17 | 4 | 420 |
| 3.1 | 10 | 1500 |
| 3.2 | 6 | 1900 |
| 3.3 | 6 | 6000 |
| 4.1 | 22 | 67 |
| 4.2 | 4 | 31 |
| 4.3 | 8 | 99 |
| 4.4 | 10 | 66 |
| 4.5 | 8 | 820 |
| 4.6 | 11 | 53 |
| 4.7 | 8 | 220 |
| 4.8 | 10 | 200 |
| 4.9 | 8 | 130 |
| 4.10 | 12 | 27 |
| 4.12 | 20 | 54 |
| 4.13 | 10 | 700 |
| 4.14 | 4 | 110 |
| 4.15 | 4 | 370 |
| 4.16 | 4 | 180 |
| 4.17 | 6 | 340 |
| 4.18 | 4 | 60 |
| 4.19 | 8 | 200 |
| 4.20 | 16 | 61 |
| 4.21 | 10 | 980 |
| 4.22 | 5 | 53 |
| 4.23 | 6 | 75 |
| 4.24 | 8 | 88 |
| 4.25 | 6 | 94 |
| 4.26 | 6 | 57 |
| 4.27 | 2 | 310 |
| 4.28 | 2 | 56 |
| 4.29 | 4 | 570 |
| 4.30 | 6 | 71 |
| 4.31 | 6 | 55 |
| 4.32 | 6 | 2700 |
| 4.33 | 4 | 280 |
| 4.34 | 7 | 120 |

Human Glucaqon SPA Assay

The Glucagon SPA assay is used to determine the ability of test compounds to block the binding of glucagon-cex to the glucagon receptor. Test compounds are re-suspended and serially diluted in 100% DMSO. 1 ul of test compound at the desired concentrations is spotted into the appropriate wells of 96 well low binding white clear bottom plate (Corning). 1 ul of DMSO is spotted into total binding wells. 1 ul of a known glucagon antagonist at a concentration of 20 uM is added to non specific binding wells. 0.3-0.75 ug of membrane from chem-1 cells stably transfected with the human glucagon receptor (Millipore), 125 pM of [$^{125}$I]Glucagon-Cex (Perkin Elmer) and 175 ug of WGA PVT SPA beads (Perkin Elmer) are added to all wells of the assay plate. All assay ingredients with the exception of test compounds are re-suspended in the following buffer; 50 mM Hepes pH 7.4; 5 mM MgCl$_2$; 1 mM CaCl; 5% glycerol and 0.2% BSA. Following a 6-10 hr incubation at room temperature the amount of hot ligand bound to the cell membranes is determined by reading the plates on a Wallac Trilux radioactive emission detector. Data is analyzed using Pfizer's Data analysis program. IC$_{50}$ values are then determined from the generated sigmoidal dose response curves. Ki values are calculated using Cheng-Prusoff equation. Data for certain compounds is provided in Table 2 below.

Table 2

| SPA Binding Data | | |
| --- | --- | --- |
| Example | N | binding |
| 1.23 | 3 | 27 |
| 1.31 | 2 | 24 |
| 2.14 | 4 | 79 |
| 2.15 | 3 | 34 |
| 4.1 | 10 | 22 |
| 4.12 | 8 | 15 |
| 4.20 | 11 | 14 |
| 4.21 | 7 | 124 |

We claim:

1. A compound of Formula I

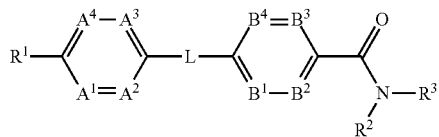

or a pharmaceutically acceptable salt thereof, wherein
R$^1$ is phenyl substituted with halo or trifluoromethyl; or a 6-membered heteroaryl group which is optionally fused with a (C$_4$-C$_7$)cycloalkyl, phenyl or 5 to 6 membered heteroaryl, and wherein the optionally fused 6-membered heteroaryl group is optionally substituted with one to four substituents each independently selected from halo, —S(O)$_2$—(C$_{1-3}$)alkyl, hydroxy, —C(O)NR$^a$R$^b$, cyano, (C$_1$-C$_6$)alkyl optionally substituted with one to three fluoro, or (C$_1$-C$_6$)alkoxy optionally substituted with one to three fluoro;
R$^a$ and R$^b$ are each independently H or (C$_1$-C$_3$)alkyl;
R$^2$ is H;
R$^3$ is —(CH$_2$)$_2$CO$_2$H;
A$^1$, A$^2$, A$^3$ and A$^4$ are each independently CR$^4$ or N, with the proviso that two of A$^1$, A$^2$, A$^3$ and A$^4$ are N and the remaining are CR$^4$;
R$^4$ at each occurrence is independently H, halo, cyano, (C$_1$-C$_3$)alkyl optionally substituted with one to three fluoro, or (C$_1$-C$_3$)alkoxy optionally substituted with one to three fluoro;
L is —CH(R$^5$)—X—;
X is NH;

R$^5$ is (C$_1$-C$_6$)alkyl which is optionally substituted with one to three fluoro, hydroxy or methoxy; (C$_3$-C$_7$)cycloalkyl which is optionally substituted with one to two (C$_1$-C$_3$) alkyl which are optionally substituted with one to three fluoro or one to two (C$_1$-C$_3$)alkyl and wherein one to two carbons of the (C$_3$-C$_7$)cycloalkyl can be replaced with a NH, N(C$_1$-C$_3$)alkyl, O or S; or (C$_3$-C$_7$)cycloalkyl-(C$_1$-C$_6$)alkyl wherein the (C$_3$-C$_7$)cycloalkyl group of said (C$_3$-C$_7$)cycloalkyl-(C$_1$-C$_6$)alkyl is optionally substituted with one to two (C$_1$-C$_3$)alkyl which are optionally substituted with one to three fluoro;
B$^1$, B$^2$, B$^3$ and B$^4$ are each independently CR$^6$ or N, with the proviso that one of B$^1$, B$^2$, B$^3$ and B$^4$ is N and the remaining are CR$^6$; and
R$^6$ at each occurrence is independently H, halo, (C$_1$-C$_3$) alkyl optionally substituted with one to three fluoro, or (C$_1$-C$_3$)alkoxy optionally substituted with one to three fluoro.

2. The compound of claim 1 or a pharmaceutically acceptable salt thereof wherein R$^5$ is ethyl, propyl, isopropyl, isobutyl, t-butyl, pentyl, neopentyl, cyclopropyl, cyclobutyl, cyclopentyl, cyclohexyl or cyclopropylmethyl each optionally substituted with 1 to 3 fluoro and wherein said cyclopropyl, cyclobutyl, cyclopentyl, cyclohexyl are each optionally substituted with 1 to 2 methyl.

3. The compound of claim 1 or a pharmaceutically acceptable salt thereof wherein R$^1$ is 4-trifluoromethylphenyl or 4-chlorophenyl; and R$^4$ and R$^6$ at each occurrence are H.

4. A pharmaceutical composition comprising (i) a compound of claim 1 or a pharmaceutically acceptable salt thereof and (ii) a pharmaceutically acceptable excipient, diluent, or carrier.

5. A method for treating obesity in a human comprising the step of administering to the human in need of such treatment a therapeutically effective amount of a compound of claim 1 or a pharmaceutically acceptable salt thereof.

6. A method for treating or delaying the progression or onset of Type 2 diabetes in a human comprising the step of administering to the human in need of such treatment a therapeutically effective amount of a compound of claim 1 or a pharmaceutically acceptable salt thereof.

7. A compound that is 3-[(6-{(S)-3-methyl-1-[2-(4-trifluoromethyl-phenyl)-pyrimidin-5-yl]-butylamino}-pyridine-3-carbonyl)-amino]-propionic acid or a pharmaceutically acceptable salt thereof.

8. A compound of structure

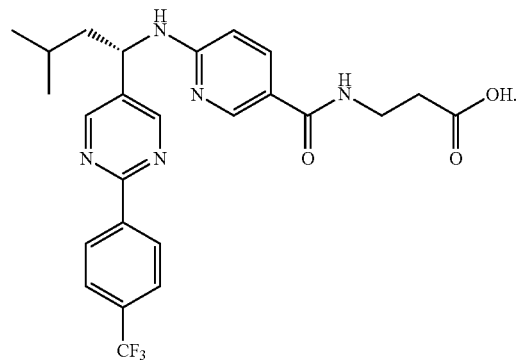 [SMILES: CC(C)C[C@H](Nc1ccc(C(=O)NCCC(=O)O)cn1)c1cnc(-c2ccc(C(F)(F)F)cc2)nc1]

* * * * *